US011753642B2

(12) United States Patent
Aumiller et al.

(10) Patent No.: US 11,753,642 B2
(45) Date of Patent: Sep. 12, 2023

(54) NUCLEIC ACIDS FOR INHIBITING EXPRESSION OF C3 IN A CELL

(71) Applicant: SILENCE THERAPEUTICS GMBH, Berlin (DE)

(72) Inventors: Verena Aumiller, Berlin (DE); Lucas Bethge, Potsdam (DE); Judith Hauptmann, Berlin (DE); Marie Wikström Lindholm, Malmö (SE); Adrien Weingärtner, Berlin (DE)

(73) Assignee: SILENCE THERAPEUTICS GMBH, Berlin (DE)

( * ) Notice: Subject to any disclaimer, the term of this patent is extended or adjusted under 35 U.S.C. 154(b) by 0 days.

(21) Appl. No.: 17/825,376

(22) Filed: May 26, 2022

(65) Prior Publication Data
US 2023/0024926 A1    Jan. 26, 2023

Related U.S. Application Data

(63) Continuation of application No. 17/612,120, filed as application No. PCT/EP2020/073904 on Aug. 26, 2020.

(51) Int. Cl.
C12N 15/113    (2010.01)
(52) U.S. Cl.
CPC ........ *C12N 15/113* (2013.01); *C12N 2310/14* (2013.01); *C12N 2310/315* (2013.01); *C12N 2310/3125* (2013.01); *C12N 2310/351* (2013.01); *C12N 2320/30* (2013.01)
(58) Field of Classification Search
CPC ............. C12N 15/113; C12N 2310/14; C12N 2310/315; C12N 2310/351; C12N 2320/30
USPC ..................... 435/6.1, 91.1, 91.31, 455, 458; 514/44 A; 536/23.1, 24.5
See application file for complete search history.

(56) References Cited

U.S. PATENT DOCUMENTS

| 5,885,968 | A  | 3/1999 | Biessen et al. |
| 2003/0096775 | A1 | 5/2003 | Graham et al. |
| 2008/0090997 | A1 | 4/2008 | Khvorova et al. |
| 2022/0017899 | A1 | 1/2022 | Aumiller et al. |

FOREIGN PATENT DOCUMENTS

| EP | 0758904 A1 | 2/1997 |
| EP | 1752536 A1 | 2/2007 |
| WO | 95/29697 A1 | 11/1995 |
| WO | 2015/089368 A2 | 6/2015 |
| WO | 2017/174657 A1 | 10/2017 |
| WO | 2019/089922 A1 | 5/2019 |

OTHER PUBLICATIONS

U.S. Appl. No. 17/612,120 (Year: 2021).*
Akinc et al., Targeted delivery of RNAi therapeutics with endogenous and exogenous ligand-based mechanisms, Molecular therapy: The journal of the American Society of Gene Therapy, 18(7):1357-1364 (2010).
Berge et al., Pharmaceutical Salts, Journal of Pharmaceutical Sciences, 66:1-19 (1977).
Biessen et al., Synthesis of cluster galactosides with high affinity for the hepatic asialoglycoprotein receptor, J Med. Chem., 38(9):1538-46 (1995).
Dubber et al., Solid-phase synthesis of multivalent glycoconjugates on a DNA synthesizer, Bioconjugate Chemistry, 14(1):239-246 (2003).
Elbashir et al., Duplexes of 21-nucleotide RNAs mediate RNA interference in cultured mammalian cells, Nature, 411:494-498 (2001).
European Application No. 19171455, European Search Report and Opinion, dated Jan. 10, 2020.
Fire et al., Potent and specific genetic interference by double-stranded RNA in Caenorhabditis elegans, Nature, 391(6669):806-811 (1998).
Haraszti et al., 5-Vinylphosphonate improves tissue accumulation and efficacy of conjugated siRNAs in vivo, Nucleic Acids Res., 45(13):7581-7592 (2017).
Hillmen et al., The complement inhibitor eculizumab in paroxysmal nocturnal hemoglobinuria, N. Engl. J. Med., 355(12):1233-43 (2006).
Hoevelmann et al., LNA-enhanced DNA FIT-probes for multicolour RNA imaging, Chem. Sci., 7(1):128-135 (2016).
International Application No. PCT/EP2019/082267, International Search Report and Written Opinion, dated Mar. 25, 2020.
International Application No. PCT/EP2019/082267, International Preliminary Report on Patentability, dated Jun. 3, 2021.
International Application No. PCT/EP2020/073904, International Preliminary Report on Patentability, dated Mar. 10, 2022.
International Application No. PCT/EP2020/073904, International Search Report and Written Opinion, dated Dec. 15, 2020.
Ishibashi et al., Asialoglycoprotein receptor deficiency in mice lacking the minor receptor subunit, J. Biol. Chem., 269(45):27803-27806 (1994).
Nair et al., Multivalent N-acetylgalactosamine-conjugated siRNA localizes in hepatocytes and elicits robust RNAi-mediated gene silencing, J Am. Chem. Soc., 136(49):16958-16961 (2014).
Partial European Application No. 19171455, European Search Report and Opinion, dated Oct. 10, 2019.
Prakash et al., Identification of metabolically stable 5'-phosphate analogs that support single-stranded siRNA activity, Nucleic Acids Res., 43(6):2993-3011 (2015).

(Continued)

*Primary Examiner* — Jane J Zara
(74) *Attorney, Agent, or Firm* — MARSHALL, GERSTEIN & BORUN LLP

(57) ABSTRACT

The invention relates to nucleic acid products that interfere with complement component C3 gene expression or inhibit its expression. The nucleic acids are preferably for use as treatment, prevention or reduction of risk of suffering from complement component C3 associated diseases, disorders or syndromes, particularly C3 Glomerulopathy (C3G), Paroxysmal Nocturnal Hemoglobinuria (PNH), atypical Hemolytic Uremic Syndrome (aHUS), Lupus nephritis, IgA nephropathy (IgA N), Cold Agglutinin Disease (CAD), Myasthenia gravis (MG), and Primary Membranous Nephropathy.

29 Claims, 22 Drawing Sheets

Specification includes a Sequence Listing.

(56) References Cited

OTHER PUBLICATIONS

Ricklin et al., Complement in disease: a defence system turning offensive, Nature Reviews Nephrology, 12:383-401 (2016).
Watts et al., Silencing disease genes in the laboratory and the clinic, Journal of Pathology, 226(2):365-379 (2012).
Weigel et al., Glycans as endocytosis signals: the cases of the asialoglycoprotein and hyaluronan/chondroitin sulfate Yeceptors, Biochim. Biophys. Acta , 1572(2-3):341-363 (2002).

* cited by examiner

Figure 2A
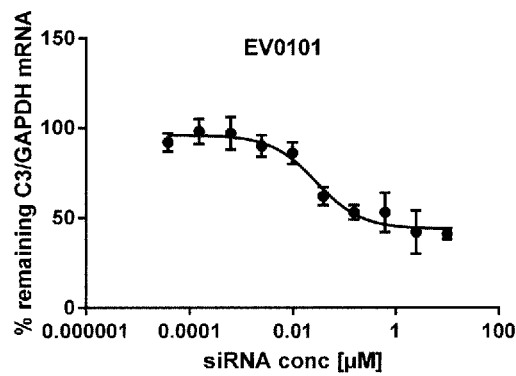
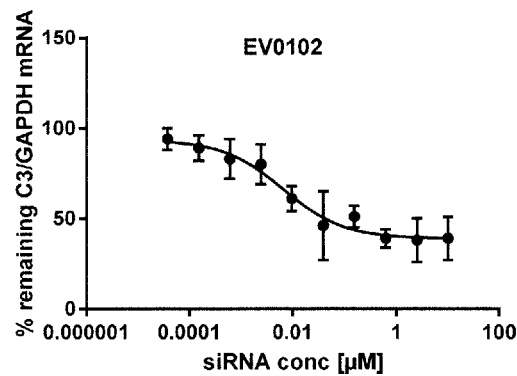
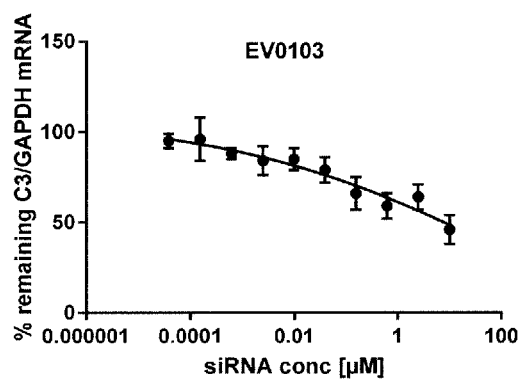
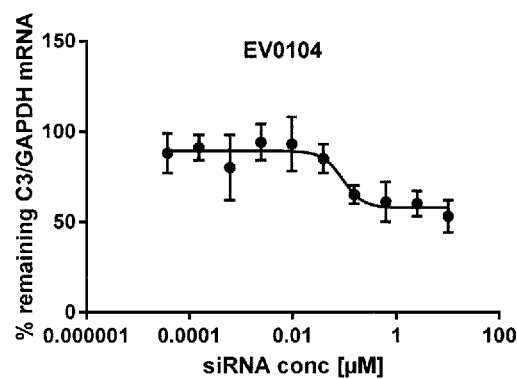
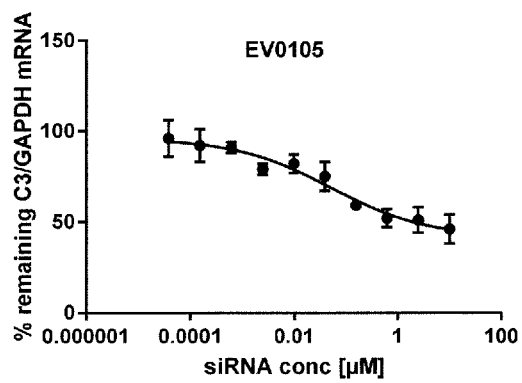
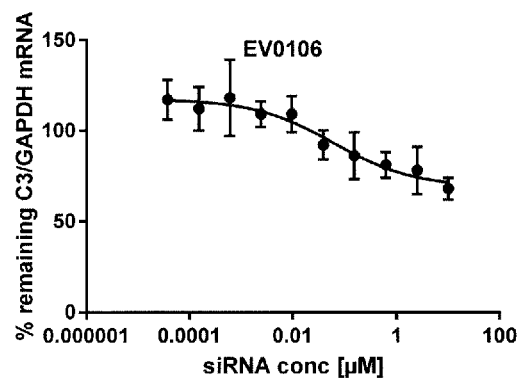

Figure 2B
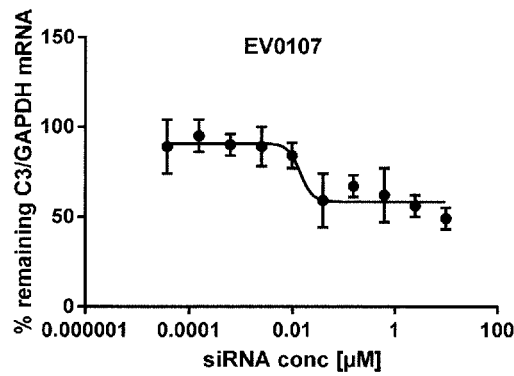
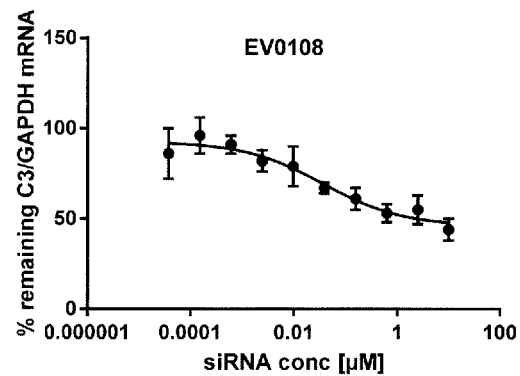
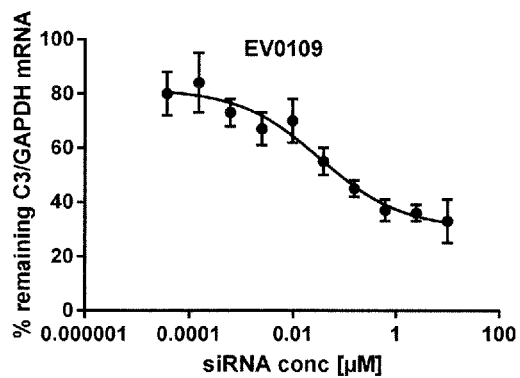
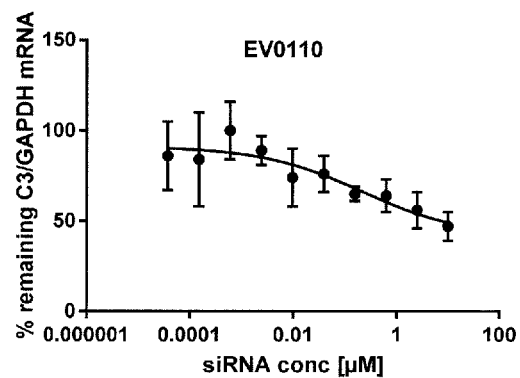
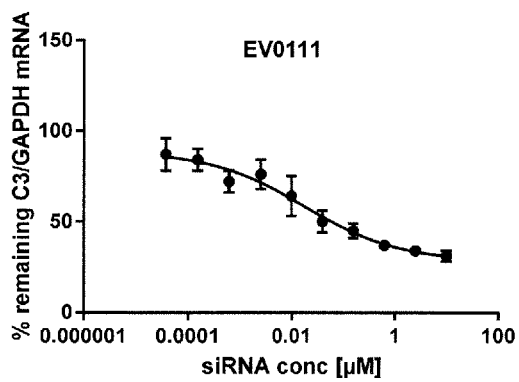
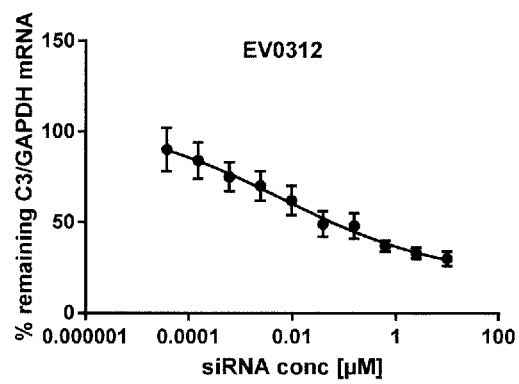

Figure 3A
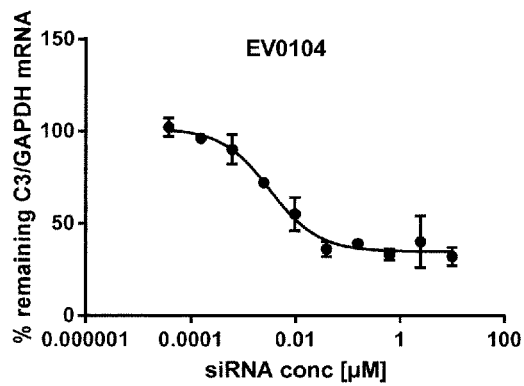
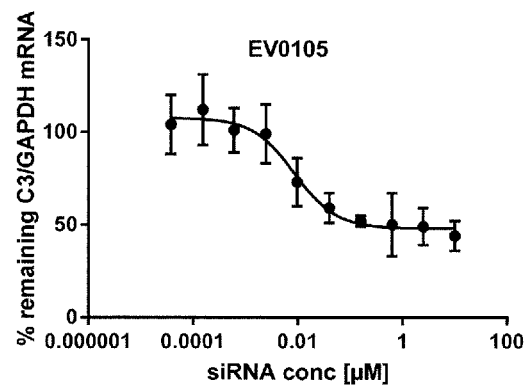
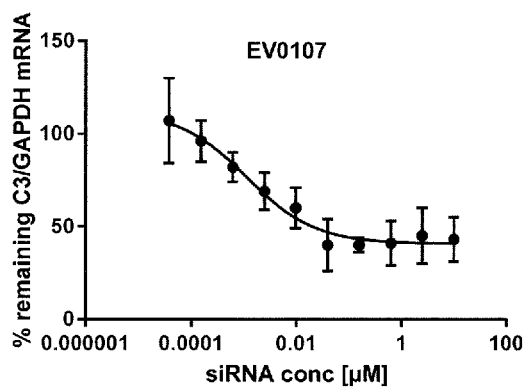
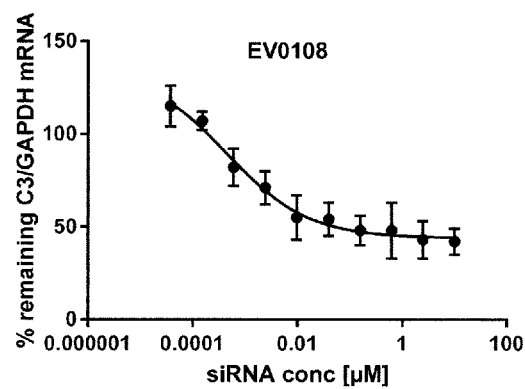
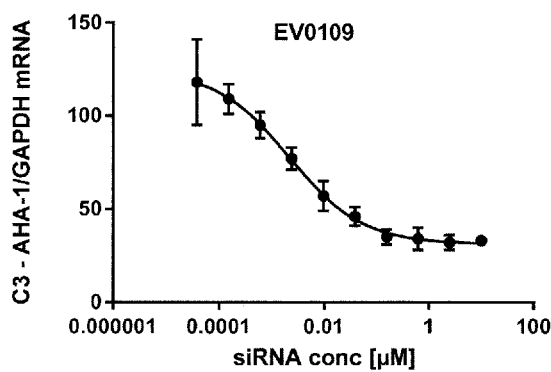

Figure 3B
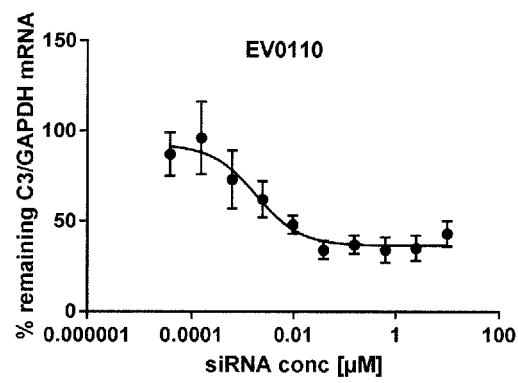
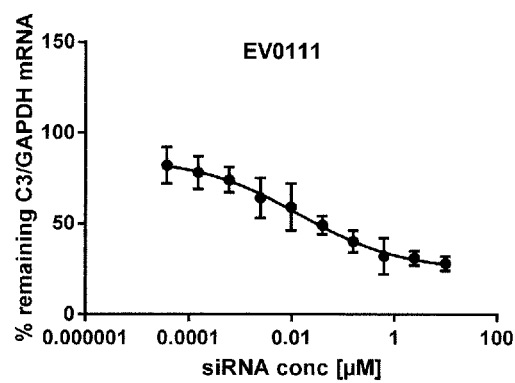
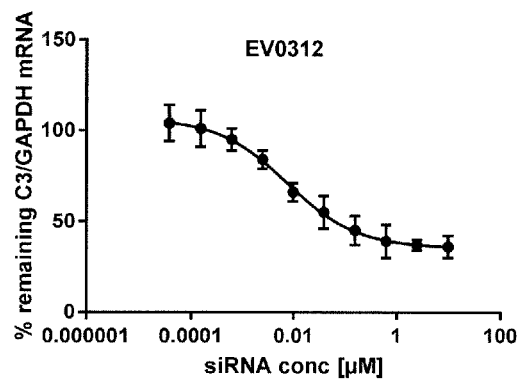

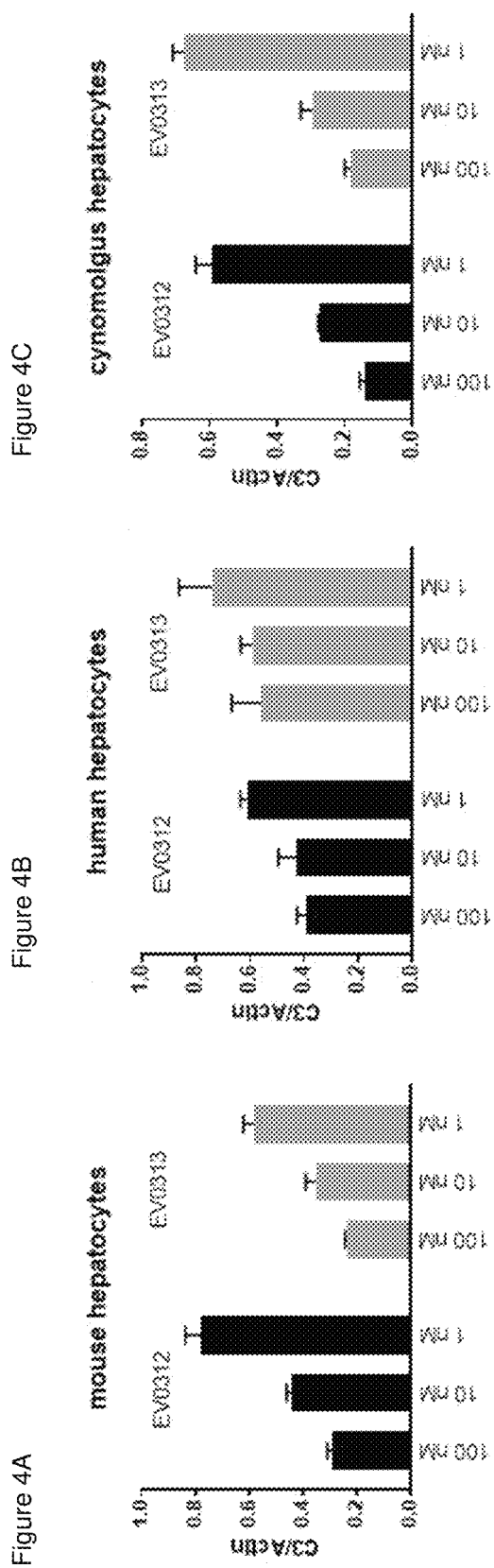

☐ Group A: Cfh def. + PBS
☐ Group B: Cfh def. + Non targeting
■ Group C: Cfh def. + siRNA C3 (10mg/kg)
☐ Group D: Cfh def. + siRNA C3 (5mg/kg)
☐ Group E: Cfh def. + siRNA C3 (1mg/kg)
☒ Group F: Wild Type female + PBS
☒ Group G: Wild Type female + siRNA C3 (10mg/kg)

☐ Group A: Cfh def. + PBS
▬ Group B: Cfh def. + Non targeting
■ Group C: Cfh def. + siRNA C3 (10mg/kg)
▨ Group D: Cfh def. + siRNA C3 (5mg/kg)
☐ Group E: Cfh def. + siRNA C3 (1mg/kg)
▨ Group F: Wild Type female + PBS
▨ Group G: Wild Type female + siRNA C3 (10mg/kg)

SEQUENCE LISTING

<160> NUMBER OF SEQ ID NOS: 425

<210> SEQ ID NO 1
<211> LENGTH: 19
<212> TYPE: RNA
<213> ORGANISM: Artificial Sequence
<220> FEATURE:
<223> OTHER INFORMATION: siRNA

<400> SEQUENCE: 1
uuucauagua ggcucggau                                                   19

<210> SEQ ID NO 2
<211> LENGTH: 19
<212> TYPE: RNA
<213> ORGANISM: Artificial Sequence

```
<220> FEATURE:
<223> OTHER INFORMATION: siRNA

<400> SEQUENCE: 2
auccgagccu acaugaaa                                                    19

<210> SEQ ID NO 3
<211> LENGTH: 19
<212> TYPE: RNA
<213> ORGANISM: Artificial Sequence
<220> FEATURE:
<223> OTHER INFORMATION: siRNA

<400> SEQUENCE: 3
uuucucugua ggcuccacu                                                   19

<210> SEQ ID NO 4
<211> LENGTH: 19
<212> TYPE: RNA
<213> ORGANISM: Artificial Sequence
<220> FEATURE:
<223> OTHER INFORMATION: siRNA

<400> SEQUENCE: 4
aguggagccu acagagaaa                                                   19

<210> SEQ ID NO 5
<211> LENGTH: 19
<212> TYPE: RNA
<213> ORGANISM: Artificial Sequence
<220> FEATURE:
<223> OTHER INFORMATION: siRNA

<400> SEQUENCE: 5
uuauagaugu aguagaauu                                                   19

<210> SEQ ID NO 6
<211> LENGTH: 19
<212> TYPE: RNA
<213> ORGANISM: Artificial Sequence
<220> FEATURE:
<223> OTHER INFORMATION: siRNA

<400> SEQUENCE: 6
aauucuacua caucuauaa                                                   19

<210> SEQ ID NO 7
<211> LENGTH: 19
<212> TYPE: RNA
<213> ORGANISM: Artificial Sequence
<220> FEATURE:
<223> OTHER INFORMATION: siRNA

<400> SEQUENCE: 7
augacaaagg cagucccu                                                    19

<210> SEQ ID NO 8
<211> LENGTH: 19
<212> TYPE: RNA
<213> ORGANISM: Artificial Sequence
<220> FEATURE:
<223> OTHER INFORMATION: siRNA

<400> SEQUENCE: 8
agggaacugc cuuugucau                                                   19
```

```
<210> SEQ ID NO 9
<211> LENGTH: 19
<212> TYPE: RNA
<213> ORGANISM: Artificial Sequence
<220> FEATURE:
<223> OTHER INFORMATION: siRNA

<400> SEQUENCE: 9
aucugguagg gagagguca                                                      19

<210> SEQ ID NO 10
<211> LENGTH: 19
<212> TYPE: RNA
<213> ORGANISM: Artificial Sequence
<220> FEATURE:
<223> OTHER INFORMATION: siRNA

<400> SEQUENCE: 10
ugaccucucc cuaccagau                                                      19

<210> SEQ ID NO 11
<211> LENGTH: 19
<212> TYPE: RNA
<213> ORGANISM: Artificial Sequence
<220> FEATURE:
<223> OTHER INFORMATION: siRNA

<400> SEQUENCE: 11
uguguguuga ugcugaguu                                                      19

<210> SEQ ID NO 12
<211> LENGTH: 19
<212> TYPE: RNA
<213> ORGANISM: Artificial Sequence
<220> FEATURE:
<223> OTHER INFORMATION: siRNA

<400> SEQUENCE: 12
aacucagcau caacacaca                                                      19

<210> SEQ ID NO 13
<211> LENGTH: 19
<212> TYPE: RNA
<213> ORGANISM: Artificial Sequence
<220> FEATURE:
<223> OTHER INFORMATION: siRNA

<400> SEQUENCE: 13
uaauuguugg aguugccca                                                      19

<210> SEQ ID NO 14
<211> LENGTH: 19
<212> TYPE: RNA
<213> ORGANISM: Artificial Sequence
<220> FEATURE:
<223> OTHER INFORMATION: siRNA

<400> SEQUENCE: 14
ugggcaacuc caacaauua                                                      19

<210> SEQ ID NO 15
<211> LENGTH: 19
<212> TYPE: RNA
<213> ORGANISM: Artificial Sequence
<220> FEATURE:
<223> OTHER INFORMATION: siRNA
```

<400> SEQUENCE: 15
aggaaguuga cguugaggg                                                      19

<210> SEQ ID NO 16
<211> LENGTH: 19
<212> TYPE: RNA
<213> ORGANISM: Artificial Sequence
<220> FEATURE:
<223> OTHER INFORMATION: siRNA

<400> SEQUENCE: 16
cccucaacgu caacuuccu                                                      19

<210> SEQ ID NO 17
<211> LENGTH: 19
<212> TYPE: RNA
<213> ORGANISM: Artificial Sequence
<220> FEATURE:
<223> OTHER INFORMATION: siRNA

<400> SEQUENCE: 17
augaagucgg uggugaugg                                                      19

<210> SEQ ID NO 18
<211> LENGTH: 19
<212> TYPE: RNA
<213> ORGANISM: Artificial Sequence
<220> FEATURE:
<223> OTHER INFORMATION: siRNA

<400> SEQUENCE: 18
ccaucaccac cgacuucau                                                      19

<210> SEQ ID NO 19
<211> LENGTH: 19
<212> TYPE: RNA
<213> ORGANISM: Artificial Sequence
<220> FEATURE:
<223> OTHER INFORMATION: siRNA

<400> SEQUENCE: 19
uuuaccacca gcgagccca                                                      19

<210> SEQ ID NO 20
<211> LENGTH: 19
<212> TYPE: RNA
<213> ORGANISM: Artificial Sequence
<220> FEATURE:
<223> OTHER INFORMATION: siRNA

<400> SEQUENCE: 20
ugggcucgcu ggugguaaa                                                      19

<210> SEQ ID NO 21
<211> LENGTH: 19
<212> TYPE: RNA
<213> ORGANISM: Artificial Sequence
<220> FEATURE:
<223> OTHER INFORMATION: siRNA

<400> SEQUENCE: 21
ucuaucuuca gggucaucu                                                      19

<210> SEQ ID NO 22

```
<211> LENGTH: 19
<212> TYPE: RNA
<213> ORGANISM: Artificial Sequence
<220> FEATURE:
<223> OTHER INFORMATION: siRNA

<400> SEQUENCE: 22
agaugacccu gaagauaga                                                      19

<210> SEQ ID NO 23
<211> LENGTH: 19
<212> TYPE: RNA
<213> ORGANISM: Artificial Sequence
<220> FEATURE:
<223> OTHER INFORMATION: siRNA

<400> SEQUENCE: 23
auguaguugc agcagucca                                                      19

<210> SEQ ID NO 24
<211> LENGTH: 19
<212> TYPE: RNA
<213> ORGANISM: Artificial Sequence
<220> FEATURE:
<223> OTHER INFORMATION: siRNA

<400> SEQUENCE: 24
uggacugcug caacuacau                                                      19

<210> SEQ ID NO 25
<211> LENGTH: 19
<212> TYPE: RNA
<213> ORGANISM: Artificial Sequence
<220> FEATURE:
<223> OTHER INFORMATION: siRNA

<400> SEQUENCE: 25
aauauauuca ugagcuucg                                                      19

<210> SEQ ID NO 26
<211> LENGTH: 19
<212> TYPE: RNA
<213> ORGANISM: Artificial Sequence
<220> FEATURE:
<223> OTHER INFORMATION: siRNA

<400> SEQUENCE: 26
cgaagcucau gaauauauu                                                      19

<210> SEQ ID NO 27
<211> LENGTH: 19
<212> TYPE: RNA
<213> ORGANISM: Artificial Sequence
<220> FEATURE:
<223> OTHER INFORMATION: siRNA

<400> SEQUENCE: 27
aaauauauuc augagcuuc                                                      19

<210> SEQ ID NO 28
<211> LENGTH: 19
<212> TYPE: RNA
<213> ORGANISM: Artificial Sequence
<220> FEATURE:
<223> OTHER INFORMATION: siRNA

<400> SEQUENCE: 28
```

```
gaagcucaug aauauauuu                                          19

<210> SEQ ID NO 29
<211> LENGTH: 19
<212> TYPE: RNA
<213> ORGANISM: Artificial Sequence
<220> FEATURE:
<223> OTHER INFORMATION: siRNA

<400> SEQUENCE: 29
uccugcauua cugugaccu                                          19

<210> SEQ ID NO 30
<211> LENGTH: 19
<212> TYPE: RNA
<213> ORGANISM: Artificial Sequence
<220> FEATURE:
<223> OTHER INFORMATION: siRNA

<400> SEQUENCE: 30
aggucacagu aaugcagga                                          19

<210> SEQ ID NO 31
<211> LENGTH: 19
<212> TYPE: RNA
<213> ORGANISM: Artificial Sequence
<220> FEATURE:
<223> OTHER INFORMATION: siRNA

<400> SEQUENCE: 31
caacagagua ggguagccg                                          19

<210> SEQ ID NO 32
<211> LENGTH: 19
<212> TYPE: RNA
<213> ORGANISM: Artificial Sequence
<220> FEATURE:
<223> OTHER INFORMATION: siRNA

<400> SEQUENCE: 32
cggcuacccu acucuguug                                          19

<210> SEQ ID NO 33
<211> LENGTH: 19
<212> TYPE: RNA
<213> ORGANISM: Artificial Sequence
<220> FEATURE:
<223> OTHER INFORMATION: siRNA

<400> SEQUENCE: 33
ucgaacaaca gaguagggu                                          19

<210> SEQ ID NO 34
<211> LENGTH: 19
<212> TYPE: RNA
<213> ORGANISM: Artificial Sequence
<220> FEATURE:
<223> OTHER INFORMATION: siRNA

<400> SEQUENCE: 34
acccuacucu guuguucga                                          19

<210> SEQ ID NO 35
<211> LENGTH: 19
<212> TYPE: RNA
```

```
<213> ORGANISM: Artificial Sequence
<220> FEATURE:
<223> OTHER INFORMATION: siRNA

<400> SEQUENCE: 35
uuucgaacaa cagaguagg                                                19

<210> SEQ ID NO 36
<211> LENGTH: 19
<212> TYPE: RNA
<213> ORGANISM: Artificial Sequence
<220> FEATURE:
<223> OTHER INFORMATION: siRNA

<400> SEQUENCE: 36
ccuacucugu uguucgaaa                                                19

<210> SEQ ID NO 37
<211> LENGTH: 19
<212> TYPE: RNA
<213> ORGANISM: Artificial Sequence
<220> FEATURE:
<223> OTHER INFORMATION: siRNA

<400> SEQUENCE: 37
guuucaucca gguaaugca                                                19

<210> SEQ ID NO 38
<211> LENGTH: 19
<212> TYPE: RNA
<213> ORGANISM: Artificial Sequence
<220> FEATURE:
<223> OTHER INFORMATION: siRNA

<400> SEQUENCE: 38
ugcauuaccu ggaugaaac                                                19

<210> SEQ ID NO 39
<211> LENGTH: 19
<212> TYPE: RNA
<213> ORGANISM: Artificial Sequence
<220> FEATURE:
<223> OTHER INFORMATION: siRNA

<400> SEQUENCE: 39
uuaucuuugg cugugguca                                                19

<210> SEQ ID NO 40
<211> LENGTH: 19
<212> TYPE: RNA
<213> ORGANISM: Artificial Sequence
<220> FEATURE:
<223> OTHER INFORMATION: siRNA

<400> SEQUENCE: 40
ugaccacagc caaagauaa                                                19

<210> SEQ ID NO 41
<211> LENGTH: 19
<212> TYPE: RNA
<213> ORGANISM: Artificial Sequence
<220> FEATURE:
<223> OTHER INFORMATION: siRNA

<400> SEQUENCE: 41
uguucauuga gccaacgca                                                19
```

```
<210> SEQ ID NO 42
<211> LENGTH: 19
<212> TYPE: RNA
<213> ORGANISM: Artificial Sequence
<220> FEATURE:
<223> OTHER INFORMATION: siRNA

<400> SEQUENCE: 42
ugcguuggcu caaugaaca                                                  19

<210> SEQ ID NO 43
<211> LENGTH: 19
<212> TYPE: RNA
<213> ORGANISM: Artificial Sequence
<220> FEATURE:
<223> OTHER INFORMATION: siRNA

<400> SEQUENCE: 43
uugguauuga gccaaggcu                                                  19

<210> SEQ ID NO 44
<211> LENGTH: 19
<212> TYPE: RNA
<213> ORGANISM: Artificial Sequence
<220> FEATURE:
<223> OTHER INFORMATION: siRNA

<400> SEQUENCE: 44
agccuuggcu caauaccaa                                                  19

<210> SEQ ID NO 45
<211> LENGTH: 19
<212> TYPE: RNA
<213> ORGANISM: Artificial Sequence
<220> FEATURE:
<223> OTHER INFORMATION: siRNA

<400> SEQUENCE: 45
uuuauuacag gugaguuga                                                  19

<210> SEQ ID NO 46
<211> LENGTH: 19
<212> TYPE: RNA
<213> ORGANISM: Artificial Sequence
<220> FEATURE:
<223> OTHER INFORMATION: siRNA

<400> SEQUENCE: 46
ucaacucacc uguaauaaa                                                  19

<210> SEQ ID NO 47
<211> LENGTH: 19
<212> TYPE: RNA
<213> ORGANISM: Artificial Sequence
<220> FEATURE:
<223> OTHER INFORMATION: siRNA

<400> SEQUENCE: 47
uuucuguuuc cggugcugg                                                  19

<210> SEQ ID NO 48
<211> LENGTH: 19
<212> TYPE: RNA
<213> ORGANISM: Artificial Sequence
<220> FEATURE:
```

```
<223> OTHER INFORMATION: siRNA

<400> SEQUENCE: 48
ccagcaccgg aaacagaaa                                                  19

<210> SEQ ID NO 49
<211> LENGTH: 19
<212> TYPE: RNA
<213> ORGANISM: Artificial Sequence
<220> FEATURE:
<223> OTHER INFORMATION: siRNA

<400> SEQUENCE: 49
ucaaggauca uaguguucu                                                  19

<210> SEQ ID NO 50
<211> LENGTH: 19
<212> TYPE: RNA
<213> ORGANISM: Artificial Sequence
<220> FEATURE:
<223> OTHER INFORMATION: siRNA

<400> SEQUENCE: 50
agaacacuau gauccuuga                                                  19

<210> SEQ ID NO 51
<211> LENGTH: 19
<212> TYPE: RNA
<213> ORGANISM: Artificial Sequence
<220> FEATURE:
<223> OTHER INFORMATION: siRNA

<400> SEQUENCE: 51
aucucaagga ucauagugu                                                  19

<210> SEQ ID NO 52
<211> LENGTH: 19
<212> TYPE: RNA
<213> ORGANISM: Artificial Sequence
<220> FEATURE:
<223> OTHER INFORMATION: siRNA

<400> SEQUENCE: 52
acacuaugau ccuugagau                                                  19

<210> SEQ ID NO 53
<211> LENGTH: 19
<212> TYPE: RNA
<213> ORGANISM: Artificial Sequence
<220> FEATURE:
<223> OTHER INFORMATION: siRNA

<400> SEQUENCE: 53
ucauacuugg agauguauc                                                  19

<210> SEQ ID NO 54
<211> LENGTH: 19
<212> TYPE: RNA
<213> ORGANISM: Artificial Sequence
<220> FEATURE:
<223> OTHER INFORMATION: siRNA

<400> SEQUENCE: 54
gauacaucuc caaguauga                                                  19
```

```
<210> SEQ ID NO 55
<211> LENGTH: 19
<212> TYPE: RNA
<213> ORGANISM: Artificial Sequence
<220> FEATURE:
<223> OTHER INFORMATION: siRNA

<400> SEQUENCE: 55
uaucggagaa ggcuuuguc                                              19

<210> SEQ ID NO 56
<211> LENGTH: 19
<212> TYPE: RNA
<213> ORGANISM: Artificial Sequence
<220> FEATURE:
<223> OTHER INFORMATION: siRNA

<400> SEQUENCE: 56
gacaaagccu ucuccgaua                                              19

<210> SEQ ID NO 57
<211> LENGTH: 19
<212> TYPE: RNA
<213> ORGANISM: Artificial Sequence
<220> FEATURE:
<223> OTHER INFORMATION: siRNA

<400> SEQUENCE: 57
augaugaggg uguuccuau                                              19

<210> SEQ ID NO 58
<211> LENGTH: 19
<212> TYPE: RNA
<213> ORGANISM: Artificial Sequence
<220> FEATURE:
<223> OTHER INFORMATION: siRNA

<400> SEQUENCE: 58
auaggaacac ccucaucau                                              19

<210> SEQ ID NO 59
<211> LENGTH: 19
<212> TYPE: RNA
<213> ORGANISM: Artificial Sequence
<220> FEATURE:
<223> OTHER INFORMATION: siRNA

<400> SEQUENCE: 59
uauuggugaa cuuugaaag                                              19

<210> SEQ ID NO 60
<211> LENGTH: 19
<212> TYPE: RNA
<213> ORGANISM: Artificial Sequence
<220> FEATURE:
<223> OTHER INFORMATION: siRNA

<400> SEQUENCE: 60
cuuucaaagu ucaccaaua                                              19

<210> SEQ ID NO 61
<211> LENGTH: 19
<212> TYPE: RNA
<213> ORGANISM: Artificial Sequence
<220> FEATURE:
<223> OTHER INFORMATION: siRNA
```

```
<400> SEQUENCE: 61
agcuuguuca gcuuccau                                                    19

<210> SEQ ID NO 62
<211> LENGTH: 19
<212> TYPE: RNA
<213> ORGANISM: Artificial Sequence
<220> FEATURE:
<223> OTHER INFORMATION: siRNA

<400> SEQUENCE: 62
auggaaagcu gaacaagcu                                                   19

<210> SEQ ID NO 63
<211> LENGTH: 19
<212> TYPE: RNA
<213> ORGANISM: Artificial Sequence
<220> FEATURE:
<223> OTHER INFORMATION: siRNA

<400> SEQUENCE: 63
uuuguaugaa gcaauucuc                                                   19

<210> SEQ ID NO 64
<211> LENGTH: 19
<212> TYPE: RNA
<213> ORGANISM: Artificial Sequence
<220> FEATURE:
<223> OTHER INFORMATION: siRNA

<400> SEQUENCE: 64
gagaauugcu ucauacaaa                                                   19

<210> SEQ ID NO 65
<211> LENGTH: 19
<212> TYPE: RNA
<213> ORGANISM: Artificial Sequence
<220> FEATURE:
<223> OTHER INFORMATION: siRNA

<400> SEQUENCE: 65
gucuuguaca cauagucca                                                   19

<210> SEQ ID NO 66
<211> LENGTH: 19
<212> TYPE: RNA
<213> ORGANISM: Artificial Sequence
<220> FEATURE:
<223> OTHER INFORMATION: siRNA

<400> SEQUENCE: 66
uggacuaugu guacaagac                                                   19

<210> SEQ ID NO 67
<211> LENGTH: 19
<212> TYPE: RNA
<213> ORGANISM: Artificial Sequence
<220> FEATURE:
<223> OTHER INFORMATION: siRNA

<400> SEQUENCE: 67
ugcucaaugg ccaugaugu                                                   19

<210> SEQ ID NO 68
<211> LENGTH: 19
```

```
<212> TYPE: RNA
<213> ORGANISM: Artificial Sequence
<220> FEATURE:
<223> OTHER INFORMATION: siRNA

<400> SEQUENCE: 68
acaucauggc cauugagca                                                    19

<210> SEQ ID NO 69
<211> LENGTH: 19
<212> TYPE: RNA
<213> ORGANISM: Artificial Sequence
<220> FEATURE:
<223> OTHER INFORMATION: siRNA

<400> SEQUENCE: 69
uuggcauucg uccuccucg                                                    19

<210> SEQ ID NO 70
<211> LENGTH: 19
<212> TYPE: RNA
<213> ORGANISM: Artificial Sequence
<220> FEATURE:
<223> OTHER INFORMATION: siRNA

<400> SEQUENCE: 70
cgaggaggac gaaugccaa                                                    19

<210> SEQ ID NO 71
<211> LENGTH: 19
<212> TYPE: RNA
<213> ORGANISM: Artificial Sequence
<220> FEATURE:
<223> OTHER INFORMATION: siRNA

<400> SEQUENCE: 71
gucuggauga agagguacc                                                    19

<210> SEQ ID NO 72
<211> LENGTH: 19
<212> TYPE: RNA
<213> ORGANISM: Artificial Sequence
<220> FEATURE:
<223> OTHER INFORMATION: siRNA

<400> SEQUENCE: 72
gguaccucuu cauccagac                                                    19

<210> SEQ ID NO 73
<211> LENGTH: 19
<212> TYPE: RNA
<213> ORGANISM: Artificial Sequence
<220> FEATURE:
<223> OTHER INFORMATION: siRNA

<400> SEQUENCE: 73
ugucuggaug aagagguac                                                    19

<210> SEQ ID NO 74
<211> LENGTH: 19
<212> TYPE: RNA
<213> ORGANISM: Artificial Sequence
<220> FEATURE:
<223> OTHER INFORMATION: siRNA

<400> SEQUENCE: 74
```
guaccucuuc auccagaca                                              19

<210> SEQ ID NO 75
<211> LENGTH: 19
<212> TYPE: RNA
<213> ORGANISM: Artificial Sequence
<220> FEATURE:
<223> OTHER INFORMATION: siRNA

<400> SEQUENCE: 75
ucugucugga ugaagaggu                                              19

<210> SEQ ID NO 76
<211> LENGTH: 19
<212> TYPE: RNA
<213> ORGANISM: Artificial Sequence
<220> FEATURE:
<223> OTHER INFORMATION: siRNA

<400> SEQUENCE: 76
accucuucau ccagacaga                                              19

<210> SEQ ID NO 77
<211> LENGTH: 19
<212> TYPE: RNA
<213> ORGANISM: Artificial Sequence
<220> FEATURE:
<223> OTHER INFORMATION: siRNA

<400> SEQUENCE: 77
cuugucuguc uggaugaag                                              19

<210> SEQ ID NO 78
<211> LENGTH: 19
<212> TYPE: RNA
<213> ORGANISM: Artificial Sequence
<220> FEATURE:
<223> OTHER INFORMATION: siRNA

<400> SEQUENCE: 78
cuucauccag acagacaag                                              19

<210> SEQ ID NO 79
<211> LENGTH: 19
<212> TYPE: RNA
<213> ORGANISM: Artificial Sequence
<220> FEATURE:
<223> OTHER INFORMATION: siRNA

<400> SEQUENCE: 79
auggucuugu cugucugga                                              19

<210> SEQ ID NO 80
<211> LENGTH: 19
<212> TYPE: RNA
<213> ORGANISM: Artificial Sequence
<220> FEATURE:
<223> OTHER INFORMATION: siRNA

<400> SEQUENCE: 80
uccagacaga caagaccau                                              19

<210> SEQ ID NO 81
<211> LENGTH: 19
<212> TYPE: RNA
<213> ORGANISM: Artificial Sequence

```
<220> FEATURE:
<223> OTHER INFORMATION: siRNA

<400> SEQUENCE: 81
agauggucuu gucugucug                                                      19

<210> SEQ ID NO 82
<211> LENGTH: 19
<212> TYPE: RNA
<213> ORGANISM: Artificial Sequence
<220> FEATURE:
<223> OTHER INFORMATION: siRNA

<400> SEQUENCE: 82
cagacagaca agaccaucu                                                      19

<210> SEQ ID NO 83
<211> LENGTH: 19
<212> TYPE: RNA
<213> ORGANISM: Artificial Sequence
<220> FEATURE:
<223> OTHER INFORMATION: siRNA

<400> SEQUENCE: 83
guagaugguc uugucuguc                                                      19

<210> SEQ ID NO 84
<211> LENGTH: 19
<212> TYPE: RNA
<213> ORGANISM: Artificial Sequence
<220> FEATURE:
<223> OTHER INFORMATION: siRNA

<400> SEQUENCE: 84
gacagacaag accaucuac                                                      19

<210> SEQ ID NO 85
<211> LENGTH: 19
<212> TYPE: RNA
<213> ORGANISM: Artificial Sequence
<220> FEATURE:
<223> OTHER INFORMATION: siRNA

<400> SEQUENCE: 85
guguagaugg ucuugucug                                                      19

<210> SEQ ID NO 86
<211> LENGTH: 19
<212> TYPE: RNA
<213> ORGANISM: Artificial Sequence
<220> FEATURE:
<223> OTHER INFORMATION: siRNA

<400> SEQUENCE: 86
cagacaagac caucuacac                                                      19

<210> SEQ ID NO 87
<211> LENGTH: 19
<212> TYPE: RNA
<213> ORGANISM: Artificial Sequence
<220> FEATURE:
<223> OTHER INFORMATION: siRNA

<400> SEQUENCE: 87
gggguguaga uggucuugu                                                      19
```

<210> SEQ ID NO 88
<211> LENGTH: 19
<212> TYPE: RNA
<213> ORGANISM: Artificial Sequence
<220> FEATURE:
<223> OTHER INFORMATION: siRNA

<400> SEQUENCE: 88
acaagaccau cuacacccc                                                    19

<210> SEQ ID NO 89
<211> LENGTH: 19
<212> TYPE: RNA
<213> ORGANISM: Artificial Sequence
<220> FEATURE:
<223> OTHER INFORMATION: siRNA

<400> SEQUENCE: 89
uaggcucgga ucuuccacu                                                    19

<210> SEQ ID NO 90
<211> LENGTH: 19
<212> TYPE: RNA
<213> ORGANISM: Artificial Sequence
<220> FEATURE:
<223> OTHER INFORMATION: siRNA

<400> SEQUENCE: 90
aguggaagau ccgagccua                                                    19

<210> SEQ ID NO 91
<211> LENGTH: 19
<212> TYPE: RNA
<213> ORGANISM: Artificial Sequence
<220> FEATURE:
<223> OTHER INFORMATION: siRNA

<400> SEQUENCE: 91
cucgaaacug ggcagcacg                                                    19

<210> SEQ ID NO 92
<211> LENGTH: 19
<212> TYPE: RNA
<213> ORGANISM: Artificial Sequence
<220> FEATURE:
<223> OTHER INFORMATION: siRNA

<400> SEQUENCE: 92
cgugcugccc aguuucgag                                                    19

<210> SEQ ID NO 93
<211> LENGTH: 19
<212> TYPE: RNA
<213> ORGANISM: Artificial Sequence
<220> FEATURE:
<223> OTHER INFORMATION: siRNA

<400> SEQUENCE: 93
uuggugaagu ggaucuggu                                                    19

<210> SEQ ID NO 94
<211> LENGTH: 19
<212> TYPE: RNA
<213> ORGANISM: Artificial Sequence
<220> FEATURE:
<223> OTHER INFORMATION: siRNA

```
<400> SEQUENCE: 94
accagaucca cuucaccaa                                                    19

<210> SEQ ID NO 95
<211> LENGTH: 19
<212> TYPE: RNA
<213> ORGANISM: Artificial Sequence
<220> FEATURE:
<223> OTHER INFORMATION: siRNA

<400> SEQUENCE: 95
ucuuggugaa guggaucug                                                    19

<210> SEQ ID NO 96
<211> LENGTH: 19
<212> TYPE: RNA
<213> ORGANISM: Artificial Sequence
<220> FEATURE:
<223> OTHER INFORMATION: siRNA

<400> SEQUENCE: 96
cagauccacu ucaccaaga                                                    19

<210> SEQ ID NO 97
<211> LENGTH: 19
<212> TYPE: RNA
<213> ORGANISM: Artificial Sequence
<220> FEATURE:
<223> OTHER INFORMATION: siRNA

<400> SEQUENCE: 97
gucuugguga aguggaucu                                                    19

<210> SEQ ID NO 98
<211> LENGTH: 19
<212> TYPE: RNA
<213> ORGANISM: Artificial Sequence
<220> FEATURE:
<223> OTHER INFORMATION: siRNA

<400> SEQUENCE: 98
agauccacuu caccaagac                                                    19

<210> SEQ ID NO 99
<211> LENGTH: 19
<212> TYPE: RNA
<213> ORGANISM: Artificial Sequence
<220> FEATURE:
<223> OTHER INFORMATION: siRNA

<400> SEQUENCE: 99
ggugucuugg ugaagugga                                                    19

<210> SEQ ID NO 100
<211> LENGTH: 19
<212> TYPE: RNA
<213> ORGANISM: Artificial Sequence
<220> FEATURE:
<223> OTHER INFORMATION: siRNA

<400> SEQUENCE: 100
uccacuucac caagacacc                                                    19

<210> SEQ ID NO 101
```

```
<211> LENGTH: 19
<212> TYPE: RNA
<213> ORGANISM: Artificial Sequence
<220> FEATURE:
<223> OTHER INFORMATION: siRNA

<400> SEQUENCE: 101
aacaccauga ggucaaagg                                                    19

<210> SEQ ID NO 102
<211> LENGTH: 19
<212> TYPE: RNA
<213> ORGANISM: Artificial Sequence
<220> FEATURE:
<223> OTHER INFORMATION: siRNA

<400> SEQUENCE: 102 ccuugaccu cauggguguu                                                    19

<210> SEQ ID NO 103
<211> LENGTH: 19
<212> TYPE: RNA
<213> ORGANISM: Artificial Sequence
<220> FEATURE:
<223> OTHER INFORMATION: siRNA

<400> SEQUENCE: 103
gaacaccaug aggucaaag                                                    19

<210> SEQ ID NO 104
<211> LENGTH: 19
<212> TYPE: RNA
<213> ORGANISM: Artificial Sequence
<220> FEATURE:
<223> OTHER INFORMATION: siRNA

<400> SEQUENCE: 104
cuuugaccuc augguguuc                                                    19

<210> SEQ ID NO 105
<211> LENGTH: 19
<212> TYPE: RNA
<213> ORGANISM: Artificial Sequence
<220> FEATURE:
<223> OTHER INFORMATION: siRNA

<400> SEQUENCE: 105
gucacgaaca ccaugaggu                                                    19

<210> SEQ ID NO 106
<211> LENGTH: 19
<212> TYPE: RNA
<213> ORGANISM: Artificial Sequence
<220> FEATURE:
<223> OTHER INFORMATION: siRNA

<400> SEQUENCE: 106
accucauggu guucgugac                                                    19

<210> SEQ ID NO 107
<211> LENGTH: 19
<212> TYPE: RNA
<213> ORGANISM: Artificial Sequence
<220> FEATURE:
<223> OTHER INFORMATION: siRNA

<400> SEQUENCE: 107
```
acacagaucc cuuucuugu                                            19

<210> SEQ ID NO 108
<211> LENGTH: 19
<212> TYPE: RNA
<213> ORGANISM: Artificial Sequence
<220> FEATURE:
<223> OTHER INFORMATION: siRNA

<400> SEQUENCE: 108
acaagaaagg gaucugugu                                            19

<210> SEQ ID NO 109
<211> LENGTH: 19
<212> TYPE: RNA
<213> ORGANISM: Artificial Sequence
<220> FEATURE:
<223> OTHER INFORMATION: siRNA

<400> SEQUENCE: 109
ccuugcagga gaauucugg                                            19

<210> SEQ ID NO 110
<211> LENGTH: 19
<212> TYPE: RNA
<213> ORGANISM: Artificial Sequence
<220> FEATURE:
<223> OTHER INFORMATION: siRNA

<400> SEQUENCE: 110
ccagaauucu ccugcaagg                                            19

<210> SEQ ID NO 111
<211> LENGTH: 19
<212> TYPE: RNA
<213> ORGANISM: Artificial Sequence
<220> FEATURE:
<223> OTHER INFORMATION: siRNA

<400> SEQUENCE: 111
agagagaaga ccuugacca                                            19

<210> SEQ ID NO 112
<211> LENGTH: 19
<212> TYPE: RNA
<213> ORGANISM: Artificial Sequence
<220> FEATURE:
<223> OTHER INFORMATION: siRNA

<400> SEQUENCE: 112
uggucaaggu cuucucucu                                            19

<210> SEQ ID NO 113
<211> LENGTH: 19
<212> TYPE: RNA
<213> ORGANISM: Artificial Sequence
<220> FEATURE:
<223> OTHER INFORMATION: siRNA

<400> SEQUENCE: 113
gagucgaugg cgaugaggu                                            19

<210> SEQ ID NO 114
<211> LENGTH: 19
<212> TYPE: RNA

```
<213> ORGANISM: Artificial Sequence
<220> FEATURE:
<223> OTHER INFORMATION: siRNA

<400> SEQUENCE: 114
accucaucgc caucgacuc                                                      19

<210> SEQ ID NO 115
<211> LENGTH: 19
<212> TYPE: RNA
<213> ORGANISM: Artificial Sequence
<220> FEATURE:
<223> OTHER INFORMATION: siRNA

<400> SEQUENCE: 115
gcuuggaaca ccaugaagg                                                      19

<210> SEQ ID NO 116
<211> LENGTH: 19
<212> TYPE: RNA
<213> ORGANISM: Artificial Sequence
<220> FEATURE:
<223> OTHER INFORMATION: siRNA

<400> SEQUENCE: 116
ccuucauggu guuccaagc                                                      19

<210> SEQ ID NO 117
<211> LENGTH: 19
<212> TYPE: RNA
<213> ORGANISM: Artificial Sequence
<220> FEATURE:
<223> OTHER INFORMATION: siRNA

<400> SEQUENCE: 117 ucauuuccu uggucucuu                                                       19

<210> SEQ ID NO 118
<211> LENGTH: 19
<212> TYPE: RNA
<213> ORGANISM: Artificial Sequence
<220> FEATURE:
<223> OTHER INFORMATION: siRNA

<400> SEQUENCE: 118
aagagaccaa ggaaaauga                                                      19

<210> SEQ ID NO 119
<211> LENGTH: 19
<212> TYPE: RNA
<213> ORGANISM: Artificial Sequence
<220> FEATURE:
<223> OTHER INFORMATION: siRNA

<400> SEQUENCE: 119
ugugucugga gcaaagcca                                                      19

<210> SEQ ID NO 120
<211> LENGTH: 19
<212> TYPE: RNA
<213> ORGANISM: Artificial Sequence
<220> FEATURE:
<223> OTHER INFORMATION: siRNA

<400> SEQUENCE: 120
uggcuuugcu ccagacaca                                                      19
```

<210> SEQ ID NO 121
<211> LENGTH: 19
<212> TYPE: RNA
<213> ORGANISM: Artificial Sequence
<220> FEATURE:
<223> OTHER INFORMATION: siRNA

<400> SEQUENCE: 121
agguagauga ugagggugu                                                19

<210> SEQ ID NO 122
<211> LENGTH: 19
<212> TYPE: RNA
<213> ORGANISM: Artificial Sequence
<220> FEATURE:
<223> OTHER INFORMATION: siRNA

<400> SEQUENCE: 122
acacccucau caucuaccu                                                19

<210> SEQ ID NO 123
<211> LENGTH: 19
<212> TYPE: RNA
<213> ORGANISM: Artificial Sequence
<220> FEATURE:
<223> OTHER INFORMATION: siRNA

<400> SEQUENCE: 123
uuguaauagg cguagaccu                                                19

<210> SEQ ID NO 124
<211> LENGTH: 19
<212> TYPE: RNA
<213> ORGANISM: Artificial Sequence
<220> FEATURE:
<223> OTHER INFORMATION: siRNA

<400> SEQUENCE: 124
aggucuacgc cuauuacaa                                                19

<210> SEQ ID NO 125
<211> LENGTH: 19
<212> TYPE: RNA
<213> ORGANISM: Artificial Sequence
<220> FEATURE:
<223> OTHER INFORMATION: siRNA

<400> SEQUENCE: 125
guuguaauag gcguagacc                                                19

<210> SEQ ID NO 126
<211> LENGTH: 19
<212> TYPE: RNA
<213> ORGANISM: Artificial Sequence
<220> FEATURE:
<223> OTHER INFORMATION: siRNA

<400> SEQUENCE: 126
ggucuacgcc uauuacaac                                                19

<210> SEQ ID NO 127
<211> LENGTH: 19
<212> TYPE: RNA
<213> ORGANISM: Artificial Sequence
<220> FEATURE:

```
<223> OTHER INFORMATION: siRNA

<400> SEQUENCE: 127 ggucuugua cacauaguc                                                    19

<210> SEQ ID NO 128
<211> LENGTH: 19
<212> TYPE: RNA
<213> ORGANISM: Artificial Sequence
<220> FEATURE:
<223> OTHER INFORMATION: siRNA

<400> SEQUENCE: 128
gacuaugugu acaagaccc                                                   19

<210> SEQ ID NO 129
<211> LENGTH: 19
<212> TYPE: RNA
<213> ORGANISM: Artificial Sequence
<220> FEATURE:
<223> OTHER INFORMATION: siRNA

<400> SEQUENCE: 129
cacuugaugg ggcugauga                                                   19

<210> SEQ ID NO 130
<211> LENGTH: 19
<212> TYPE: RNA
<213> ORGANISM: Artificial Sequence
<220> FEATURE:
<223> OTHER INFORMATION: siRNA

<400> SEQUENCE: 130
ucaucagccc caucaagug                                                   19

<210> SEQ ID NO 131
<211> LENGTH: 19
<212> TYPE: RNA
<213> ORGANISM: Artificial Sequence
<220> FEATURE:
<223> OTHER INFORMATION: siRNA

<400> SEQUENCE: 131
auuguaauag gcguagacc                                                   19

<210> SEQ ID NO 132
<211> LENGTH: 19
<212> TYPE: RNA
<213> ORGANISM: Artificial Sequence
<220> FEATURE:
<223> OTHER INFORMATION: siRNA

<400> SEQUENCE: 132
ggucuacgcc uauuacaau                                                   19

<210> SEQ ID NO 133
<211> LENGTH: 19
<212> TYPE: RNA
<213> ORGANISM: Artificial Sequence
<220> FEATURE:
<223> OTHER INFORMATION: siRNA

<400> SEQUENCE: 133
auguagaugg ucuugucug                                                   19
```

```
<210> SEQ ID NO 134
<211> LENGTH: 19
<212> TYPE: RNA
<213> ORGANISM: Artificial Sequence
<220> FEATURE:
<223> OTHER INFORMATION: siRNA

<400> SEQUENCE: 134
cagacaagac caucuacau                                               19

<210> SEQ ID NO 135
<211> LENGTH: 19
<212> TYPE: RNA
<213> ORGANISM: Artificial Sequence
<220> FEATURE:
<223> OTHER INFORMATION: siRNA

<400> SEQUENCE: 135
gguaccucuu cauccagaa                                               19

<210> SEQ ID NO 136
<211> LENGTH: 19
<212> TYPE: RNA
<213> ORGANISM: Artificial Sequence
<220> FEATURE:
<223> OTHER INFORMATION: siRNA

<400> SEQUENCE: 136
cuucauccag acagacaaa                                               19

<210> SEQ ID NO 137
<211> LENGTH: 19
<212> TYPE: RNA
<213> ORGANISM: Artificial Sequence
<220> FEATURE:
<223> OTHER INFORMATION: siRNA

<400> SEQUENCE: 137
uccagacaga caagaccaa                                               19

<210> SEQ ID NO 138
<211> LENGTH: 19
<212> TYPE: RNA
<213> ORGANISM: Artificial Sequence
<220> FEATURE:
<223> OTHER INFORMATION: siRNA

<400> SEQUENCE: 138
cagacagaca agaccauca                                               19

<210> SEQ ID NO 139
<211> LENGTH: 19
<212> TYPE: RNA
<213> ORGANISM: Artificial Sequence
<220> FEATURE:
<223> OTHER INFORMATION: siRNA

<400> SEQUENCE: 139
gacagacaag accaucuaa                                               19

<210> SEQ ID NO 140
<211> LENGTH: 19
<212> TYPE: RNA
<213> ORGANISM: Artificial Sequence
<220> FEATURE:
<223> OTHER INFORMATION: siRNA
```

```
<400> SEQUENCE: 140
cagacaagac caucuacaa                                          19

<210> SEQ ID NO 141
<211> LENGTH: 19
<212> TYPE: RNA
<213> ORGANISM: Artificial Sequence
<220> FEATURE:
<223> OTHER INFORMATION: siRNA

<400> SEQUENCE: 141
acaagaccau cuacaccca                                          19

<210> SEQ ID NO 142
<211> LENGTH: 19
<212> TYPE: RNA
<213> ORGANISM: Artificial Sequence
<220> FEATURE:
<223> OTHER INFORMATION: siRNA

<400> SEQUENCE: 142
cgugcugccc aguuucgaa                                          19

<210> SEQ ID NO 143
<211> LENGTH: 19
<212> TYPE: RNA
<213> ORGANISM: Artificial Sequence
<220> FEATURE:
<223> OTHER INFORMATION: siRNA

<400> SEQUENCE: 143
agauccacuu caccaagaa                                          19

<210> SEQ ID NO 144
<211> LENGTH: 19
<212> TYPE: RNA
<213> ORGANISM: Artificial Sequence
<220> FEATURE:
<223> OTHER INFORMATION: siRNA

<400> SEQUENCE: 144
uccacuucac caagacaca                                          19

<210> SEQ ID NO 145
<211> LENGTH: 19
<212> TYPE: RNA
<213> ORGANISM: Artificial Sequence
<220> FEATURE:
<223> OTHER INFORMATION: siRNA

<400> SEQUENCE: 145
ccuuugaccu cauggugua                                          19

<210> SEQ ID NO 146
<211> LENGTH: 19
<212> TYPE: RNA
<213> ORGANISM: Artificial Sequence
<220> FEATURE:
<223> OTHER INFORMATION: siRNA

<400> SEQUENCE: 146
cuuugaccuc augguguua                                          19

<210> SEQ ID NO 147
<211> LENGTH: 19
```

<212> TYPE: RNA
<213> ORGANISM: Artificial Sequence
<220> FEATURE:
<223> OTHER INFORMATION: siRNA

<400> SEQUENCE: 147
accucauggu guucgugaa                                              19

<210> SEQ ID NO 148
<211> LENGTH: 19
<212> TYPE: RNA
<213> ORGANISM: Artificial Sequence
<220> FEATURE:
<223> OTHER INFORMATION: siRNA

<400> SEQUENCE: 148
acaagaaagg gaucuguga                                              19

<210> SEQ ID NO 149
<211> LENGTH: 19
<212> TYPE: RNA
<213> ORGANISM: Artificial Sequence
<220> FEATURE:
<223> OTHER INFORMATION: siRNA

<400> SEQUENCE: 149
agggaucugu guggcagaa                                              19

<210> SEQ ID NO 150
<211> LENGTH: 19
<212> TYPE: RNA
<213> ORGANISM: Artificial Sequence
<220> FEATURE:
<223> OTHER INFORMATION: siRNA

<400> SEQUENCE: 150
aaugcaggac uucuucaua                                              19

<210> SEQ ID NO 151
<211> LENGTH: 19
<212> TYPE: RNA
<213> ORGANISM: Artificial Sequence
<220> FEATURE:
<223> OTHER INFORMATION: siRNA

<400> SEQUENCE: 151
ccagaauucu ccugcaaga                                              19

<210> SEQ ID NO 152
<211> LENGTH: 19
<212> TYPE: RNA
<213> ORGANISM: Artificial Sequence
<220> FEATURE:
<223> OTHER INFORMATION: siRNA

<400> SEQUENCE: 152
uggucaaggu cuucucuca                                              19

<210> SEQ ID NO 153
<211> LENGTH: 19
<212> TYPE: RNA
<213> ORGANISM: Artificial Sequence
<220> FEATURE:
<223> OTHER INFORMATION: siRNA

<400> SEQUENCE: 153
accucaucgc caucgacua                                            19

<210> SEQ ID NO 154
<211> LENGTH: 19
<212> TYPE: RNA
<213> ORGANISM: Artificial Sequence
<220> FEATURE:
<223> OTHER INFORMATION: siRNA

<400> SEQUENCE: 154
ccuucauggu guuccaaga                                            19

<210> SEQ ID NO 155
<211> LENGTH: 19
<212> TYPE: RNA
<213> ORGANISM: Artificial Sequence
<220> FEATURE:
<223> OTHER INFORMATION: siRNA

<400> SEQUENCE: 155
acacccucau caucuacca                                            19

<210> SEQ ID NO 156
<211> LENGTH: 19
<212> TYPE: RNA
<213> ORGANISM: Artificial Sequence
<220> FEATURE:
<223> OTHER INFORMATION: siRNA

<400> SEQUENCE: 156
ggucuacgcc uauuacaaa                                            19

<210> SEQ ID NO 157
<211> LENGTH: 19
<212> TYPE: RNA
<213> ORGANISM: Artificial Sequence
<220> FEATURE:
<223> OTHER INFORMATION: siRNA

<400> SEQUENCE: 157
gacuaugugu acaagacca                                            19

<210> SEQ ID NO 158
<211> LENGTH: 19
<212> TYPE: RNA
<213> ORGANISM: Artificial Sequence
<220> FEATURE:
<223> OTHER INFORMATION: siRNA

<400> SEQUENCE: 158
ucaucagccc caucaagua                                            19

<210> SEQ ID NO 159
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 159
uuucauagua ggcucggau                                            19

<210> SEQ ID NO 160
<211> LENGTH: 19
<212> TYPE: RNA

<213> ORGANISM: Artificial Sequence
<220> FEATURE:
<223> OTHER INFORMATION: siRNA - modified_base, modified as per summary
      sequence table at the end of the description

<400> SEQUENCE: 160
auccgagccu acuaugaaa                                                    19

<210> SEQ ID NO 161
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 161
uuucucugua ggcuccacu                                                    19

<210> SEQ ID NO 162
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 162
aguggagccu acagagaaa                                                    19

<210> SEQ ID NO 163
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 163
uuauagaugu aguagaauu                                                    19

<210> SEQ ID NO 164
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 164
aauucuacua caucuauaa                                                    19

<210> SEQ ID NO 165
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 165
augacaaagg caguucccu                                                    19

<210> SEQ ID NO 166
<211> LENGTH: 19
<212> TYPE: RNA
<213> ORGANISM: Artificial Sequence

```
<220> FEATURE:
<223> OTHER INFORMATION: siRNA - modified_base, modified as per summary
      sequence table at the end of the description

<400> SEQUENCE: 166
agggaacugc cuuugucau                                                19

<210> SEQ ID NO 167
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 167
aucugguagg gagagguca                                                19

<210> SEQ ID NO 168
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 168
ugaccucucc cuaccagau                                                19

<210> SEQ ID NO 169
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 169
uguguguuga ugcugaguu                                                19

<210> SEQ ID NO 170
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 170
aacucagcau caacacaca                                                19

<210> SEQ ID NO 171
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 171
uaauuguugg aguugccca                                                19

<210> SEQ ID NO 172
<211> LENGTH: 19
<212> TYPE: RNA
<213> ORGANISM: Artificial Sequence
<220> FEATURE:
```

```
<223> OTHER INFORMATION: siRNA - modified_base, modified as per summary
      sequence table at the end of the description

<400> SEQUENCE: 172
ugggcaacuc caacaauua                                                      19

<210> SEQ ID NO 173
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 173
aggaaguuga cguugaggg                                                      19

<210> SEQ ID NO 174
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 174
cccucaacgu caacuuccu                                                      19

<210> SEQ ID NO 175
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 175
augaagucgg uggugaugg                                                      19

<210> SEQ ID NO 176
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 176
ccaucaccac cgacuucau                                                      19

<210> SEQ ID NO 177
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 177
uuuaccacca gcgagccca                                                      19

<210> SEQ ID NO 178
<211> LENGTH: 19
<212> TYPE: RNA
<213> ORGANISM: Artificial Sequence
<220> FEATURE:
<223> OTHER INFORMATION: siRNA - modified_base, modified as per summary
```

-continued sequence table at the end of the description

<400> SEQUENCE: 178
ugggcucgcu ggugguaaa                                              19

<210> SEQ ID NO 179
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 179
ucuaucuuca gggucaucu                                              19

<210> SEQ ID NO 180
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 180
agaugacccu gaagauaga                                              19

<210> SEQ ID NO 181
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 181
auguaguugc agcagucca                                              19

<210> SEQ ID NO 182
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 182
uggacugcug caacuacau                                              19

<210> SEQ ID NO 183
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 183
aauauauuca ugagcuucg                                              19

<210> SEQ ID NO 184
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

```
<400> SEQUENCE: 184
cgaagcucau gaauauauu                                                19

<210> SEQ ID NO 185
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 185
aaauauauuc augagcuuc                                                19

<210> SEQ ID NO 186
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 186
gaagcucaug aauauauuu                                                19

<210> SEQ ID NO 187
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 187
uccugcauua cugugaccu                                                19

<210> SEQ ID NO 188
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 188
aggucacagu aaugcagga                                                19

<210> SEQ ID NO 189
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 189
caacagagua ggguagccg                                                19

<210> SEQ ID NO 190
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description
```

```
<400> SEQUENCE: 190
cggcuacccu acucuguug                                            19

<210> SEQ ID NO 191
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 191
ucgaacaaca gaguagggu                                            19

<210> SEQ ID NO 192
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 192
acccuacucu guuguucga                                            19

<210> SEQ ID NO 193
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 193
uuucgaacaa cagaguagg                                            19

<210> SEQ ID NO 194
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 194
ccuacucugu uguucgaaa                                            19

<210> SEQ ID NO 195
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 195
guuucaucca gguaaugca                                            19

<210> SEQ ID NO 196
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 196
```
ugcauuaccu ggaugaaac                                                    19

<210> SEQ ID NO 197
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 197
uuaucuuugg cugugguca                                                    19

<210> SEQ ID NO 198
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 198
ugaccacagc caaagauaa                                                    19

<210> SEQ ID NO 199
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 199
uguucauuga gccaacgca                                                    19

<210> SEQ ID NO 200
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 200
ugcguuggcu caaugaaca                                                    19

<210> SEQ ID NO 201
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 201
aacaccauga agguggccu                                                    19

<210> SEQ ID NO 202
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 202
aggccaccuu cauggguguu                                          19

<210> SEQ ID NO 203
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 203
uugguauuga gccaaggcu                                           19

<210> SEQ ID NO 204
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 204
agccuuggcu caauaccaa                                           19

<210> SEQ ID NO 205
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 205
uuuauuacag gugaguuga                                           19

<210> SEQ ID NO 206
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 206
ucaacucacc uguaauaaa                                           19

<210> SEQ ID NO 207
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 207
uuucuguuuc cggugcugg                                           19

<210> SEQ ID NO 208
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 208
ccagcaccgg aaacagaaa                                           19

```
<210> SEQ ID NO 209
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 209
ucaaggauca uaguguucu                                                    19

<210> SEQ ID NO 210
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 210
agaacacuau gauccuuga                                                    19

<210> SEQ ID NO 211
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 211
aucucaagga ucauagugu                                                    19

<210> SEQ ID NO 212
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 212
acacuaugau ccuugagau                                                    19

<210> SEQ ID NO 213
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 213
ucauacuugg agauguauc                                                    19

<210> SEQ ID NO 214
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 214
gauacaucuc caaguauga                                                    19
```

<210> SEQ ID NO 215
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 215
uaucggagaa ggcuuuguc                                                 19

<210> SEQ ID NO 216
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 216
gacaaagccu ucuccgaua                                                 19

<210> SEQ ID NO 217
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 217
augaugaggg uguuccuau                                                 19

<210> SEQ ID NO 218
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 218
auaggaacac ccucaucau                                                 19

<210> SEQ ID NO 219
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 219
uauuggugaa cuuugaaag                                                 19

<210> SEQ ID NO 220
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 220
cuuucaaagu ucaccaaua                                                 19

-continued

```
<210> SEQ ID NO 221
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 221
agcuuguuca gcuuccau                                                        19

<210> SEQ ID NO 222
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 222
auggaaagcu gaacaagcu                                                       19

<210> SEQ ID NO 223
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 223
uuuguaugaa gcaauucuc                                                       19

<210> SEQ ID NO 224
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 224
gagaauugcu ucauacaaa                                                       19

<210> SEQ ID NO 225
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 225
gucuuguaca cauagucca                                                       19

<210> SEQ ID NO 226
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 226
uggacuaugu guacaagac                                                       19

<210> SEQ ID NO 227
```

```
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 227
ugcucaaugg ccaugaugu                                                    19

<210> SEQ ID NO 228
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 228
acaucauggc cauugagca                                                    19

<210> SEQ ID NO 229
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 229
uuggcauucg uccuccucg                                                    19

<210> SEQ ID NO 230
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 230
cgaggaggac gaaugccaa                                                    19

<210> SEQ ID NO 231
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 231
gucuggauga agagguacc                                                    19

<210> SEQ ID NO 232
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 232
gguaccucuu cauccagac                                                    19

<210> SEQ ID NO 233
<211> LENGTH: 19
```

<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 233
ugucuggaug aagagguac                                           19

<210> SEQ ID NO 234
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 234
guaccucuuc auccagaca                                           19

<210> SEQ ID NO 235
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 235
ucugucugga ugaagaggu                                           19

<210> SEQ ID NO 236
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 236
accucuucau ccagacaga                                           19

<210> SEQ ID NO 237
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 237
cuugucuguc uggaugaag                                           19

<210> SEQ ID NO 238
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 238
cuucauccag acagacaag                                           19

<210> SEQ ID NO 239
<211> LENGTH: 19
<212> TYPE: RNA

```
<213> ORGANISM: Artificial Sequence
<220> FEATURE:
<223> OTHER INFORMATION: siRNA - modified_base, modified as per summary
      sequence table at the end of the description

<400> SEQUENCE: 239
auggucuugu cugucugga                                                    19

<210> SEQ ID NO 240
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 240
uccagacaga caagaccau                                                    19

<210> SEQ ID NO 241
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 241
agauggucuu gucugucug                                                    19

<210> SEQ ID NO 242
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 242
cagacagaca agaccaucu                                                    19

<210> SEQ ID NO 243
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 243
guagaugguc uugucuguc                                                    19

<210> SEQ ID NO 244
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 244
gacagacaag accaucuac                                                    19

<210> SEQ ID NO 245
<211> LENGTH: 19
<212> TYPE: RNA
<213> ORGANISM: Artificial Sequence
```

```
<220> FEATURE:
<223> OTHER INFORMATION: siRNA - modified_base, modified as per summary
      sequence table at the end of the description

<400> SEQUENCE: 245
guguagaugg ucuugucug                                              19

<210> SEQ ID NO 246
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 246
cagacaagac caucuacac                                              19

<210> SEQ ID NO 247
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 247
gggguguaga uggucuugu                                              19

<210> SEQ ID NO 248
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 248
acaagaccau cuacacccc                                              19

<210> SEQ ID NO 249
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 249
uaggcucgga ucuuccacu                                              19

<210> SEQ ID NO 250
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 250
aguggaagau ccgagccua                                              19

<210> SEQ ID NO 251
<211> LENGTH: 19
<212> TYPE: RNA
<213> ORGANISM: Artificial Sequence
<220> FEATURE:
```

```
<223> OTHER INFORMATION: siRNA - modified_base, modified as per summary
      sequence table at the end of the description

<400> SEQUENCE: 251
cucgaaacug ggcagcacg                                                 19

<210> SEQ ID NO 252
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 252
cgugcugccc aguuucgag                                                 19

<210> SEQ ID NO 253
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 253
uuggugaagu ggaucuggu                                                 19

<210> SEQ ID NO 254
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 254
accagaucca cuucaccaa                                                 19

<210> SEQ ID NO 255
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 255
ucuuggugaa guggaucug                                                 19

<210> SEQ ID NO 256
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 256
cagauccacu ucaccaaga                                                 19

<210> SEQ ID NO 257
<211> LENGTH: 19
<212> TYPE: RNA
<213> ORGANISM: Artificial Sequence
<220> FEATURE:
<223> OTHER INFORMATION: siRNA - modified_base, modified as per summary
```

-continued sequence table at the end of the description

<400> SEQUENCE: 257
gucuugguga aguggaucu                                                19

<210> SEQ ID NO 258
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 258
agauccacuu caccaagac                                                19

<210> SEQ ID NO 259
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 259
ggugucuugg ugaagugga                                                19

<210> SEQ ID NO 260
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 260
uccacuucac caagacacc                                                19

<210> SEQ ID NO 261
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 261
aacaccauga ggucaaagg                                                19

<210> SEQ ID NO 262
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 262
ccuuugaccu caugguguu                                                19

<210> SEQ ID NO 263
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description -continued

<400> SEQUENCE: 263
gaacaccaug aggucaaag                                                    19

<210> SEQ ID NO 264
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 264
cuuugaccuc augguguuc                                                    19

<210> SEQ ID NO 265
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 265
gucacgaaca ccaugaggu                                                    19

<210> SEQ ID NO 266
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 266
accucauggu guucgugac                                                    19

<210> SEQ ID NO 267
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 267
acacagaucc cuuucuugu                                                    19

<210> SEQ ID NO 268
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 268
acaagaaagg gaucugugu                                                    19

<210> SEQ ID NO 269
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

```
<400> SEQUENCE: 269
gucugccaca cagauccccu                                               19

<210> SEQ ID NO 270
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 270
agggaucugu guggcagac                                                19

<210> SEQ ID NO 271
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 271
gaugaagaag uccugcauu                                                19

<210> SEQ ID NO 272
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 272
aaugcaggac uucuucauc                                                19

<210> SEQ ID NO 273
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 273
ccuugcagga gaauucugg                                                19

<210> SEQ ID NO 274
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 274
ccagaauucu ccugcaagg                                                19

<210> SEQ ID NO 275
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 275
```

```
agagagaaga ccuugacca                                               19

<210> SEQ ID NO 276
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 276
uggucaaggu cuucucucu                                               19

<210> SEQ ID NO 277
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 277
gagucgaugg cgaugaggu                                               19

<210> SEQ ID NO 278
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 278
accucaucgc caucgacuc                                               19

<210> SEQ ID NO 279
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 279
gcuuggaaca ccaugaagg                                               19

<210> SEQ ID NO 280
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 280
ccuucauggu guuccaagc                                               19

<210> SEQ ID NO 281
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 281
```
ucauuuuccu uggucucuu          19

<210> SEQ ID NO 282
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 282
aagagaccaa ggaaaauga          19

<210> SEQ ID NO 283
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 283
ugugucugga gcaaagcca          19

<210> SEQ ID NO 284
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 284
uggcuuugcu ccagacaca          19

<210> SEQ ID NO 285
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 285
agguagauga ugagggugu          19

<210> SEQ ID NO 286
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 286
acacccucau caucuaccu          19

<210> SEQ ID NO 287
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 287
uuguaauagg cguagaccu          19

```
<210> SEQ ID NO 288
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 288
aggucuacgc cuauuacaa                                                  19

<210> SEQ ID NO 289
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 289
guuguaauag gcguagacc                                                  19

<210> SEQ ID NO 290
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 290
ggucuacgcc uauuacaac                                                  19

<210> SEQ ID NO 291
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 291
gggucuugua cacauaguc                                                  19

<210> SEQ ID NO 292
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 292
gacuaugugu acaagaccc                                                  19

<210> SEQ ID NO 293
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 293
cacuugaugg ggcugauga                                                  19
```

```
<210> SEQ ID NO 294
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 294
ucaucagccc caucaagug                                                      19

<210> SEQ ID NO 295
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 295
gguaccucuu cauccagaa                                                      19

<210> SEQ ID NO 296
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 296
guaccucuuc auccagaca                                                      19

<210> SEQ ID NO 297
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 297
accucuucau ccagacaga                                                      19

<210> SEQ ID NO 298
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 298
cuucauccag acagacaaa                                                      19

<210> SEQ ID NO 299
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 299
uccagacaga caagaccaa                                                      19
```

```
<210> SEQ ID NO 300
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 300
cagacagaca agaccauca                                                      19

<210> SEQ ID NO 301
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 301
gacagacaag accaucuaa                                                      19

<210> SEQ ID NO 302
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 302
cagacaagac caucuacaa                                                      19

<210> SEQ ID NO 303
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 303
acaagaccau cuacaccca                                                      19

<210> SEQ ID NO 304
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 304
aguggaagau ccgagccua                                                      19

<210> SEQ ID NO 305
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 305
cgugcugccc aguuucgaa                                                      19

<210> SEQ ID NO 306
```

```
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 306
accagaucca cuucaccaa                                                   19

<210> SEQ ID NO 307
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 307
cagauccacu ucaccaaga                                                   19

<210> SEQ ID NO 308
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 308
agauccacuu caccaagaa                                                   19

<210> SEQ ID NO 309
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 309
uccacuucac caagacaca                                                   19

<210> SEQ ID NO 310
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 310
ccuuugaccu cauggugua                                                   19

<210> SEQ ID NO 311
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 311
cuuugaccuc augguguua                                                   19

<210> SEQ ID NO 312
<211> LENGTH: 19
```

<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 312
accucauggu guucgugaa                                                    19

<210> SEQ ID NO 313
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 313
acaagaaagg gaucuguga                                                    19

<210> SEQ ID NO 314
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 314
agggaucugu guggcagaa                                                    19

<210> SEQ ID NO 315
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 315
aaugcaggac uucuucaua                                                    19

<210> SEQ ID NO 316
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 316
ccagaauucu ccugcaaga                                                    19

<210> SEQ ID NO 317
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 317
uggucaaggu cuucucuca                                                    19

<210> SEQ ID NO 318
<211> LENGTH: 19
<212> TYPE: RNA

<213> ORGANISM: Artificial Sequence
<220> FEATURE:
<223> OTHER INFORMATION: siRNA - modified_base, modified as per summary
      sequence table at the end of the description

<400> SEQUENCE: 318
accucaucgc caucgacua                                                      19

<210> SEQ ID NO 319
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 319
ccuucauggu guuccaaga                                                      19

<210> SEQ ID NO 320
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 320
aagagaccaa ggaaaauga                                                      19

<210> SEQ ID NO 321
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 321
uggcuuugcu ccagacaca                                                      19

<210> SEQ ID NO 322
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 322
acacccucau caucuacca                                                      19

<210> SEQ ID NO 323
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 323
aggucuacgc cuauuacaa                                                      19

<210> SEQ ID NO 324
<211> LENGTH: 19
<212> TYPE: RNA
<213> ORGANISM: Artificial Sequence

```
<220> FEATURE:
<223> OTHER INFORMATION: siRNA - modified_base, modified as per summary
      sequence table at the end of the description

<400> SEQUENCE: 324
ggucuacgcc uauuacaaa                                                       19

<210> SEQ ID NO 325
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 325
gacuaugugu acaagacca                                                       19

<210> SEQ ID NO 326
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 326
ucaucagccc caucaagua                                                       19

<210> SEQ ID NO 327
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 327
aggaaguuga cguugaggg                                                       19

<210> SEQ ID NO 328
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 328
cccucaacgu caacuuccu                                                       19

<210> SEQ ID NO 329
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 329
aauauauuca ugagcuucg                                                       19

<210> SEQ ID NO 330
<211> LENGTH: 19
<212> TYPE: RNA
<213> ORGANISM: Artificial Sequence
<220> FEATURE:
```

```
<223> OTHER INFORMATION: siRNA - modified_base, modified as per summary
      sequence table at the end of the description

<400> SEQUENCE: 330
cgaagcucau gaauauauu                                                     19

<210> SEQ ID NO 331
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 331
augaugaggg uguuccuau                                                     19

<210> SEQ ID NO 332
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 332
auaggaacac ccucaucau                                                     19

<210> SEQ ID NO 333
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 333
ucugucugga ugaagaggu                                                     19

<210> SEQ ID NO 334
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 334
accucuucau ccagacaga                                                     19

<210> SEQ ID NO 335
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 335
guagaugguc uugucuguc                                                     19

<210> SEQ ID NO 336
<211> LENGTH: 19
<212> TYPE: RNA
<213> ORGANISM: Artificial Sequence
<220> FEATURE:
<223> OTHER INFORMATION: siRNA - modified_base, modified as per summary
``` sequence table at the end of the description

<400> SEQUENCE: 336
gacagacaag accaucuac                                              19

<210> SEQ ID NO 337
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 337
gaacaccaug aggucaaag                                              19

<210> SEQ ID NO 338
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 338
cuuugaccuc augguguuc                                              19

<210> SEQ ID NO 339
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 339
agagagaaga ccuugacca                                              19

<210> SEQ ID NO 340
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 340
uggucaaggu cuucucucu                                              19

<210> SEQ ID NO 341
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 341
cuugucuguc uggaugaag                                              19

<210> SEQ ID NO 342
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 342
cuucauccag acagacaaa                                                    19

<210> SEQ ID NO 343
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 343
guagaugguc uugucuguc                                                    19

<210> SEQ ID NO 344
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 344
gacagacaag accaucuaa                                                    19

<210> SEQ ID NO 345
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 345
ucuuggugaa guggaucug                                                    19

<210> SEQ ID NO 346
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 346
cagauccacu ucaccaaga                                                    19

<210> SEQ ID NO 347
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 347
guuguaauag gcguagacc                                                    19

<210> SEQ ID NO 348
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

```
<400> SEQUENCE: 348 ggcucuacgcc uauuacaaa                                               19

<210> SEQ ID NO 349
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 349
auuguaauag gcguagacc                                                19

<210> SEQ ID NO 350
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 350 ggcucuacgcc uauuacaau                                               19

<210> SEQ ID NO 351
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 351
auguagaugg ucuugucug                                                19

<210> SEQ ID NO 352
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 352
cagacaagac caucuacau                                                19

<210> SEQ ID NO 353
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 353
ugagagaaga ccuugacca                                                19

<210> SEQ ID NO 354
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 354
```

```
uggucaaggu cuucucucu                                              19

<210> SEQ ID NO 355
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 355
uggucaaggu cuucucucu                                              19

<210> SEQ ID NO 356
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 356
ugagagaaga ccuugacca                                              19

<210> SEQ ID NO 357
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 357
cagauccacu ucaccaaga                                              19

<210> SEQ ID NO 358
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 358
cagauccacu ucaccaaga                                              19

<210> SEQ ID NO 359
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 359
ucuuggugaa guggaucug                                              19

<210> SEQ ID NO 360
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 360
```
ucuuggugaa guggaucug                                                19

<210> SEQ ID NO 361
<211> LENGTH: 19
<212> TYPE: RNA
<213> ORGANISM: Artificial Sequence
<220> FEATURE:
<223> OTHER INFORMATION: siRNA

<400> SEQUENCE: 361
ugagagaaga ccuugacca                                                19

<210> SEQ ID NO 362
<211> LENGTH: 19
<212> TYPE: RNA
<213> ORGANISM: Artificial Sequence
<220> FEATURE:
<223> OTHER INFORMATION: siRNA

<400> SEQUENCE: 362
ugagagaaga ccuugacca                                                19

<210> SEQ ID NO 363
<211> LENGTH: 19
<212> TYPE: RNA
<213> ORGANISM: Artificial Sequence
<220> FEATURE:
<223> OTHER INFORMATION: siRNA

<400> SEQUENCE: 363
uggucaaggu cuucucucu                                                19

<210> SEQ ID NO 364
<211> LENGTH: 19
<212> TYPE: RNA
<213> ORGANISM: Artificial Sequence
<220> FEATURE:
<223> OTHER INFORMATION: siRNA

<400> SEQUENCE: 364
ugagagacga ccuugacca                                                19

<210> SEQ ID NO 365
<211> LENGTH: 19
<212> TYPE: RNA
<213> ORGANISM: Artificial Sequence
<220> FEATURE:
<223> OTHER INFORMATION: siRNA

<400> SEQUENCE: 365
ugagagaaua ccuugacca                                                19

<210> SEQ ID NO 366
<211> LENGTH: 19
<212> TYPE: RNA
<213> ORGANISM: Artificial Sequence
<220> FEATURE:
<223> OTHER INFORMATION: siRNA

<400> SEQUENCE: 366
ugagagaaga ccuugaccg                                                19

<210> SEQ ID NO 367
<211> LENGTH: 19
<212> TYPE: RNA
<213> ORGANISM: Artificial Sequence

```
<220> FEATURE:
<223> OTHER INFORMATION: siRNA

<400> SEQUENCE: 367
cggucaaggu cuucucucu                                                    19

<210> SEQ ID NO 368
<211> LENGTH: 19
<212> TYPE: RNA
<213> ORGANISM: Artificial Sequence
<220> FEATURE:
<223> OTHER INFORMATION: siRNA

<400> SEQUENCE: 368
augagcuucg uagagauuc                                                    19

<210> SEQ ID NO 369
<211> LENGTH: 19
<212> TYPE: RNA
<213> ORGANISM: Artificial Sequence
<220> FEATURE:
<223> OTHER INFORMATION: siRNA

<400> SEQUENCE: 369
gaaucucuac gaagcucau                                                    19

<210> SEQ ID NO 370
<211> LENGTH: 19
<212> TYPE: RNA
<213> ORGANISM: Artificial Sequence
<220> FEATURE:
<223> OTHER INFORMATION: siRNA

<400> SEQUENCE: 370
uuguaguagc ggaucuugg                                                    19

<210> SEQ ID NO 371
<211> LENGTH: 19
<212> TYPE: RNA
<213> ORGANISM: Artificial Sequence
<220> FEATURE:
<223> OTHER INFORMATION: siRNA

<400> SEQUENCE: 371
ccaagauccg cuacuacac                                                    19

<210> SEQ ID NO 372
<211> LENGTH: 19
<212> TYPE: RNA
<213> ORGANISM: Artificial Sequence
<220> FEATURE:
<223> OTHER INFORMATION: siRNA

<400> SEQUENCE: 372
uucugucugg augaagagg                                                    19

<210> SEQ ID NO 373
<211> LENGTH: 19
<212> TYPE: RNA
<213> ORGANISM: Artificial Sequence
<220> FEATURE:
<223> OTHER INFORMATION: siRNA

<400> SEQUENCE: 373
ccucuucauc cagacagac                                                    19
```

```
<210> SEQ ID NO 374
<211> LENGTH: 19
<212> TYPE: RNA
<213> ORGANISM: Artificial Sequence
<220> FEATURE:
<223> OTHER INFORMATION: siRNA

<400> SEQUENCE: 374
uggucaaggu cuucucuca                                                   19

<210> SEQ ID NO 375
<211> LENGTH: 19
<212> TYPE: RNA
<213> ORGANISM: Artificial Sequence
<220> FEATURE:
<223> OTHER INFORMATION: siRNA

<400> SEQUENCE: 375
uggucaaggu cgucucuca                                                   19

<210> SEQ ID NO 376
<211> LENGTH: 19
<212> TYPE: RNA
<213> ORGANISM: Artificial Sequence
<220> FEATURE:
<223> OTHER INFORMATION: siRNA

<400> SEQUENCE: 376
cggucaaggu cuucucuca                                                   19

<210> SEQ ID NO 377
<211> LENGTH: 19
<212> TYPE: RNA
<213> ORGANISM: Artificial Sequence
<220> FEATURE:
<223> OTHER INFORMATION: siRNA

<400> SEQUENCE: 377
ugagagacga ccuugaccg                                                   19

<210> SEQ ID NO 378
<211> LENGTH: 19
<212> TYPE: RNA
<213> ORGANISM: Artificial Sequence
<220> FEATURE:
<223> OTHER INFORMATION: siRNA

<400> SEQUENCE: 378
cggucaaggu cgucucuca                                                   19

<210> SEQ ID NO 379
<211> LENGTH: 19
<212> TYPE: RNA
<213> ORGANISM: Artificial Sequence
<220> FEATURE:
<223> OTHER INFORMATION: siRNA

<400> SEQUENCE: 379
ccaagauccg cuacuacaa                                                   19

<210> SEQ ID NO 380
<211> LENGTH: 19
<212> TYPE: RNA
<213> ORGANISM: Artificial Sequence
<220> FEATURE:
<223> OTHER INFORMATION: siRNA
```

```
<400> SEQUENCE: 380
ccucuucauc cagacagaa                                                    19

<210> SEQ ID NO 381
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 381
ugagagaaga ccuugacca                                                    19

<210> SEQ ID NO 382
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 382
uggucaaggu cuucucucu                                                    19

<210> SEQ ID NO 383
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 383
ugagagacga ccuugacca                                                    19

<210> SEQ ID NO 384
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 384
ugagagaaua ccuugacca                                                    19

<210> SEQ ID NO 385
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 385
ugagagaaga ccuugaccg                                                    19

<210> SEQ ID NO 386
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description
```

```
<400> SEQUENCE: 386
cggucaaggu cuucucucu                                           19

<210> SEQ ID NO 387
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 387
augagcuucg uagagauuc                                           19

<210> SEQ ID NO 388
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 388
gaaucucuac gaagcucau                                           19

<210> SEQ ID NO 389
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 389
uuguaguagc ggaucuugg                                           19

<210> SEQ ID NO 390
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 390
ccaagauccg cuacuacac                                           19

<210> SEQ ID NO 391
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 391
uucugucugg augaagagg                                           19

<210> SEQ ID NO 392
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 392
```

```
ccucuucauc cagacagac                                                19
```

<210> SEQ ID NO 393
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 393

```
uggucaaggu cuucucucu                                                19
```

<210> SEQ ID NO 394
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 394

```
uggucaaggu cuucucuca                                                19
```

<210> SEQ ID NO 395
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 395

```
ugagagacga ccuugacca                                                19
```

<210> SEQ ID NO 396
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 396

```
uggucaaggu cgucucuca                                                19
```

<210> SEQ ID NO 397
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 397

```
cggucaaggu cuucucuca                                                19
```

<210> SEQ ID NO 398
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 398
ugagagacga ccuugaccg                                                19

<210> SEQ ID NO 399
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 399
cggucaaggu cgucucuca                                                19

<210> SEQ ID NO 400
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 400
gaaucucuac gaagcucau                                                19

<210> SEQ ID NO 401
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 401
ccaagauccg cuacuacaa                                                19

<210> SEQ ID NO 402
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 402
ccucuucauc cagacagaa                                                19

<210> SEQ ID NO 403
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 403
ugagagacga ccuugaccg                                                19

<210> SEQ ID NO 404
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 404
ugagagacga ccuugaccg                                            19

<210> SEQ ID NO 405
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 405
cggucaaggu cgucucuca                                            19

<210> SEQ ID NO 406
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 406
ugagagacga ccuugaccg                                            19

<210> SEQ ID NO 407
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 407
cggucaaggu cgucucuca                                            19

<210> SEQ ID NO 408
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 408
uuguaguagc ggaucuugg                                            19

<210> SEQ ID NO 409
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 409
uuguaguagc ggaucuugg                                            19

<210> SEQ ID NO 410
<211> LENGTH: 19
<212> TYPE: RNA
<213> ORGANISM: Artificial Sequence

```
<220> FEATURE:
<223> OTHER INFORMATION: siRNA - modified_base, modified as per summary
      sequence table at the end of the description

<400> SEQUENCE: 410
ccaagauccg cuacuacaa                                                 19

<210> SEQ ID NO 411
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 411
uucugucugg augaagagg                                                 19

<210> SEQ ID NO 412
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 412
uucugucugg augaagagg                                                 19

<210> SEQ ID NO 413
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 413
ccucuucauc cagacagaa                                                 19

<210> SEQ ID NO 414
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 414
uucugucugg augaagagg                                                 19

<210> SEQ ID NO 415
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 415
ccucuucauc cagacagaa                                                 19

<210> SEQ ID NO 416
<211> LENGTH: 19
<212> TYPE: RNA
<213> ORGANISM: Artificial Sequence
```

-continued

<220> FEATURE:
<223> OTHER INFORMATION: siRNA

<400> SEQUENCE: 416
uauauauuca ugagcuucg                                                   19

<210> SEQ ID NO 417
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 417
uauauauuca ugagcuucg                                                   19

<210> SEQ ID NO 418
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 418
cgaagcucau gaauauauu                                                   19

<210> SEQ ID NO 419
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 419
uauauauuca ugagcuucg                                                   19

<210> SEQ ID NO 420
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 420
uauauauuca ugagcuucg                                                   19

<210> SEQ ID NO 421
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

```
<400> SEQUENCE: 421
cgaagcucau gaauauauu                                                      19

<210> SEQ ID NO 422
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 422
uauauauuca ugagcuucg                                                      19

<210> SEQ ID NO 423
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 423
ccaagauccg cuacuacaa                                                      19

<210> SEQ ID NO 424
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 424
cgaagcucau gaauauauu                                                      19

<210> SEQ ID NO 425
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 425
cgaagcucau gaauauauu                                                      19
```

NUCLEIC ACIDS FOR INHIBITING EXPRESSION OF C3 IN A CELL

CROSS REFERENCE TO RELATED APPLICATIONS

This application is a continuation of U.S. patent application Ser. No. 17/612,120, filed Nov. 17, 2021, which is a U.S. national stage under 35 U.S.C. § 371 of International Patent Application No. PCT/EP2020/073904, filed Aug. 26, 2020, which claims the benefit of European Patent Application No. 19193840.6, filed Aug. 27, 2019, European Patent Application No. 19219497.5, filed Dec. 23, 2019, and European Patent Application No. 20176947.8, filed May 27, 2020, the entire contents of each of which are fully incorporated herein by reference.

INCORPORATION BY REFERENCE OF MATERIAL SUBMITTED ELECTRONICALLY

A Sequence Listing, which is a part of the present disclosure, is submitted concurrently with the specification as a text file. The name of the text file containing the Sequence Listing is "57310A_Seqlisting.txt." The Sequence Listing was created on May 26, 2022, and is 100,092 bytes in size. The subject matter of the Sequence Listing is incorporated by reference herein in its entirety.

FIELD OF THE INVENTION

The invention relates to nucleic acid products that interfere with or inhibit complement component C3 gene expression. It further relates to therapeutic uses of such inhibition such as for the treatment of diseases and disorders associated with complement pathway deregulation and/or over-activation or with ectopic expression or localisation or accumulation of the complement component C3 in the body.

BACKGROUND

Double-stranded RNAs (dsRNA) able to bind through complementary base pairing to expressed mRNAs have been shown to block gene expression (Fire et al., 1998, Nature. 1998 Feb. 19; 391(6669):806-11 and Elbashir et al., 2001, Nature. 2001 May 24; 411(6836):494-8) by a mechanism that has been termed "RNA interference (RNAi)". Short dsRNAs direct gene specific, post transcriptional silencing in many organisms, including vertebrates, and have become a useful tool for studying gene function. RNAi is mediated by the RNA induced silencing complex (RISC), a sequence specific, multi component nuclease that degrades messenger RNAs having sufficient complementary or homology to the silencing trigger loaded into the RISC complex. Interfering RNAs such as siRNAs, antisense RNAs, and micro RNAs, are oligonucleotides that prevent the formation of proteins by gene silencing, i.e., inhibiting gene translation of the protein through degradation of mRNA molecules. Gene silencing agents are becoming increasingly important for therapeutic applications in medicine.

According to Watts and Corey in the Journal of Pathology (2012; Vol 226, p 365-379), there are algorithms that can be used to design nucleic acid silencing triggers, but all of these have severe limitations. It may take various experimental methods to identify potent siRNAs, as algorithms do not take into account factors such as tertiary structure of the target mRNA or the involvement of RNA binding proteins. Therefore, the discovery of a potent nucleic acid silencing trigger with minimal off-target effects is a complex process. For the pharmaceutical development of these highly charged molecules, it is necessary that they can be synthesised economically, distributed to target tissues, enter cells and function within acceptable limits of toxicity.

The complement system or pathway is part of the innate immune system of host defence against invading pathogens. It mainly consists of a number of proteins that circulate in the bloodstream in the form of precursors. Most of the proteins that form the complement system, including the complement component protein C3 (also referred to herein simply as C3), are largely synthesised and secreted into the bloodstream by hepatocytes in the liver. Activation of the system leads to inflammatory responses resulting in phagocyte attraction and opsonization and consequently clearance of pathogens, immune complexes and cellular debris (Janeway's Immunobiology 9th Edition). The complement system consists of 3 pathways (Classical, Leptin and Alternative pathways), which all converge at the formation of so-called complement component 3 convertase enzyme complexes. These enzyme complexes cleave the complement component C3 protein into C3a and C3b. Once cleaved, C3b forms part of a complex that in turn cleaves C5 into C5a and C5b. After cleavage, C5b is one of the key components of the main complement pathway effectors, the membrane attack complex. C3 is therefore a key component of the complement system activation pathway.

Several diseases are associated with aberrant acquired or genetic activation of the complement pathway as well as with aberrant or over-expression of C3. Among others, these are C3 Glomerulopathy (C3G), atypical Hemolytic Uremic Syndrome (aHUS), Immune Complex-mediated Glomerulonephritis (IC-mediated GN), post-Infectious Glomerulonephritis (PIGN), Systemic Lupus Erythematosus, Lupus nephritis, Ischemia/reperfusion injury and IgA nephropathy (IgA N; reviewed in Ricklin et al., Nephrology, 2016 and others). Most of these diseases are associated with the kidney, as this organ is uniquely sensitive to complement-induced damage. However, diseases of other organs are also known to be related to complement dysfunction, such as age-related macular degeneration (AMD), Rheumatoid arthritis (RA), antineutrophil Cytoplasmic Autoantibodies-associated Vasculitis (ANCA-AV), dysbiotic periodontal Disease, Malarial Anaemia, Paroxysmal Nocturnal Hemoglobinuria (PNH) and sepsis.

In C3G, C3 accumulates in the glomeruli in the kidney and clogs them. The accumulation of C3 also leads to kidney damage. In atypical Hemolytic Uremic Syndrome (aHUS), the complement system targets red blood cells, which leads to lysis of the red blood cells.

There are currently only few treatments for complement system mediated diseases, disorders and syndromes. The monoclonal humanized antibody Eculizumab is one of them. It is known to bind complement protein C5, thereby blocking the membrane attack complex at the end of the complement cascade (Hillmen et al., 2006 NEJM). However, only a subset of patients suffering from the above listed diseases respond to Eculizumab therapy. There is thus a high unmet need for medical treatments of complement mediated or associated diseases. C3 is a pivotal factor in the complement pathway activation. Inhibiting C3 expression therefore presents a promising therapeutic strategy for many complement-mediated diseases.

SUMMARY OF THE INVENTION

One aspect of the invention is a double-stranded nucleic acid for inhibiting expression of complement component C3, wherein the nucleic acid comprises a first strand and a second strand, wherein the first strand sequence comprises a sequence of at least 15 nucleotides differing by no more than 3 nucleotides from any one of the sequences SEQ ID NO: 370, 364, 365, 366, 368, 372, 377, 361, 95, 111, 125, 131, 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 97, 99, 101, 103, 105, 107, 109, 113, 115, 117, 119, 121, 123, 127, 129, 133 or 416.

One aspect relates to a double-stranded nucleic acid that is capable of inhibiting expression of complement component C3, preferably in a cell, for use as a medicament or in associated diagnostic or therapeutic methods, wherein the nucleic acid preferably comprises or consists of a first strand and a second strand and preferably wherein the first strand comprises sequences sufficiently complementary to a complement component C3 mRNA so as to mediate RNA interference.

One aspect relates to a composition comprising a nucleic acid as disclosed herein and a solvent (preferably water) and/or a delivery vehicle and/or a physiologically acceptable excipient and/or a carrier and/or a salt and/or a diluent and/or a buffer and/or a preservative.

One aspect relates to a composition comprising a nucleic acid as disclosed herein and a further therapeutic agent selected from e.g., an oligonucleotide, a small molecule, a monoclonal antibody, a polyclonal antibody and a peptide.

One aspect relates to a nucleic acid or a composition comprising it as disclosed herein for use as a medicament or in associated methods.

One aspect relates to a nucleic acid or a composition comprising it as disclosed herein for use in the prevention, decrease of the risk of suffering from, or treatment of a disease, disorder or syndrome.

One aspect relates to the use of a nucleic acid or a composition comprising it as disclosed herein in the prevention, decrease of the risk of suffering from, or treatment of a disease, disorder or syndrome, wherein the disease, disorder or syndrome is preferably C3 Glomerulopathy (C3G).

One aspect relates to a method of preventing, decreasing the risk of suffering from, or treating a disease, disorder or syndrome comprising administering a pharmaceutically effective dose or amount of a nucleic acid or composition comprising it as disclosed herein to an individual in need of treatment, preferably wherein the nucleic acid or composition is administered to the subject subcutaneously, intravenously or by oral, rectal, pulmonary, intramuscular or intraperitoneal administration.

DETAILED DESCRIPTION OF THE INVENTION

The present invention relates to a nucleic acid which is double-stranded and which comprises a sequence homologous to an expressed RNA transcript of the complement component C3, and compositions thereof. These nucleic acids, or conjugates or compositions thereof, may be used in the treatment and prevention of a variety of diseases, disorders and syndromes in which reduced expression of the C3 gene product is desirable.

A first aspect of the invention is a double-stranded nucleic acid for inhibiting expression of C3, preferably in a cell, wherein the nucleic acid comprises a first strand and a second strand, wherein the first strand sequence comprises a sequence of at least 15 nucleotides differing by no more than 3 nucleotides from any one of the sequences selected from SEQ ID NO: 370, 364, 365, 366, 368, 372, 377, 361, 95, 111, 125, 131, 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 97, 99, 101, 103, 105, 107, 109, 113, 115, 117, 119, 121, 123, 127, 129, 133 or 416. These nucleic acids among others have the advantage of being active in various species that are relevant for pre-clinical and clinical development and/or of having few relevant off-target effects. Having few relevant off-target effects means that a nucleic acid specifically inhibits the intended target and does not significantly inhibit other genes or inhibits only one or few other genes at a therapeutically acceptable level.

Preferably, the first strand sequence comprises a sequence of at least 16, more preferably at least 17, yet more preferably at least 18 and most preferably all 19 nucleotides differing by no more than 3 nucleotides, preferably by no more than 2 nucleotides, more preferably by no more than 1 nucleotide, and most preferably not differing by any nucleotide from any one of the sequences selected from SEQ ID NO: 370, 364, 365, 366, 368, 372, 377, 361, 95, 111, 125, 131, 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 97, 99, 101, 103, 105, 107, 109, 113, 115, 117, 119, 121, 123, 127, 129, 133 or 416.

Preferably, the first strand sequence of the nucleic acid consists of one of the sequences selected from SEQ ID NOs: 370, 364, 365, 366, 368, 372, 377, 361, 95, 111, 125, 131, 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 97, 99, 101, 103, 105, 107, 109, 113, 115, 117, 119, 121, 123, 127, 129, 133 or 416. The sequence may however be modified by a number of nucleic acid modifications that do not change the identity of the nucleotide. For example, modifications of the backbone or sugar residues of the nucleic acid do not change the identity of the nucleotide because the base itself remains the same as in the reference sequence.

A nucleic acid that comprises a sequence according to a reference sequence herein means that the nucleic acid comprises a sequence of contiguous nucleotides in the order as defined in the reference sequence.

When reference is made herein to a reference sequence comprising or consisting of nucleotides, this reference is not limited to the sequence with unmodified nucleotides. The same reference also encompasses the same nucleotide sequence in which one, several, such as two, three, four, five, six, seven or more, including all, nucleotides are modified by modifications such as 2'-OMe, 2'-F, a ligand, a linker, a 3' end or 5' end modification or any other modification. It also refers to sequences in which two or more nucleotides are linked to each other by the natural phosphodiester linkage or by any other linkage such as a phosphorothioate or a phosphorodithioate linkage.

A double-stranded nucleic acid is a nucleic acid in which the first strand and the second strand hybridise to each other over at least part of their lengths and are therefore capable of forming a duplex region under physiological conditions, such as in PBS at 37° C. at a concentration of 1 μM of each strand. The first and second strand are preferably able to hybridise to each other and therefore to form a duplex region over a region of at least 15 nucleotides, preferably 16, 17, 18 or 19 nucleotides. This duplex region comprises nucleotide base parings between the two strands, preferably based on Watson-Crick base pairing and/or wobble base pairing (such as GU base pairing). All the nucleotides of the two strands within a duplex region do not have to base pair to each other to form a duplex region. A certain number of mismatches, deletions or insertions between the nucleotide sequences of the two strands are acceptable. Overhangs on either end of the first or second strand or unpaired nucleotides at either end of the double-stranded nucleic acid are also possible. The double-stranded nucleic acid is preferably a stable double-stranded nucleic acid under physiological conditions, and preferably has a melting temperature (Tm) of 45° C. or more, preferably 50° C. or more, and more preferably 55° C. or more for example in PBS at a concentration of 1 µM of each strand.

A stable double-stranded nucleic acid under physiological conditions is a double-stranded nucleic acid that has a Tm of 45° C. or more, preferably 50° C. or more, and more preferably 55° C. or more, for example in PBS at a concentration of 1 µM of each strand.

The first strand and the second strand are preferably capable of forming a duplex region (i.e., are complementary to each other) over i) at least a portion of their lengths, preferably over at least 15 nucleotides of both of their lengths, ii) over the entire length of the first strand, iii) over the entire length of the second strand or iv) over the entire length of both the first and the second strand. Strands being complementary to each other over a certain length means that the strands are able to base pair to each other, either via Watson-Crick or wobble base pairing, over that length. Each nucleotide of the length does not necessarily have to be able to base pair with its counterpart in the other strand over the entire given length as long as a stable double-stranded nucleotide under physiological conditions can be formed. It is however, preferred, in certain embodiments, if each nucleotide of the length can base pair with its counterpart in the other strand over the entire given length.

A certain number of mismatches, deletions or insertions between the first strand and the target sequence, or between the first strand and the second strand can be tolerated in the context of the siRNA and even have the potential in certain cases to increase RNA interference (e.g., inhibition) activity.

The inhibition activity of the nucleic acids according to the present invention relies on the formation of a duplex region between all or a portion of the first strand and a portion of a target nucleic acid. The portion of the target nucleic acid that forms a duplex region with the first strand, defined as beginning with the first base pair formed between the first strand and the target sequence and ending with the last base pair formed between the first strand and the target sequence, inclusive, is the target nucleic acid sequence or simply, target sequence. The duplex region formed between the first strand and the second strand need not be the same as the duplex region formed between the first strand and the target sequence. That is, the second strand may have a sequence different from the target sequence; however, the first strand must be able to form a duplex structure with both the second strand and the target sequence, at least under physiological conditions.

The complementarity between the first strand and the target sequence may be perfect (i.e., 100% identity with no nucleotide mismatches or insertions or deletions in the first strand as compared to the target sequence).

The complementarity between the first strand and the target sequence may not be perfect. The complementarity may be from about 70% to about 100%. More specifically, the complementarity may be at least 70%, 80%, 85%, 90% or 95% and intermediate values.

The identity between the first strand and the complementary sequence of the target sequence may range from about 75% to about 100%. More specifically, the complementarity may be at least 75%, 80%, 85%, 90% or 95% and intermediate values, provided a nucleic acid is capable of reducing or inhibiting the expression of the complement component C3.

A nucleic acid having less than 100% complementarity between the first strand and the target sequence may be able to reduce the expression of the complement component C3 to the same level as a nucleic acid having perfect complementarity between the first strand and target sequence. Alternatively, it may be able to reduce expression of the complement component C3 to a level that is 15%, 20%, 25%, 30%, 35%, 40%, 45%, 50%, 55%, 60%, 65%, 70%, 75%, 80%, 85%, 90%, 95%, 98%, 99% or 100% of the level of reduction achieved by the nucleic acid with perfect complementarity.

In one aspect, a nucleic acid of the present disclosure is a nucleic acid wherein (a) the first strand sequence comprises a sequence differing by no more than 3 nucleotides from any one of the first strand sequences of Table 1 and optionally wherein the second strand sequence comprises a sequence differing by no more than 3 nucleotides from the second strand sequence in the same line of the table;

(b) the first strand sequence comprises a sequence differing by no more than 2 nucleotides from any one of the first strand sequences of Table 1 and optionally wherein the second strand sequence comprises a sequence differing by no more than 2 nucleotides from the second strand sequence in the same line of the table;

(c) the first strand sequence comprises a sequence differing by no more than 1 nucleotide from any one of the first strand sequences of Table 1 and optionally wherein the second strand sequence comprises a sequence differing by no more than 1 nucleotide from the second strand sequence in the same line of the table;

(d) the first strand sequence comprises a sequence corresponding to nucleotides 2 to 17 from the 5' end of any one of the first strand sequences of Table 1 and optionally wherein the second strand sequence comprises a sequence corresponding to nucleotides 2 to 17 from the 5' end of the second strand sequence in the same line of the table;

(e) the first strand sequence comprises a sequence corresponding to nucleotides 2 to 18 from the 5' end of any one of the first strand sequences of Table 1 and optionally wherein the second strand sequence comprises a sequence corresponding to nucleotides 2 to 18 from the 5' end of the second strand sequence in the same line of the table;

(f) the first strand sequence comprises a sequence corresponding to nucleotides 2 to 19 from the 5' end of any one of the first strand sequences of Table 1 and optionally wherein the second strand sequence comprises a sequence corresponding to nucleotides 2 to 19 from the 5' end of the second strand sequence in the same line of the table;

(g) the first strand sequence comprises a sequence corresponding to nucleotides 2 to 19 from the 5' end of any one of the first strand sequences of Table 1 and optionally wherein the second strand sequence comprises a sequence corresponding to nucleotides 1 to 18 from the 5' end of the second strand sequence in the same line of the table;

(h) the first strand sequence comprises a sequence of any one of the first strand sequences of Table 1 and optionally wherein the second strand sequence comprises a sequence of the second strand sequence in the same line of the table; or (i) the first strand sequence consists of any one of the first strand sequences of Table 1 and optionally wherein the second strand sequence consists of the sequence of the second strand sequence in the same line of the table;

wherein Table 1 is:

TABLE 1

| First strand sequence (SEQ ID NO:) | Second strand sequence (SEQ ID NO:) |
|---|---|
| 364 | 363 or 375 |
| 365 | 363 |
| 366 | 367 or 376 |
| 368 | 369 |
| 370 | 379 or 371, preferably 379 |
| 372 | 373 |
| 362 | 374 |
| 377 | 378 |
| 361 | 112 |
| 95 | 96 |
| 111 | 112 |
| 125 | 126 |
| 131 | 132 |
| 1 | 2 |
| 3 | 4 |
| 5 | 6 |
| 7 | 8 |
| 9 | 10 |
| 11 | 12 |
| 13 | 14 |
| 15 | 16 |
| 17 | 18 |
| 19 | 20 |
| 21 | 22 |
| 23 | 24 |
| 25 | 26 |
| 27 | 28 |
| 29 | 30 |
| 31 | 32 |
| 33 | 34 |
| 35 | 36 |
| 37 | 38 |
| 39 | 40 |
| 41 | 42 |
| 43 | 44 |
| 45 | 46 |
| 47 | 48 |
| 49 | 50 |
| 51 | 52 |
| 53 | 54 |
| 55 | 56 |
| 57 | 58 |
| 59 | 60 |
| 61 | 62 |
| 63 | 64 |
| 65 | 66 |
| 67 | 68 |
| 69 | 70 |
| 71 | 72 |
| 73 | 74 |
| 75 | 76 |
| 77 | 78 |
| 79 | 80 |
| 81 | 82 |
| 83 | 84 |
| 85 | 86 |
| 87 | 88 |
| 89 | 90 |
| 91 | 92 |
| 93 | 94 |
| 97 | 98 |
| 99 | 100 |
| 101 | 102 |

TABLE 1-continued

| First strand sequence (SEQ ID NO:) | Second strand sequence (SEQ ID NO:) |
|---|---|
| 103 | 104 |
| 105 | 106 |
| 107 | 108 |
| 109 | 110 |
| 113 | 114 |
| 115 | 116 |
| 117 | 118 |
| 119 | 120 |
| 121 | 122 |
| 123 | 124 |
| 127 | 128 |
| 129 | 130 |
| 133 | 134 |
| 416 | 26 |

In one aspect, the nucleic acid is a nucleic acid wherein:

(a) the first strand sequence comprises the sequence of SEQ ID NO 361 and optionally wherein the second strand sequence comprises the sequence of SEQ ID NO: 112; or (b) the first strand sequence comprises the sequence of SEQ ID NO 95 and optionally wherein the second strand sequence comprises the sequence of SEQ ID NO: 96; or (c) the first strand sequence comprises the sequence of SEQ ID NO 111 and optionally wherein the second strand sequence comprises the sequence of SEQ ID NO: 112; or (d) the first strand sequence comprises the sequence of SEQ ID NO 125 and optionally wherein the second strand sequence comprises the sequence of SEQ ID NO: 126; or (e) the first strand sequence comprises the sequence of SEQ ID NO 131 and optionally wherein the second strand sequence comprises the sequence of SEQ ID NO: 132; or (f) the first strand sequence consists of SEQ ID NO: 361 and optionally wherein the second strand sequence consists of SEQ ID NO: 112; or (g) the first strand sequence consists of SEQ ID NO: 95 and optionally wherein the second strand sequence consists of SEQ ID NO: 96; or (h) the first strand sequence consists of SEQ ID NO: 111 and optionally wherein the second strand sequence consists of SEQ ID NO: 112; or (i) the first strand sequence consists of SEQ ID NO: 125 and optionally wherein the second strand sequence consists of SEQ ID NO: 126; or (j) the first strand sequence consists of SEQ ID NO: 131 and optionally wherein the second strand sequence consists of SEQ ID NO: 132; or (k) the first strand sequence comprises or consists of the sequence of SEQ ID NO 364 and optionally wherein the second strand sequence comprises or consists of the sequence of SEQ ID NO: 363 or 375; or (l) the first strand sequence comprises or consists of the sequence of SEQ ID NO 365 and optionally wherein the second strand sequence comprises or consists of the sequence of SEQ ID NO: 363; or (m) the first strand sequence comprises or consists of the sequence of SEQ ID NO 366 and optionally wherein the second strand sequence comprises or consists of the sequence of SEQ ID NO: 367 or 376; or (n) the first strand sequence comprises or consists of the sequence of SEQ ID NO 368 and optionally wherein the second strand sequence comprises or consists of the sequence of SEQ ID NO: 369; or
(o) the first strand sequence comprises or consists of the sequence of SEQ ID NO 370 and optionally wherein the second strand sequence comprises or consists of the sequence of SEQ ID NO: 371 or 379, preferably 379; or
(p) the first strand sequence comprises or consists of the sequence of SEQ ID NO 372 and optionally wherein the second strand sequence comprises or consists of the sequence of SEQ ID NO: 373 or 380; or
(q) the first strand sequence comprises or consists of the sequence of SEQ ID NO 362 and optionally wherein the second strand sequence comprises or consists of the sequence of SEQ ID NO: 374; or
(r) the first strand sequence comprises or consists of the sequence of SEQ ID NO 377 and optionally wherein the second strand sequence comprises or consists of the sequence of SEQ ID NO: 378; or
(s) the first strand sequence comprises or consists of the sequence of SEQ ID NO 416 and optionally wherein the second strand sequence comprises or consists of the sequence of SEQ ID NO: 26.

In one aspect, if the 5'-most nucleotide of the first strand is a nucleotide other than A or U, this nucleotide is replaced by an A or U. Preferably, if the 5'-most nucleotide of the first strand is a nucleotide other than U, this nucleotide is replaced by U, and more preferably by U with a 5' vinylphosphonate.

When a nucleic acid of the invention does not comprise the entire sequence of a reference first strand and/or second strand sequence, as for example given in Table 1, or one or both strands differ from the corresponding reference sequence by one, two or three nucleotides, this nucleic acid preferably retains at least 30%, more preferably at least 50%, more preferably at least 70%, more preferably at least 80%, even more preferably at least 90%, yet more preferably at least 95% and most preferably at least 100% of the C3 inhibition activity compared to the inhibition activity of the corresponding nucleic acid that comprises the entire first strand and second strand reference sequences in a comparable experiment.

In one aspect, the nucleic acid is a nucleic acid wherein the first strand sequence comprises, or preferably consists of, the sequence of SEQ ID NO: 361 and optionally wherein the second strand sequence comprises, or consists of, a sequence of at least 15, preferably at least 16, more preferably at least 17, yet more preferably at least 18 and most preferably all nucleotides of the sequence of SEQ ID NO: 112; or wherein the first strand sequence comprises, or preferably consists of, the sequence of SEQ ID NO: 95 and optionally wherein the second strand sequence comprises, or consists of, a sequence of at least 15, preferably at least 16, more preferably at least 17, yet more preferably at least 18 and most preferably all nucleotides of the sequence of SEQ ID NO: 96; or wherein the first strand sequence comprises, or preferably consists of, the sequence of SEQ ID NO: 111 and optionally wherein the second strand sequence comprises, or consists of, a sequence of at least 15, preferably at least 16, more preferably at least 17, yet more preferably at least 18 and most preferably all nucleotides of the sequence of SEQ ID NO: 112; or wherein the first strand sequence comprises, or preferably consists of, the sequence of SEQ ID NO: 125 and optionally wherein the second strand sequence comprises, or consists of, a sequence of at least 15, preferably at least 16, more preferably at least 17, yet more preferably at least 18 and most preferably all nucleotides of the sequence of SEQ ID NO: 126; or wherein the first strand sequence comprises, or preferably consists of, the sequence of SEQ ID NO: 131 and optionally wherein the second strand sequence comprises, or consists of, a sequence of at least 15, preferably at least 16, more preferably at least 17, yet more preferably at least 18 and most preferably all nucleotides of the sequence of SEQ ID NO: 132; or wherein the first strand sequence comprises, or preferably consists of, the sequence of SEQ ID NO: 364 and optionally wherein the second strand sequence comprises, or consists of, a sequence of at least 15, preferably at least 16, more preferably at least 17, yet more preferably at least 18 and most preferably all nucleotides of the sequence of SEQ ID NO: 363 or 375; or wherein the first strand sequence comprises, or preferably consists of, the sequence of SEQ ID NO: 365 and optionally wherein the second strand sequence comprises, or consists of, a sequence of at least 15, preferably at least 16, more preferably at least 17, yet more preferably at least 18 and most preferably all nucleotides of the sequence of SEQ ID NO: 363; or wherein the first strand sequence comprises, or preferably consists of, the sequence of SEQ ID NO: 366 and optionally wherein the second strand sequence comprises, or consists of, a sequence of at least 15, preferably at least 16, more preferably at least 17, yet more preferably at least 18 and most preferably all nucleotides of the sequence of SEQ ID NO: 367 or 376; or wherein the first strand sequence comprises, or preferably consists of, the sequence of SEQ ID NO: 368 and optionally wherein the second strand sequence comprises, or consists of, a sequence of at least 15, preferably at least 16, more preferably at least 17, yet more preferably at least 18 and most preferably all nucleotides of the sequence of SEQ ID NO: 369; or wherein the first strand sequence comprises, or preferably consists of, the sequence of SEQ ID NO: 370 and optionally wherein the second strand sequence comprises, or consists of, a sequence of at least 15, preferably at least 16, more preferably at least 17, yet more preferably at least 18 and most preferably all nucleotides of the sequence of SEQ ID NO: 371 or 379, preferably 379; or wherein the first strand sequence comprises, or preferably consists of, the sequence of SEQ ID NO: 372 and optionally wherein the second strand sequence comprises, or consists of, a sequence of at least 15, preferably at least 16, more preferably at least 17, yet more preferably at least 18 and most preferably all nucleotides of the sequence of SEQ ID NO: 373 or 380; or wherein the first strand sequence comprises, or preferably consists of, the sequence of SEQ ID NO: 362 and optionally wherein the second strand sequence comprises, or consists of, a sequence of at least 15, preferably at least 16, more preferably at least 17, yet more preferably at least 18 and most preferably all nucleotides of the sequence of SEQ ID NO: 374; or wherein the first strand sequence comprises, or preferably consists of, the sequence of SEQ ID NO: 377 and optionally wherein the second strand sequence comprises, or consists of, a sequence of at least 15, preferably at least 16, more preferably at least 17, yet more preferably at least 18 and most preferably all nucleotides of the sequence of SEQ ID NO: 378; or wherein the first strand sequence comprises, or preferably consists of, the sequence of SEQ ID NO: 416 and optionally wherein the second strand sequence comprises, or consists of, a sequence of at least 15, preferably at least 16, more preferably at least 17, yet more preferably at least 18 and most preferably all nucleotides of the sequence of SEQ ID NO: 26.

In one aspect, the nucleic acid is a double-stranded nucleic acid for inhibiting expression of C3, preferably in a cell, wherein the nucleic acid comprises a first nucleic acid strand and a second nucleic acid strand, wherein the first strand is capable of hybridising under physiological conditions to a nucleic acid of sequence selected from SEQ ID NO: 379, 363, 375, 367, 376, 369, 371, 373, 380, 374, 378, 112, 96, 126, 132, 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 98, 100, 102, 104, 106, 108, 110, 114, 116, 118, 120, 122, 124, 128, 130 or 134; and wherein the second strand is capable of hybridising under physiological conditions to the first strand to form a duplex region.

Nucleic acids that are capable of hybridising under physiological conditions are nucleic acids that are capable of forming base pairs, preferably Watson-Crick or wobble base-pairs, between at least a portion of the opposed nucleotides in the strands so as to form at least a duplex region. Such a double-stranded nucleic acid is preferably a stable double-stranded nucleic acid under physiological conditions (for example in PBS at 37° C. at a concentration of 1 µM of each strand), meaning that under such conditions, the two strands stay hybridised to each other. The Tm of the double-stranded nucleotide is preferably 45° C. or more, preferably 50° C. or more and more preferably 55° C. or more.

One aspect of the present invention relates to a nucleic acid for inhibiting expression of the complement component C3, wherein the nucleic acid comprises a first sequence of at least 15, preferably at least 16, more preferably at least 17, yet more preferably at least 18 and most preferably all nucleotides differing by no more than 3 nucleotides, preferably no more than 2 nucleotides, more preferably no more than 1 nucleotide and most preferably not differing by any nucleotide from any of the sequences of Table 5, the first sequence being able to hybridise to a target gene transcript (such as an mRNA) under physiological conditions. Preferably, the nucleic acid further comprises a second sequence of at least 15, preferably at least 16, more preferably at least 17, yet more preferably at least 18 and most preferably all nucleotides differing by no more than 3 nucleotides, preferably no more than 2 nucleotides, more preferably no more than 1 nucleotide and most preferably not differing by any nucleotide from any of the sequences of Table 5, the second sequence being able to hybridise to the first sequence under physiological conditions and preferably the nucleic acid being an siRNA that is capable of inhibiting C3 expression via the RNAi pathway.

One aspect relates to any double-stranded nucleic acid as disclosed in Table 3, preferably for inhibiting expression of the complement component C3, provided that the double-stranded nucleic acid is able to inhibit expression of complement component C3. These nucleic acids are all siRNAs with various nucleotide modifications. Some of them are conjugates comprising GalNAc moieties that can be specifically targeted to cells with GalNAc receptors, such as hepatocytes.

One aspect relates to a double-stranded nucleic acid that is capable of inhibiting expression of complement component C3, preferably in a cell, for use as a medicament or in associated diagnostic or therapeutic methods, wherein the nucleic acid preferably comprises or consists of a first strand and a second strand and preferably wherein the first strand comprises sequences sufficiently complementary to a complement component C3 mRNA so as to mediate RNA interference.

The nucleic acids described herein may be capable of inhibiting the expression of the complement component C3. Inhibition may be complete, i.e., 0% remaining expression. Inhibition of C3 expression may be partial, i.e., it may be 15%, 20%, 30%, 40%, 50%, 60%, 70%, 75%, 80%, 85%, 90%, 95% or more, or intermediate values of inhibition of the level of C3 expression in the absence of a nucleic acid of the invention. The level of inhibition may be measured by comparing a treated sample with an untreated sample or with a sample treated with a control such as for example a siRNA that does not target C3. Inhibition may be measured by measuring C3 mRNA and/or protein levels or levels of a biomarker or indicator that correlates with C3 presence or activity. It may be measured in cells that may have been treated in vitro with a nucleic acid described herein. Alternatively, or in addition, inhibition may be measured in cells, such as hepatocytes, or tissue, such as liver tissue, or an organ, such as the liver, or in a body fluid such as blood, serum, lymph or any other body part or fluid that has been taken from a subject previously treated with a nucleic acid disclosed herein. Preferably, inhibition of C3 expression is determined by comparing the C3 mRNA level measured in C3-expressing cells after 24 or 48 hours in vitro treatment with a double-stranded RNA disclosed herein under ideal conditions (see the examples for appropriate concentrations and conditions) to the C3 mRNA level measured in control cells that were untreated or mock treated or treated with a control double-stranded RNA under the same conditions.

One aspect of the present invention relates to a nucleic acid, wherein the first strand and the second strand are present on a single strand of a nucleic acid that loops around so that the first strand and the second strand are able to hybridise to each other and to thereby form a double-stranded nucleic acid with a duplex region.

Preferably, the first strand and the second strand of the nucleic acid are separate strands. The two separate strands are preferably each 17-25 nucleotides in length, more preferably 18-25 nucleotides in length. The two strands may be of the same or different lengths. The first strand may be 17-25 nucleotides in length, preferably it may be 18-24 nucleotides in length, it may be 18, 19, 20, 21, 22, 23 or 24 nucleotides in length. Most preferably, the first strand is 19 nucleotides in length. The second strand may independently be 17-25 nucleotides in length, preferably it may be 18-24 nucleotides in length, it may be 18, 19, 20, 21, 22, 23 or 24 nucleotides in length. More preferably, the second strand is 18 or 19 or 20 nucleotides in length, and most preferably it is 19 nucleotides in length.

Preferably, the first strand and the second strand of the nucleic acid form a duplex region of 17-25 nucleotides in length. More preferably, the duplex region is 18-24 nucleotides in length. The duplex region may be 17, 18, 19, 20, 21, 22, 23, 24 or 25 nucleotides in length. In the most preferred embodiment, the duplex region is 18 or 19 nucleotides in length. The duplex region is defined here as the region between and including the 5'-most nucleotide of the first strand that is base paired to a nucleotide of the second strand to the 3'-most nucleotide of the first strand that is base paired to a nucleotide of the second strand. The duplex region may comprise nucleotides in either or both strands that are not base-paired to a nucleotide in the other strand. It may comprise one, two, three or four such nucleotides on the first strand and/or on the second strand. However, preferably, the duplex region consists of 17-25 consecutive nucleotide base pairs. That is to say that it preferably comprises 17-25 consecutive nucleotides on both of the strands that all base pair to a nucleotide in the other strand. More preferably, the duplex region consists of 18 or 19 consecutive nucleotide base pairs, most preferably 18.

In each of the embodiments disclosed herein, the nucleic acid may be blunt ended at both ends; have an overhang at one end and a blunt end at the other end; or have an overhang at both ends.

The nucleic acid may have an overhang at one end and a blunt end at the other end. The nucleic acid may have an overhang at both ends. The nucleic acid may be blunt ended at both ends. The nucleic acid may be blunt ended at the end with the 5' end of the first strand and the 3' end of the second strand or at the 3' end of the first strand and the 5' end of the second strand.

The nucleic acid may comprise an overhang at a 3' or 5' end. The nucleic acid may have a 3' overhang on the first strand. The nucleic acid may have a 3' overhang on the second strand. The nucleic acid may have a 5' overhang on the first strand. The nucleic acid may have a 5' overhang on the second strand. The nucleic acid may have an overhang at both the 5' end and 3' end of the first strand. The nucleic acid may have an overhang at both the 5' end and 3' end of the second strand. The nucleic acid may have a 5' overhang on the first strand and a 3' overhang on the second strand. The nucleic acid may have a 3' overhang on the first strand and a 5' overhang on the second strand. The nucleic acid may have a 3' overhang on the first strand and a 3' overhang on the second strand. The nucleic acid may have a 5' overhang on the first strand and a 5' overhang on the second strand.

An overhang at the 3' end or 5' end of the second strand or the first strand may consist of 1, 2, 3, 4 and 5 nucleotides in length. Optionally, an overhang may consist of 1 or 2 nucleotides, which may or may not be modified.

In one embodiment, the 5' end of the first strand is a single-stranded overhang of one, two or three nucleotides, preferably of one nucleotide.

Preferably, the nucleic acid is an siRNA. siRNAs are short interfering or short silencing RNAs that are able to inhibit the expression of a target gene through the RNA interference (RNAi) pathway. Inhibition occurs through targeted degradation of mRNA transcripts of the target gene after transcription. The siRNA forms part of the RISC complex. The RISC complex specifically targets the target RNA by sequence complementarity of the first (antisense) strand with the target sequence.

Preferably, the nucleic acid mediates RNA interference (RNAi). Preferably, the nucleic acid mediates RNA interference with an efficacy of at least 50% inhibition, more preferably at least 70%, more preferably at least 80%, even more preferably at least 90%, yet more preferably at least 95% and most preferably 100% inhibition. The inhibition efficacy is preferably measured by comparing the C3 mRNA level in cells, such as hepatocytes, treated with a C3 specific siRNA to the C3 mRNA level in cells treated with a control in a comparable experiment. The control can be a treatment with a non-C3 targeting siRNA or without a siRNA. The nucleic acid, or at least the first strand of the nucleic acid, is therefore preferably able to be incorporated into the RISC complex. As a result, the nucleic acid, or at least the first strand of the nucleic acid, is therefore able to guide the RISC complex to a specific target RNA with which the nucleic acid, or at least the first strand of the nucleic acid, is at least partially complementary. The RISC complex then specifically cleaves this target RNA and as a result leads to inhibition of the expression of the gene from which the RNA stems.

Nucleic Acid Modifications

Nucleic acids discussed herein include unmodified RNA as well as RNA which has been modified, e.g., to improve efficacy or stability. Unmodified RNA refers to a molecule in which the components of the nucleic acid, namely sugars, bases, and phosphate moieties, are the same or essentially the same as those which occur in nature, for example as occur naturally in the human body. The term "modified nucleotide" as used herein refers to a nucleotide in which one or more of the components of the nucleotide, namely the sugar, base, and phosphate moiety, is/are different from those which occur in nature. The term "modified nucleotide" also refers in certain cases to molecules that are not nucleotides in the strict sense of the term because they lack, or have a substitute of, an essential component of a nucleotide, such as the sugar, base or phosphate moiety. A nucleic acid comprising such modified nucleotides is still to be understood as being a nucleic acid, even if one or more of the nucleotides of the nucleic acid has been replaced by a modified nucleotide that lacks, or has a substitution of, an essential component of a nucleotide.

Modifications of the nucleic acid of the present invention generally provide a powerful tool in overcoming potential limitations including, but not limited to, in vitro and in vivo stability and bioavailability inherent to native RNA molecules. The nucleic acids according to the invention may be modified by chemical modifications. Modified nucleic acids can also minimise the possibility of inducing interferon activity in humans. Modifications can further enhance the functional delivery of a nucleic acid to a target cell. The modified nucleic acids of the present invention may comprise one or more chemically modified ribonucleotides of either or both of the first strand or the second strand. A ribonucleotide may comprise a chemical modification of the base, sugar or phosphate moieties. The ribonucleic acid may be modified by substitution with or insertion of analogues of nucleic acids or bases.

Throughout the description of the invention, "same or common modification" means the same modification to any nucleotide, be that A, G, C or U modified with a group such as a methyl group (2'-OMe) or a fluoro group (2'-F). For example, 2"-F-dU, 2"-F-dA, 2"-F-dC, 2"-F-dG are all considered to be the same or common modification, as are 2'-OMe-rU, 2'-OMe-rA; 2'-OMe-rC; 2'-OMe-rG. In contrast, a 2'-F modification is a different modification compared to a 2'-OMe modification.

Preferably, at least one nucleotide of the first and/or second strand of the nucleic acid is a modified nucleotide, preferably a non-naturally occurring nucleotide such as preferably a 2'-F modified nucleotide.

A modified nucleotide can be a nucleotide with a modification of the sugar group. The 2' hydroxyl group (OH) can be modified or replaced with a number of different "oxy" or "deoxy" substituents.

Examples of "oxy"-2' hydroxyl group modifications include alkoxy or aryloxy (OR, e.g., R=H, alkyl (such as methyl), cycloalkyl, aryl, aralkyl, heteroaryl or sugar); polyethyleneglycols (PEG), $O(CH_2CH_2O)_nCH_2CH_2OR$; "locked" nucleic acids (LNA) in which the 2' hydroxyl is connected, e.g., by a methylene bridge, to the 4' carbon of the same ribose sugar; O-AMINE (AMINE=$NH_2$, alkylamino, dialkylamino, heterocyclyl, arylamino, diaryl amino, heteroaryl amino, or diheteroaryl amino, ethylene diamine, or polyamino) and aminoalkoxy, $O(CH_2)nAMINE$, (e.g., AMINE=$NH_2$, alkylamino, dialkylamino, heterocyclyl, arylamino, diaryl amino, heteroaryl amino, or diheteroaryl amino, ethylene diamine, or polyamino).

"Deoxy" modifications include hydrogen, halogen, amino (e.g., $NH_2$, alkylamino, dialkylamino, heterocyclyl, arylamino, diaryl amino, heteroaryl amino, diheteroaryl amino, or amino acid); $NH(CH_2CH_2NH)_nCH_2CH_2$-AMINE (AMINE=$NH_2$, alkylamino, dialkylamino, heterocyclyl, arylamino, diaryl amino, heteroaryl amino, or diheteroaryl amino), —NHC(O)R (R=alkyl, cycloalkyl, aryl, aralkyl, heteroaryl or sugar), cyano; mercapto; alkyl-thio-alkyl; thio-alkoxy; and alkyl, cycloalkyl, aryl, alkenyl and alkynyl, which may be optionally substituted with e.g., an amino functionality. Other substituents of certain embodiments include 2'-methoxyethyl, 2'-OCH$_3$, 2'-O-allyl, 2'-C-allyl, and 2'-fluoro.

The sugar group can also contain one or more carbons that possess the opposite stereochemical configuration than that of the corresponding carbon in ribose. Thus, a modified nucleotide may contain a sugar such as arabinose.

Modified nucleotides can also include "abasic" sugars, which lack a nucleobase at C-1'. These abasic sugars can further contain modifications at one or more of the constituent sugar atoms. The 2' modifications may be used in combination with one or more phosphate internucleoside linker modifications (e.g., phosphorothioate or phosphorodithioate).

One or more nucleotides of a nucleic acid of the present invention may be modified. The nucleic acid may comprise at least one modified nucleotide. The modified nucleotide may be in the first strand. The modified nucleotide may be in the second strand. The modified nucleotide may be in the duplex region. The modified nucleotide may be outside the duplex region, i.e., in a single-stranded region. The modified nucleotide may be on the first strand and may be outside the duplex region. The modified nucleotide may be on the second strand and may be outside the duplex region. The 3'-terminal nucleotide of the first strand may be a modified nucleotide. The 3'-terminal nucleotide of the second strand may be a modified nucleotide. The 5'-terminal nucleotide of the first strand may be a modified nucleotide. The 5'-terminal nucleotide of the second strand may be a modified nucleotide.

A nucleic acid of the invention may have 1 modified nucleotide or a nucleic acid of the invention may have about 2-4 modified nucleotides, or a nucleic acid may have about 4-6 modified nucleotides, about 6-8 modified nucleotides, about 8-10 modified nucleotides, about 10-12 modified nucleotides, about 12-14 modified nucleotides, about 14-16 modified nucleotides about 16-18 modified nucleotides, about 18-20 modified nucleotides, about 20-22 modified nucleotides, about 22-24 modified nucleotides, about 24-26 modified nucleotides or about 26-28 modified nucleotides. In each case the nucleic acid comprising said modified nucleotides retains at least 50% of its activity as compared to the same nucleic acid but without said modified nucleotides or vice versa. The nucleic acid may retain 55%, 60%, 65%, 70%, 75%, 80%, 85%, 90%, 95% or 100% and intermediate values of its activity as compared to the same nucleic acid but without said modified nucleotides, or may have more than 100% of the activity of the same nucleic acid without said modified nucleotides.

The modified nucleotide may be a purine or a pyrimidine. At least half of the purines may be modified. At least half of the pyrimidines may be modified. All of the purines may be modified. All of the pyrimidines may be modified. The modified nucleotides may be selected from the group consisting of a 3' terminal deoxy thymine (dT) nucleotide, a 2'-O-methyl (2'-OMe) modified nucleotide, a 2' modified nucleotide, a 2' deoxy modified nucleotide, a locked nucleotide, an abasic nucleotide, a 2' amino modified nucleotide, a 2' alkyl modified nucleotide, a 2'-deoxy-2'-fluoro (2'-F) modified nucleotide, a morpholino nucleotide, a phosphoramidate, a non-natural base comprising nucleotide, a nucleotide comprising a 5'-phosphorothioate group, a nucleotide comprising a 5' phosphate or 5' phosphate mimic and a terminal nucleotide linked to a cholesteryl derivative or a dodecanoic acid bisdecylamide group.

The nucleic acid may comprise a nucleotide comprising a modified base, wherein the base is selected from 2-aminoadenosine, 2,6-diaminopurine, inosine, pyridin-4-one, pyridin-2-one, phenyl, pseudouracil, 2,4,6-trimethoxy benzene, 3-methyl uracil, dihydrouridine, naphthyl, aminophenyl, 5-alkylcytidine (e.g., 5-methylcytidine), 5-alkyluridine (e.g., ribothymidine), 5-halouridine (e.g., 5-bromouridine), 6-azapyrimidine, 6-alkylpyrimidine (e.g. 6-methyluridine), propyne, quesosine, 2-thiouridine, 4-thiouridine, wybutosine, wybutoxosine, 4-acetylcytidine, 5-(carboxyhydroxymethyl)uridine, 5'-carboxymethylaminomethyl-2-thiouridine, 5-carboxymethylaminomethyluridine, beta-D-galactosylqueosine, 1-methyladenosine, 1-methylinosine, 2,2-dimethylguanosine, 3-methylcytidine, 2-methyladenosine, 2-methylguanosine, N6-methyladenosine, 7-methylguanosine, 5-methoxyaminomethyl-2-thiouridine, 5-methylaminomethyluridine, 5-methylcarbonylmethyluridine, 5-methyloxyuridine, 5-methyl-2-thiouridine, 2-methylthio-N6-isopentenyladenosine, beta-D-mannosylqueosine, uridine-5-oxyacetic acid and 2-thiocytidine.

Many of the modifications described herein and that occur within a nucleic acid will be repeated within a polynucleotide molecule, such as a modification of a base, or a phosphate moiety, or a non-linking O of a phosphate moiety. In some cases, the modification will occur at all of the possible positions/nucleotides in the polynucleotide but in many cases it will not. A modification may only occur at a 3' or 5' terminal position, may only occur in a terminal region, such as at a position on a terminal nucleotide or in the last 2, 3, 4, 5, or 10 nucleotides of a strand. A modification may occur in a double-strand region, a single-strand region, or in both. A modification may occur only in the double-strand region of a nucleic acid of the invention or may only occur in a single-strand region of a nucleic acid of the invention. A phosphorothioate or phosphorodithioate modification at a non-linking O position may only occur at one or both termini, may only occur in a terminal region, e.g., at a position on a terminal nucleotide or in the last 2, 3, 4 or 5 nucleotides of a strand, or may occur in duplex and/or in single-strand regions, particularly at termini. The 5' end and/or 3' end may be phosphorylated.

Stability of a nucleic acid of the invention may be increased by including particular bases in overhangs, or by including modified nucleotides, in single-strand overhangs, e.g., in a 5' or 3' overhang, or in both. Purine nucleotides may be included in overhangs. All or some of the bases in a 3' or 5' overhang may be modified. Modifications can include the use of modifications at the 2' OH group of the ribose sugar, the use of deoxyribonucleotides, instead of ribonucleotides, and modifications in the phosphate group, such as phosphorothioate or phosphorodithioate modifications. Overhangs need not be homologous with the target sequence.

Nucleases can hydrolyse nucleic acid phosphodiester bonds. However, chemical modifications to nucleic acids can confer improved properties, and, can render oligoribonucleotides more stable to nucleases.

Modified nucleic acids, as used herein, can include one or more of:
(i) alteration, e.g., replacement, of one or both of the non-linking phosphate oxygens and/or of one or more of the linking phosphate oxygens (referred to as linking even if at the 5' and 3' terminus of the nucleic acid of the invention);
(ii) alteration, e.g., replacement, of a constituent of the ribose sugar, e.g., of the 2' hydroxyl on the ribose sugar;
(iii) replacement of the phosphate moiety with "dephospho" linkers;

(iv) modification or replacement of a naturally occurring base;

(v) replacement or modification of the ribose-phosphate backbone; and (vi) modification of the 3' end or 5' end of the first strand and/or the second strand, e.g., removal, modification or replacement of a terminal phosphate group or conjugation of a moiety, e.g., a fluorescently labelled moiety, to either the 3' or 5' end of one or both strands.

The terms replacement, modification and alteration indicate a difference from a naturally occurring molecule.

Specific modifications are discussed in more detail below.

The nucleic acid may comprise one or more nucleotides on the second and/or first strands that are modified. Alternating nucleotides may be modified, to form modified nucleotides.

Alternating as described herein means to occur one after another in a regular way. In other words, alternating means to occur in turn repeatedly. For example, if one nucleotide is modified, the next contiguous nucleotide is not modified and the following contiguous nucleotide is modified and so on. One nucleotide may be modified with a first modification, the next contiguous nucleotide may be modified with a second modification and the following contiguous nucleotide is modified with the first modification and so on, where the first and second modifications are different.

Some representative modified nucleic acid sequences of the present invention are shown in the examples. These examples are meant to be representative and not limiting.

In one aspect of the nucleic acid, at least nucleotides 2 and 14 of the first strand are modified, preferably by a first common modification, the nucleotides being numbered consecutively starting with nucleotide number 1 at the 5' end of the first strand. The first modification is preferably 2'-F.

In one aspect, at least one, several or preferably all the even-numbered nucleotides of the first strand are modified, preferably by a first common modification, the nucleotides being numbered consecutively starting with nucleotide number 1 at the 5' end of the first strand. The first modification is preferably 2'-F.

In one aspect, at least one, several or preferably all the odd-numbered nucleotides of the first strand are modified, the nucleotides being numbered consecutively starting with nucleotide number 1 at the 5' end of the first strand. Preferably, they are modified by a second modification. This second modification is preferably different from the first modification if the nucleic acid also comprises a first modification, for example of nucleotides 2 and 14 or of all the even-numbered nucleotides of the first strand. The first modification is preferably any 2' ribose modification that is of the same size or smaller in volume than a 2'-OH group, or a locked nucleic acid (LNA), or an unlocked nucleic acid (UNA), or a 2'-Fluoroarabino Nucleic Acid (FANA) modification. A 2' ribose modification that is of the same size or smaller in volume than a 2'-OH group can for example be a 2'-F, 2'-H, 2'-halo, or 2'-NH$_2$. The second modification is preferably any 2' ribose modification that is larger in volume than a 2'-OH group. A 2' ribose modification that is larger in volume than a 2'-OH group can for example be a 2'-OMe, 2'-O-MOE (2'-O-methoxyethyl), 2'-O-allyl or 2'-O-alkyl, with the proviso that the nucleic is capable of reducing the expression of the target gene to at least the same extent as the same nucleic acid without the modification(s) under comparable conditions. The first modification is preferably 2'-F and/or the second modification is preferably 2'-OMe.

In the context of this disclosure, the size or volume of a substituent, such as a 2' ribose modification, is preferably measured as the van der Waals volume.

In one aspect, at least one, several or preferably all the nucleotides of the second strand in a position corresponding to an even-numbered nucleotide of the first strand are modified, preferably by a third modification. Preferably in the same nucleic acid nucleotides 2 and 14 or all the even numbered nucleotides of the first strand are modified with a first modification. In addition, or alternatively, the odd-numbered nucleotides of the first strand are modified with a second modification. Preferably, the third modification is different from the first modification and/or the third modification is the same as the second modification. The first modification is preferably any 2' ribose modification that is of the same size or smaller in volume than a 2'-OH group, or a locked nucleic acid (LNA), or an unlocked nucleic acid (UNA), or a 2'-Fluoroarabino Nucleic Acid (FANA) modification. A 2' ribose modification that is of the same size or smaller in volume than a 2'-OH group can for example be a 2'-F, 2'-H, 2'-halo, or 2'-NH$_2$. The second and/or third modification is preferably any 2' ribose modification that is larger in volume than a 2'-OH group. A 2' ribose modification that is larger in volume than a 2'-OH group can for example be a 2'-OMe, 2'-O-MOE (2'-O-methoxyethyl), 2'-O-allyl or 2'-O-alkyl, with the proviso that the nucleic is capable of reducing the expression of the target gene to at least the same extent as the same nucleic acid without the modification(s) under comparable conditions. The first modification is preferably 2'-F and/or the second and/or third modification is/are preferably 2'-OMe. The nucleotides on the first strand are numbered consecutively starting with nucleotide number 1 at the 5' end of the first strand.

A nucleotide of the second strand that is in a position corresponding, for example, to an even-numbered nucleotide of the first strand is a nucleotide of the second strand that is base-paired to an even-numbered nucleotide of the first strand.

In one aspect, at least one, several or preferably all the nucleotides of the second strand in a position corresponding to an odd-numbered nucleotide of the first strand are modified, preferably by a fourth modification. Preferably in the same nucleic acid nucleotides 2 and 14 or all the even numbered nucleotides of the first strand are modified with a first modification. In addition, or alternatively, the odd-numbered nucleotides of the first strand are modified with a second modification. In addition, or alternatively, all the nucleotides of the second strand in a position corresponding to an even-numbered nucleotide of the first strand are modified with a third modification. The fourth modification is preferably different from the second modification and preferably different from the third modification and the fourth modification is preferably the same as the first modification. The first and/or fourth modification is preferably any 2' ribose modification that is of the same size or smaller in volume than a 2'-OH group, or a locked nucleic acid (LNA), or an unlocked nucleic acid (UNA), or a 2'-Fluoroarabino Nucleic Acid (FANA) modification. A 2' ribose modification that is of the same size or smaller in volume than a 2'-OH group can for example be a 2'-F, 2'-H, 2'-halo, or 2'-NH$_2$. The second and/or third modification is preferably any 2' ribose modification that is larger in volume than a 2'-OH group. A 2' ribose modification that is larger in volume than a 2'-OH group can for example be a 2'-OMe, 2'-O-MOE (2'-O-methoxyethyl), 2'-O-allyl or 2'-O-alkyl, with the proviso that the nucleic is capable of reducing the expression of the target gene to at least the same extent as the same nucleic acid without the modification(s) under comparable conditions. The first and/or the fourth modification is/are preferably a 2'-OMe modification and/or the second and/or third modification is/are preferably a 2'-F modification. The nucleotides on the first strand are numbered consecutively starting with nucleotide number 1 at the 5' end of the first strand.

In one aspect of the nucleic acid, the nucleotide/nucleotides of the second strand in a position corresponding to nucleotide 11 or nucleotide 13 or nucleotides 11 and 13 or nucleotides 11-13 of the first strand is/are modified by a fourth modification. Preferably, all the nucleotides of the second strand other than the nucleotide/nucleotides in a position corresponding to nucleotide 11 or nucleotide 13 or nucleotides 11 and 13 or nucleotides 11-13 of the first strand is/are modified by a third modification. Preferably in the same nucleic acid nucleotides 2 and 14 or all the even numbered nucleotides of the first strand are modified with a first modification. In addition, or alternatively, the odd-numbered nucleotides of the first strand are modified with a second modification. The fourth modification is preferably different from the second modification and preferably different from the third modification and the fourth modification is preferably the same as the first modification. The first and/or fourth modification is preferably any 2' ribose modification that is of the same size or smaller in volume than a 2'-OH group, or a locked nucleic acid (LNA), or an unlocked nucleic acid (UNA), or a 2'-Fluoroarabino Nucleic Acid (FANA) modification. A 2' ribose modification that is of the same size or smaller in volume than a 2'-OH group can for example be a 2'-F, 2'-H, 2'-halo, or 2'-NH$_2$. The second and/or third modification is preferably any 2' ribose modification that is larger in volume than a 2'-OH group. A 2' ribose modification that is larger in volume than a 2'-OH group can for example be a 2'-OMe, 2'-O-MOE (2'-O-methoxyethyl), 2'-O-allyl or 2'-O-alkyl, with the proviso that the nucleic is capable of reducing the expression of the target gene to at least the same extent as the same nucleic acid without the modification(s) under comparable conditions. The first and/or the fourth modification is/are preferably a 2'-OMe modification and/or the second and/or third modification is/are preferably a 2'-F modification. The nucleotides on the first strand are numbered consecutively starting with nucleotide number 1 at the 5' end of the first strand.

In one aspect of the nucleic acid, all the even-numbered nucleotides of the first strand are modified by a first modification, all the odd-numbered nucleotides of the first strand are modified by a second modification, all the nucleotides of the second strand in a position corresponding to an even-numbered nucleotide of the first strand are modified by a third modification, all the nucleotides of the second strand in a position corresponding to an odd-numbered nucleotide of the first strand are modified by a fourth modification, wherein the first and/or fourth modification is/are 2'-F and/or the second and/or third modification is/are 2'-OMe. In one aspect of the nucleic acid, all the even-numbered nucleotides of the first strand are modified by a first modification, all the odd-numbered nucleotides of the first strand are modified by a second modification, all the nucleotides of the second strand in positions corresponding to nucleotides 11-13 of the first strand are modified by a fourth modification, all the nucleotides of the second strand other than the nucleotides corresponding to nucleotides 11-13 of the first strand are modified by a third modification, wherein the first and fourth modification are 2'-F and the second and third modification are 2'-OMe. In one embodiment in this aspect, the 3' terminal nucleotide of the second strand is an inverted RNA nucleotide (i.e., the nucleotide is linked to the 3' end of the strand through its 3' carbon, rather than through its 5' carbon as would normally be the case). When the 3' terminal nucleotide of the second strand is an inverted RNA nucleotide, the inverted RNA nucleotide is preferably an unmodified nucleotide in the sense that it does not comprise any modifications compared to the natural nucleotide counterpart. Specifically, the inverted RNA nucleotide is preferably a 2'-OH nucleotide. Preferably, in this aspect when the 3' terminal nucleotide of the second strand is an inverted RNA nucleotide, the nucleic acid is blunt-ended at least at the end that comprises the 5' end of the first strand.

One aspect of the present invention is a nucleic acid as disclosed herein for inhibiting expression of the C3 gene, preferably in a cell, wherein said first strand includes modified nucleotides or unmodified nucleotides at a plurality of positions in order to facilitate processing of the nucleic acid by RISC.

In one aspect, "facilitate processing by RISC" means that the nucleic acid can be processed by RISC, for example any modification present will permit the nucleic acid to be processed by RISC and preferably, will be beneficial to processing by RISC, suitably such that siRNA activity can take place.

A nucleic acid as disclosed herein, wherein the nucleotides at positions 2 and 14 from the 5' end of the first strand are not modified with a 2' OMe modification, and the nucleotide/nucleotides on the second strand which corresponds to position 11 or position 13 or positions 11 and 13 or positions 11, 12 and 13 of the first strand is/are not modified with a 2'-OMe modification (in other words, they are not modified or are modified with a modification other than 2'-OMe).

In one aspect, the nucleotide on the second strand which corresponds to position 13 of the first strand is the nucleotide that forms a base pair with position 13 (from the 5' end) of the first strand.

In one aspect, the nucleotide on the second strand which corresponds to position 11 of the first strand is the nucleotide that forms a base pair with position 11 (from the 5' end) of the first strand.

In one aspect, the nucleotide on the second strand which corresponds to position 12 of the first strand is the nucleotide that forms a base pair with position 12 (from the 5' end) of the first strand.

For example, in a 19-mer nucleic acid which is double-stranded and blunt ended, position 13 (from the 5' end) of the first strand would pair with position 7 (from the 5' end) of the second strand. Position 11 (from the 5' end) of the first strand would pair with position 9 (from the 5' end) of the second strand. This nomenclature may be applied to other positions of the second strand.

In one aspect, in the case of a partially complementary first and second strand, the nucleotide on the second strand that "corresponds to" a position on the first strand may not necessarily form a base pair if that position is the position in which there is a mismatch, but the principle of the nomenclature still applies.

One aspect is a nucleic acid as disclosed herein, wherein the nucleotides at positions 2 and 14 from the 5' end of the first strand are not modified with a 2'-OMe modification, and the nucleotides on the second strand which correspond to position 11, or 13, or 11 and 13, or 11-13 of the first strand are modified with a 2'-F modification.

One aspect is a nucleic acid as disclosed herein, wherein the nucleotides at positions 2 and 14 from the 5' end of the first strand are modified with a 2'-F modification, and the nucleotides on the second strand which correspond to position 11, or 13, or 11 and 13, or 11-13 of the first strand are not modified with a 2'-OMe modification.

One aspect is a nucleic acid as disclosed herein, wherein the nucleotides at positions 2 and 14 from the 5' end of the first strand are modified with a 2'-F modification, and the nucleotides on the second strand which correspond to position 11, or 13, or 11 and 13, or 11-13 of the first strand are modified with a 2'-F modification.

One aspect is a nucleic acid as disclosed herein wherein greater than 50% of the nucleotides of the first and/or second strand comprise a 2'-OMe modification, such as greater than 55%, 60%, 65%, 70%, 75%, 80%, or 85%, or more, of the first and/or second strand comprise a 2'-OMe modification, preferably measured as a percentage of the total nucleotides of both the first and second strands.

One aspect is a nucleic acid as disclosed herein wherein greater than 50% of the nucleotides of the first and/or second strand comprise a naturally occurring RNA modification, such as wherein greater than 55%, 60%, 65%, 70%, 75%, 80%, or 85% or more of the first and/or second strands comprise such a modification, preferably measured as a percentage of the total nucleotides of both the first and second strands. Suitable naturally occurring modifications include, as well as 2'-OMe, other 2' sugar modifications, in particular a 2'-H modification resulting in a DNA nucleotide.

One aspect is a nucleic acid as disclosed herein comprising no more than 20%, such as no more than 15% such as no more than 10%, of nucleotides which have 2' modifications that are not 2'-OMe modifications on the first and/or second strand, preferably as a percentage of the total nucleotides of both the first and second strands.

One aspect is a nucleic acid as disclosed herein, wherein the number of nucleotides in the first and/or second strand with a 2'-modification that is not a 2'-OMe modification is no more than 7, more preferably no more than 5, and most preferably no more than 3.

One aspect is a nucleic acid as disclosed herein comprising no more than 20%, (such as no more than 15% or no more than 10%) of 2'-F modifications on the first and/or second strand, preferably as a percentage of the total nucleotides of both strands.

One aspect is a nucleic acid as disclosed herein, wherein the number of nucleotides in the first and/or second strand with a 2'-F modification is no more than 7, more preferably no more than 5, and most preferably no more than 3.

One aspect is a nucleic acid as disclosed herein, wherein all nucleotides are modified with a 2'-OMe modification except positions 2 and 14 from the 5' end of the first strand and the nucleotides on the second strand which correspond to position 11, or 13, or 11 and 13, or 11-13 of the first strand. Preferably the nucleotides that are not modified with 2'-OMe are modified with fluoro at the 2' position (2'-F modification).

Preferred is a nucleic acid as disclosed herein wherein all nucleotides of the nucleic acid are modified at the 2' position of the sugar. Preferably these nucleotides are modified with a 2'-F modification where the modification is not a 2'-OMe modification.

In one aspect the nucleic acid is modified on the first strand with alternating 2'-OMe modifications and 2-F modifications, and positions 2 and 14 (starting from the 5' end) are modified with 2'-F. Preferably the second strand is modified with 2'-F modifications at nucleotides on the second strand which correspond to position 11, or 13, or 11 and 13, or 11-13 of the first strand. Preferably the second strand is modified with 2'-F modifications at positions 11-13 counting from the 3' end starting at the first position of the complementary (double-stranded) region, and the remaining modifications are naturally occurring modifications, preferably 2'-OMe. The complementary region at least in this case starts at the first position of the second strand that has a corresponding nucleotide in the first strand, regardless of whether the two nucleotides are able to base pair to each other.

In one aspect of the nucleic acid, each of the nucleotides of the first strand and of the second strand is a modified nucleotide.

The term "odd numbered" as described herein means a number not divisible by two. Examples of odd numbers are 1, 3, 5, 7, 9, 11 and so on. The term "even numbered" as described herein means a number which is evenly divisible by two. Examples of even numbers are 2, 4, 6, 8, 10, 12, 14 and so on.

Unless specifically stated otherwise, herein the nucleotides of the first strand are numbered contiguously starting with nucleotide number 1 at the 5' end of the first strand. Nucleotides of the second strand are numbered contiguously starting with nucleotide number 1 at the 3' end of the second strand.

One or more nucleotides on the first and/or second strand may be modified, to form modified nucleotides. One or more of the odd-numbered nucleotides of the first strand may be modified. One or more of the even-numbered nucleotides of the first strand may be modified by at least a second modification, wherein the at least second modification is different from the modification on the one or more odd nucleotides. At least one of the one or more modified even numbered-nucleotides may be adjacent to at least one of the one or more modified odd-numbered nucleotides.

A plurality of odd-numbered nucleotides in the first strand may be modified in the nucleic acid of the invention. A plurality of even-numbered nucleotides in the first strand may be modified by a second modification. The first strand may comprise adjacent nucleotides that are modified by a common modification. The first strand may also comprise adjacent nucleotides that are modified by a second different modification (i.e. the first strand may comprise nucleotides that are adjacent to each other and modified by a first modification as well as other nucleotides that are adjacent to each other and modified by a second modification that is different to the first modification).

One or more of the odd-numbered nucleotides of the second strand (wherein the nucleotides are numbered contiguously starting with nucleotide number 1 at the 3' end of the second strand) may be modified by a modification that is different to the modification of the odd-numbered nucleotides on the first strand (wherein the nucleotides are numbered contiguously starting with nucleotide number 1 at the 5' end of the first strand) and/or one or more of the even-numbered nucleotides of the second strand may be modified by the same modification of the odd-numbered nucleotides of the first strand. At least one of the one or more modified even-numbered nucleotides of the second strand may be adjacent to the one or more modified odd-numbered nucleotides. A plurality of odd-numbered nucleotides of the second strand may be modified by a common modification and/or a plurality of even-numbered nucleotides may be modified by the same modification that is present on the first stand odd-numbered nucleotides. A plurality of odd-numbered nucleotides on the second strand may be modified by a modification that is different from the modification of the first strand odd-numbered nucleotides.

The second strand may comprise adjacent nucleotides that are modified by a common modification, which may be a modification that is different from the modification of the odd-numbered nucleotides of the first strand.

In the nucleic acid of the invention, each of the odd-numbered nucleotides in the first strand and each of the even-numbered nucleotides in the second strand may be modified with a common modification and, each of the even-numbered nucleotides may be modified in the first strand with a different modification and each of the odd-numbered nucleotides may be modified in the second strand with the different modification.

The nucleic acid of the invention may have the modified nucleotides of the first strand shifted by at least one nucleotide relative to the unmodified or differently modified nucleotides of the second strand.

One or more or each of the odd numbered-nucleotides may be modified in the first strand and one or more or each of the even-numbered nucleotides may be modified in the second strand. One or more or each of the alternating nucleotides on either or both strands may be modified by a second modification. One or more or each of the even-numbered nucleotides may be modified in the first strand and one or more or each of the even-numbered nucleotides may be modified in the second strand. One or more or each of the alternating nucleotides on either or both strands may be modified by a second modification. One or more or each of the odd-numbered nucleotides may be modified in the first strand and one or more of the odd-numbered nucleotides may be modified in the second strand by a common modification. One or more or each of the alternating nucleotides on either or both strands may be modified by a second modification. One or more or each of the even-numbered nucleotides may be modified in the first strand and one or more or each of the odd-numbered nucleotides may be modified in the second strand by a common modification. One or more or each of the alternating nucleotides on either or both strands may be modified by a second modification.

The nucleic acid of the invention may comprise single- or double-stranded constructs that comprise at least two regions of alternating modifications in one or both of the strands. These alternating regions can comprise up to about 12 nucleotides but preferably comprise from about 3 to about 10 nucleotides. The regions of alternating nucleotides may be located at the termini of one or both strands of the nucleic acid of the invention. The nucleic acid may comprise from 4 to about 10 nucleotides of alternating nucleotides at each of the termini (3' and 5') and these regions may be separated by from about 5 to about 12 contiguous unmodified or differently or commonly modified nucleotides.

The odd numbered nucleotides of the first strand may be modified and the even numbered nucleotides may be modified with a second modification. The second strand may comprise adjacent nucleotides that are modified with a common modification, which may be the same as the modification of the odd-numbered nucleotides of the first strand. One or more nucleotides of the second strand may also be modified with the second modification. One or more nucleotides with the second modification may be adjacent to each other and to nucleotides having a modification that is the same as the modification of the odd-numbered nucleotides of the first strand. The first strand may also comprise phosphorothioate linkages between the two nucleotides at the 3' end and at the 5' end or a phosphorodithioate linkage between the two nucleotides at the 3' end. The second strand may comprise a phosphorothioate or phosphorodithioate linkage between the two nucleotides at the 5' end. The second strand may also be conjugated to a ligand at the 5' end.

The nucleic acid of the invention may comprise a first strand comprising adjacent nucleotides that are modified with a common modification. One or more such nucleotides may be adjacent to one or more nucleotides which may be modified with a second modification. One or more nucleotides with the second modification may be adjacent. The second strand may comprise adjacent nucleotides that are modified with a common modification, which may be the same as one of the modifications of one or more nucleotides of the first strand. One or more nucleotides of the second strand may also be modified with the second modification. One or more nucleotides with the second modification may be adjacent. The first strand may also comprise phosphorothioate linkages between the two nucleotides at the 3' end and at the 5' end or a phosphorodithioate linkage between the two nucleotides at the 3' end. The second strand may comprise a phosphorothioate or phosphorodithioate linkage between the two nucleotides at the 3' end. The second strand may also be conjugated to a ligand at the 5' end.

The nucleotides numbered from 5' to 3' on the first strand and 3' to 5' on the second strand, 1, 3, 5, 7, 9, 11, 13, 15, 17, 19, 21, 23 and 25 may be modified by a modification on the first strand. The nucleotides numbered 2, 4, 6, 8, 10, 12, 14, 16, 18, 20, 22 and 24 may be modified by a second modification on the first strand. The nucleotides numbered 1, 3, 5, 7, 9, 11, 13, 15, 17, 19, 21, 23 may be modified by a modification on the second strand. The nucleotides numbered 2, 4, 6, 8, 10, 12, 14, 16, 18, 20, 22 and 24 may be modified by a second modification on the second strand. Nucleotides are numbered for the sake of the nucleic acid of the present invention from 5' to 3' on the first strand and 3' to 5' on the second strand.

The nucleotides numbered 2, 4, 6, 8, 10, 12, 14, 16, 18, 20, 22 and 24 may be modified by a modification on the first strand. The nucleotides numbered 1, 3, 5, 7, 9, 11, 13, 15, 17, 19, 21, 23 may be modified by a second modification on the first strand. The nucleotides numbered 1, 3, 5, 7, 9, 11, 13, 15, 17, 19, 21, 23 may be modified by a modification on the second strand. The nucleotides numbered 2, 4, 6, 8, 10, 12, 14, 16, 18, 20, 22 and 24 may be modified by a second modification on the second strand.

Clearly, if the first and/or the second strand are shorter than 25 nucleotides in length, such as 19 nucleotides in length, there are no nucleotides numbered 20, 21, 22, 23, 24 and 25 to be modified. The skilled person understands the description above to apply to shorter strands, accordingly.

One or more modified nucleotides on the first strand may be paired with modified nucleotides on the second strand having a common modification. One or more modified nucleotides on the first strand may be paired with modified nucleotides on the second strand having a different modification. One or more modified nucleotides on the first strand may be paired with unmodified nucleotides on the second strand. One or more modified nucleotides on the second strand may be paired with unmodified nucleotides on the first strand. In other words, the alternating nucleotides can be aligned on the two strands such as, for example, all the modifications in the alternating regions of the second strand are paired with identical modifications in the first strand or alternatively the modifications can be offset by one nucleotide with the common modifications in the alternating regions of one strand pairing with dissimilar modifications (i.e. a second or further modification) in the other strand. Another option is to have dissimilar modifications in each of the strands.

The modifications on the first strand may be shifted by one nucleotide relative to the modified nucleotides on the second strand, such that common modified nucleotides are not paired with each other.

The modification and/or modifications may each and individually be selected from the group consisting of 3' terminal deoxy thymine, 2'-OMe, a 2' deoxy modification, a 2' amino modification, a 2' alkyl modification, a morpholino modification, a phosphoramidate modification, 5'-phosphorothioate group modification, a 5' phosphate or 5' phosphate mimic modification and a cholesteryl derivative or a dodecanoic acid bisdecylamide group modification and/or the modified nucleotide may be any one of a locked nucleotide, an abasic nucleotide or a non-natural base comprising nucleotide.

At least one modification may be 2'-OMe and/or at least one modification may be 2'-F. Further modifications as described herein may be present on the first and/or second strand.

The nucleic acid of the invention may comprise an inverted RNA nucleotide at one or several of the strand ends. Such inverted nucleotides provide stability to the nucleic acid. Preferably, the nucleic acid comprises at least an inverted nucleotide at the 3' end of the first and/or the second strand and/or at the 5' end of the second strand. More preferably, the nucleic acid comprises an inverted nucleotide at the 3' end of the second strand. Most preferably, the nucleic acid comprises an inverted RNA nucleotide at the 3' end of the second strand and this nucleotide is preferably an inverted A. An inverted nucleotide is a nucleotide that is linked to the 3' end of a nucleic acid through its 3' carbon, rather than its 5' carbon as would normally be the case or is linked to the 5' end of a nucleic acid through its 5' carbon, rather than its 3' carbon as would normally be the case. The inverted nucleotide is preferably present at an end of a strand not as an overhang but opposite a corresponding nucleotide in the other strand.

Accordingly, the nucleic acid is preferably blunt-ended at the end that comprises the inverted RNA nucleotide. An inverted RNA nucleotide being present at the end of a strand preferably means that the last nucleotide at this end of the strand is the inverted RNA nucleotide. A nucleic acid with such a nucleotide is stable and easy to synthesise. The inverted RNA nucleotide is preferably an unmodified nucleotide in the sense that it does not comprise any modifications compared to the natural nucleotide counterpart. Specifically, the inverted RNA nucleotide is preferably a 2'-OH nucleotide.

Nucleic acids of the invention may comprise one or more nucleotides modified at the 2' position with a 2'-H, and therefore having a DNA nucleotide within the nucleic acid. Nucleic acids of the invention may comprise DNA nucleotides at positions 2 and/or 14 of the first strand counting from the 5' end of the first strand. Nucleic acids may comprise DNA nucleotides on the second strand which correspond to position 11, or 13, or 11 and 13, or 11-13 of the first strand.

In one aspect there is no more than one DNA nucleotide per nucleic acid of the invention.

Nucleic acids of the invention may comprise one or more LNA nucleotides. Nucleic acids of the invention may comprise LNA nucleotides at positions 2 and/or 14 of the first strand counting from the 5' end of the first strand. Nucleic acids may comprise LNA on the second strand which correspond to position 11, or 13, or 11 and 13, or 11-13 of the first strand.

Some representative modified nucleic acid sequences of the present invention are shown in the examples. These examples are meant to be representative and not limiting.

Preferably, the nucleic acid may comprise a first modification and a second or further modification which are each and individually selected from the group comprising 2'-OMe modification and 2'-F modification. The nucleic acid may comprise a modification that is 2'-OMe that may be a first modification, and a second modification that is 2'-F. The nucleic acid of the invention may also include a phosphorothioate or phosphorodithioate modification and/or a deoxy modification which may be present in or between the terminal 2 or 3 nucleotides of each or any end of each or both strands.

In one aspect of the nucleic acid, at least one nucleotide of the first and/or second strand is a modified nucleotide, wherein if the first strand comprises at least one modified nucleotide:
  (i) at least one or both of the nucleotides 2 and 14 of the first strand is/are modified by a first modification; and/or
  (ii) at least one, several, or all the even-numbered nucleotides of the first strand is/are modified by a first modification; and/or
  (iii) at least one, several, or all the odd-numbered nucleotides of the first strand is/are modified by a second modification; and/or
wherein if the second strand comprises at least one modified nucleotide:
  (iv) at least one, several, or all the nucleotides of the second strand in a position corresponding to an even-numbered nucleotide of the first strand is/are modified by a third modification; and/or
  (v) at least one, several, or all the nucleotides of the second strand in a position corresponding to an odd-numbered nucleotide of the first strand is/are modified by a fourth modification; and/or
  (vi) at least one, several, or all the nucleotides of the second strand in a position corresponding to nucleotide 11 or nucleotide 13 or nucleotides 11 and 13 or nucleotides 11-13 of the first strand is/are modified by a fourth modification; and/or
  (vii) at least one, several, or all the nucleotides of the second strand in a position other than the position corresponding to nucleotide 11 or nucleotide 13 or nucleotides 11 and 13 or nucleotides 11-13 of the first strand is/are modified by a third modification;
wherein the nucleotides on the first strand are numbered consecutively starting with nucleotide number 1 at the 5' end of the first strand;
wherein the modifications are preferably at least one of the following:
  (a) the first modification is preferably different from the second and from the third modification;
  (b) the first modification is preferably the same as the fourth modification;
  (c) the second and the third modification are preferably the same modification;
  (d) the first modification is preferably a 2'-F modification;
  (e) the second modification is preferably a 2'-OMe modification;
  (f) the third modification is preferably a 2'-OMe modification; and/or (g) the fourth modification is preferably a 2'-F modification; and wherein optionally the nucleic acid is conjugated to a ligand.

One aspect is a double-stranded nucleic acid for inhibiting expression of C3, preferably in a cell, wherein the nucleic acid comprises a first strand and a second strand, wherein the first strand sequence comprises a sequence of at least 15 nucleotides differing by no more than 3 nucleotides from any one of the sequences SEQ ID NO: 370, 364, 365, 366, 368, 372, 377, 361, 95, 111, 125, 131, 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 97, 99, 101, 103, 105, 107, 109, 113, 115, 117, 119, 121, 123, 127, 129, 133 or 416, preferably SEQ ID NO: 370, 364, 365, 366, 368, 372, 377 or 416, wherein all the even-numbered nucleotides of the first strand are modified by a first modification, all the odd-numbered nucleotides of the first strand are modified by a second modification, all the nucleotides of the second strand in a position corresponding to an even-numbered nucleotide of the first strand are modified by a third modification, all the nucleotides of the second strand in a position corresponding to an odd-numbered nucleotide of the first strand are modified by a fourth modification, wherein the first and fourth modification are 2'-F and the second and third modification are 2'-OMe.

One aspect is a double-stranded nucleic acid for inhibiting expression of C3, preferably in a cell, wherein the nucleic acid comprises a first strand and a second strand, wherein the first strand sequence comprises a sequence of at least 15 nucleotides differing by no more than 3 nucleotides from any one of the sequences SEQ ID NO: 370, 364, 365, 366, 368, 372, 377, 361, 95, 111, 125, 131, 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 97, 99, 101, 103, 105, 107, 109, 113, 115, 117, 119, 121, 123, 127, 129, 133 or 416, preferably SEQ ID NO: 370, 364, 365, 366, 368, 372, 377 or 416, wherein all the even-numbered nucleotides of the first strand are modified by a first modification, all the odd-numbered nucleotides of the first strand are modified by a second modification, all the nucleotides of the second strand in positions corresponding to nucleotides 11-13 of the first strand are modified by a fourth modification, all the nucleotides of the second strand other than the nucleotides corresponding to nucleotides 11-13 of the first strand are modified by a third modification, wherein the first and fourth modification are 2'-F and the second and third modification are 2'-OMe.

The 3' and 5' ends of an oligonucleotide can be modified. Such modifications can be at the 3' end or the 5' end or both ends of the molecule. They can include modification or replacement of an entire terminal phosphate or of one or more of the atoms of the phosphate group. For example, the 3' and 5' ends of an oligonucleotide can be conjugated to other functional molecular entities such as labelling moieties, e.g., fluorophores (e.g., pyrene, TAMRA, fluorescein, Cy3 or Cy5 dyes) or protecting groups (based e.g., on sulfur, silicon, boron or ester). The functional molecular entities can be attached to the sugar through a phosphate group and/or a linker. The terminal atom of the linker can connect to or replace the linking atom of the phosphate group or the C-3' or C-5' O, N, S or C group of the sugar. Alternatively, the linker can connect to or replace the terminal atom of a nucleotide surrogate (e.g., PNAs). These spacers or linkers can include e.g., —($CH_2$)$_n$—, —($CH_2$)$_n$N—, —($CH_2$)$_n$O—, —($CH_2$)$_n$S—, —($CH_2CH_2O$)$_n$$CH_2CH_2O$— (e.g., n=3 or 6), abasic sugars, amide, carboxy, amine, oxyamine, oxyimine, thioether, disulfide, thiourea, sulfonamide, or morpholino, or biotin and fluorescein reagents. The 3' end can be an —OH group.

Other examples of terminal modifications include dyes, intercalating agents (e.g., acridines), cross-linkers (e.g., psoralene, mitomycin C), porphyrins (TPPC4, texaphyrin, Sapphyrin), polycyclic aromatic hydrocarbons (e.g., phenazine, dihydrophenazine), artificial endonucleases, EDTA, lipophilic carriers (e.g., cholesterol, cholic acid, adamantane acetic acid, 1-pyrene butyric acid, dihydrotestosterone, 1,3-Bis-O(hexadecyl)glycerol, geranyloxyhexyl group, hexadecylglycerol, borneol, menthol, 1,3-propanediol, heptadecyl group, palmitic acid, myristic acid, O3-(oleoyl) lithocholic acid, O3-(oleoyl)cholenic acid, dimethoxytrityl, or phenoxazine) and peptide conjugates (e.g., antennapedia peptide, Tat peptide), alkylating agents, phosphate, amino, mercapto, PEG (e.g., PEG-40K), MPEG, [MPEG]2, polyamino, alkyl, substituted alkyl, radiolabeled markers, enzymes, haptens (e.g., biotin), transport/absorption facilitators (e.g., aspirin, vitamin E, folic acid), synthetic ribonucleases (e.g., imidazole, bisimidazole, histamine, imidazole clusters, acridine-imidazole conjugates, Eu3+ complexes of tetraazamacrocycles).

Terminal modifications can also be useful for monitoring distribution, and in such cases the groups to be added may include fluorophores, e.g., fluorescein or an Alexa dye. Terminal modifications can also be useful for enhancing uptake, useful modifications for this include cholesterol. Terminal modifications can also be useful for cross-linking an RNA agent to another moiety.

Terminal modifications can be added for a number of reasons, including to modulate activity or to modulate resistance to degradation. Terminal modifications useful for modulating activity include modification of the 5' end with phosphate or phosphate analogues. Nucleic acids of the invention, on the first or second strand, may be 5' phosphorylated or include a phosphoryl analogue at the 5' prime terminus. 5'-phosphate modifications include those which are compatible with RISC mediated gene silencing. Suitable modifications include: 5'-monophosphate (($HO$)$_2$(O)P—O-5'); 5'-diphosphate (($HO$)$_2$(O)P—O—P(HO)(O)—O-5'); 5'-triphosphate (($HO$)$_2$P—O—(HO)(O)P—O—P(HO)(O)—O-5'); 5'-guanosine cap (7-methylated or non-methylated) (7m-G-O-5'-(HO)(O)P—O—(HO)(O)P—O—P(HO)(O)—O-5'); 5'-adenosine cap (Appp), and any modified or unmodified nucleotide cap structure (N—O-5'-(HO)(O)P—O—(HO)(O)P—O—P(HO)(O)—O-5'); 5'-monothiophosphate (phosphorothioate; ($HO$)$_2$(S)P—O-5'); 5'-monodithiophosphate (phosphorodithioate; (HO)(HS)(S)P—O-5'), 5'-phosphorothiolate (($HO$)$_2$(O)P—S-5'); any additional combination of oxygen/sulfur replaced monophosphate, diphosphate and triphosphates (e.g., 5'-alpha-thiotriphosphate, 5'-gamma-thiotriphosphate, etc.), 5'-phosphoramidates (($HO$)$_2$(O)P—NH-5', (HO)($NH_2$)(O)P—O-5'), 5'-alkylphosphonates (alkyl=methyl, ethyl, isopropyl, propyl, etc., e.g. RP(OH)(O)—O-5'- (wherein R is an alkyl), ($OH$)$_2$(O)P-5'-$CH_2$—), 5' vinylphosphonate, 5'-alkyletherphosphonates (alkylether=methoxymethyl ($MeOCH_2$—), ethoxymethyl, etc., e.g. RP(OH)(O)—O-5'- (wherein R is an alkylether)).

Certain moieties may be linked to the 5' terminus of the first strand or the second strand. These include abasic ribose moiety, abasic deoxyribose moiety, modifications abasic ribose and abasic deoxyribose moieties including 2'-O alkyl modifications; inverted abasic ribose and abasic deoxyribose moieties and modifications thereof, C6-imino-Pi; a mirror nucleotide including L-DNA and L-RNA; 5'OMe nucleotide; and nucleotide analogues including 4',5'-methylene nucleotide; 1-(β-D-erythrofuranosyl)nucleotide; 4'-thio nucleotide, carbocyclic nucleotide; 5'-amino-alkyl phosphate; 1,3-diamino-2-propyl phosphate, 3-aminopropyl phosphate; 6-aminohexyl phosphate; 12-aminododecyl phosphate; hydroxypropyl phosphate; 1,5-anhydrohexitol nucleotide; alpha-nucleotide; threo-pentofuranosyl nucleotide; acyclic 3',4'-seco nucleotide; 3,4-dihydroxybutyl nucleotide; 3,5-dihydroxypentyl nucleotide, 5'-5'-inverted abasic moiety; 1,4-butanediol phosphate; 5'-amino; and bridging or non-bridging methylphosphonate and 5'-mercapto moieties.

In each sequence described herein, a C-terminal "—OH" moiety may be substituted for a C-terminal "—NH$_2$" moiety, and vice-versa.

The invention also provides a nucleic acid according to any aspect of the invention described herein, wherein the first strand has a terminal 5' (E)-vinylphosphonate nucleotide at its 5' end. This terminal 5' (E)-vinylphosphonate nucleotide is preferably linked to the second nucleotide in the first strand by a phosphodiester linkage.

The first strand of the nucleic acid may comprise formula (I):

where '(vp)-' is the 5' (E)-vinylphosphonate, 'N' is a nucleotide, 'po' is a phosphodiester linkage, and n is from 1 to (the total number of nucleotides in the first strand–2), preferably wherein n is from 1 to (the total number of nucleotides in the first strand–3), more preferably wherein n is from 1 to (the total number of nucleotides in the first strand–4).

Preferably, the terminal 5' (E)-vinylphosphonate nucleotide is an RNA nucleotide, preferably a (vp)-U.

A terminal 5' (E)-vinylphosphonate nucleotide is a nucleotide wherein the natural phosphate group at the 5'-end has been replaced with a E-vinylphosphonate, in which the bridging 5'-oxygen atom of the terminal nucleotide of the 5' phosphorylated strand is replaced with a methynyl (—CH=) group:

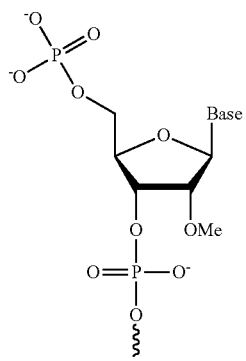

Nucleotides with a natural phosphate at the 5'-end

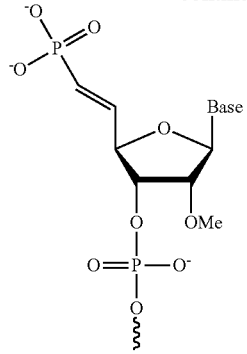

Nucleotide with a E-vinylphosphonate at the 5'-end

A 5' (E)-vinylphosphonate is a 5' phosphate mimic. A biological mimic is a molecule that is capable of carrying out the same function as and is structurally very similar to the original molecule that is being mimicked. In the context of the present invention, 5' (E)-vinylphosphonate mimics the function of a normal 5' phosphate, e.g. enabling efficient RISC loading. In addition, because of its slightly altered structure, 5' (E) vinylphosphonate is capable of stabilizing the 5'-end nucleotide by protecting it from dephosphorylation by enzymes such as phosphatases.

In one aspect, the first strand has a terminal 5' (E)-vinylphosphonate nucleotide at its 5' end, the terminal 5' (E)-vinylphosphonate nucleotide is linked to the second nucleotide in the first strand by a phosphodiester linkage and the first strand comprises a) more than 1 phosphodiester linkage; b) phosphodiester linkages between at least the terminal three 5' nucleotides and/or c) phosphodiester linkages between at least the terminal four 5' nucleotides.

In one aspect, the first strand and/or the second strand of the nucleic acid comprises at least one phosphorothioate (ps) and/or at least one phosphorodithioate (ps2) linkage between two nucleotides.

In one aspect, the first strand and/or the second strand of the nucleic acid comprises more than one phosphorothioate and/or more than one phosphorodithioate linkage.

In one aspect, the first strand and/or the second strand of the nucleic acid comprises a phosphorothioate or phosphorodithioate linkage between the terminal two 3' nucleotides or phosphorothioate or phosphorodithioate linkages between the terminal three 3' nucleotides. Preferably, the linkages between the other nucleotides in the first strand and/or the second strand are phosphodiester linkages.

In one aspect, the first strand and/or the second strand of the nucleic acid comprises a phosphorothioate linkage between the terminal two 5' nucleotides or a phosphorothioate linkages between the terminal three 5' nucleotides.

In one aspect, the nucleic acid of the present invention comprises one or more phosphorothioate or phosphorodithioate modifications on one or more of the terminal ends of the first and/or the second strand. Optionally, each or either end of the first strand may comprise one or two or three phosphorothioate or phosphorodithioate modified nucleotides (internucleoside linkage). Optionally, each or either end of the second strand may comprise one or two or three phosphorothioate or phosphorodithioate modified nucleotides (internucleoside linkage).

In one aspect, the nucleic acid comprises a phosphorothioate linkage between the terminal two or three 3' nucleotides and/or 5' nucleotides of the first and/or the second strand. Preferably, the nucleic acid comprises a phosphorothioate linkage between each of the terminal three 3' nucleotides and the terminal three 5' nucleotides of the first strand and of the second strand. Preferably, all remaining linkages between nucleotides of the first and/or of the second strand are phosphodiester linkages.

In one aspect, the nucleic acid comprises a phosphorodithioate linkage between each of the two, three or four terminal nucleotides at the 3' end of the first strand and/or comprises a phosphorodithioate linkage between each of the two, three or four terminal nucleotides at the 3' end of the second strand and/or a phosphorodithioate linkage between each of the two, three or four terminal nucleotides at the 5' end of the second strand and comprises a linkage other than a phosphorodithioate linkage between the two, three or four terminal nucleotides at the 5' end of the first strand.

In one aspect, the nucleic acid comprises a phosphorothioate linkage between the terminal three 3' nucleotides and the terminal three 5' nucleotides of the first strand and of the second strand. Preferably, all remaining linkages between nucleotides of the first and/or of the second strand are phosphodiester linkages.

In one aspect, the nucleic acid:
(i) has a phosphorothioate linkage between the terminal three 3' nucleotides and the terminal three 5' nucleotides of the first strand;
(ii) is conjugated to a triantennary ligand either on the 3' end nucleotide or on the 5' end nucleotide of the second strand;
(iii) has a phosphorothioate linkage between the terminal three nucleotides of the second strand at the end opposite to the one conjugated to the triantennary ligand; and
(iv) optionally all remaining linkages between nucleotides of the first and/or of the second strand are phosphodiester linkages.

In one aspect, the nucleic acid:
(i) has a terminal 5' (E)-vinylphosphonate nucleotide at the 5' end of the first strand;
(ii) has a phosphorothioate linkage between the terminal three 3' nucleotides on the first and second strand and between the terminal three 5' nucleotides on the second strand or it has a phosphorodithioate linkage between the terminal two 3' nucleotides on the first and second strand and between the terminal two 5' nucleotides on the second strand; and
(iii) optionally all remaining linkages between nucleotides of the first and/or of the second strand are phosphodiester linkages.

The use of a phosphorodithioate linkage in the nucleic acid of the invention reduces the variation in the stereochemistry of a population of nucleic acid molecules compared to molecules comprising a phosphorothioate in that same position. Phosphorothioate linkages introduce chiral centres and it is difficult to control which non-linking oxygen is substituted for sulphur. The use of a phosphorodithioate ensures that no chiral centre exists in that linkage and thus reduces or eliminates any variation in the population of nucleic acid molecules, depending on the number of phosphorodithioate and phosphorothioate linkages used in the nucleic acid molecule.

In one aspect, the nucleic acid comprises a phosphorodithioate linkage between the two terminal nucleotides at the 3' end of the first strand and a phosphorodithioate linkage between the two terminal nucleotides at the 3' end of the second strand and a phosphorodithioate linkage between the two terminal nucleotides at the 5' end of the second strand and comprises a linkage other than a phosphorodithioate linkage between the two, three or four terminal nucleotides at the 5' end of the first strand. Preferably, the first strand has a terminal 5' (E)-vinylphosphonate nucleotide at its 5' end. This terminal 5' (E)-vinylphosphonate nucleotide is preferably linked to the second nucleotide in the first strand by a phosphodiester linkage. Preferably, all the linkages between the nucleotides of both strands other than the linkage between the two terminal nucleotides at the 3' end of the first strand and the linkages between the two terminal nucleotides at the 3' end and at the 5' end of the second strand are phosphodiester linkages.

In one aspect, the nucleic acid comprises a phosphorothioate linkage between each of the three terminal 3' nucleotides and/or between each of the three terminal 5' nucleotides on the first strand, and/or between each of the three terminal 3' nucleotides and/or between each of the three terminal 5' nucleotides of the second strand when there is no phosphorodithioate linkage present at that end. No phosphorodithioate linkage being present at an end means that the linkage between the two terminal nucleotides, or preferably between the three terminal nucleotides of the nucleic acid end in question are linkages other than phosphorodithioate linkages.

In one aspect, all the linkages of the nucleic acid between the nucleotides of both strands other than the linkage between the two terminal nucleotides at the 3' end of the first strand and the linkages between the two terminal nucleotides at the 3' end and at the 5' end of the second strand are phosphodiester linkages.

Other phosphate linkage modifications are possible.

The phosphate linker can also be modified by replacement of a linking oxygen with nitrogen (bridged phosphoroamidates), sulfur (bridged phosphorothioates) and carbon (bridged methylenephosphonates). The replacement can occur at a terminal oxygen. Replacement of the non-linking oxygens with nitrogen is possible.

The phosphate groups can also individually be replaced by non-phosphorus containing connectors.

Examples of moieties which can replace the phosphate group include siloxane, carbonate, carboxymethyl, carbamate, amide, thioether, ethylene oxide linker, sulfonate, sulfonamide, thioformacetal, formacetal, oxime, methyleneimino, methylenemethylimino, methylenehydrazo, methylenedimethylhydrazo and methyleneoxymethylimino. In certain embodiments, replacements may include the methylenecarbonylamino and methylenemethylimino groups.

The phosphate linker and ribose sugar may be replaced by nuclease resistant nucleotides. Examples include the morpholino, cyclobutyl, pyrrolidine and peptide nucleic acid (PNA) nucleoside surrogates. In certain embodiments, PNA surrogates may be used.

In one aspect, the nucleic acid, which is preferably an siRNA that inhibits expression of the complement component C3, preferably via RNAi, and preferably in a cell, comprises one or more or all of:
(i) a modified nucleotide;
(ii) a modified nucleotide other than a 2'-OMe modified nucleotide at positions 2 and 14 from the 5' end of the first strand, preferably a 2'-F modified nucleotide;
(iii) each of the odd-numbered nucleotides of the first strand as numbered starting from one at the 5' end of the first strand are 2'-OMe modified nucleotides;
(iv) each of the even-numbered nucleotides of the first strand as numbered starting from one at the 5' end of the first strand are 2'-F modified nucleotides;

(v) the second strand nucleotide corresponding to position 11 and/or 13 or 11-13 of the first strand is modified by a modification other than a 2'-OMe modification, preferably wherein one or both or all of these positions comprise a 2'-F modification;

(vi) an inverted nucleotide, preferably a 3'-3' linkage at the 3' end of the second strand;

(vii) one or more phosphorothioate linkages;

(viii) one or more phosphorodithioate linkages; and/or (ix) the first strand has a terminal 5' (E)-vinylphosphonate nucleotide at its 5' end, in which case the terminal 5' (E)-vinylphosphonate nucleotide is preferably a uridine and is preferably linked to the second nucleotide in the first strand by a phosphodiester linkage.

All the features of the nucleic acids can be combined with all other aspects of the invention disclosed herein.

Ligands

The nucleic acids of the invention may be conjugated to a ligand. Efficient delivery of oligonucleotides, in particular double-stranded nucleic acids of the invention, to cells in vivo is important and requires specific targeting and substantial protection from the extracellular environment, particularly serum proteins. One method of achieving specific targeting is to conjugate a ligand to the nucleic acid. In some embodiments, the ligand helps in targeting the nucleic acid to a target cell which has a cell surface receptor that binds to and internalizes the conjugated ligand. In such embodiments, there is a need to conjugate appropriate ligands for the desired receptor molecules in order for the conjugated molecules to be taken up by the target cells by mechanisms such as different receptor-mediated endocytosis pathways or functionally analogous processes. In other embodiments, a ligand which can mediate internalization of the nucleic acid into a target cell by mechanisms other than receptor mediated endocytosis may alternatively be conjugated to a nucleic acid of the invention for cell or tissue specific targeting.

One example of a conjugate that mediates receptor mediated endocytosis is the asialoglycoprotein receptor complex (ASGP-R) which has high affinity to the GalNAc moiety described herein. The ASGP-R complex is composed of varying ratios of multimers of membrane ASGR1 and ASGR2 receptors, which are highly abundant on hepatocytes. One of the first disclosures of the use of triantennary cluster glycosides as conjugated ligands was in U.S. Pat. No. 5,885,968. Conjugates having three GalNAc ligands and comprising phosphate groups are known and are described in Dubber et al. (Bioconjug. Chem. 2003 January-February; 14(1):239-46). The ASGP-R complex shows a 50-fold higher affinity for N-Acetyl-D-Galactosamine (GalNAc) than D-Gal.

The ASGP-R complex recognizes specifically terminal β-galactosyl subunits of glycosylated proteins or other oligosaccharides (Weigel, P. H. et. al., Biochim. Biophys. Acta. 2002 Sep. 19; 1572(2-3):341-63) and can be used for delivering a drug to the liver's hepatocytes expressing the receptor complex by covalent coupling of galactose or galactosamine to the drug substance (Ishibashi, S.; et. al., J Biol. Chem. 1994 Nov. 11; 269(45):27803-6). Furthermore, the binding affinity can be significantly increased by the multi-valency effect, which is achieved by the repetition of the targeting moiety (Biessen E A, et al., J Med Chem. 1995 Apr. 28; 38(9):1538-46).

The ASGP-R complex is a mediator for an active uptake of terminal β-galactosyl containing glycoproteins to the cell's endosomes. Thus, the ASGPR is highly suitable for targeted delivery of drug candidates conjugated to such ligands like, e.g., nucleic acids into receptor-expressing cells (Akinc et al., Mol Ther. 2010 July; 18(7):1357-64).

More generally the ligand can comprise a saccharide that is selected to have an affinity for at least one type of receptor on a target cell. In particular, the receptor is on the surface of a mammalian liver cell, for example, the hepatic asialoglycoprotein receptor complex described before (ASGP-R).

The saccharide may be selected from N-acetyl galactosamine, mannose, galactose, glucose, glucosamine and fucose. The saccharide may be N-acetyl galactosamine (GalNAc).

A ligand for use in the present invention may therefore comprise (i) one or more N-acetyl galactosamine (GalNAc) moieties and derivatives thereof, and (ii) a linker, wherein the linker conjugates the GalNAc moieties to a nucleic acid as defined in any preceding aspects. The linker may be a monovalent structure or bivalent or trivalent or tetravalent branched structure.

The nucleotides may be modified as defined herein.

The ligand may therefore comprise GalNAc.

In one aspect, the nucleic acid is conjugated to a ligand comprising a compound of formula (II):

$$[S-X^1-P-X^2]_3-A-X^3-\qquad(II)$$

wherein:

S represents a saccharide, preferably wherein the saccharide is N-acetyl galactosamine;

$X^1$ represents $C_3$-$C_6$ alkylene or $(-CH_2-CH_2-O)_m(-CH_2)_2-$ wherein m is 1, 2, or 3;

P is a phosphate or modified phosphate, preferably a thiophosphate;

$X^2$ is alkylene or an alkylene ether of the formula $(-CH_2)_n-O-CH_2-$ where n=1-6;

A is a branching unit;

$X^3$ represents a bridging unit;

wherein a nucleic acid according to the present invention is conjugated to $X^3$ via a phosphate or modified phosphate, preferably a thiophosphate.

In formula (II), the branching unit "A" preferably branches into three in order to accommodate three saccharide ligands. The branching unit is preferably covalently attached to the remaining tethered portions of the ligand and the nucleic acid. The branching unit may comprise a branched aliphatic group comprising groups selected from alkyl, amide, disulphide, polyethylene glycol, ether, thioether and hydroxyamino groups. The branching unit may comprise groups selected from alkyl and ether groups.

The branching unit A may have a structure selected from:

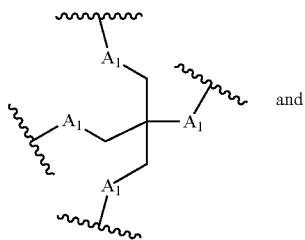 and

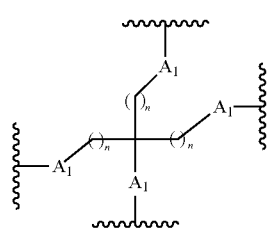

wherein each $A_1$ independently represents O, S, C=O or NH; and each n independently represents an integer from 1 to 20.

The branching unit may have a structure selected from:

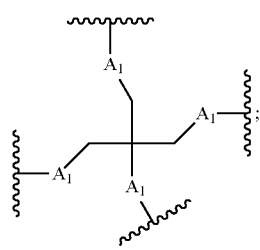;

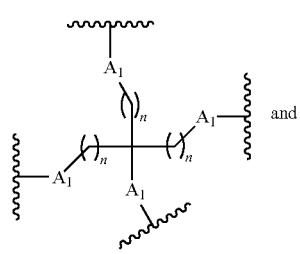 and

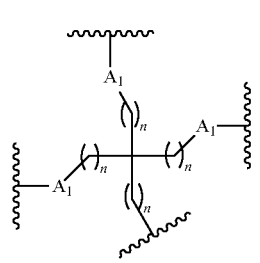

wherein each $A_1$ independently represents O, S, C=O or NH; and each n independently represents an integer from 1 to 20.

The branching unit may have a structure selected from:

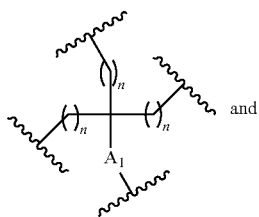 and

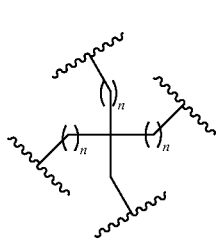

wherein $A_1$ is O, S, C=O or NH; and each n independently represents an integer from 1 to 20.

The branching unit may have the structure:

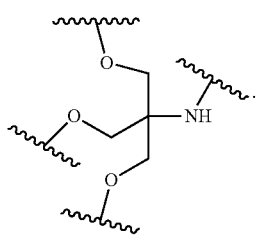 [SMILES: *NC(CO*)(CO*)CO*]

The branching unit may have the structure:

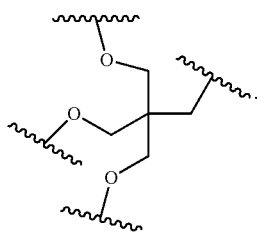 [SMILES: *CC(CO*)(CO*)CO*]

The branching unit may have the structure:

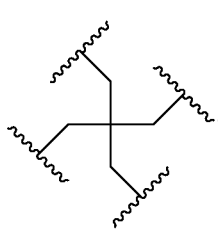

Alternatively, the branching unit A may have a structure selected from:

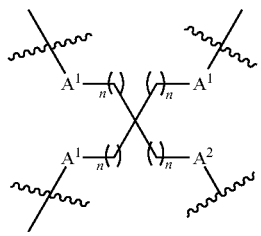

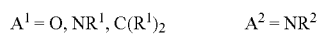

$A^1 = O, NR^1, C(R^1)_2$  $A^2 = NR^2$ n = 1 to 4

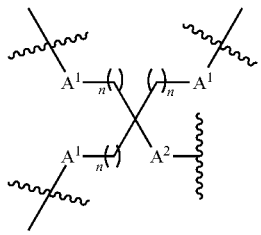

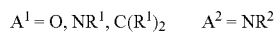

$A^1 = O, NR^1, C(R^1)_2$  $A^2 = NR^2$ n = 1 to 4 wherein:
R1 is hydrogen or C1-C10 alkylene;
and R2 is C1-C10 alkylene.

Optionally, the branching unit consists of only a carbon atom.

The "$X^3$" portion is a bridging unit. The bridging unit is linear and is covalently bound to the branching unit and the nucleic acid.

$X^3$ may be selected from —$C_1$-$C_{20}$ alkylene-, —$C_2$-$C_{20}$ alkenylene-, an alkylene ether of formula —($C_1$-$C_{20}$ alkylene)-O—($C_1$-$C_{20}$ alkylene)-, —C(O)—$C_1$-$C_{20}$ alkylene-, —$C_0$-$C_4$ alkylene(Cy)$C_0$-$C_4$ alkylene- wherein Cy represents a substituted or unsubstituted 5 or 6 membered cycloalkylene, arylene, heterocyclylene or heteroarylene ring, —$C_1$-$C_4$ alkylene-NHC(O)—$C_1$-$C_4$ alkylene-, —$C_1$-$C_4$ alkylene-C(O)NH—$C_1$-$C_4$ alkylene-, —$C_1$-$C_4$ alkylene-SC(O)—$C_1$-$C_4$ alkylene-, —$C_1$-$C_4$ alkylene-C(O)S—$C_1$-$C_4$ alkylene-, —$C_1$-$C_4$ alkylene-OC(O)—$C_1$-$C_4$ alkylene-, —$C_1$-$C_4$ alkylene-C(O)O—$C_1$-$C_4$ alkylene-, and —$C_1$-$C_6$ alkylene-S—S—$C_1$-$C_6$ alkylene-.

$X^3$ may be an alkylene ether of formula —($C_1$-$C_{20}$ alkylene)-O—($C_1$-$C_{20}$ alkylene)-. $X^3$ may be an alkylene ether of formula —($C_1$-$C_{20}$ alkylene)-O—($C_4$-$C_{20}$ alkylene)-, wherein said ($C_4$-$C_{20}$ alkylene) is linked to Z. $X^3$ may be selected from the group consisting of —$CH_2$—O—$C_3H_6$—, —$CH_2$—O—$C_4H_8$—, —$CH_2$—O—$C_6H_{12}$— and —$CH_2$—O—$C_8H_{16}$—, especially —$CH_2$—O—$C_4H_8$—, —$CH_2$—O—$C_6H_{12}$— and —$CH_2$—O—$C_8H_{16}$—, wherein in each case the —$CH_2$— group is linked to A.

In one aspect, the nucleic acid is conjugated to a ligand comprising a compound of formula (III):

wherein:

S represents a saccharide, preferably GalNAc;

$X^1$ represents $C_3$-$C_6$ alkylene or (—$CH_2$—$CH_2$—O)$_m$(—$CH_2$)$_2$— wherein m is 1, 2, or 3;

P is a phosphate or modified phosphate, preferably a thiophosphate;

$X^2$ is $C_1$-$C_8$ alkylene;

A is a branching unit selected from:

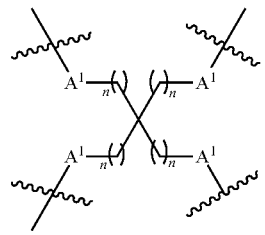

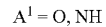

$A^1 = O, NH$ n = 1 to 4

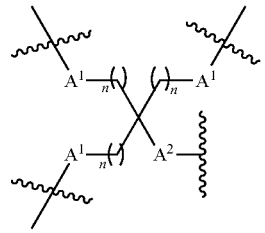

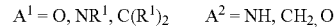

$A^1 = O, NR^1, C(R^1)_2$  $A^2 = NH, CH_2, O$ n = 1 to 4

$X^3$ is a bridging unit;

wherein a nucleic acid according to the present invention is conjugated to $X^3$ via a phosphate or a modified phosphate, preferably a thiophosphate.

The branching unit A may have the structure:

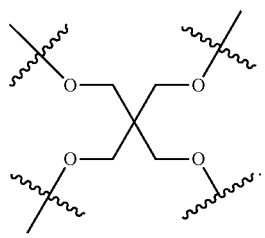 [SMILES: *OCC(CO*)(CO*)CO*]

The branching unit A may have the structure:

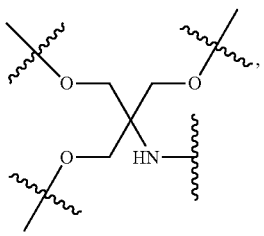

wherein $X^3$ is attached to the nitrogen atom.

$X^3$ may be $C_1$-$C_{20}$ alkylene. Preferably, $X^3$ is selected from the group consisting of —$C_3H_6$—, —$C_4H_8$—, —$C_6H_{12}$— and —$C_8H_{16}$—, especially —$C_4H_8$—, —$C_6H_{12}$— and —$C_8H_{16}$—.

In one aspect, the nucleic acid is conjugated to a ligand comprising a compound of formula (IV):

$$[S—X^1—P—X^2]_3\text{-}A\text{-}X^3— \qquad (IV)$$

wherein:
S represents a saccharide, preferably GalNAc;
$X^1$ represents $C_3$-$C_6$ alkylene or (—$CH_2$—$CH_2$—O)$_m$(—$CH_2$)$_2$— wherein m is 1, 2, or 3;
P is a phosphate or modified phosphate, preferably a thiophosphate;
$X^2$ is an alkylene ether of formula —$C_3H_6$—O—$CH_2$—;
A is a branching unit;
$X^3$ is an alkylene ether of formula selected from the group consisting of —$CH_2$—O—$CH_2$—, —$CH_2$—O—$C_2H_4$—, —$CH_2$—O—$C_3H_6$—, —$CH_2$—O—$C_4H_8$—, —$CH_2$—O—$C_5H_{10}$—, —$CH_2$—O—$C_6H_{12}$—, —$CH_2$—O—$C_7H_{14}$—, and —$CH_2$—O—$C_8H_{16}$—, wherein in each case the —$CH_2$— group is linked to A, and wherein $X^3$ is conjugated to a nucleic acid according to the present invention by a phosphate or modified phosphate, preferably a thiophosphate.

The branching unit may comprise carbon. Preferably, the branching unit is a carbon.

$X^3$ may be selected from the group consisting of —$CH_2$—O—$C_4H_8$—, —$CH_2$—O—$C_5H_{10}$—, —$CH_2$—O—$C_6H_{12}$—, —$CH_2$—O—$C_7H_{14}$—, and —$CH_2$—O—$C_8H_{16}$—. Preferably, $X^3$ is selected from the group consisting of —$CH_2$—O—$C_4H_8$—, —$CH_2$—O—$C_6H_{12}$— and —$CH_2$—O—$C_8H_{16}$.

$X^1$ may be (—$CH_2$—$CH_2$—O)(—$CH_2$)$_2$—. $X^1$ may be (—$CH_2$—$CH_2$—O)$_2$(—$CH_2$)$_2$—. $X^1$ may be (—$CH_2$—$CH_2$—O)$_3$(—$CH_2$)$_2$—. Preferably, $X^1$ is (—$CH_2$—$CH_2$—O)$_2$(—$CH_2$)$_2$—. Alternatively, $X^1$ represents $C_3$-$C_6$ alkylene. $X^1$ may be propylene. $X^1$ may be butylene. $X^1$ may be pentylene. $X^1$ may be hexylene. Preferably the alkyl is a linear alkylene. In particular, $X^1$ may be butylene.

$X^2$ represents an alkylene ether of formula —$C_3H_6$—O—$CH_2$— i.e. $O_3$ alkoxy methylene, or —$CH_2CH_2$$CH_2OCH_2$—.

For any of the above aspects, when P represents a modified phosphate group, P can be represented by:

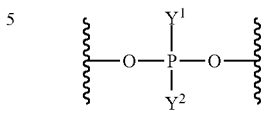

wherein $Y^1$ and $Y^2$ each independently represent =O, =S, —O⁻, —OH, —SH, —BH$_3$, —OCH$_2$CO$_2$, —OCH$_2$CO$_2$R$^x$, —OCH$_2$C(S)OR$^x$, and —OR$^x$, wherein R$^x$ represents $C_1$-$C_6$ alkyl and wherein

indicates attachment to the remainder of the compound.

By modified phosphate it is meant a phosphate group wherein one or more of the non-linking oxygens is replaced. Examples of modified phosphate groups include phosphorothioate, phosphorodithioates, phosphoroselenates, borano phosphates, borano phosphate esters, hydrogen phosphonates, phosphoroamidates, alkyl or aryl phosphonates and phosphotriesters. Phosphorodithioates have both non-linking oxygens replaced by sulphur. One, each or both non-linking oxygens in the phosphate group can be independently any one of S, Se, B, C, H, N, or OR (R is alkyl or aryl).

The phosphate can also be modified by replacement of a linking oxygen with nitrogen (bridged phosphoroamidates), sulfur (bridged phosphorothioates) and carbon (bridged methylenephosphonates). The replacement can occur at a terminal oxygen. Replacement of the non-linking oxygens with nitrogen is possible.

For example, r may represent —OH and $Y^2$ may represent =O or =S; or $Y^1$ may represent —O⁻ and $Y^2$ may represent =O or =S;

$Y^1$ may represent =O and $Y^2$ may represent —CH$_3$, —SH, —OR$^x$, or —BH$_3$ $Y^1$ may represent =S and $Y^2$ may represent —CH$_3$, OR$^x$ or —SH.

It will be understood by the skilled person that in certain instances there will be delocalisation between $Y^1$ and $Y^2$.

Preferably, the modified phosphate group is a thiophosphate group. Thiophosphate groups include bithiophosphate (i.e. where V represents =S and $Y^2$ represents —S⁻) and monothiophosphate (i.e. where V represents —O⁻ and $Y^2$ represents =S, or where V represents =O and $Y^2$ represents —S⁻). Preferably, P is a monothiophosphate. The inventors have found that conjugates having thiophosphate groups in replacement of phosphate groups have improved potency and duration of action in vivo.

P may also be an ethylphosphate (i.e. where $Y^1$ represents =O and $Y^2$ represents OCH$_2$CH$_3$).

The saccharide may be selected to have an affinity for at least one type of receptor on a target cell. In particular, the receptor is on the surface of a mammalian liver cell, for example, the hepatic asialoglycoprotein receptor complex (ASGP-R).

For any of the above or below aspects, the saccharide may be selected from N-acetyl with one or more of galactosamine, mannose, galactose, glucose, glucosamine and fructose. Typically a ligand to be used in the present invention may include N-acetyl galactosamine (GalNAc). Preferably the compounds of the invention may have 3 ligands, which will each preferably include N-acetyl galactosamine.

"GalNAc" refers to 2-(Acetylamino)-2-deoxy-D-galactopyranose, commonly referred to in the literature as N-acetyl galactosamine. Reference to "GalNAc" or "N-acetyl galactosamine" includes both the β-form: 2-(Acetylamino)-2-deoxy-β-D-galactopyranose and the α-form: 2-(Acetylamino)-2-deoxy-α-D-galactopyranose. In certain embodiments, both the β-form: 2-(Acetylamino)-2-deoxy-β-D-galactopyranose and α-form: 2-(Acetylamino)-2-deoxy-α-D-galactopyranose may be used interchangeably. Preferably, the compounds of the invention comprise the β-form, 2-(Acetylamino)-2-deoxy-β-D-galactopyranose.

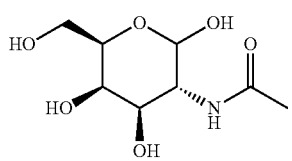

2-(Acetylamino)-2-deoxy-D-galactopyranose

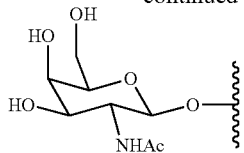

2-(Acetylamino)-2-deoxy-β-D-galactopyranose

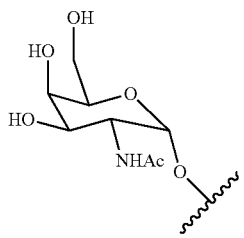

2-(Acetylamino)-2-deoxy-α-D-galactopyranose

In one aspect, the nucleic acid is a conjugated nucleic acid, wherein the nucleic acid is conjugated to a triantennary ligand with one of the following structures:

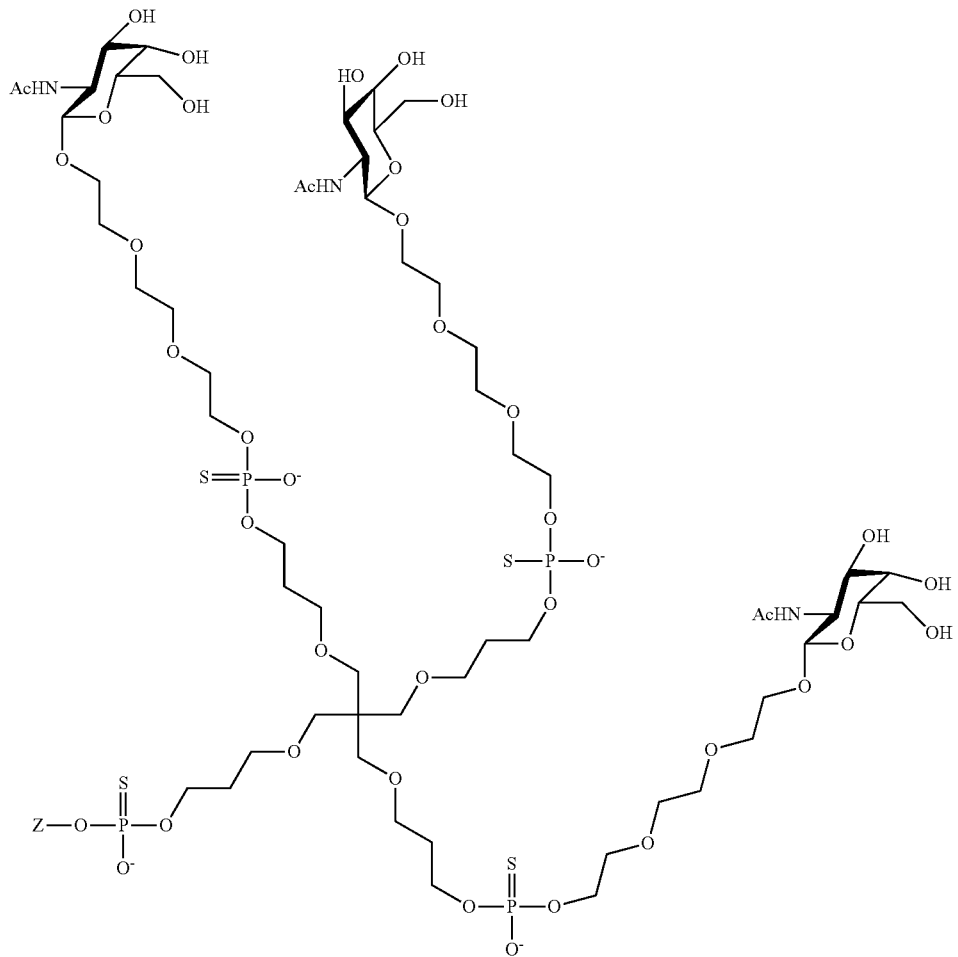

-continued
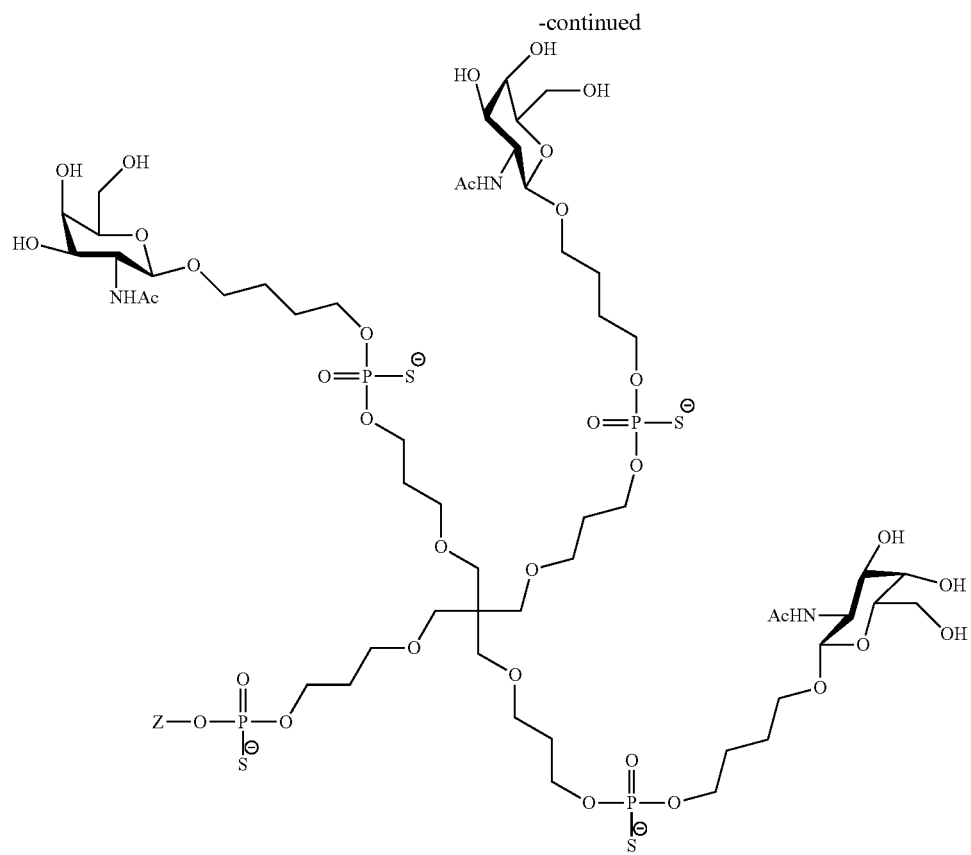
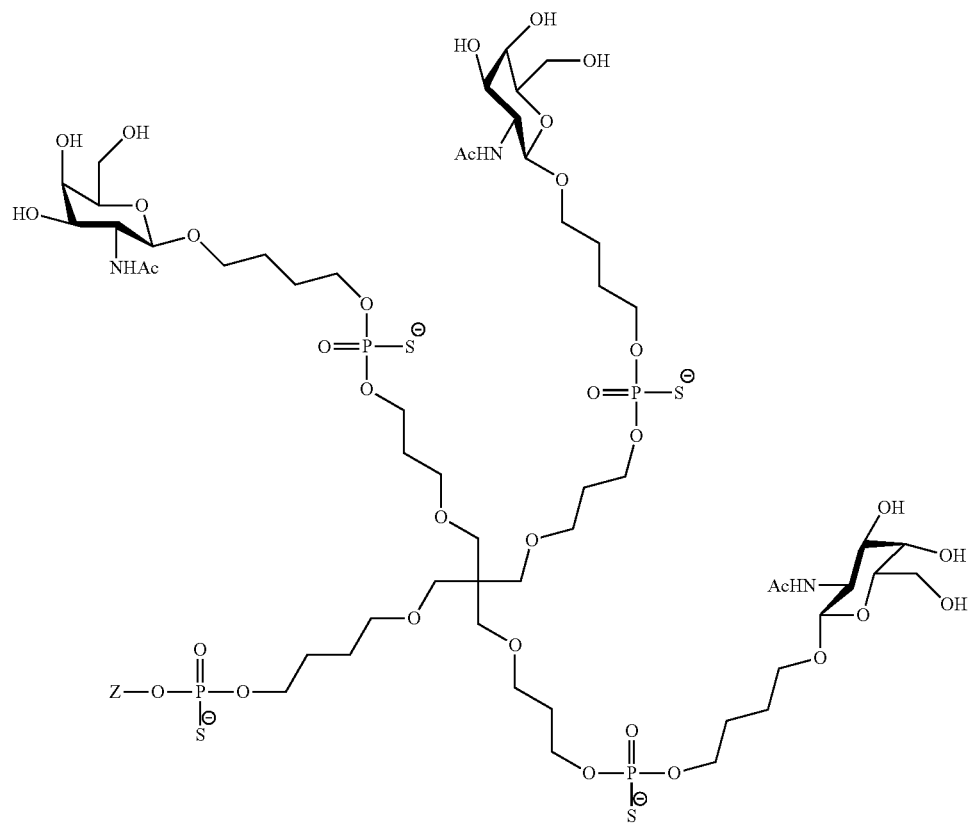

-continued
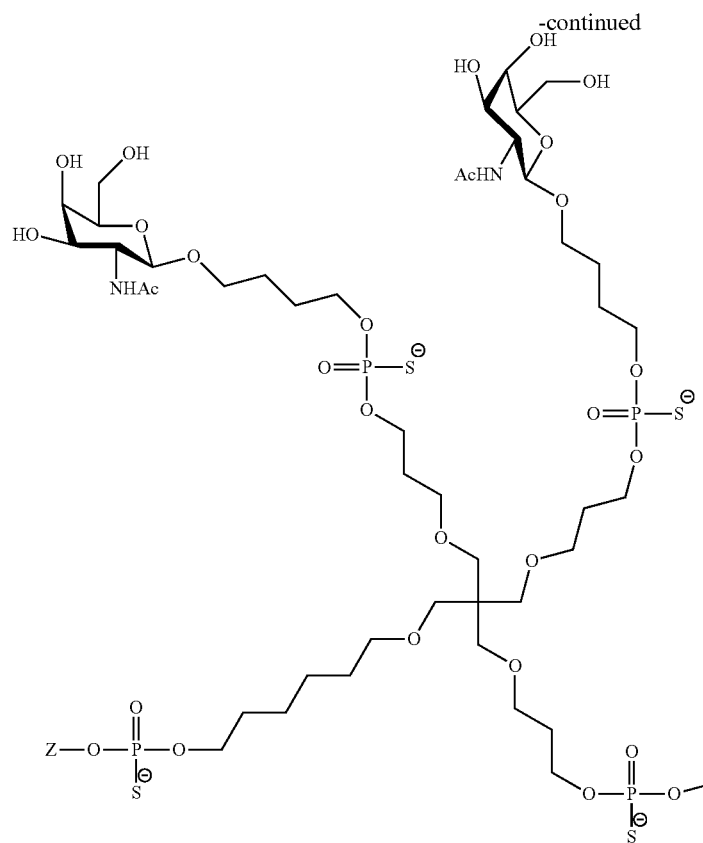
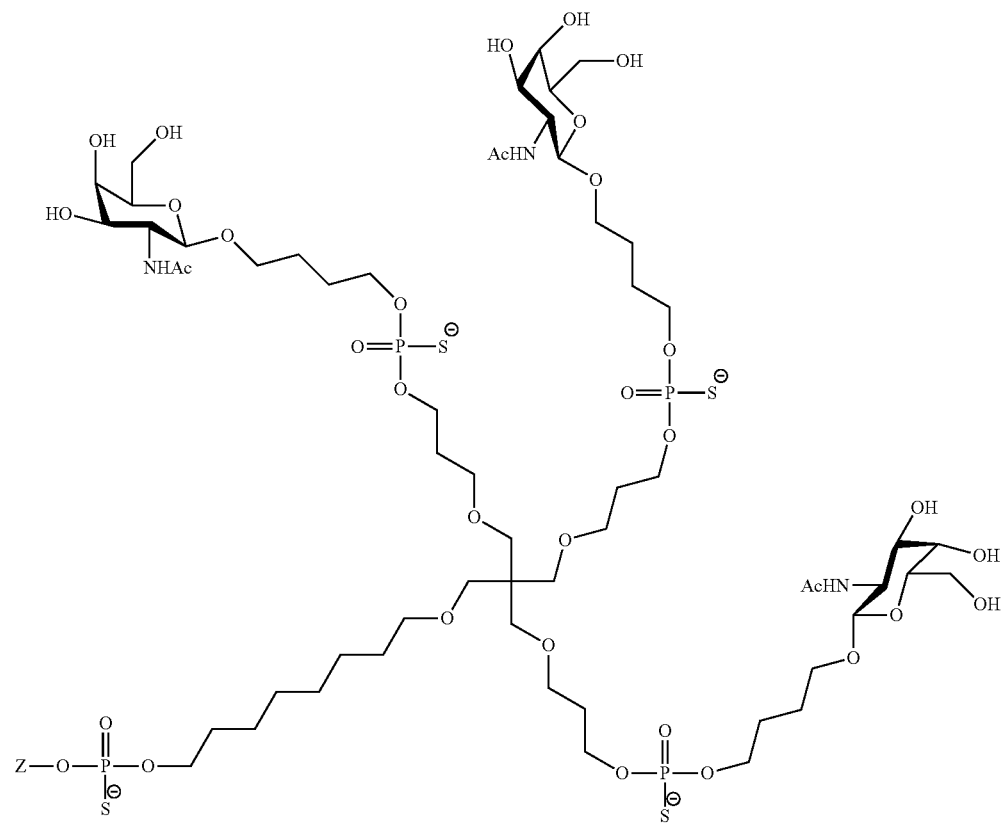

-continued
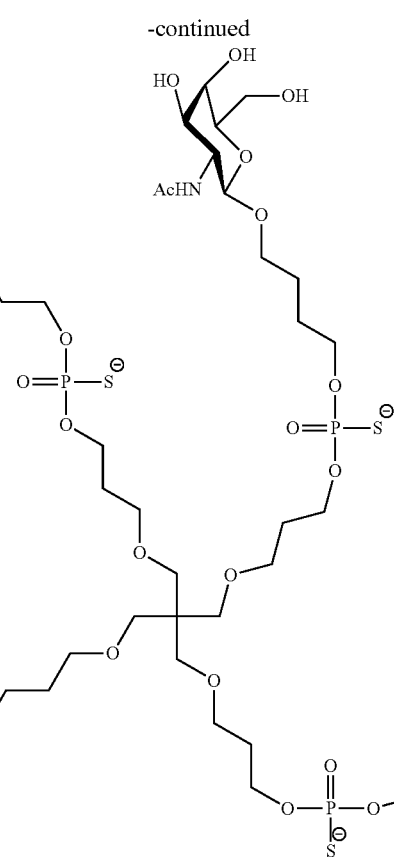
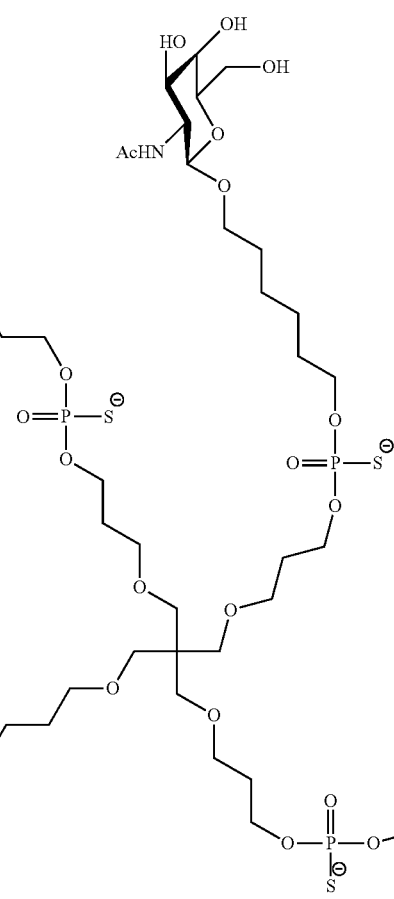

-continued
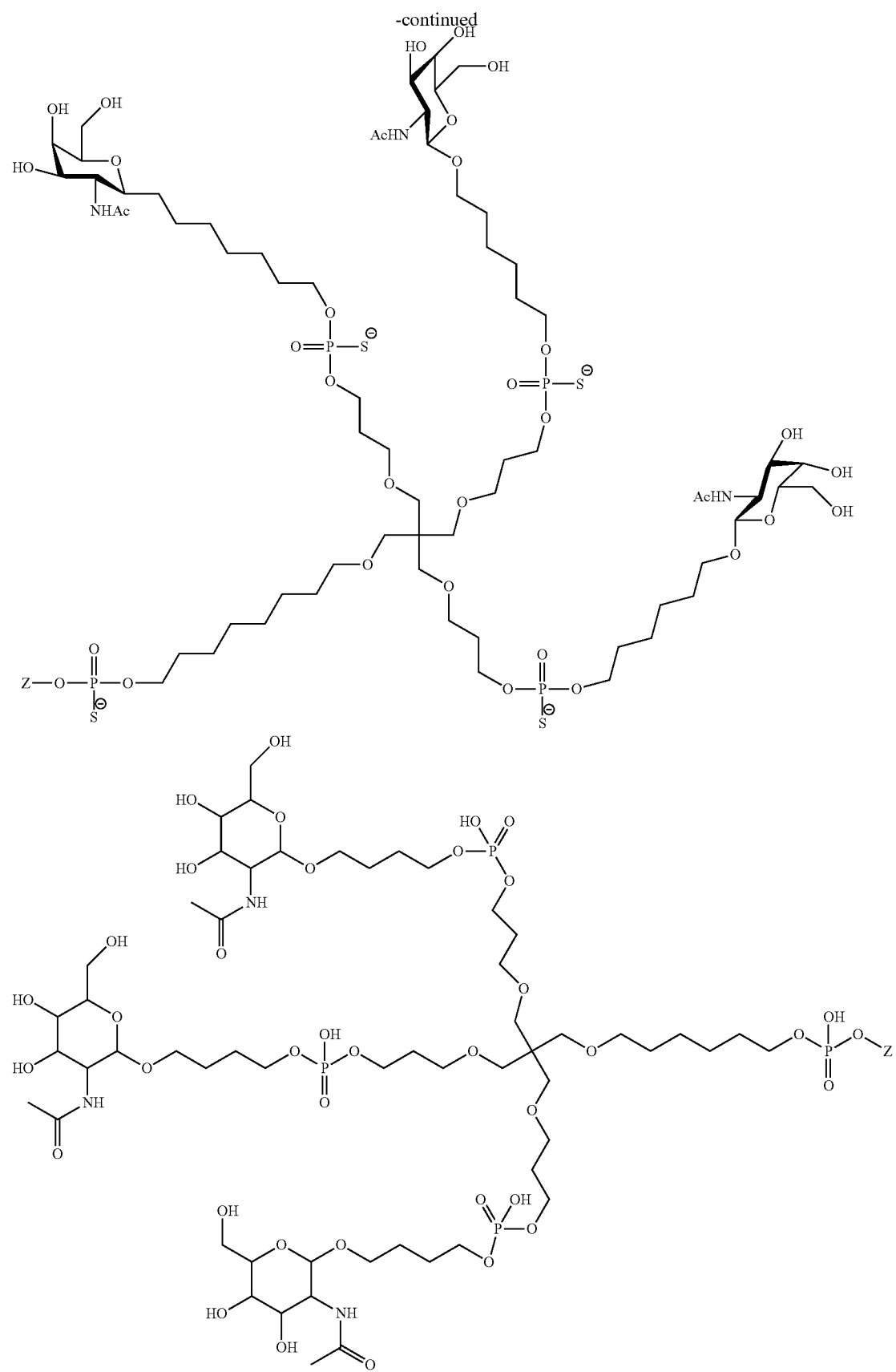
wherein Z is any nucleic acid as defined herein.

Preferably, the nucleic acid is a conjugated nucleic acid, wherein the nucleic acid is conjugated to a triantennary ligand with the following structures:

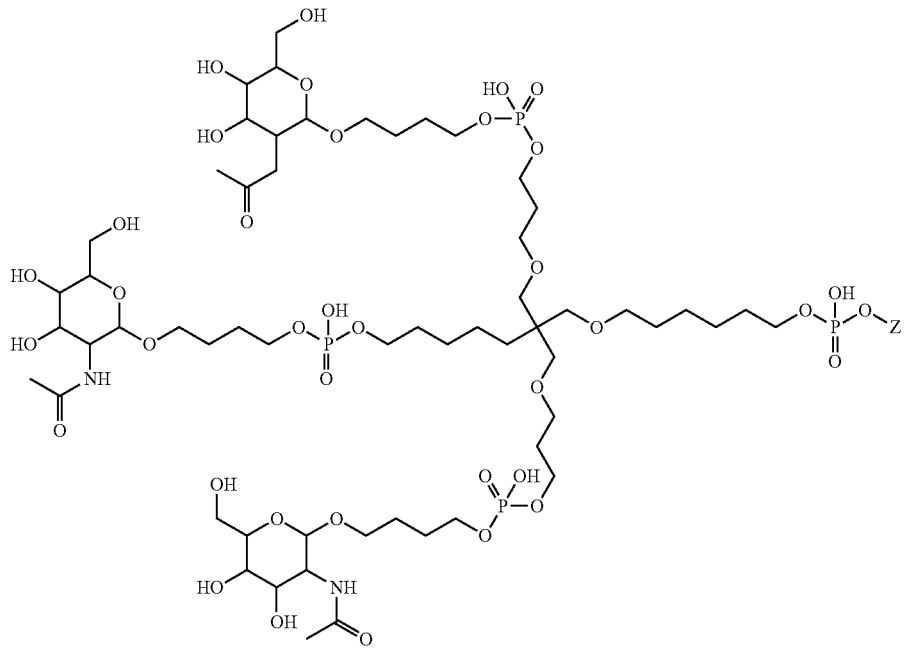

wherein Z is any nucleic acid as defined herein.

A ligand of formula (II), (III) or (IV) or any one of the triantennary ligands disclosed herein can be attached at the 3'-end of the first (antisense) strand and/or at any of the 3' and/or 5' end of the second (sense) strand. The nucleic acid can comprise more than one ligand of formula (II), (III) or (IV) or any one of the triantennary ligands disclosed herein. However, a single ligand of formula (II), (III) or (IV) or any one of the triantennary ligands disclosed herein is preferred because a single such ligand is sufficient for efficient targeting of the nucleic acid to the target cells. Preferably in that case, at least the last two, preferably at least the last three and more preferably at least the last four nucleotides at the end of the nucleic acid to which the ligand is attached are linked by a phosphodiester linkage.

Preferably, the 5'-end of the first (antisense) strand is not attached to a ligand of formula (II), (III) or (IV) or any one of the triantennary ligands disclosed herein, since a ligand in this position can potentially interfere with the biological activity of the nucleic acid.

A nucleic acid with a single ligand of formula (II), (III) or (IV) or any one of the triantennary ligands disclosed herein at the 5' end of a strand is easier and therefore cheaper to synthesise than the same nucleic acid with the same ligand at the 3' end. Preferably therefore, a single ligand of any of formulae (II), (III) or (IV) or any one of the triantennary ligands disclosed herein is covalently attached to (conjugated with) the 5' end of the second strand of the nucleic acid.

In one aspect, the first strand of the nucleic acid is a compound of formula (V):

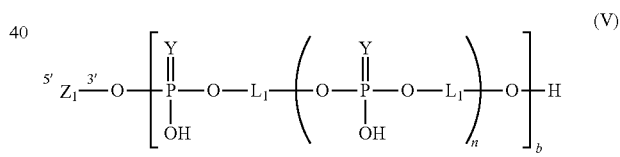

wherein b is preferably 0 or 1; and
the second strand is a compound of formula (VI):

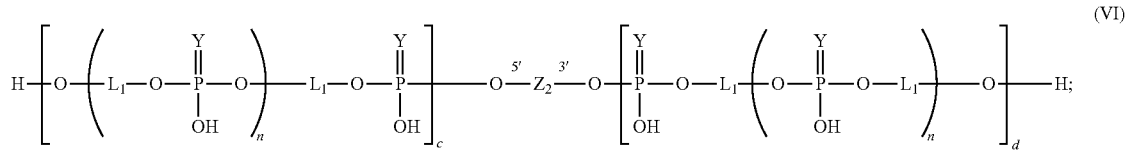

wherein:
c and d are independently preferably 0 or 1;
$Z_1$ and $Z_2$ are respectively the first and second strand of the nucleic acid;
Y is independently O or S;
n is independently 0, 1, 2 or 3; and $L_1$ is a linker to which a ligand is attached, wherein $L_1$ is the same or different in formulae (V) and (VI), and is the same or different within formulae (V) and (VI) when $L_1$ is present more than once within the same formula, wherein $L_1$ is preferably of formula (VII); and wherein b+c+d is preferably 2 or 3.

Preferably, $L_1$ in formulae (V) and (VI) is of formula (VII):

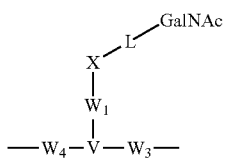
(VII)

wherein:
L is selected from the group comprising, or preferably consisting of:
- —(CH$_2$)$_r$—C(O)—, wherein r=2-12;
- —(CH$_2$—CH$_2$—O)$_s$—CH$_2$—C(O)—, wherein s=1-5;
- —(CH$_2$)$_t$—CO—NH—(CH$_2$)$_t$—NH—C(O)—, wherein t is independently 1-5;
- —(CH$_2$)$_u$—CO—NH—(CH$_2$)$_u$—C(O)—, wherein u is independently 1-5; and
- —(CH$_2$)$_v$—NH—C(O)—, wherein v is 2-12; and wherein the terminal C(O), if present, is attached to X of formula (VII), or if X is absent, to $W_1$ of formula (VII), or if $W_1$ is absent, to V of formula (VII);

$W_1$, $W_3$ and $W_5$ are individually absent or selected from the group comprising, or preferably consisting of:
- —(CH$_2$)$_r$—, wherein r=1-7;
- —(CH$_2$)$_s$—O—(CH$_2$)$_s$—, wherein s is independently 0-5;
- —(CH$_2$)$_t$—S—(CH$_2$)$_t$—, wherein t is independently 0-5;

X is absent or is selected from the group comprising, or preferably consisting of: NH, NCH$_3$ or NC$_2$H$_5$;

V is selected from the group comprising, or preferably consisting of:
CH, N,

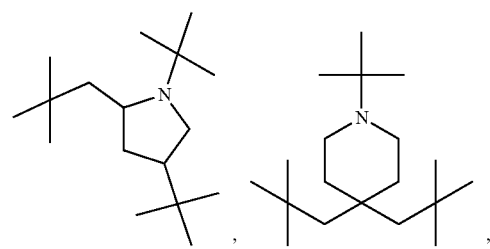

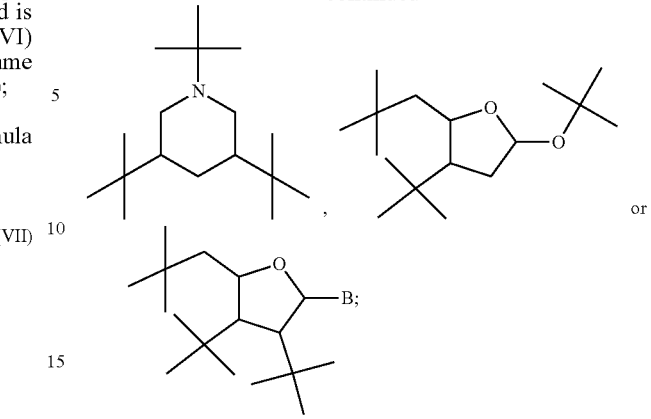

wherein B, if present, is a modified or natural nucleobase.

In one aspect, the first strand is a compound of formula (VIII)

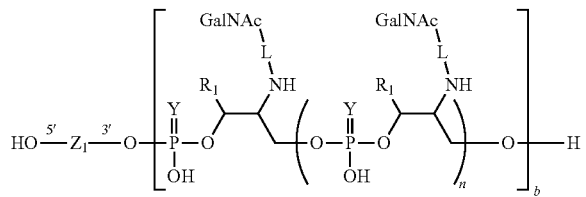
(VIII)

wherein b is preferably 0 or 1; and
the second strand is a compound of formula (IX):

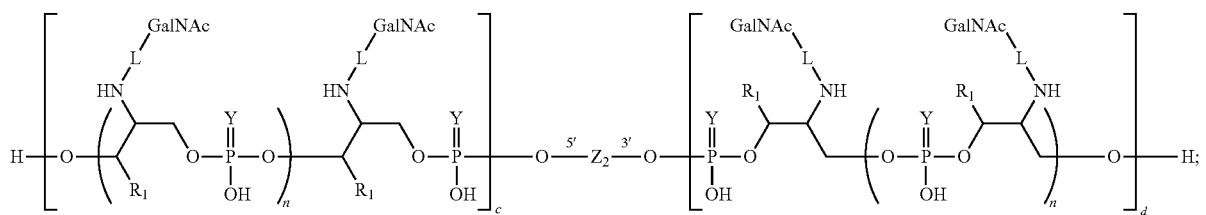
(IX)

wherein c and d are independently preferably 0 or 1;
wherein:
$Z_1$ and $Z_2$ are respectively the first and second strand of the nucleic acid;
Y is independently O or S;
$R_1$ is H or methyl;
n is independently preferably 0, 1, 2 or 3; and
L is the same or different in formulae (VIII) and (IX), and is the same or different within formulae (VIII) and (IX) when L is present more than once within the same formula, and is selected from the group comprising, or preferably consisting of:
- —(CH$_2$)$_r$—C(O)—, wherein r=2-12;
- —(CH$_2$—CH$_2$—O)$_s$—CH$_2$—C(O)—, wherein s=1-5;
- —(CH$_2$)$_t$—CO—NH—(CH$_2$)$_t$—NH—C(O)—, wherein t is independently 1-5;
- —(CH$_2$)$_u$—CO—NH—(CH$_2$)$_u$—C(O)—, wherein u is independently 1-5; and
- —(CH$_2$)$_v$—NH—C(O)—, wherein v is 2-12; and
wherein the terminal C(O), if present, is attached to the NH group (of the linker, not of the targeting ligand); and wherein b+c+d is preferably 2 or 3.

In one aspect, the first strand of the nucleic acid is a compound of formula (X):

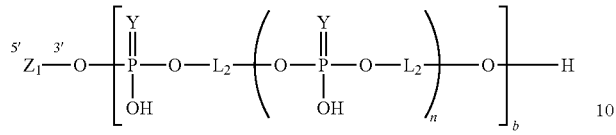
(X)

wherein b is preferably 0 or 1; and
the second strand is a compound of formula (XI):

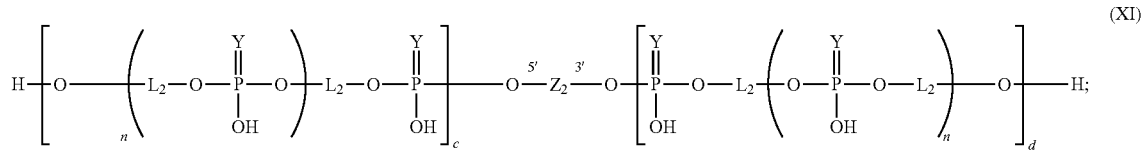
(XI)

wherein:
c and d are independently preferably 0 or 1;
$Z_1$ and $Z_2$ are respectively the first and second RNA strand of the nucleic;
Y is independently O or S;
n is independently preferably 0, 1, 2 or 3; and
$L_2$ is the same or different in formulae (X) and (XI) and is the same or different in moieties bracketed by b, c and d, and is selected from the group comprising, or preferably consisting of:

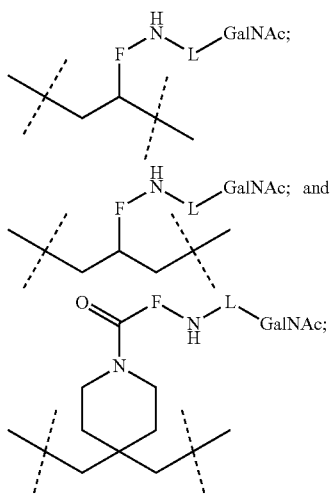

or
n is 0 and $L_2$ is:

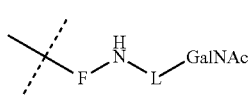

and the terminal OH group is absent such that the following moiety is formed:

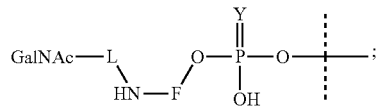

wherein:
F is a saturated branched or unbranched (such as unbranched) $C_{1-8}$alkyl (e.g. $C_{1-6}$alkyl) chain wherein one of the carbon atoms is optionally replaced with an oxygen atom provided that said oxygen atom is separated from another heteroatom (e.g. an O or N atom) by at least 2 carbon atoms;

L is the same or different in formulae (X) and (XI) and is selected from the group comprising, or preferably consisting of:
—$(CH_2)_r$—C(O)—, wherein r=2-12;
—$(CH_2—CH_2—O)_s$—$CH_2$—C(O)—, wherein s=1-5;
—$(CH_2)_t$—CO—NH—$(CH_2)_t$—NH—C(O)—, wherein t is independently 1-5;
—$(CH_2)_u$—CO—NH—$(CH_2)_u$—C(O)—, wherein u is independently 1-5; and
—$(CH_2)_v$—NH—C(O)—, wherein v is 2-12; and
wherein the terminal C(O), if present, is attached to the NH group (of the linker, not of the targeting ligand); and wherein b+c+d is preferably 2 or 3.

In one aspect, b is 0, c is 1 and d is 1; b is 1, c is 0 and d is 1; b is 1, c is 1 and d is 0; or b is 1, c is 1 and d is 1 in any of the nucleic acids of formulae (V) and (VI) or (VIII) and (IX) or (X) and (XI). Preferably, b is 0, c is 1 and d is 1; b is 1, c is 0 and d is 1; or b is 1, c is 1 and d is 1. Most preferably, b is 0, c is 1 and d is 1.

In one aspect, Y is O in any of the nucleic acids of formulae (V) and (VI) or (VIII) and (IX) or (X) and (XI). In another aspect, Y is S. In a preferred aspect, Y is independently selected from O or S in the different positions in the formulae.

In one aspect, $R_1$ is H or methyl in any of the nucleic acids of formulae (VIII) and (IX). In one aspect, $R_1$ is H. In another aspect, $R_1$ is methyl.

In one aspect, n is 0, 1, 2 or 3 in any of the nucleic acids of formulae (V) and (VI) or (VIII) and (IX) or (X) and (XI). Preferably, n is 0.

Examples of F moieties in any of the nucleic acids of formulae (X) and (XI) include $(CH_2)_{1-6}$ e.g. $(CH_2)_{1-4}$ e.g. $CH_2$, $(CH_2)_4$, $(CH_2)_5$ or $(CH_2)_6$, or $CH_2O(CH_2)_{2-3}$, e.g. $CH_2O(CH_2)CH_3$.

In one aspect, $L_2$ in formulae (X) and (XI) is:

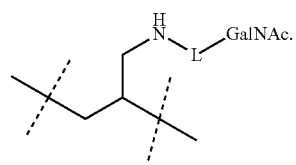

In one aspect, $L_2$ is:

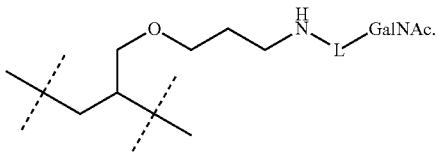

In one aspect, $L_2$ is:

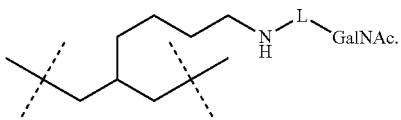

In one aspect, $L_2$ is:

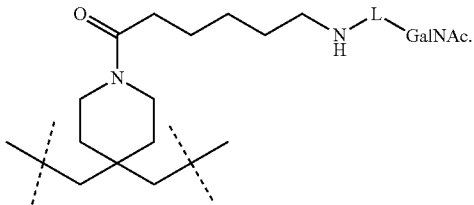

In one aspect, n is 0 and $L_2$ is:

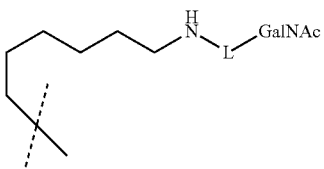

and the terminal OH group is absent such that the following moiety is formed:

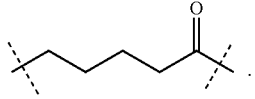

wherein Y is O or S.

In one aspect, L in the nucleic acids of formulae (V) and (VI) or (VIII) and (IX) or (X) and (XI), is selected from the group comprising, or preferably consisting of:
—$(CH_2)_r$—C(O)—, wherein r=2-12;
—$(CH_2$—$CH_2$—O$)_s$—$CH_2$—C(O)—, wherein s=1-5;
—$(CH_2)_t$—CO—NH—$(CH_2)_t$—NH—C(O)—, wherein t is independently 1-5;
—$(CH_2)_u$—CO—NH—$(CH_2)_u$—C(O)—, wherein u is independently 1-5; and
—$(CH_2)_v$—NH—C(O)—, wherein v is 2-12;
wherein the terminal C(O) is attached to the NH group.
Preferably, L is —$(CH_2)_r$—C(O)—, wherein r=2-12, more preferably r=2-6 even more preferably, r=4 or 6 e.g. 4.
Preferably, L is:

Within the moiety bracketed by b, c and d, $L_2$ in the nucleic acids of formulae (X) and (XI) is typically the same. Between moieties bracketed by b, c and d, $L_2$ may be the same or different.

In an embodiment, $L_2$ in the moiety bracketed by c is the same as the $L_2$ in the moiety bracketed by d. In an embodiment, $L_2$ in the moiety bracketed by c is not the same as $L_2$ in the moiety bracketed by d. In an embodiment, the $L_2$ in the moieties bracketed by b, c and d is the same, for example when the linker moiety is a serinol-derived linker moiety.

Serinol derived linker moieties may be based on serinol in any stereochemistry i.e. derived from L-serine isomer, D-serine isomer, a racemic serine or other combination of isomers. In a preferred aspect of the invention, the serinol-GalNAc moiety (SerGN) has the following stereochemistry:

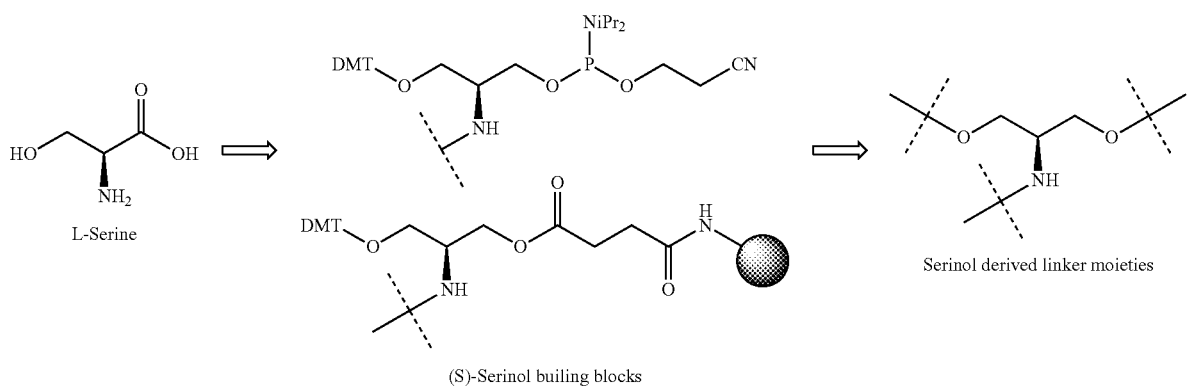

i.e. is based on an (S)-serinol-amidite or (S)-serinol succinate solid supported building block derived from L-serine isomer.

In a preferred aspect, the first strand of the nucleic acid is a compound of formula (VIII) and the second strand of the nucleic acid is a compound of formula (IX), wherein:
b is 0;
c and d are 1,
n is 0,
$Z_1$ and $Z_2$ are respectively the first and second strand of the nucleic acid,
Y is S,
$R_1$ is H, and
L is —$(CH_2)_4$—C(O)—, wherein the terminal C(O) of L is attached to the N atom of the linker (ie not a possible N atom of a targeting ligand).

In another preferred aspect, the first strand of the nucleic acid is a compound of formula (V) and the second strand of the nucleic acid is a compound of formula (VI), wherein:

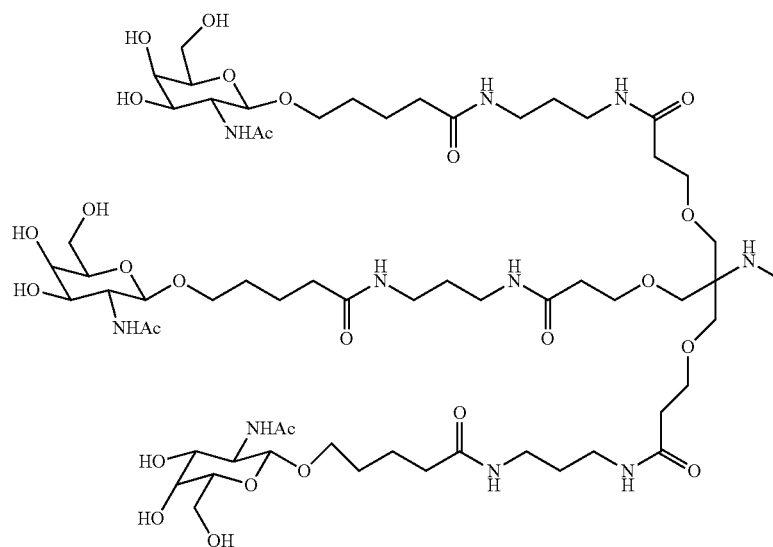

b is 0,
c and d are 1,
n is 0,
$Z_1$ and $Z_2$ are respectively the first and second strand of the nucleic acid,
Y is S,
$L_1$ is of formula (VII), wherein:
 $W_1$ is —$CH_2$—O—$(CH_2)_3$—,
 $W_3$ is —$CH_2$—,
 $W_5$ is absent,
 V is CH,
 X is NH, and
 L is —$(CH_2)_4$—C(O)— wherein the terminal C(O) of L is attached to the N atom of X in formula (VII).

In another preferred aspect, the first strand of the nucleic acid is a compound of formula (V) and the second strand of the nucleic acid is a compound of formula (VI), wherein:
b is 0,
c and d are 1,
n is 0,
$Z_1$ and $Z_2$ are respectively the first and second strand of the nucleic acid,
Y is S, $L_1$ is of formula (VII), wherein:
 $W_1$, $W_3$ and $W_5$ are absent,
 V is

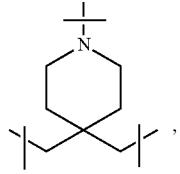

X is absent, and
 L is —$(CH_2)_4$—C(O)—NH—$(CH_2)_5$—C(O)—, wherein the terminal C(O) of L is attached to the N atom of V in formula (VII).

In one aspect, the nucleic acid is conjugated to a triantennary ligand with the following structure:

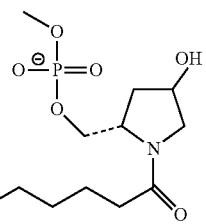

wherein the nucleic acid is conjugated to the ligand via the phosphate group of the ligand a) to the last nucleotide at the 5' end of the second strand; b) to the last nucleotide at the 3' end of the second strand; or c) to the last nucleotide at the 3' end of the first strand.

In one aspect of the nucleic acid, the cells that are targeted by the nucleic acid with a ligand are hepatocytes.

In any one of the above ligands where GalNAc is present, the GalNAc may be substituted for any other targeting ligand, such as those mentioned herein, in particular mannose, galactose, glucose, glucosamine and fucose.

A particularly preferred embodiment is a nucleic acid wherein the first strand comprises or consists of SEQ ID NO: 409 and the second strand optionally comprises or consists of SEQ ID NO: 423. This nucleic acid can be further conjugated to a ligand. Even more preferred is a nucleic acid wherein the first strand comprises or consists of SEQ ID NO: 409 and the second strand optionally comprises or consists of SEQ ID NO: 410. Most preferred is an siRNA that consists of SEQ ID NO: 409 and SEQ ID NO: 410. One aspect of the invention is EJ0020.

An alternative particularly preferred embodiment is a nucleic acid wherein the first strand comprises or consists of SEQ ID NO: 420 and the second strand optionally comprises or consists of SEQ ID NO: 424. This nucleic acid can be further conjugated to a ligand. Even more preferred is a nucleic acid wherein the first strand comprises or consists of SEQ ID NO: 420 and the second strand optionally comprises or consists of SEQ ID NO: 421. Most preferred is an siRNA that consists of SEQ ID NO: 420 and SEQ ID NO: 421. One aspect of the invention is EV0212.

An alternative particularly preferred embodiment is a nucleic acid wherein the first strand comprises or consists of SEQ ID NO: 417 and the second strand optionally comprises or consists of SEQ ID NO: 425. This nucleic acid can be further conjugated to a ligand. Even more preferred is a nucleic acid wherein the first strand comprises or consists of SEQ ID NO: 417 and the second strand optionally comprises or consists of SEQ ID NO: 418. Most preferred is an siRNA that consists of SEQ ID NO: 417 and SEQ ID NO: 418. One aspect of the invention is EV0210. Preliminary NHP data show that this siRNA is surprisingly potent in vivo in higher species.

In one aspect, the nucleic acid is conjugated to a ligand that comprises a lipid, and more preferably, a ligand that comprises a cholesterol.

Compositions, Uses and Methods

The present invention also provides compositions comprising a nucleic acid of the invention. The nucleic acids and compositions may be used as medicaments or as diagnostic agents, alone or in combination with other agents. For example, one or more nucleic acid(s) of the invention can be combined with a delivery vehicle (e.g., liposomes) and/or excipients, such as carriers, diluents. Other agents such as preservatives and stabilizers can also be added. Pharmaceutically acceptable salts or solvates of any of the nucleic acids of the invention are likewise within the scope of the present invention. Methods for the delivery of nucleic acids are known in the art and within the knowledge of the person skilled in the art.

Compositions disclosed herein are particularly pharmaceutical compositions. Such compositions are suitable for administration to a subject.

In one aspect, the composition comprises a nucleic acid disclosed herein, or a pharmaceutically acceptable salt or solvate thereof, and a solvent (preferably water) and/or a delivery vehicle and/or a physiologically acceptable excipient and/or a carrier and/or a salt and/or a diluent and/or a buffer and/or a preservative.

Pharmaceutically acceptable carriers or diluents include those used in formulations suitable for oral, rectal, nasal or parenteral (including subcutaneous, intramuscular, intravenous, intradermal, and transdermal) administration. The formulations may conveniently be presented in unit dosage form and may be prepared by any of the methods well known in the art of pharmacy. Subcutaneous or transdermal modes of administration may be particularly suitable for the compounds described herein.

The therapeutically effective amount of a nucleic acid of the present invention will depend on the route of administration, the type of mammal being treated, and the physical characteristics of the specific mammal under consideration. These factors and their relationship to determining this amount are well known to skilled practitioners in the medical arts. This amount and the method of administration can be tailored to achieve optimal efficacy, and may depend on such factors as weight, diet, concurrent medication and other factors, well known to those skilled in the medical arts. The dosage sizes and dosing regimen most appropriate for human use may be guided by the results obtained by the present invention, and may be confirmed in properly designed clinical trials.

An effective dosage and treatment protocol may be determined by conventional means, starting with a low dose in laboratory animals and then increasing the dosage while monitoring the effects, and systematically varying the dosage regimen as well. Numerous factors may be taken into consideration by a clinician when determining an optimal dosage for a given subject. Such considerations are known to the skilled person.

Nucleic acids of the present invention, or salts thereof, may be formulated as pharmaceutical compositions prepared for storage or administration, which typically comprise a therapeutically effective amount of a nucleic acid of the invention, or a salt thereof, in a pharmaceutically acceptable carrier.

The nucleic acid or conjugated nucleic acid of the present invention can also be administered in combination with other therapeutic compounds, either administrated separately or simultaneously, e.g., as a combined unit dose. The invention also includes a composition comprising one or more nucleic acids according to the present invention in a physiologically/pharmaceutically acceptable excipient, such as a stabilizer, preservative, diluent, buffer, and the like.

In one aspect, the composition comprises a nucleic acid disclosed herein and a further therapeutic agent selected from the group comprising an oligonucleotide, a small molecule, a monoclonal antibody, a polyclonal antibody and a peptide. Preferably, the further therapeutic agent is an agent that targets, preferably inhibits the expression or the activity, of the complement component C3 or of another element, such as a protein, of the immune system or more specifically of the complement pathway. Preferably, the further therapeutic agent is one of the following: a) a peptide that inhibits the expression or activity of one of the components of the complement pathway, preferably either C3 or C5 or one of their subunits; b) an antibody that specifically binds under physiological conditions to one of the components of the complement pathway, preferably either C3 or C5 or one of their subunits; c) Eculizumab or an antigen-binding derivative thereof.

Eculizumab is a humanised monoclonal antibody that specifically binds to the complement component C5 and is commercialised under the trade name SOLIRIS®. It specifically binds the complement component C5 with high affinity and inhibits cleavage of C5 to C5a and C5b. The antibody is for example described in the patent EP 0 758 904 B1 and its family members.

In certain embodiments, two or more nucleic acids of the invention with different sequences may be administered simultaneously or sequentially.

In another aspect, the present invention provides a composition, e.g., a pharmaceutical composition, comprising one or a combination of different nucleic acids of the invention and at least one pharmaceutically acceptable carrier.

Dosage levels for the medicament and compositions of the invention can be determined by those skilled in the art by experimentation. In one aspect, a unit dose may contain between about 0.01 mg/kg and about 100 mg/kg body weight of nucleic acid or conjugated nucleic acid. Alternatively, the dose can be from 10 mg/kg to 25 mg/kg body weight, or 1 mg/kg to 10 mg/kg body weight, or 0.05 mg/kg to 5 mg/kg body weight, or 0.1 mg/kg to 5 mg/kg body weight, or 0.1 mg/kg to 1 mg/kg body weight, or 0.1 mg/kg to 0.5 mg/kg body weight, or 0.5 mg/kg to 1 mg/kg body weight. Alternatively, the dose can be from about 0.5 mg/kg to about 10 mg/kg body weight, or about 0.6 mg/kg to about 8 mg/kg body weight, or about 0.7 mg/kg to about 7 mg/kg body weight, or about 0.8 mg/kg to about 6 mg/kg body weight, or about 0.9 mg/kg to about 5.5 mg/kg body weight, or about 1 mg/kg to about 5 mg/kg body weight, or about 1 mg/kg body weight, or about 3 mg/kg body weight, or about 5 mg/kg body weight, wherein "about" is a deviation of up to 30%, preferably up to 20%, more preferably up to 10%, yet more preferably up to 5% and most preferably 0% from the indicated value. Dosage levels may also be calculated via other parameters such as, e.g., body surface area.

A particularly preferred embodiment is a nucleic acid wherein the first strand comprises or consists of SEQ ID NO: 409 and the second strand optionally comprises or consists of SEQ ID NO: 423. This nucleic acid can be further conjugated to a ligand. Even more preferred is a nucleic acid wherein the first strand comprises or consists of SEQ ID NO: 409 and the second strand optionally comprises or consists of SEQ ID NO: 410. Most preferred is an siRNA that consists of SEQ ID NO: 409 and SEQ ID NO: 410. One aspect of the invention is EJ0020. A dose unit of these nucleic acids preferably comprises about 1 mg/kg to about 5 mg/kg body weight, or about 1 mg/kg to about 3 mg/kg body weight, or about 1 mg/kg body weight, or about 3 mg/kg body weight, or about 5 mg/kg body weight. The C3 mRNA level in the liver and/or the C3 protein level in the plasma or blood of a subject treated by a dose unit of the nucleic acid is preferably decreased at the time point of maximum effect by at least 30%, at least 40%, at least 50%, at least 60% or at least 70% as compared to a control that was not treatment with the nucleic acid or treated with a control nucleic acid under comparable conditions.

The dosage and frequency of administration may vary depending on whether the treatment is therapeutic or prophylactic (e.g., preventative), and may be adjusted during the course of treatment. In certain prophylactic applications, a relatively low dosage is administered at relatively infrequent intervals over a relatively long period of time. Some subjects may continue to receive treatment over their lifetime. In certain therapeutic applications, a relatively high dosage at relatively short intervals is sometimes required until progression of the disease is reduced or until the patient shows partial or complete amelioration of symptoms of disease. Thereafter, the patient may be switched to a suitable prophylactic dosing regimen.

Actual dosage levels of a nucleic acid of the invention alone or in combination with one or more other active ingredients in the pharmaceutical compositions of the present invention may be varied so as to obtain an amount of the active ingredient which is effective to achieve the desired therapeutic response for a particular patient, composition, and mode of administration, without causing deleterious side effects to the subject or patient. A selected dosage level will depend upon a variety of factors, such as pharmacokinetic factors, including the activity of the particular nucleic acid or composition employed, the route of administration, the time of administration, the rate of excretion of the particular nucleic acid being employed, the duration of the treatment, other drugs, compounds and/or materials used in combination with the particular compositions employed, the age, sex, weight, condition, general health and prior medical history of the subject or patient being treated, and similar factors well known in the medical arts.

The pharmaceutical composition may be a sterile injectable aqueous suspension or solution, or in a lyophilized form.

The pharmaceutical compositions can be in unit dosage form. In such form, the composition is divided into unit doses containing appropriate quantities of the active component. The unit dosage form can be a packaged preparation, the package containing discrete quantities of the preparations, for example, packeted tablets, capsules, and powders in vials or ampoules. The unit dosage form can also be a capsule, cachet, or tablet itself, or it can be the appropriate number of any of these packaged forms. It may be provided in single dose injectable form, for example in the form of a pen. Compositions may be formulated for any suitable route and means of administration.

The pharmaceutical compositions and medicaments of the present invention may be administered to a mammalian subject in a pharmaceutically effective dose. The mammal may be selected from a human, a non-human primate, a simian or prosimian, a dog, a cat, a horse, cattle, a pig, a goat, a sheep, a mouse, a rat, a hamster, a hedgehog and a guinea pig, or other species of relevance. On this basis, "C3" as used herein denotes nucleic acid or protein in any of the above-mentioned species, if expressed therein naturally or artificially, but preferably this wording denotes human nucleic acids or proteins.

Pharmaceutical compositions of the invention may be administered alone or in combination with one or more other therapeutic or diagnostic agents. A combination therapy may include a nucleic acid of the present invention combined with at least one other therapeutic agent selected based on the particular patient, disease or condition to be treated. Examples of other such agents include, inter alia, a therapeutically active small molecule or polypeptide, a single chain antibody, a classical antibody or fragment thereof, or a nucleic acid molecule which modulates gene expression of one or more additional genes, and similar modulating therapeutics which may complement or otherwise be beneficial in a therapeutic or prophylactic treatment regimen.

Pharmaceutical compositions are typically sterile and stable under the conditions of manufacture and storage. The composition may be formulated as a solution, microemulsion, liposome, or other ordered structure suitable to high drug concentration. The carrier may be a solvent or dispersion medium containing, for example, water, alcohol such as ethanol, polyol (e.g., glycerol, propylene glycol, and liquid polyethylene glycol), or any suitable mixtures. The proper fluidity may be maintained, for example, by the use of a coating such as lecithin, by the maintenance of the required particle size in the case of dispersion and by use of surfactants according to formulation chemistry well known in the art. In certain embodiments, isotonic agents, e.g., sugars, polyalcohols such as mannitol, sorbitol, or sodium chloride may be desirable in the composition. Prolonged absorption of injectable compositions may be brought about by including in the composition an agent that delays absorption for example, monostearate salts and gelatine.

One aspect of the invention is a nucleic acid or a composition disclosed herein for use as a medicament. The nucleic acid or composition is preferably for use in the prevention, decrease of the risk of suffering from, or treatment of a disease, disorder or syndrome.

The present invention provides a nucleic acid for use, alone or in combination with one or more additional therapeutic agents in a pharmaceutical composition, for treatment or prophylaxis of conditions, diseases and disorders responsive to inhibition of C3 expression.

One aspect of the invention is the use of a nucleic acid or a composition as disclosed herein in the prevention, decrease of the risk of suffering from, or treatment of a disease, disorder or syndrome.

Nucleic acids and pharmaceutical compositions of the invention may be used in the treatment of a variety of conditions, disorders or diseases. Treatment with a nucleic acid of the invention preferably leads to in vivo C3 depletion, preferably in the liver and/or in blood. As such, nucleic acids of the invention, and compositions comprising them, will be useful in methods for treating a variety of pathological disorders in which inhibiting the expression of C3 may be beneficial. The present invention provides methods for treating a disease, disorder or syndrome comprising the step of administering to a subject in need thereof a therapeutically effective amount of a nucleic acid of the invention.

The invention thus provides methods of treatment or prevention of a disease, disorder or syndrome, the method comprising the step of administering to a subject (e.g., a patient) in need thereof a therapeutically effective amount of a nucleic acid or pharmaceutical composition comprising a nucleic acid of the invention.

The most desirable therapeutically effective amount is an amount that will produce a desired efficacy of a particular treatment selected by one of skill in the art for a given subject in need thereof. This amount will vary depending upon a variety of factors understood by the skilled worker, including but not limited to the characteristics of the therapeutic compound (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through experimentation, namely by monitoring a subject's response to administration of a compound and adjusting the dosage accordingly. See, e.g., Remington: The Science and Practice of Pharmacy 21st Ed., Univ. of Sciences in Philadelphia (USIP), Lippincott Williams & Wilkins, Philadelphia, Pa., 2005.

In certain embodiments, nucleic acids and pharmaceutical compositions of the invention may be used to treat or prevent a disease, disorder or syndrome.

In certain embodiments, the present invention provides methods for treating a disease, disorder or syndrome in a mammalian subject, such as a human, the method comprising the step of administering to a subject in need thereof a therapeutically effective amount of a nucleic acid as disclosed herein.

Administration of a "therapeutically effective dosage" of a nucleic acid of the invention may result in a decrease in severity of disease symptoms, an increase in frequency and duration of disease symptom-free periods, or a prevention of impairment or disability due to the disease affliction.

Nucleic acids of the invention may be beneficial in treating or diagnosing a disease, disorder or syndrome that may be diagnosed or treated using the methods described herein. Treatment and diagnosis of other diseases, disorders or syndromes are also considered to fall within the scope of the present invention.

One aspect of the invention is a method of preventing, decreasing the risk of suffering from, or treating a disease, disorder or syndrome comprising administering a pharmaceutically effective dose or amount a nucleic acid or a composition disclosed herein to an individual in need of treatment, preferably wherein the nucleic acid or composition is administered to the subject subcutaneously, intravenously or by oral, rectal, pulmonary, intramuscular or intraperitoneal administration. Preferably, it is administered subcutaneously.

The disease, disorder or syndrome to be prevented, or treated with a nucleic acid or composition disclosed herein is preferably a complement-mediated disease, disorder or syndrome or a disease disorder or syndrome associated with the complement pathway.

The disease, disorder or syndrome to be prevented or treated with a nucleic acid or composition disclosed herein is preferably associated with aberrant activation and/or over-activation (hyper-activation) of the complement pathway and/or with over-expression or ectopic expression or localisation or accumulation of the complement component C3. One example of a disease that involves accumulation of C3 is C3 Glomerulopathy (C3G). In this disease, C3 accumulates in the kidney glomeruli. The aberrant or over activation of the complement pathway to be prevented or treated can have genetic causes or can be acquired. Preferably, the disease, disorder or syndrome to be prevented or treated is C3 Glomerulopathy (C3G).

The disease, disorder or syndrome to be prevented or treated with a nucleic acid or composition disclosed herein is preferably a) selected from the group comprising, and preferably consisting of C3 Glomerulopathy (C3G), Paroxysmal Nocturnal Hemoglobinuria (PNH), atypical Hemolytic Uremic Syndrome (aHUS), Lupus nephritis, IgA nephropathy (IgA N), Cold Agglutinin Disease (CAD), Myasthenia gravis (MG), Primary Membranous Nephropathy, Immune Complex-mediated Glomerulonephritis (IC-mediated GN), post-Infectious Glomerulonephritis (PIGN), Systemic Lupus Erythematosus (SLE), Ischemia/reperfusion injury, age-related macular degeneration (AMD), Rheumatoid arthritis (RA), antineutrophil Cytoplasmic Autoantibodies-associated Vasculitis (ANCA-AV), dysbiotic periodontal Disease, Malarial Anaemia, Neuromyelitis Optica, Post-HCT/Solid Organ Transplant (TMAs), Guillain-Barré Syndrome, Membranous Glomerulonephritis, Thrombotic Thrombocytopenic Purpura and sepsis; or b) selected from the group comprising, or preferably consisting of C3 Glomerulopathy (C3G), Paroxysmal Nocturnal Hemoglobinuria (PNH), atypical Hemolytic Uremic Syndrome (aHUS), Lupus nephritis, IgA nephropathy (IgA N) and Primary Membranous Nephropathy; or c) selected from the group comprising, or preferably consisting of C3 Glomerulopathy (C3G), antineutrophil Cytoplasmic Autoantibodies-associated Vasculitis (ANCA-AV), atypical Hemolytic Uremic Syndrome (aHUS), Cold Agglutinin Disease (CAD), Myasthenia gravis (MG), IgA nephropathy (IgA N), Paroxysmal Nocturnal Hemoglobinuria (PNH); d) selected from the group comprising, or preferably consisting of C3 Glomerulopathy (C3G), Cold Agglutinin Disease (CAD), Myasthenia gravis (MG), Neuromyelitis Optica, atypical Hemolytic Uremic Syndrome (aHUS), antineutrophil Cytoplasmic Autoantibodies-associated Vasculitis (ANCA-AV), IgA nephropathy (IgA N), Post-HCT/Solid Organ Transplant (TMAs), Guillain-Barré Syndrome, Paroxysmal Nocturnal Hemoglobinuria (PNH), Membranous Glomerulonephritis, Lupus nephritis and Thrombotic Thrombocytopenic Purpura; e) C3 Glomerulopathy (C3G), Cold Agglutinin Disease (CAD) and IgA nephropathy (IgA N) or f) it is C3 Glomerulopathy (C3G). The subjects to be treated with a nucleic acid or composition according to the invention are preferably subjects that suffer from one of these diseases, disorders or syndromes.

A nucleic acid or compositions disclosed herein may be for use in a regimen comprising treatments once or twice weekly, every week, every two weeks, every three weeks, every four weeks, every five weeks, every six weeks, every seven weeks, every eight weeks, every nine weeks, every ten weeks, every eleven weeks, every twelve weeks, every three months, every four months, every five months, every six months or in regimens with varying dosing frequency such as combinations of the before-mentioned intervals. The nucleic acid or composition may be for use subcutaneously, intravenously or using any other application routes such as oral, rectal, pulmonary, or intraperitoneal. Preferably, it is for use subcutaneously.

In cells and/or subjects treated with or receiving a nucleic acid or composition as disclosed herein, the C3 expression may be inhibited compared to untreated cells and/or subjects by a range from 15% up to 100% but at least about 30%, 35%, 40%, 45%, 50%, 55%, 60%, 65%, 70%, 75%, 80%, 85%, 90%, 95%, 98%, or 100% or intermediate values. The level of inhibition may allow treatment of a disease associated with C3 expression or overexpression or complement over-activation, or may serve to further investigate the functions and physiological roles of the C3 gene products. The level of inhibition is preferably measured in the liver or in the blood or in the kidneys, preferably in the blood, of the subject treated with the nucleic acid or composition.

One aspect is the use of a nucleic acid or composition as disclosed herein in the manufacture of a medicament for treating a disease, disorder or syndromes, such as those as listed above or additional pathologies associated with elevated levels of C3, preferably in the blood or in the kidneys, or over activation of the complement pathway, or additional therapeutic approaches where inhibition of C3 expression is desired. A medicament is a pharmaceutical composition.

Each of the nucleic acids of the invention and pharmaceutically acceptable salts and solvates thereof constitutes an individual embodiment of the invention.

Also included in the invention is a method of treating or preventing a disease, disorder or syndrome, such as those listed above, comprising administration of a composition comprising a nucleic acid or composition as described herein, to an individual in need of treatment (to improve such pathologies). The nucleic acid or composition may be administered in a regimen comprising treatments twice every week, once every week, every two weeks, every three weeks, every four weeks, every five weeks, every six weeks, every seven weeks, or every eight to twelve or more weeks or in regimens with varying dosing frequency such as combinations of the before-mentioned intervals. The nucleic acid or conjugated nucleic acid may be for use subcutaneously or intravenously or other application routes such as oral, rectal or intraperitoneal.

A nucleic acid of the invention may be administered by any appropriate administration pathway known in the art, including but not limited to aerosol, enteral, nasal, ophthalmic, oral, parenteral, rectal, vaginal, or transdermal (e.g., topical administration of a cream, gel or ointment, or by means of a transdermal patch). "Parenteral administration" is typically associated with injection at or in communication with the intended site of action, including infraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal administration.

The use of a chemical modification pattern of the nucleic acids confers nuclease stability in serum and makes for example subcutaneous application route feasible.

Solutions or suspensions used for intradermal or subcutaneous application typically include one or more of: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates; and/or tonicity adjusting agents such as, e.g., sodium chloride or dextrose. The pH can be adjusted with acids or bases, such as hydrochloric acid or sodium hydroxide, or buffers with citrate, phosphate, acetate and the like. Such preparations may be enclosed in ampoules, disposable syringes or multiple dose vials made of glass or plastic.

Sterile injectable solutions may be prepared by incorporating a nucleic acid in the required amount in an appropriate solvent with one or a combination of ingredients described above, as required, followed by sterilization microfiltration. Dispersions may be prepared by incorporating the active compound into a sterile vehicle that contains a dispersion medium and optionally other ingredients, such as those described above. In the case of sterile powders for the preparation of sterile injectable solutions, the methods of preparation are vacuum drying and freeze-drying (lyophilization) that yield a powder of the active ingredient in addition to any additional desired ingredient from a sterile-filtered solution thereof.

When a therapeutically effective amount of a nucleic acid of the invention is administered by, e.g., intravenous, cutaneous or subcutaneous injection, the nucleic acid will be in the form of a pyrogen-free, parenterally acceptable aqueous solution. Methods for preparing parenterally acceptable solutions, taking into consideration appropriate pH, isotonicity, stability, and the like, are within the skill in the art. A preferred pharmaceutical composition for intravenous, cutaneous, or subcutaneous injection will contain, in addition to a nucleic acid, an isotonic vehicle such as sodium chloride injection, Ringer's injection, dextrose injection, dextrose and sodium chloride injection, lactated Ringer's injection, or other vehicle as known in the art. A pharmaceutical composition of the present invention may also contain stabilizers, preservatives, buffers, antioxidants, or other additives well known to those of skill in the art.

The amount of nucleic acid which can be combined with a carrier material to produce a single dosage form will vary depending on a variety of factors, including the subject being treated, and the particular mode of administration. In general, it will be an amount of the composition that produces an appropriate therapeutic effect under the particular circumstances. Generally, out of one hundred percent, this amount will range from about 0.01% to about 99% of nucleic acid, from about 0.1% to about 70%, or from about 1% to about 30% of nucleic acid in combination with a pharmaceutically acceptable carrier.

The nucleic acid may be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., Sustained and Controlled Release Drug Delivery Systems, J. R. Robinson, ed., Marcel Dekker, Inc., New York, 1978.

Dosage regimens may be adjusted to provide the optimum desired response (e.g., a therapeutic response). For example, a dose may be administered, several divided doses may be administered over time, or the dose may be proportionally reduced or increased as indicated by the particular circumstances of the therapeutic situation, on a case by case basis. It is especially advantageous to formulate parenteral compositions in dosage unit forms for ease of administration and uniformity of dosage when administered to the subject or patient. As used herein, a dosage unit form refers to physically discrete units suitable as unitary dosages for the subjects to be treated; each unit containing a predetermined quantity of active compound calculated to produce a desired therapeutic effect. The specification for the dosage unit forms of the invention depend on the specific characteristics of the active compound and the particular therapeutic effect(s) to be achieved and the treatment and sensitivity of any individual patient.

The nucleic acid or composition of the present invention can be produced using routine methods in the art including chemical synthesis, such as solid phase chemical synthesis.

Nucleic acids or compositions of the invention may be administered with one or more of a variety of medical devices known in the art. For example, in one embodiment, a nucleic acid of the invention may be administered with a needleless hypodermic injection device. Examples of well-known implants and modules useful in the present invention are in the art, including e.g., implantable micro-infusion pumps for controlled rate delivery; devices for administering through the skin; infusion pumps for delivery at a precise infusion rate; variable flow implantable infusion devices for continuous drug delivery; and osmotic drug delivery systems. These and other such implants, delivery systems, and modules are known to those skilled in the art.

In certain embodiments, the nucleic acid or composition of the invention may be formulated to ensure a desired distribution in vivo. To target a therapeutic compound or composition of the invention to a particular in vivo location, they can be formulated, for example, in liposomes which may comprise one or more moieties that are selectively transported into specific cells or organs, thus enhancing targeted drug delivery.

The invention is characterized by high specificity at the molecular and tissue-directed delivery level. The sequences of the nucleic acids of the invention are highly specific for their target, meaning that they do not inhibit the expression of genes that they are not designed to target or only minimally inhibit the expression of genes that they are not designed to target and/or only inhibit the expression of a low number of genes that they are not designed to target. A further level of specificity is achieved when nucleic acids are linked to a ligand that is specifically recognised and internalised by a particular cell type. This is for example the case when a nucleic acid is linked to a ligand comprising GalNAc moieties, which are specifically recognised and internalised by hepatocytes. This leads to the nucleic acid inhibiting the expression of their target only in the cells that are targeted by the ligand to which they are linked. These two levels of specificity potentially confer a better safety profile than the currently available treatments. In certain embodiments, the present invention thus provides nucleic acids of the invention linked to a ligand comprising one or more GalNAc moieties, or comprising one or more other moieties that confer cell-type or tissue-specific internalisation of the nucleic acid thereby conferring additional specificity of target gene knockdown by RNA interference.

The nucleic acid as described herein may be formulated with a lipid in the form of a liposome. Such a formulation may be described in the art as a lipoplex. The composition with a lipid/liposome may be used to assist with delivery of the nucleic acid of the invention to the target cells. The lipid delivery system herein described may be used as an alternative to a conjugated ligand. The modifications herein described may be present when using the nucleic acid of the invention with a lipid delivery system or with a ligand conjugate delivery system.

Such a lipoplex may comprise a lipid composition comprising:
i) a cationic lipid, or a pharmaceutically acceptable salt thereof;
ii) a steroid;
iii) a phosphatidylethanolamine phospholipid; and/or
iv) a PEGylated lipid.

The cationic lipid may be an amino cationic lipid.

The cationic lipid may have the formula (XII):

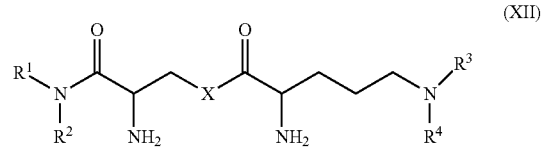

or a pharmaceutically acceptable salt thereof, wherein:
X represents O, S or NH;
$R^1$ and $R^2$ each independently represents a $C_4$-$C_{22}$ linear or branched alkyl chain or a $C_4$-$C_{22}$ linear or branched alkenyl chain with one or more double bonds, wherein the alkyl or alkenyl chain optionally contains an intervening ester, amide or disulfide;
when X represents S or NH, $R^3$ and $R^4$ each independently represent hydrogen, methyl, ethyl, a mono- or polyamine moiety, or $R^3$ and $R^4$ together form a heterocyclyl ring;
when X represents O, R3 and R4 each independently represent hydrogen, methyl, ethyl, a mono- or polyamine moiety, or $R^3$ and $R^4$ together form a heterocyclyl ring, or $R^3$ represents hydrogen and $R^4$ represents $C(NH)(NH_2)$.

The cationic lipid may have the formula (XIII):

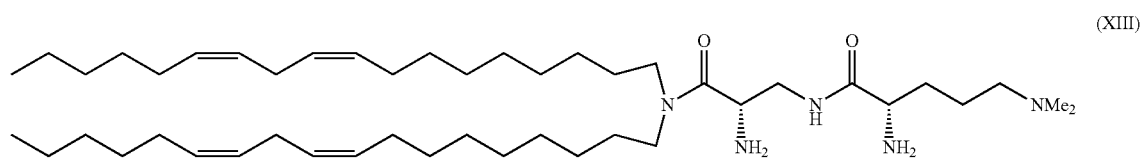 [SMILES: CCCCC/C=C\C/C=C\CCCCCCCCN(CCCCCCCC/C=C\C/C=C\CCCCC)C(=O)[C@@H](N)CNC(=O)[C@@H](N)CCCN(C)C]

or a pharmaceutically acceptable salt thereof.

The cationic lipid may have the formula (XIV):

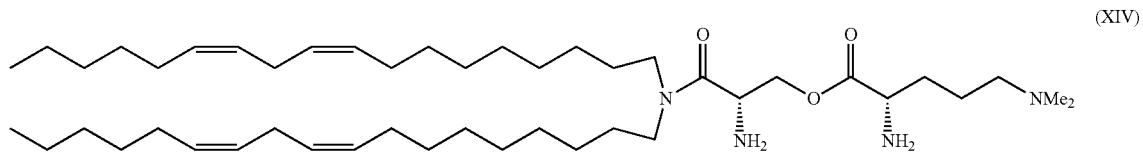 [SMILES: CCCCC/C=C\C/C=C\CCCCCCCCN(CCCCCCCC/C=C\C/C=C\CCCCC)C(=O)[C@@H](N)COC(=O)[C@@H](N)CCCN(C)C]

(XIV)

or a pharmaceutically acceptable salt thereof.

The content of the cationic lipid component may be from about 55 mol % to about 65 mol % of the overall lipid content of the composition. In particular, the cationic lipid component is about 59 mol % of the overall lipid content of the composition.

The compositions can further comprise a steroid. The steroid may be cholesterol. The content of the steroid may be from about 26 mol % to about 35 mol % of the overall lipid content of the lipid composition. More particularly, the content of steroid may be about 30 mol % of the overall lipid content of the lipid composition.

The phosphatidylethanolamine phospholipid may be selected from the group consisting of 1,2-diphytanoyl-sn-glycero-3-phosphoethanolamine (DPhyPE), 1,2-dioleoyl-sn-glycero-3-phosphoethanolamine (DOPE), 1,2-distearoyl-sn-glycero-3-phosphoethanolamine (DSPE), 1,2-Dilauroyl-sn-glycero-3-phosphoethanolamine (DLPE), 1,2-Dimyristoyl-sn-glycero-3-phosphoethanolamine (DMPE), 1,2-Dipalmitoyl-sn-glycero-3-phosphoethanolamine (DPPE), 1,2-Dilinoleoyl-sn-glycero-3-phosphoethanolamine (DLoPE), 1-Palmitoyl-2-oleoyl-sn-glycero-3-phosphoethanolamine (POPE), 1,2-Dierucoyl-sn-glycero-3-phosphoethanolamine (DEPE), 1,2-Disqualeoyl-sn-glycero-3-phosphoethanolamine (DSQPE) and 1-Stearoyl-2-linoleoyl-sn-glycero-3-phosphoethanolamine (SLPE). The content of the phospholipid may be about 10 mol % of the overall lipid content of the composition.

The PEGylated lipid may be selected from the group consisting of 1,2-dimyristoyl-sn-glycerol, methoxypolyethylene glycol (DMG-PEG) and C16-Ceramide-PEG. The content of the PEGylated lipid may be about 1 to 5 mol % of the overall lipid content of the composition.

The content of the cationic lipid component in the composition may be from about 55 mol % to about 65 mol % of the overall lipid content of the lipid composition, preferably about 59 mol % of the overall lipid content of the lipid composition.

The composition may have a molar ratio of the components of i):ii):iii):iv) selected from 55:34:10:1; 56:33:10:1; 57:32:10:1; 58:31:10:1; 59:30:10:1; 60:29:10:1; 61:28:10:1; 62:27:10:1; 63:26:10:1; 64:25:10:1; and 65:24:10:1.

The composition may comprise a cationic lipid having the structure

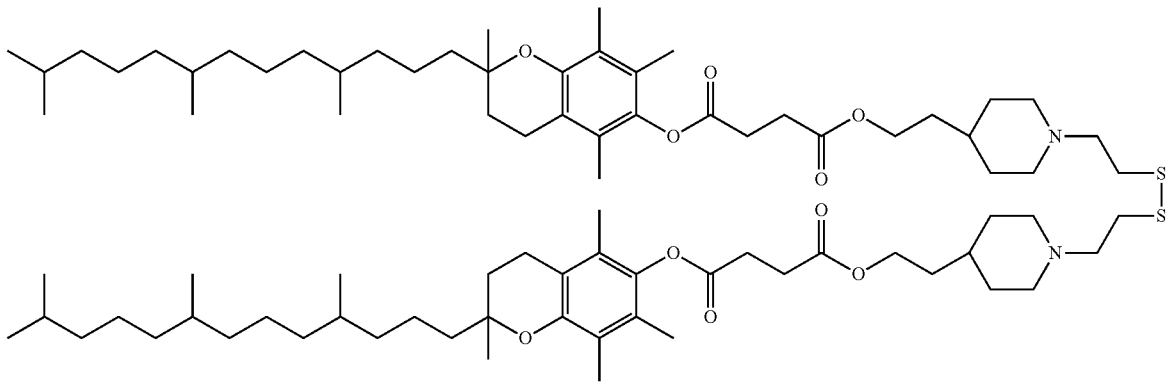 [SMILES: Cc1c(C)c2c(c(C)c1OC(=O)CCC(=O)OCCC1CCN(CCSSCCN3CCC(CCOC(=O)CCC(=O)Oc4c(C)c(C)c5c(c4C)CCC(C)(CCCC(C)CCCC(C)CCCC(C)C)O5)CC3)CC1)CCC(C)(CCCC(C)CCCC(C)CCCC(C)C)O2]

a steroid having the structure

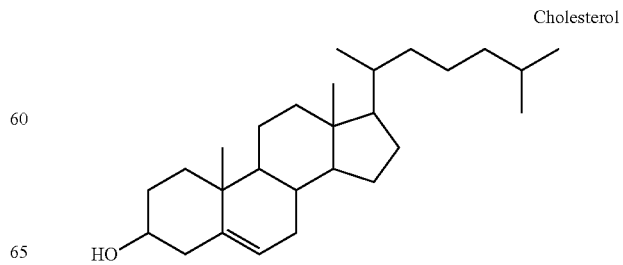

Cholesterol a phosphatidylethanolamine phospholipid having the structure

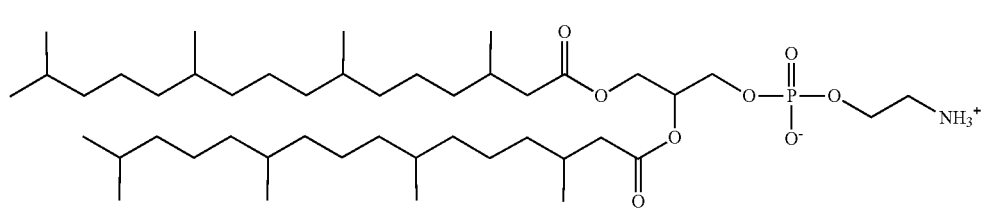

DPhyPE and a PEGylated lipid having the structure

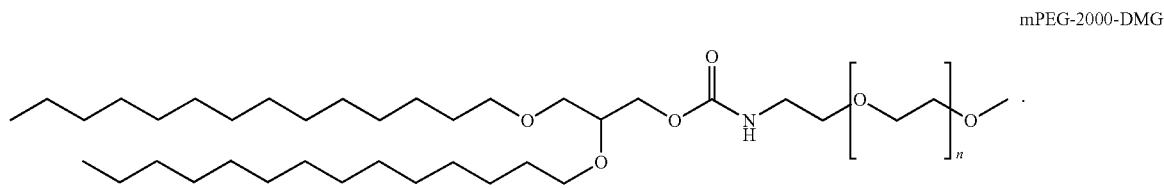

mPEG-2000-DMG

Neutral liposome compositions may be formed from, for example, dimyristoyl phosphatidylcholine (DMPC) or dipalmitoyl phosphatidylcholine (DPPC). Anionic liposome compositions may be formed from dimyristoyl phosphatidylglycerol, while anionic fusogenic liposomes may be formed primarily from dioleoyl phosphatidylethanolamine (DOPE). Another type of liposomal composition may be formed from phosphatidylcholine (PC) such as, for example, soybean PC, and egg PC. Another type is formed from mixtures of phospholipid and/or phosphatidylcholine and/or cholesterol.

A positively charged synthetic cationic lipid, N-[1-(2,3-dioleyloxy)propyl]-N,N,N-trimethylammonium chloride (DOTMA) can be used to form small liposomes that interact spontaneously with nucleic acid to form lipid-nucleic acid complexes which are capable of fusing with the negatively charged lipids of the cell membranes of tissue culture cells. DOTMA analogues can also be used to form liposomes.

Derivatives and analogues of lipids described herein may also be used to form liposomes.

A liposome containing a nucleic acid can be prepared by a variety of methods. In one example, the lipid component of a liposome is dissolved in a detergent so that micelles are formed with the lipid component. For example, the lipid component can be an amphipathic cationic lipid or lipid conjugate. The detergent can have a high critical micelle concentration and may be nonionic. Exemplary detergents include cholate, CHAPS, octylglucoside, deoxycholate, and lauroyl sarcosine. The nucleic acid preparation is then added to the micelles that include the lipid component. The cationic groups on the lipid interact with the nucleic acid and condense around the nucleic acid to form a liposome. After condensation, the detergent is removed, e.g., by dialysis, to yield a liposomal preparation of nucleic acid.

If necessary, a carrier compound that assists in condensation can be added during the condensation reaction, e.g., by controlled addition. For example, the carrier compound can be a polymer other than a nucleic acid (e.g., spermine or spermidine). pH can also be adjusted to favour condensation.

Nucleic acid formulations of the present invention may include a surfactant. In one embodiment, the nucleic acid is formulated as an emulsion that includes a surfactant.

A surfactant that is not ionized is a non-ionic surfactant. Examples include non-ionic esters, such as ethylene glycol esters, propylene glycol esters, glyceryl esters etc., nonionic alkanolamides, and ethers such as fatty alcohol ethoxylates, propoxylated alcohols, and ethoxylated/propoxylated block polymers.

A surfactant that carries a negative charge when dissolved or dispersed in water is an anionic surfactant. Examples include carboxylates, such as soaps, acyl lactylates, acyl amides of amino acids, esters of sulfuric acid such as alkyl sulfates and ethoxylated alkyl sulfates, sulfonates such as alkyl benzene sulfonates, acyl isethionates, acyl taurates and sulfosuccinates, and phosphates.

A surfactant that carries a positive charge when dissolved or dispersed in water is a cationic surfactant. Examples include quaternary ammonium salts and ethoxylated amines.

A surfactant that has the ability to carry either a positive or negative charge is an amphoteric surfactant. Examples include acrylic acid derivatives, substituted alkylamides, N-alkylbetaines and phosphatides.

"Micelles" are defined herein as a particular type of molecular assembly in which amphipathic molecules are arranged in a spherical structure such that all the hydrophobic portions of the molecules are directed inward, leaving the hydrophilic portions in contact with the surrounding aqueous phase. The converse arrangement exists if the environment is hydrophobic. A micelle may be formed by mixing an aqueous solution of the nucleic acid, an alkali metal alkyl sulphate, and at least one micelle forming compound.

Exemplary micelle forming compounds include lecithin, hyaluronic acid, pharmaceutically acceptable salts of hyaluronic acid, glycolic acid, lactic acid, chamomile extract, cucumber extract, oleic acid, linoleic acid, linolenic acid, monoolein, monooleates, monolaurates, borage oil, evening of primrose oil, menthol, trihydroxy oxo cholanyl glycine and pharmaceutically acceptable salts thereof, glycerol, polyglycerol, lysine, polylysine, triolein, polyoxyethylene ethers and analogues thereof, polidocanol alkyl ethers and analogues thereof, chenodeoxycholate, deoxycholate, and mixtures thereof.

Phenol and/or m-cresol may be added to the mixed micellar composition to act as a stabiliser and preservative. An isotonic agent such as glycerine may as be added.

A nucleic acid preparation may be incorporated into a particle such as a microparticle. Microparticles can be produced by spray-drying, lyophilisation, evaporation, fluid bed drying, vacuum drying, or a combination of these methods.

Definitions

As used herein, the terms "inhibit", "down-regulate", or "reduce" with respect to gene expression mean that the expression of the gene, or the level of RNA molecules or equivalent RNA molecules encoding one or more proteins or protein subunits (e.g., mRNA), or the activity of one or more proteins or protein subunits, is reduced below that observed either in the absence of the nucleic acid or conjugated nucleic acid of the invention or as compared to that obtained with an siRNA molecule with no known homology to the human transcript (herein termed non-silencing control). Such control may be conjugated and modified in an analogous manner to the molecule of the invention and delivered into the target cell by the same route. The expression after treatment with the nucleic acid of the invention may be reduced to 95%, 90%, 80%, 70%, 60%, 50%, 40%, 30%, 20%, 15%, 10%, 5% or 0% or to intermediate values, or less than that observed in the absence of the nucleic acid or conjugated nucleic acid. The expression may be measured in the cells to which the nucleic acid is applied. Alternatively, especially if the nucleic acid is administered to a subject, the level can be measured in a different group of cells or in a tissue or an organ or in a body fluid such as blood or plasma. The level of inhibition is preferably measured in conditions that have been selected because they show the greatest effect of the nucleic acid on the target mRNA level in cells treated with the nucleic acid in vitro. The level of inhibition may for example be measured after 24 hours or 48 hours of treatment with a nucleic acid at a concentration of between 0.038 nM-10 μM, preferably 1 nM, 10 nM or 100 nM. These conditions may be different for different nucleic acid sequences or for different types of nucleic acids, such as for nucleic acids that are unmodified or modified or conjugated to a ligand or not. Examples of suitable conditions for determining levels of inhibition are described in the examples.

By nucleic acid it is meant a nucleic acid comprising two strands comprising nucleotides, that is able to interfere with gene expression. Inhibition may be complete or partial and results in down regulation of gene expression in a targeted manner. The nucleic acid comprises two separate polynucleotide strands; the first strand, which may also be a guide strand; and a second strand, which may also be a passenger strand. The first strand and the second strand may be part of the same polynucleotide molecule that is self-complementary which 'folds' back to form a double-stranded molecule. The nucleic acid may be an siRNA molecule.

The nucleic acid may comprise ribonucleotides, modified ribonucleotides, deoxynucleotides, deoxyribonucleotides, or nucleotide analogues non-nucleotides that are able to mimic nucleotides such that they may 'pair' with the corresponding base on the target sequence or complementary strand. The nucleic acid may further comprise a double-stranded nucleic acid portion or duplex region formed by all or a portion of the first strand (also known in the art as a guide strand) and all or a portion of the second strand (also known in the art as a passenger strand). The duplex region is defined as beginning with the first base pair formed between the first strand and the second strand and ending with the last base pair formed between the first strand and the second strand, inclusive.

By duplex region it is meant the region in two complementary or substantially complementary oligonucleotides that form base pairs with one another, either by Watson-Crick base pairing or any other manner that allows for a duplex between oligonucleotide strands that are complementary or substantially complementary. For example, an oligonucleotide strand having 21 nucleotide units can base pair with another oligonucleotide of 21 nucleotide units, yet only 19 nucleotides on each strand are complementary or substantially complementary, such that the "duplex region" consists of 19 base pairs. The remaining base pairs may exist as 5' and 3' overhangs, or as single-stranded regions. Further, within the duplex region, 100% complementarity is not required; substantial complementarity is allowable within a duplex region. Substantial complementarity refers to complementarity between the strands such that they are capable of annealing under biological conditions. Techniques to empirically determine if two strands are capable of annealing under biological conditions are well known in the art. Alternatively, two strands can be synthesised and added together under biological conditions to determine if they anneal to one another. The portion of the first strand and second strand that forms at least one duplex region may be fully complementary and is at least partially complementary to each other. Depending on the length of a nucleic acid, a perfect match in terms of base complementarity between the first strand and the second strand is not necessarily required. However, the first and second strands must be able to hybridise under physiological conditions.

As used herein, the terms "non-pairing nucleotide analogue" means a nucleotide analogue which includes a non-base pairing moiety including but not limited to: 6 des amino adenosine (Nebularine), 4-Me-indole, 3-nitropyrrole, 5-nitroindole, Ds, Pa, N3-Me ribo U, N3-Me riboT, N3-Me dC, N3-Me-dT, N1-Me-dG, N1-Me-dA, N3-ethyl-dC, and N3-Me dC. In some embodiments the non-base pairing nucleotide analogue is a ribonucleotide. In other embodiments it is a deoxyribonucleotide.

As used herein, the term, "terminal functional group" includes without limitation a halogen, alcohol, amine, carboxylic, ester, amide, aldehyde, ketone, and ether groups.

An "overhang" as used herein has its normal and customary meaning in the art, i.e. a single-stranded portion of a nucleic acid that extends beyond the terminal nucleotide of a complementary strand in a double-strand nucleic acid. The term "blunt end" includes double-stranded nucleic acid whereby both strands terminate at the same position, regardless of whether the terminal nucleotide(s) are base-paired. The terminal nucleotide of a first strand and a second strand at a blunt end may be base paired. The terminal nucleotide of a first strand and a second strand at a blunt end may not be paired. The terminal two nucleotides of a first strand and a second strand at a blunt end may be base-paired. The terminal two nucleotides of a first strand and a second strand at a blunt end may not be paired.

The term "serinol-derived linker moiety" means the linker moiety comprises the following structure:

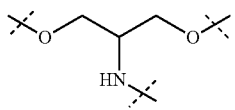

An O atom of said structure typically links to an RNA strand and the N atom typically links to the targeting ligand.

The terms "patient," "subject," and "individual" may be used interchangeably and refer to either a human or a non-human animal. These terms include mammals such as humans, primates, livestock animals (e.g., bovines, porcines), companion animals (e.g., canines, felines) and rodents (e.g., mice and rats).

As used herein, "treating" or "treatment" and grammatical variants thereof refer to an approach for obtaining beneficial or desired clinical results. The term may refer to slowing the onset or rate of development of a condition, disorder or disease, reducing or alleviating symptoms associated with it, generating a complete or partial regression of the condition, or some combination of any of the above. For the purposes of this invention, beneficial or desired clinical results include, but are not limited to, reduction or alleviation of symptoms, diminishment of extent of disease, stabilization (i.e., not worsening) of state of disease, delay or slowing of disease progression, amelioration or palliation of the disease state, and remission (whether partial or total), whether detectable or undetectable. "Treatment" can also mean prolonging survival relative to expected survival time if not receiving treatment. A subject (e.g., a human) in need of treatment may thus be a subject already afflicted with the disease or disorder in question. The term "treatment" includes inhibition or reduction of an increase in severity of a pathological state or symptoms relative to the absence of treatment, and is not necessarily meant to imply complete cessation of the relevant disease, disorder or condition.

As used herein, the terms "preventing" and grammatical variants thereof refer to an approach for preventing the development of, or altering the pathology of, a condition, disease or disorder. Accordingly, "prevention" may refer to prophylactic or preventive measures. For the purposes of this invention, beneficial or desired clinical results include, but are not limited to, prevention or slowing of symptoms, progression or development of a disease, whether detectable or undetectable. A subject (e.g., a human) in need of prevention may thus be a subject not yet afflicted with the disease or disorder in question. The term "prevention" includes slowing the onset of disease relative to the absence of treatment, and is not necessarily meant to imply permanent prevention of the relevant disease, disorder or condition. Thus "preventing" or "prevention" of a condition may in certain contexts refer to reducing the risk of developing the condition, or preventing or delaying the development of symptoms associated with the condition.

As used herein, an "effective amount," "therapeutically effective amount" or "effective dose" is an amount of a composition (e.g., a therapeutic composition or agent) that produces at least one desired therapeutic effect in a subject, such as preventing or treating a target condition or beneficially alleviating a symptom associated with the condition.

As used herein, the term "pharmaceutically acceptable salt" refers to a salt that is not harmful to a patient or subject to which the salt in question is administered. It may be a salt chosen, e.g., among acid addition salts and basic salts. Examples of acid addition salts include chloride salts, citrate salts and acetate salts. Examples of basic salts include salts wherein the cation is selected from alkali metal cations, such as sodium or potassium ions, alkaline earth metal cations, such as calcium or magnesium ions, as well as substituted ammonium ions, such as ions of the type $N(R^1)(R^2)(R^3)(R^4)+$, wherein $R^1$, $R^2$, $R^3$ and $R^4$ independently will typically designate hydrogen, optionally substituted C1-6-alkyl groups or optionally substituted C2-6-alkenyl groups. Examples of relevant C1-6-alkyl groups include methyl, ethyl, 1-propyl and 2-propyl groups. Examples of C2-6-alkenyl groups of possible relevance include ethenyl, 1-propenyl and 2-propenyl. Other examples of pharmaceutically acceptable salts are described in "Remington's Pharmaceutical Sciences", 17th edition, Alfonso R. Gennaro (Ed.), Mark Publishing Company, Easton, Pa., USA, 1985 (and more recent editions thereof), in the "Encyclopaedia of Pharmaceutical Technology", 3rd edition, James Swarbrick (Ed.), Informa Healthcare USA (Inc.), NY, USA, 2007, and in J. Pharm. Sci. 66: 2 (1977). A "pharmaceutically acceptable salt" retains qualitatively a desired biological activity of the parent compound without imparting any undesired effects relative to the compound. Examples of pharmaceutically acceptable salts include acid addition salts and base addition salts. Acid addition salts include salts derived from nontoxic inorganic acids, such as hydrochloric, nitric, phosphorous, phosphoric, sulfuric, hydrobromic, hydroiodic and the like, or from nontoxic organic acids such as aliphatic mono- and di-carboxylic acids, phenyl-substituted alkanoic acids, hydroxy alkanoic acids, aromatic acids, aliphatic and aromatic sulfonic acids and the like. Base addition salts include salts derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

The term "pharmaceutically acceptable carrier" includes any of the standard pharmaceutical carriers. Pharmaceutically acceptable carriers for therapeutic use are well known in the pharmaceutical art, and are described, for example, in Remington's Pharmaceutical Sciences, Mack Publishing Co. (A. R. Gennaro edit. 1985). For example, sterile saline and phosphate-buffered saline at slightly acidic or physiological pH may be used. Exemplary pH buffering agents include phosphate, citrate, acetate, tris/hydroxymethyl)aminomethane (TRIS), N-Tris(hydroxymethyl)methyl-3-aminopropanesulphonic acid (TAPS), ammonium bicarbonate, diethanolamine, histidine, which is a preferred buffer, arginine, lysine, or acetate or mixtures thereof. The term further encompasses any agents listed in the US Pharmacopeia for use in animals, including humans. A "pharmaceutically acceptable carrier" includes any and all physiologically acceptable, i.e., compatible, solvents, dispersion media, coatings, antimicrobial agents, isotonic and absorption delaying agents, and the like. In certain embodiments, the carrier is suitable for intravenous, intramuscular, subcutaneous, parenteral, spinal or epidermal administration (e.g., by injection or infusion). Depending on selected route of administration, the nucleic acid may be coated in a material or materials intended to protect the compound from the action of acids and other natural inactivating conditions to which the nucleic acid may be exposed when administered to a subject by a particular route of administration.

The term "solvate" in the context of the present invention refers to a complex of defined stoichiometry formed between a solute (in casu, a nucleic acid compound or pharmaceutically acceptable salt thereof according to the invention) and a solvent. The solvent in this connection may, for example, be water or another pharmaceutically acceptable, typically small-molecular organic species, such as, but not limited to, acetic acid or lactic acid. When the solvent in question is water, such a solvate is normally referred to as a hydrate.

The invention will now be described with reference to the following non-limiting Figures and Examples.

BRIEF DESCRIPTION OF THE FIGURES

The nucleic acid sequences of the siRNAs referenced in the figures are found in Table 5.

FIGS. 2A and 2B show concentration-response-curves of selected siRNA GalNAc conjugates in human primary hepatocytes.

FIGS. 3A and 3B show concentration-response-curves of selected siRNA GalNAc conjugates in mouse primary hepatocytes.

FIGS. 4A, 4B and 4C show concentration-dependent C3 mRNA inhibition of selected siRNA GalNAc conjugates respectively in primary mouse, human and cynomolgus hepatocytes.

FIG. 9F shows normalized C3 serum levels after dosing of 0.3, 1, 3, and 5 mg/kg EV0203 at days 7, 14, 21 and 28 post administration.

EXAMPLES

Example 1

Figure 1A:
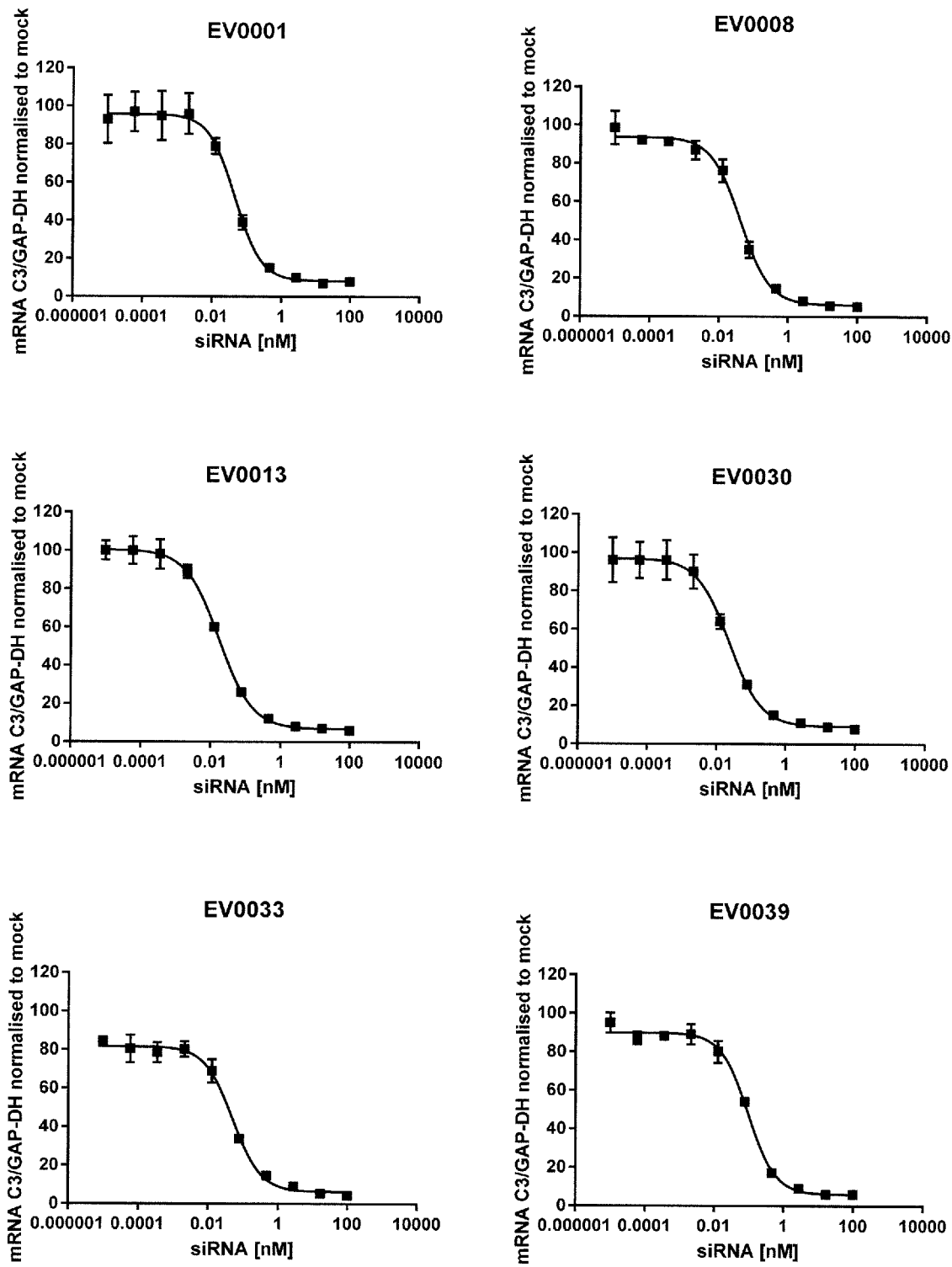
FIGS. 1A, 1B and 1C show concentration-response-curves of selected siRNAs.

In Vitro Study in HepG2 Cells Showing C3 mRNA Knockdown Efficacy of Tested siRNAs After Transfection of 10 nM siRNA.

C3 knockdown efficacy of siRNAs EV0001-EV0100 was determined after transfection of 10 nM siRNA in HepG2 cells. The results are shown in Table 2 below. Remaining C3 mRNA levels after knockdown were in the range of 6 to 83%. The most potent siRNAs were EV0001, EV0007, EV0008, EV0009, EV0012, EV0013, EV0018, EV0020, EV0030, EV0033, and EV0004.

For transfection of HepG2 cells with siRNAs, cells were seeded at a density of 15,000 cells/well into collagen-coated 96-well tissue culture plates (#655150, GBO, Germany). Transfection of siRNAs was carried out with Lipofectamine RNAiMax (Invitrogen/Life Technologies, Karlsruhe, Germany) according to the manufacturer's instructions directly after seeding. The screen was performed with C3 siRNAs in quadruplicates at 10 nM, with siRNAs targeting Aha1, Firefly-Luciferase and Factor VII as unspecific controls and a mock transfection. After 24 h of incubation with siRNAs, medium was removed, and cells were lysed in 150 μl Medium-Lysis Mixture (1 volume lysis mixture, 2 volumes cell culture medium) and then incubated at 53° C. for 30 minutes. bDNA assay was performed according to the manufacturer's instructions.

Luminescence was read using 1420 Luminescence Counter (WALLAC VICTOR Light, Perkin Elmer, Rodgau-Jügesheim, Germany) following 30 minutes of incubation at RT in the dark. For each well, the C3 mRNA level was normalized to the respective GAPDH mRNA level. The activity of a given C3 siRNA was expressed as percent remaining C3 mRNA concentration (normalized to GAPDH mRNA) in treated cells, relative to the C3 mRNA concentration (normalized to GAPDH mRNA) averaged across control wells.

TABLE 2

| Duplex ID | % remaining mRNA Mean | SD | Duplex ID | % remaining mRNA Mean | SD |
|---|---|---|---|---|---|
| EV0001 | 8.87 | 0.61 | EV0051 | 11.84 | 0.60 |
| EV0002 | 10.61 | 0.72 | EV0052 | 18.23 | 1.26 |
| EV0003 | 10.68 | 0.82 | EV0053 | 15.40 | 0.60 |
| EV0004 | 9.59 | 0.43 | EV0054 | 12.80 | 0.69 |
| EV0005 | 22.27 | 0.97 | EV0055 | 44.97 | 4.50 |
| EV0006 | 13.10 | 1.16 | EV0056 | 83.23 | 5.03 |
| EV0007 | 8.89 | 0.90 | EV0057 | 55.45 | 3.76 |
| EV0008 | 6.02 | 0.47 | EV0058 | 22.12 | 0.84 |
| EV0009 | 6.80 | 0.45 | EV0059 | 12.74 | 0.48 |
| EV0010 | 20.18 | 1.32 | EV0060 | 14.38 | 0.79 |
| EV0011 | 10.09 | 0.34 | EV0061 | 12.92 | 0.83 |
| EV0012 | 9.48 | 1.06 | EV0062 | 13.26 | 0.83 |
| EV0013 | 7.40 | 1.08 | EV0063 | 21.32 | 1.61 |
| EV0014 | 9.75 | 1.25 | EV0064 | 15.14 | 0.86 |
| EV0015 | 13.08 | 1.52 | EV0065 | 12.01 | 0.42 |
| EV0016 | 16.68 | 0.66 | EV0066 | 13.14 | 1.32 |
| EV0017 | 47.72 | 1.80 | EV0067 | 13.57 | 0.61 |
| EV0018 | 7.86 | 0.77 | EV0068 | 24.89 | 0.87 |
| EV0019 | 18.83 | 1.08 | EV0069 | 15.36 | 2.68 |
| EV0020 | 8.80 | 0.87 | EV0070 | 16.50 | 1.29 |
| EV0021 | 13.88 | 0.98 | EV0071 | 9.69 | 0.71 |
| EV0022 | 79.91 | 4.20 | EV0072 | 25.55 | 1.40 |
| EV0023 | 13.32 | 1.29 | EV0073 | 12.79 | 1.34 |
| EV0024 | 11.11 | 0.76 | EV0074 | 14.63 | 0.51 |
| EV0025 | 16.35 | 0.50 | EV0075 | 13.05 | 0.83 |
| EV0026 | 10.03 | 0.88 | EV0076 | 16.29 | 0.87 |
| EV0027 | 10.11 | 1.03 | EV0077 | 18.63 | 0.98 |
| EV0028 | 11.83 | 0.53 | EV0078 | 21.78 | 1.18 |
| EV0029 | 9.71 | 1.02 | EV0079 | 20.78 | 1.04 |
| EV0030 | 9.05 | 0.49 | EV0080 | 17.59 | 1.31 |
| EV0031 | 10.70 | 0.64 | EV0081 | 15.27 | 0.70 |
| EV0032 | 12.93 | 0.55 | EV0082 | 20.75 | 1.03 |
| EV0033 | 9.29 | 0.59 | EV0083 | 11.84 | 0.60 |
| EV0034 | 15.20 | 0.50 | EV0084 | 18.23 | 1.26 |
| EV0035 | 16.87 | 0.62 | EV0085 | 15.40 | 0.60 |
| EV0036 | 14.37 | 1.05 | EV0086 | 12.80 | 0.69 |
| EV0037 | 15.36 | 2.68 | EV0087 | 44.97 | 4.50 |
| EV0038 | 16.50 | 1.29 | EV0088 | 83.23 | 5.03 |
| EV0039 | 9.69 | 0.71 | EV0089 | 55.45 | 3.76 |
| EV0040 | 25.55 | 1.40 | EV0090 | 22.12 | 0.84 |
| EV0041 | 12.79 | 1.34 | EV0091 | 12.74 | 0.48 |
| EV0042 | 14.63 | 0.51 | EV0092 | 14.38 | 0.79 |
| EV0043 | 13.05 | 0.83 | EV0093 | 12.92 | 0.83 |
| EV0044 | 16.29 | 0.87 | EV0094 | 13.26 | 0.83 |
| EV0045 | 18.63 | 0.98 | EV0095 | 21.32 | 1.61 |
| EV0046 | 21.78 | 1.18 | EV0096 | 15.14 | 0.86 |
| EV0047 | 20.78 | 1.04 | EV0097 | 12.01 | 0.42 |
| EV0048 | 17.59 | 1.31 | EV0098 | 13.14 | 1.32 |
| EV0049 | 15.27 | 0.70 | EV0099 | 13.57 | 0.61 |
| EV0050 | 20.75 | 1.03 | EV0100 | 24.89 | 0.87 |

Table 2: Results of screening of C3 siRNAs—the identity of the single strands forming each of the siRNA duplexes as well as their sequences and modifications are to be found in the tables at the end of the description.

Example 2

In Vitro Study in HepG2 Cells Showing C3 mRNA Knockdown Efficacy of Tested siRNAs after Transfection of 0.01 µM-100 nM siRNA (Concentration-Response-Curve Experiment).

Figure 1B:
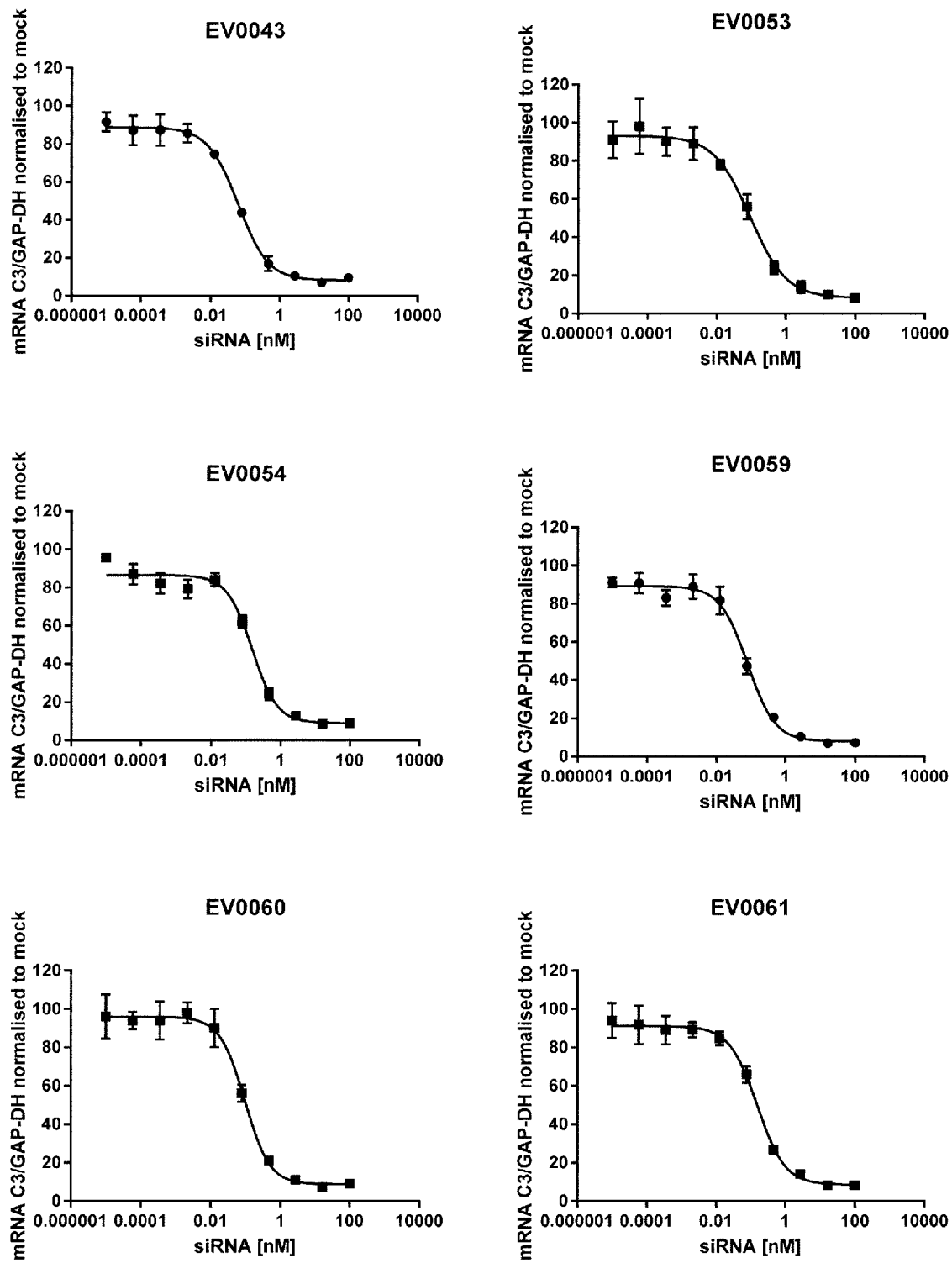
Figure 1C:
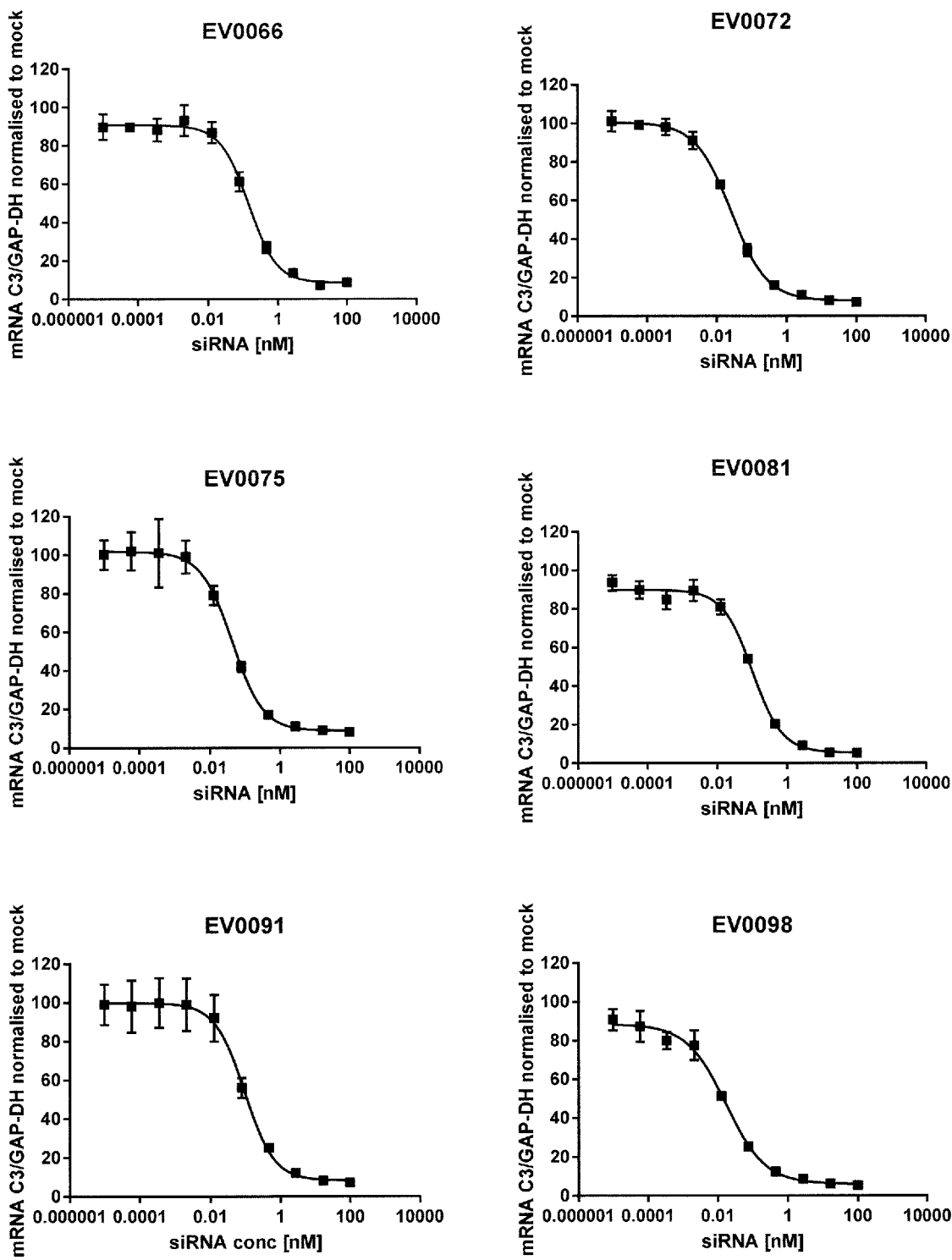

C3 knockdown efficacy of siRNAs EV0001, EV0008, EV0013, EV0030, EV0033, EV0039, EV0043, EV0053, EV0054, EV0059, EV0060, EV0061, EV0066, EV0072, EV0075, EV0081, EV0091 and EV0098 was determined after transfection of 0.01 µM-100 nM siRNA in HepG2 cells. The identity of the single strands forming each of the siRNA duplexes as well as their sequences are to be found in the tables at the end of the description. Results are presented in FIGS. 1A, 1B and 1C. All siRNAs showed a dose-dependent knockdown of C3 mRNA after transfection. The most potent siRNAs were EV0008, EV0033 and EV0081, with a residual C3 expression of 4.3, 5.3 and 5.3% at 100 nM siRNA, respectively.

For transfection of HepG2 cells with siRNAs, cells were seeded at a density of 15,000 cells/well into collagen-coated 96-well tissue culture plates (#655150, GBO, Germany). Transfection of siRNA was carried out with Lipofectamine RNAiMax (Invitrogen/Life Technologies, Karlsruhe, Germany) according to the manufacturer's instructions directly after seeding. Concentration-response experiments were done with C3 siRNA in 10 concentrations transfected in quadruplicates, starting at 100 nM in 6-fold dilution steps down to 0.01 µM. Mock transfected cells served as control in CRC experiments. After 24 h of incubation with siRNAs, medium was removed and cells were lysed in 150 µl Medium-Lysis Mixture (1 volume lysis mixture, 2 volumes cell culture medium) and then incubated at 53° C. for 30 minutes. bDNA assay was performed according to the manufacturer's instructions. Luminescence was read using 1420 Luminescence Counter (WALLAC VICTOR Light, Perkin Elmer, Rodgau-Jügesheim, Germany) following 30 minutes of incubation at RT in the dark. For each well, the C3 mRNA level was normalized to the respective GAPDH mRNA level. The activity of a given C3 siRNA was expressed as percent remaining C3 mRNA (normalized to GAPDH mRNA) in treated cells, relative to the C3 mRNA concentration (normalized to GAPDH mRNA) averaged across control wells. Concentration-response-curves were fitted with GraphPad Prism version 7.05 using a four-parameter logistic (4PL) model without further constraints.

Example 3

In Vitro Study in Primary Human Hepatocytes Showing C3 mRNA Knockdown Efficacy of Tested siRNA-GalNAc Conjugates in Concentration-Response-Curve Format (0.038 nM-10 µM siRNA Conjugate).

Expression of C3 mRNA after incubation with the GalNAc siRNA conjugates EV0101, EV0102, EV0103, EV0104, EV0105, EV0106, EV0107, EV0108, EV0109, EV0110, EV0111 and EV0312 was analysed in a concentration-response format. The identity of the single strands forming each of the siRNA duplexes as well as their sequences are to be found in the tables at the end of the description. Results are shown in FIGS. 2A and 2B. The mRNA level of the house keeping gene GAPDH served as control for all experiments. All siRNA GalNAc conjugates were able to decrease C3 mRNA level in a concentration-dependent fashion with maximal inhibition at 10 µM between 32 and 70%, respectively. The most potent siRNAs were EV0102 with 61%, EV0109 with 67%, EV0111 with 69% and EV0312 with 70% reduction of the C3 mRNA level at 10 µM.

Human cryopreserved primary hepatocytes were purchased from Primacyt (Schwerin, Germany, cat #GuCPI, Lot #BHum16061-P). Directly before treatment, cells were thawed, transferred to a tube with thawing medium (Primacyt, cat #HTM), centrifuged and washed with washing Medium (Primacyt, cat #HWM). Cells were seeded at a density of 90,000 cells per well in plating medium (Primacyt, cat #MPM-cryo) on collagen coated 96-well plates (Greiner-Bio-One, #655150). Directly after seeding, cells were treated with the siRNAs as they adhered as a monolayer in plating medium. Each siRNA was applied to the cells for the concentration-response-curve at concentrations starting with 10 µM, sequentially diluted in 4-fold dilution steps down to 38 µM. Each concentration was applied as quadruplicate. After 5 hours, the medium was changed to maintenance medium (Primacyt cat #HHMM). The medium was changed every 24 hours and the cells were harvested for analysis by Quantigene bDNA assay 48 hours after seeding. The C3 mRNA concentrations were normalised to GAPDH mRNA. Concentration-response-curves were fitted with GraphPad Prism version 7.05 using a four-parameter logistic (4PL) model without further constraints.

Example 4

In Vitro Study in Primary Mouse Hepatocytes Showing C3 mRNA Knockdown Efficacy of Tested siRNA-GalNAc Conjugates in Concentration-Response-Curve Format (0.038 nM-10 µM siRNA Conjugate).

Expression of C3 mRNA after incubation with the GalNAc siRNA conjugates EV0104, EV0105, EV0107, EV0108, EV0109, EV0110, EV0111 and EV0312 in a concentration-response format was analysed. The identity of the single strands forming each of the siRNA duplexes as well as their sequences are to be found in the tables at the end of the description. The mRNA level of the house keeping gene GAPDH served as control. The siRNA GalNAc conjugates were able to decrease C3 mRNA levels in a concentration dependent fashion with maximal inhibition at 10 µM between 56 and 72%. The most potent siRNAs were EV0104 with 68%, EV0109 with 67% and EV0111 with 72% reduction of C3 mRNA at 10 µM, respectively.

Cryopreserved murine hepatocytes were purchased from Thermo Fisher (#MSCP10, Lot #MC817) and plated in plating medium (Thermo Fisher Sci, Cat. No. CM3000 supplement pack added to William's E Medium, no phenol red-to 500 ml total, Thermo Fisher Sci, Cat. No. A12176-01). On the day of seeding, the cells were thawed and plated at a density of 60,000 cells per well into a collagen-coated 96-well plate (Greiner-Bio-One, #655150). Directly after seeding, cells were treated with the siRNAs as they adhered as a monolayer in plating medium. Each siRNA was applied to the cells as concentration-response-curve at concentrations starting with 10 µM, sequentially diluted in 4-fold dilution steps down to 0.038 nM. Each concentration was applied as quadruplicate. After 5 hours, the medium was changed to maintenance medium (Thermo Fisher Sci, Cat. No. CM4000 supplement pack added to William's E Medium, no phenol red-to 500 ml total, Thermo Fisher Sci, Cat. No. A12176-01). The medium was changed every 24 hours and the cells were harvested for analysis by Quantigene bDNA assay 48 hours after seeding.

The results are shown in FIGS. 3A and 3B. They depict % remaining C3 mRNA expression in primary mouse hepatocytes after incubation with siRNA GalNAc conjugates (0.038 nM-10 µM) normalized to GAPDH mRNA. Concentration-response curves were fitted with Graph Pad Prism version 7.05 using a four-parameter logistic (4PL) model without further constraints.

Example 5

In Vitro Study in Primary Mouse, Human and Cynomolgus Hepatocytes Showing C3 mRNA Knockdown Efficacy of Tested siRNA-GalNAc Conjugates at 1, 10 and 100 nM.

The expression of C3 mRNA after incubation with the GalNAc siRNA conjugates EV0312 and EV0313 at 1, 10 and 100 nM was analysed. The identity of the single strands forming each of the siRNA duplexes as well as their sequences are to be found in the tables at the end of the description. The mRNA level of the house keeping gene Actin served as control.

40,000 (human), 30,000 (mouse) or 45,000 (cynomolgus) cells were seeded on collagen-coated 96-well plates. siRNAs in indicated concentrations were added immediately after seeding. 24 hours post treatment, cells were lysed using InviTrap RNA Cell HTS96 Kit/C (Stratec). qPCR was performed using mRNA-specific primers and probes against C3 and Actin.

The results are shown in FIGS. 4A, 4B and 4C.

Example 6—Synthesis of Building Blocks

Figure 5:
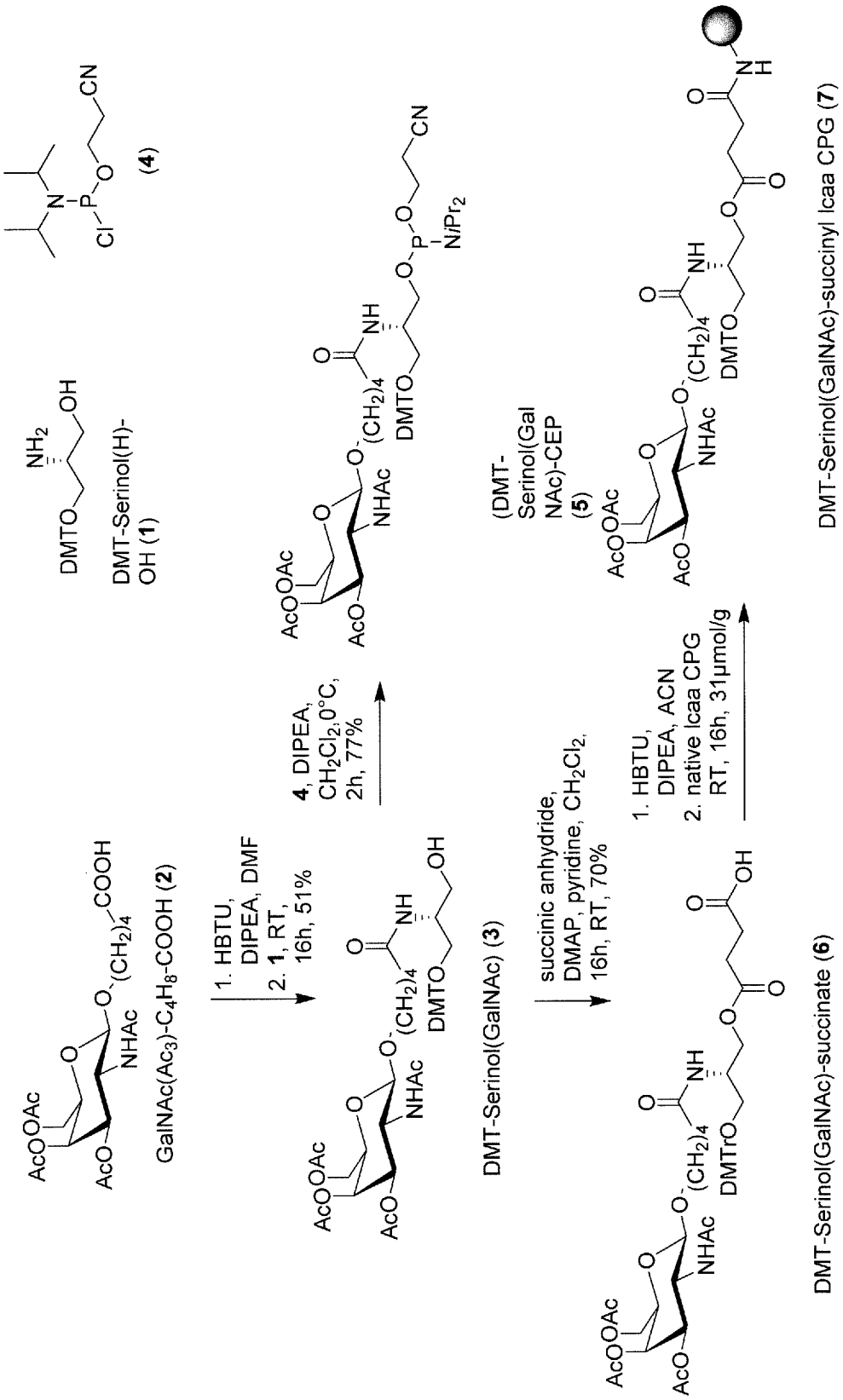
FIG. 5 shows a possible synthesis route to DMT-Serinol (GalNAc)-CEP and CPG.

The synthesis route for DMT-Serinol(GalNAc)-CEP and CPG as described below is outlined in FIG. 5. Starting material DMT-Serinol(H) (1) was made according to literature published methods (Hoevelmann et al. Chem. Sci., 2016, 7, 128-135) from commercially available L-Serine. GalNAc(Ac$_3$)—C$_4$H$_8$—COOH (2) was prepared according to literature published methods (Nair et al. J. Am. Chem. Soc., 2014, 136 (49), pp 16958-1696), starting from commercially available per-acetylated galactose amine. Phosphitylation reagent 2-Cyanoethyl-N,N-diisopropylchlorophosphor-amidite (4) is commercially available. Synthesis of (vp)-mU-phos was performed as described in Prakash, Nucleic Acids Res. 2015, 43(6), 2993-3011 and Haraszti, Nucleic Acids Res. 2017, 45(13), 7581-7592. Synthesis of the phosphoramidite derivatives of ST43 (ST43-phos) as well as ST23 (ST23-phos) can be performed as described in WO2017/174657.

DMT-Serinol(GalNAc) (3)

HBTU (9.16 g, 24.14 mmol) was added to a stirring solution of GalNAc(Ac$_3$)—C4H$_8$-000H (2) (11.4 g, 25.4 mmol) and DIPEA (8.85 ml, 50.8 mmol). After 2 minutes activation time a solution of DMT-Serinol(H) (1) (10 g, 25.4 mmol) in Acetonitrile (anhydrous) (200 ml) was added to the stirring mixture. After 1 h LCMS showed good conversion. The reaction mixture was concentrated in vacuo. The residue was dissolved up in EtOAc, washed subsequently with water (2×) and brine. The organic layer was dried over Na$_2$SO$_4$, filtered and concentrated under reduced pressure. The residue was further purified by column chromatography (3% MeOH in CH$_2$Cl$_2$+1% Et$_3$N, 700 g silica). Product containing fractions were pooled, concentrated and stripped with CH$_2$Cl$_2$ (2×) to yield to yield 10.6 g (51%) of DMT-Serinol (GalNAc) (3) as an off-white foam.

DMT-Serinol(GalNAc)-CEP (5)

2-Cyanoethyl-N,N-diisopropylchlorophosphoramidite (4) (5.71 ml, 25.6 mmol) was added slowly to a stirring mixture of DMT-Serinol(GalNAc) (3) (15.0 g, 17.0 mmol), DIPEA (14.9 ml, 85 mmol) and 4 Å molecular sieves in Dichloromethane (dry) (150 ml) at 0° C. under argon atmosphere. The reaction mixture was stirred at 0° C. for 1 h. TLC indicated complete conversion. The reaction mixture was filtered and concentrated in vacuo to give a thick oil. The residue was dissolved in Dichloromethane and was further purified by flash chromatography (0-50% acetone in toluene 1% Et3N, 220 g silica). Product containing fractions were pooled and concentrated in vacuo. The resulting oil was stripped with MeCN (2×) to yield 13.5 g (77%) of the colorless DMT-Serinol(GalNAc)-CEP (5) foam.

DMT-Serinol(GalNAc)-Succinate (6)

DMAP (1.11 g, 9.11 mmol) was added to a stirring solution of DMT-Serinol(GalNAc) (3) (7.5 g, 9.11 mmol) and succinic anhydride (4.56 g, 45.6 mmol) in a mixture of Dichloromethane (50 ml) and Pyridine (50 ml) under argon atmosphere. After 16 h of stirring the reaction mixture was concentrated in vacuo and the residue was taken up in EtOAc and washed with 5% citric acid (aq). The aqueous layer was extracted with EtOAc. The combined organic layers were washed subsequently with sat $NaHCO_3$ (aq.) and brine, dried over $Na_2SO_4$, filtered and concentrated in vacuo. Further purification was achieved by flash chromatography (0-5% MeOH in $CH_2Cl_2$+1% $Et_3N$, 120 g silica). Product containing fractions were pooled and concentrated in vacuo. The residue was stripped with MeCN (3×) to yield 5.9 g (70%) DMT-Serinol(GalNAc)-succinate (6).

DMT-Serinol(GalNAc)-succinyl-lcaa-CPG (7)

The DMT-Serinol(GalNAc)-succinate (6) (1 eq.) and HBTU (1.1 eq.) were dissolved in $CH_3CN$ (10 ml). Diisopropylethylamine (2 eq.) was added to the solution, and the mixture was swirled for 2 min followed by addition native amino-lcaa-CPG (500 A, 88 µmol/g, 1 eq.). The suspension was gently shaken at room temperature on a wrist-action shaker for 16 h, then filtered and washed with acetonitrile. The solid support was dried under reduced pressure for 2 h. The unreacted amines on the support were capped by stirring with $Ac_2O$/2,6-lutidine/NMI at room temperature (2×15 min). The washing of the support was repeated as above. The solid was dried under vacuum to yield DMT-Serinol(GalNAc)-succinyl-lcaa-CPG (7) (loading: 34 µmol/g, determined by detritylation assay).

Example 7—Oligonucleotide Synthesis

Example compounds were synthesised according to methods described below and known to the person skilled in the art. Assembly of the oligonucleotide chain and linker building blocks was performed by solid phase synthesis applying phosphoramidite methodology.

Downstream cleavage, deprotection and purification followed standard procedures that are known in the art.

Oligonucleotide syntheses was performed on an AKTA oligopilot 10 using commercially available 2'O-Methyl RNA and 2"Fluoro-2"Deoxy RNA base loaded CPG solid support and phosphoramidites (all standard protection, ChemGenes, LinkTech) were used. Synthesis of DMT-(S)-Serinol(GalNAc)-succinyl lcaa CPG (7) and DMT-(S)-Serinol(GalNAc)-CEP (5) are described in example 6.

Ancillary reagents were purchased from EMP Biotech. Synthesis was performed using a 0.1 M solution of the phosphoramidite in dry acetonitrile (<20 ppm $H_2O$) and benzylthiotetrazole (BTT) was used as activator (0.3M in acetonitrile). Coupling time was 10 min. A Cap/OX/Cap or Cap/Thio/Cap cycle was applied (Cap: $Ac_2O$/NMI/Lutidine/Acetonitrile, Oxidizer: 0.05M $I_2$ in pyridine/$H_2O$). Phosphorothioates were introduced using commercially available thiolation reagent 50 mM EDITH in acetonitrile (Link technologies). DMT cleavage was achieved by treatment with 3% dichloroacetic acid in toluene. Upon completion of the programmed synthesis cycles a diethylamine (DEA) wash was performed. All oligonucleotides were synthesized in DMT-off mode.

Attachment of the Serinol(GalNAc) moiety was achieved by use of either base-loaded (S)-DMT-Serinol(GalNAc)-succinyl-lcaa-CPG (7) or a (S)-DMT-Serinol(GalNAc)-CEP (5). Triantennary GalNAc clusters (ST23/ST43) were introduced by successive coupling of the branching trebler amidite derivative (C6XLT-phos) followed by the GalNAc amidite (ST23-phos). Attachment of (vp)-mU moiety was achieved by use of (vp)-mU-phos in the last synthesis cycle. The (vp)-mU-phos does not provide a hydroxy group suitable for further synthesis elongation and therefore, does not possess an DMT-group. Hence coupling of (vp)-mU-phos results in synthesis termination.

For the removal of the methyl esters masking the vinylphosphonate, the CPG carrying the fully assembled oligonucleotide was dried under reduced pressure and transferred into a 20 ml PP syringe reactor for solid phase peptide synthesis equipped with a disc frit (Carl Roth GmbH). The CPG was then brought into contact with a solution of 250 µL TMSBr and 177 µL pyridine in $CH_2Cl_2$ (0.5 ml/µmol solid support bound oligonucleotide) at room temperature and the reactor was sealed with a Luer cap. The reaction vessels were slightly agitated over a period of 2×15 min, the excess reagent discarded, and the residual CPG washed 2× with 10 ml acetonitrile. Further downstream processing did not alter from any other example compound.

The single strands were cleaved off the CPG by 40% aq. methylamine treatment (90 min, RT). The resulting crude oligonucleotide was purified by ion exchange chromatography (Resource Q, 6 ml, GE Healthcare) on a AKTA Pure HPLC System using a sodium chloride gradient. Product containing fractions were pooled, desalted on a size exclusion column (Zetadex, EMP Biotech) and lyophilized until further use.

All final single-stranded products were analysed by AEX-HPLC to prove their purity. Identity of the respective single-stranded products was proved by LC-MS analysis.

Example 8— Double-Strand Formation

Individual single strands were dissolved in a concentration of 60 OD/ml in $H_2O$. Both individual oligonucleotide solutions were added together in a reaction vessel. For easier reaction monitoring a titration was performed. The first strand was added in 25% excess over the second strand as determined by UV-absorption at 260 nm. The reaction mixture was heated to 80° C. for 5 min and then slowly cooled to RT. Double-strand formation was monitored by ion pairing reverse phase HPLC. From the UV-area of the residual single strand the needed amount of the second strand was calculated and added to the reaction mixture. The reaction was heated to 80° C. again and slowly cooled to RT. This procedure was repeated until less than 10% of residual single strand was detected.

Example 9

In Vivo Study Showing Knockdown of C3 mRNA in Murine Liver Tissue and Serum Protein after Single Subcutaneous Dosing of 1 or 5 mg/kg GalNAc Conjugated siRNAs.

Figure 6A:
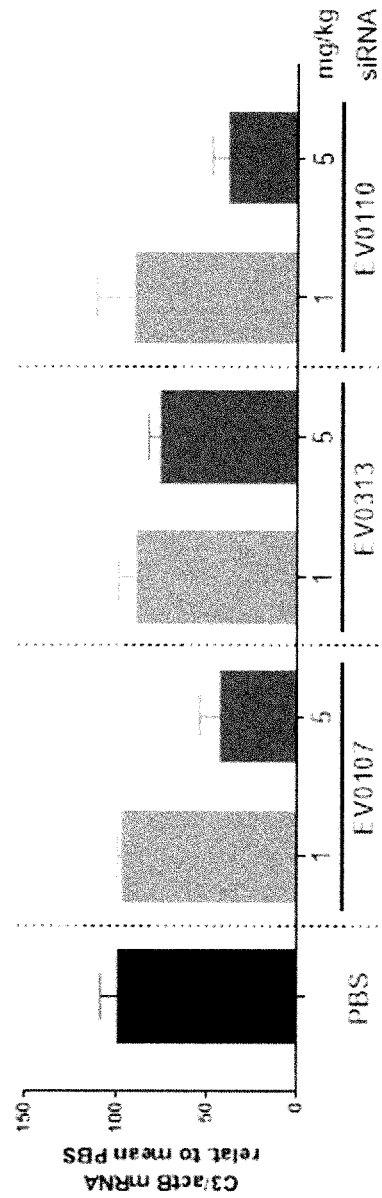
FIGS. 6A and 6B show in vivo C3 mRNA levels in hepatocytes as well as C3 protein levels in serum in response to sc treatment of mice with selected siRNA GalNAc conjugates.

Female C57BL/6N mice with an age of 8 weeks were obtained from CHARLES RIVER, Sulzfeld, Germany. Animal experiments were performed according to ethical guidelines of the German Protection of Animals Act in its version of July 2013. Mice were randomized according to weight into groups of 4 mice. On day 0 of the study animals received a single subcutaneous dose of 1 or 5 mg/kg siRNA dissolved in phosphate buffered saline (PBS) or PBS only as control. The viability, body weight and behaviour of the mice was monitored during the study without pathological findings. Serum samples were taken before the application, at day 4, day 10 and day 14. At day 14 the study was terminated, animals were euthanized, and liver samples were snap frozen and stored at −80° C. until further analysis. For analysis, RNAs were isolated using the InviTrap Spin Tissue RNA Mini Kit from Stratec according to the manufacturer's protocol. QPCR was performed using C3 and Actin specific primer probe sets and Takyon™ One-Step Low Rox Probe 5× MasterMix dTTP on the QuantStudio6 device from Applied Biosystems in single-plex 384 well format. Expression differences were calculated using the delta delta Ct method and relative expression of C3 versus the house keeping gene actin normalized to the PBS control experiment was used for comparison of the different siRNAs. EV0107, EV0313 and EV0110 induced a dose dependent knockdown of liver C3 mRNA. The maximum achieved knockdown was observed using siRNA EV0107 (57%) and EV0110 (61%) using 5 mg/kg siRNA, respectively. Results are shown in FIG. 6A. The figure shows relative C3 mRNA expression in % in murine liver 14 days after a single dosing of GalNAc conjugated siRNAs EV0107, EV0313 and EV0110. The identity of the single strands forming each of the siRNA duplexes as well as their sequences are to be found in the tables at the end of the description. Data is shown in bar charts as mean±SD (n=4 per group).

Figure 6B:
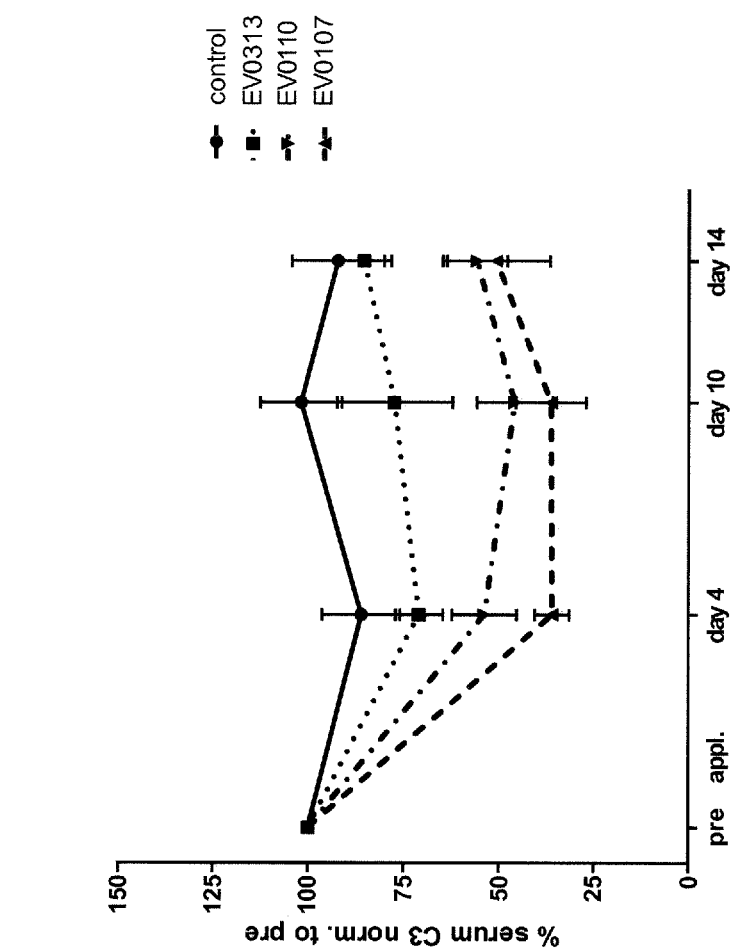

Serum samples were analysed using commercially available C3 ELISA Kits. The analyses were carried out according to the manufacturer's protocol, and C3 serum levels were calculated relative to the respective pre dose levels. Results are shown in FIG. 6B. The figure shows relative C3 protein serum levels in % from mouse serum samples taken before, at day 4, at day 10 and at day 14 of the study after dosing of 5 mg/kg EV0313, EV0110 and EV0107 GalNAc conjugated siRNAs. Data is shown as means±SD (n=3 or 4 per group).

Example 10

In Vitro Study in Primary Mouse, Human and Cynomolgus Hepatocytes Showing C3 Knockdown Efficacy of Tested siRNA-GalNAc Conjugates at 1, 10 an 100 nM.

Figure 7A:
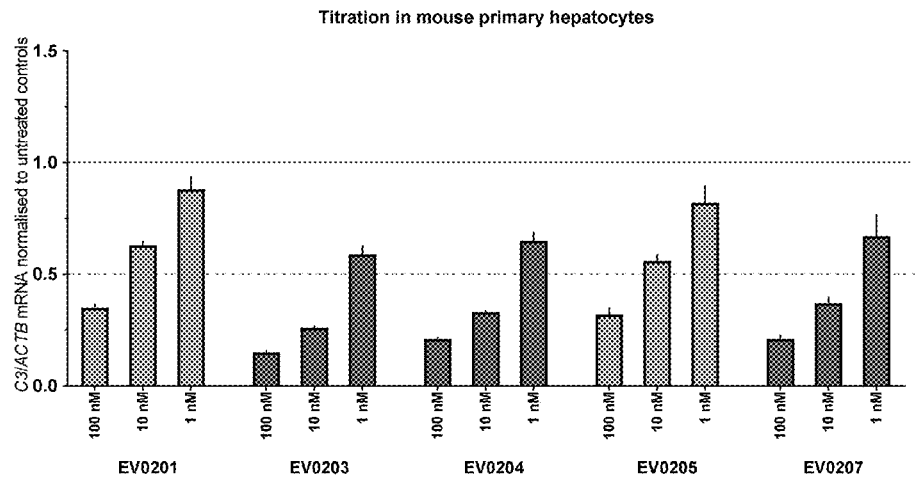
FIGS. 7A, 7B and 7C show relative C3 mRNA expression in primary mouse (A), cynomolgus (B) and human (C) hepatocytes after incubation with selected siRNA GalNac conjugates (1 nM, 10 nM and 100 nM) normalized to ACTIN mRNA.
Figure 7B:
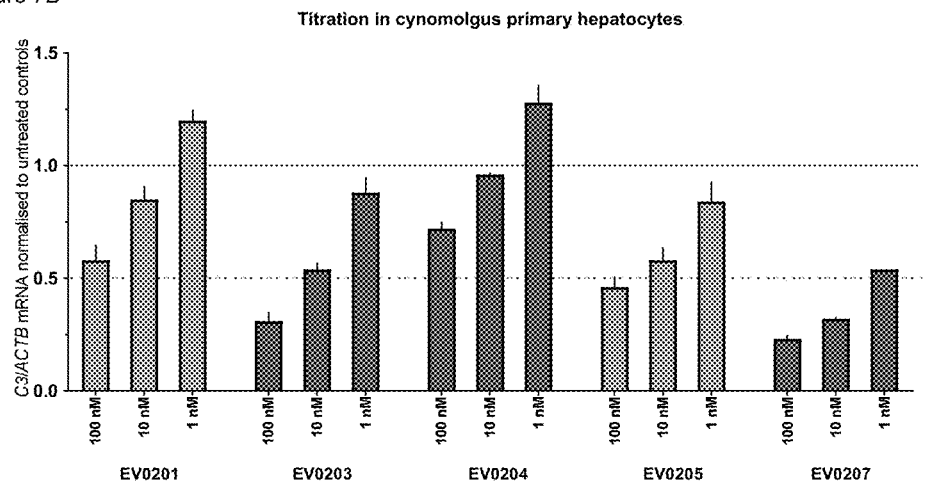
Figure 7C:
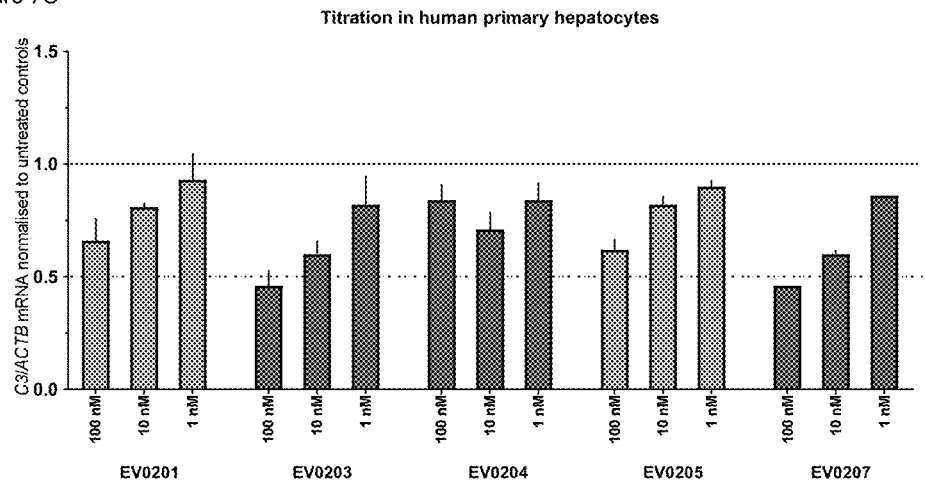

Expression of C3 mRNA after incubation with the GalNAc siRNA conjugates EV0201, EV0203, EV0204, EV0205 and EV0207 at 1, 10 and 100 nM was measured (FIG. 7). siRNA sequences and modifications are listed in Tables 3 and 5. The mRNA level of the house keeping gene ACTIN served as housekeeping control. Human and cynomolgus primary hepatocytes were seeded into collagen I-coated 96-well plates (Life Technologies) at a density of 40,000 cells per well. Mouse hepatocytes were seeded at a density of 25,000 cells per well. GalNAc-conjugated siRNAs were added immediately after plating in the previously defined media to final siRNA concentrations of 100, 10 and 1 nM. Plates were then incubated at 37° C. in a 5% CO2 atmosphere for 24 hours. Subsequently, cells were lysed and RNA was isolated using InviTrap RNA Cell HTS96 Kit/C (Stratec).

10 µl of RNA-solution was used for gene expression analysis by reverse transcription quantitative polymerase chain reaction (RT-qPCR) performed with amplicon sets/ sequences for ACTB (Eurogentec) and C3 (BioTez GmbH, Berlin, Germany), respectively. The RT-qPCR reactions were carried out with an ABI StepOne Plus (Applied Biosystems, part of Thermo Fisher Scientific, Massachusetts, USA) using standard protocols for RT-PCR (48° C. 30 min, 95° C. 10 min, 40 cycles at 95° C. 15 s followed by 60° C. 1 min). The data were calculated by using the comparative CT method also known as the 2-deltadelta Ct method. SiRNAs EV0201, EV0203, EV0204, EV0205 and EV0207 show dose-dependent inhibition of C3 mRNA expression in primary hepatocytes.

Example 11

In Vivo Study Showing Knockdown of C3 mRNA in Murine Liver Tissue and Serum Protein after a Single Subcutaneous Dosing of 5 or 10 mg/kg GalNAc Conjugated Modified siRNAs.

siRNA sequences and modifications are listed in Tables 3 and 5. The mRNA level of the house keeping gene ACTIN served as housekeeping control. Male C57BL/6N mice with an age of about 8 weeks were obtained from CHARLES RIVER, Sulzfeld, Germany. Animal experiments were conducted in compliance with the principles of the Hungarian Act 1998: XXVIII regulating animal protection (latest modified by Act 2011 CLVIII) and in Government Decree 40/2013 on animal experiments. Mice were assigned into groups of 4 mice. On day 0 of the study, the animals received a single subcutaneous dose of 5 or 10 mg/kg siRNA dissolved in phosphate buffered saline (PBS) or PBS only as control. The viability, body weight and behaviour of the mice was monitored during the study without pathological findings. Serum samples were taken before the application, at day 4, day 10, day 14, day 21, day 28, day 35 and day 42. At day 14 and at day 42 half of the groups, respectively, were terminated, the animals were euthanized, and liver samples were snap frozen and stored at −80° C. until further analysis.

For analysis, RNAs were isolated using the InviTrap Spin Tissue RNA Mini Kit from Stratec according to the manufacturer's protocol. RT-qPCR was performed using C3 and ACTIN specific primer probe sets and Takyon™ One-Step Low Rox Probe 5× MasterMix dTTP on the QuantStudio6 device from Applied Biosystems in single-plex 384 well format. Expression differences were calculated using the delta delta Ct method and relative expression of C3 versus the house keeping gene ACTIN normalized to the PBS group was used for comparison of the different siRNAs.

Figure 8A:
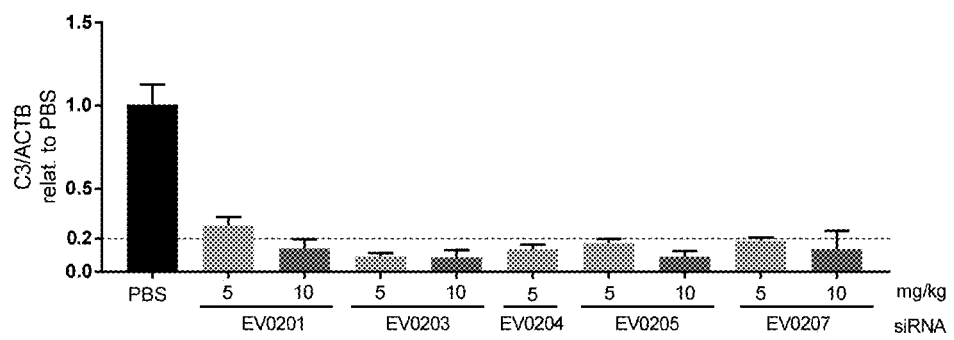
FIGS. 8A and 8B show relative C3 mRNA expression in % in murine liver 14 days (A) or 42 days (B) after a single dosing of GalNAc conjugated siRNAs EV0201, EV0203, EV0204, EV0205 and EV0207. Data is shown in bar charts as mean±SD (n=4 per group).
Figure 8B:
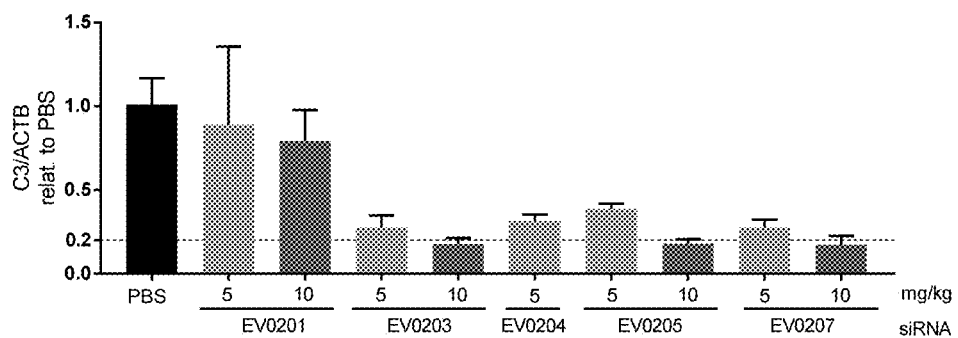

All tested siRNAs (EV0201, EV0203, EV0204, EV0205 and EV0207) inhibit C3 mRNA expression by more than 70% after 14 days after a single dose of 5 or 10 mg/kg (FIG. 8A). After 42 days, the inhibition of C3 expression by EV0203, EV0204, EV0205 and EV0207 was still more than 80% knockdown with a 10 mg/kg siRNA dose (FIG. 8B).

Figure 9A:
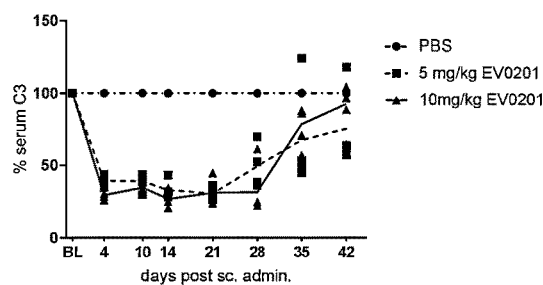
FIGS. 9A, 9B, 9C, 9D, 9E, 9F show relative C3 protein serum levels in % from mouse serum samples taken before (BL), at day 4, at day 10, day 14, day 21, day 28, day 35 and day 42 of the study after dosing of 5 or 10 mg/kg siRNA. Data points depict serum C3 level of individual animals determined using a standard C3 ELISA. Data was normalized to each group's baseline mean and then to the time matched PBS control, which was set as 100%. The plotted line connects the individual group means at the respective timepoints.
  A) Normalised C3 serum levels after dosing of 5 and 10 mg/kg EV0201
  B) Normalised C3 serum levels after dosing of 5 and 10 mg/kg EV0203
  C) Normalised C3 serum levels after dosing of 5 mg/kg EV0204
  D) Normalised C3 serum levels after dosing of 5 and 10 mg/kg EV0205
  E) Normalised C3 serum levels after dosing of 5 and 10 mg/kg EV0207
Figure 9B:
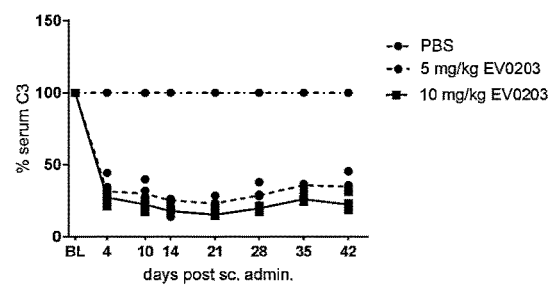
Figure 9C:
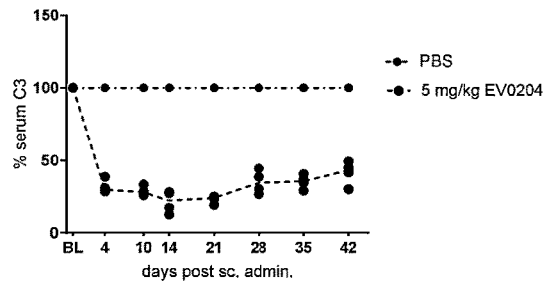
Figure 9D:
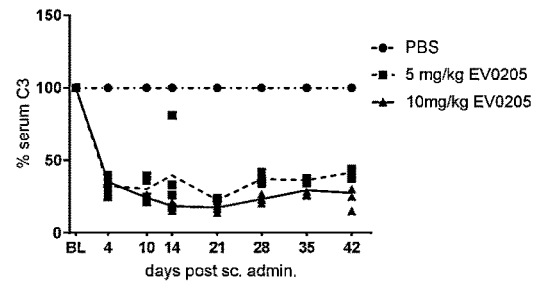
Figure 9E:
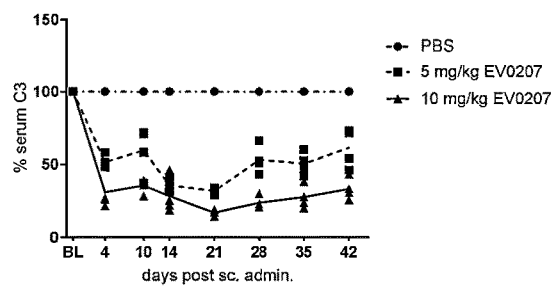
Figure 9F:
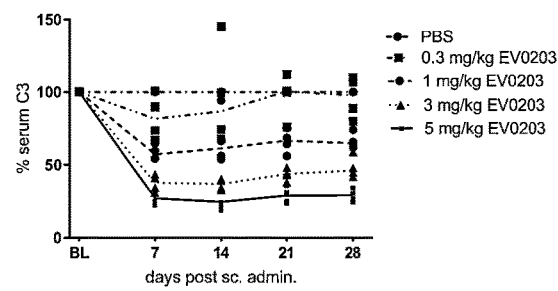

For C3 protein level analysis, serum samples were measured using commercially available C3 ELISA Kits. The analyses were carried out according the manufacturer's protocol, and % C3 serum levels were calculated relative to the group means at baseline/before the application and relative to the time matched PBS control group's means. The data for the C3 protein analyses mirror the results from the RNA analyses (FIG. 9). EV0203, EV0204, EV0205 and EV0207 were able to induce a long lasting C3 serum decrease. A reduction of up to 80% 42 days after a single application of 10 mg/kg was obtained for EV0203 (FIG. 9B).

Example 12

Various siRNAs Targeting C3 are Active In Vitro.

Figure 10:
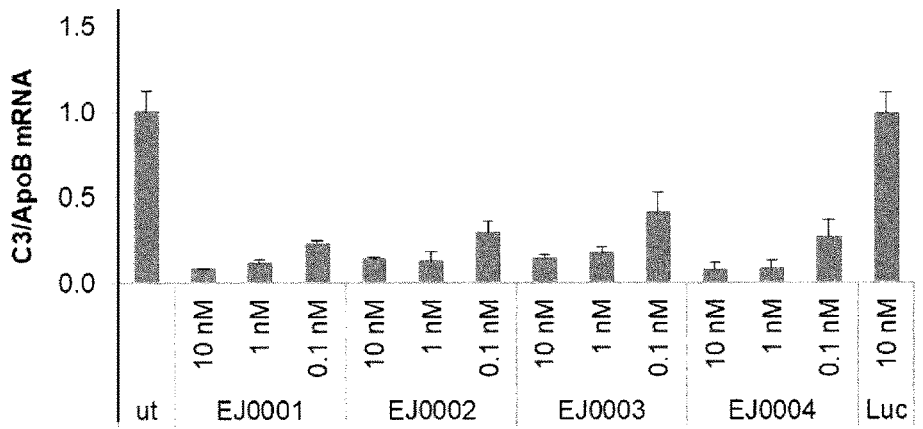
FIG. 10 shows C3 mRNA knockdown efficiency by various siRNAs in vitro.

C3 knockdown efficacy of siRNAs EJ0001, EJ0002, EJ0003 and EJ0004 was determined after transfection of 0.1-10 nM siRNA in Hep3B cells. The results are depicted in FIG. 10. After transfection with EJ0001, a dose dependent reduction of C3 mRNA levels with a maximum of ~90% knockdown is observed. EJ0002, EJ0003 and EJ0004 are in a similar activity range.

For transfection of Hep3B cells with siRNAs, cells were seeded at a density of 12,000 cells/well into 96-well tissue culture plates. Transfection of siRNA was carried out with Atufect liposomal transfection reagent 24 h after seeding. The screen was performed with siRNAs targeting C3 in triplicates at 0.1, 1 and 10 nM. An siRNA targeting Firefly Luciferase ("Luc") was used as control. After 24 h of incubation with siRNAs, medium was removed, cells were lysed, and total RNA was extracted. C3 and ApoB mRNA levels were determined by TaqMan qRT-PCR. Each bar represents mean±SD from three technical replicates.

Example 13

Various siRNAs Targeting Human C3 are Active In Vitro.

Figure 11:
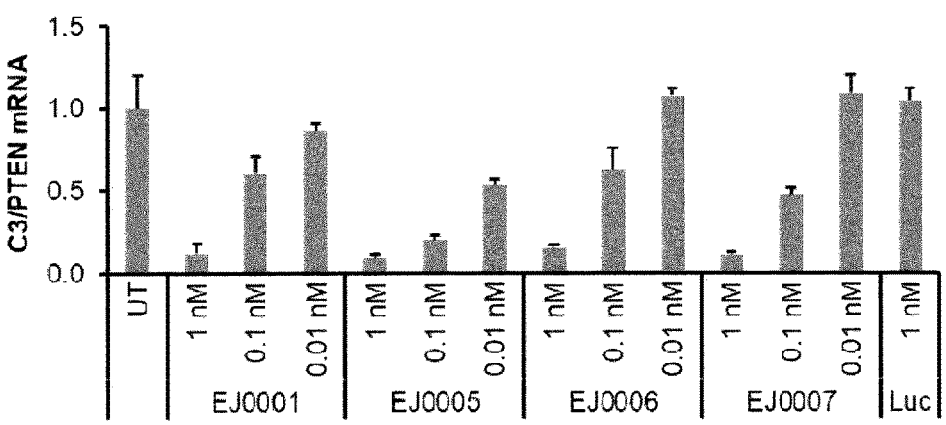
FIG. 11 shows human C3 mRNA knockdown efficiency by various siRNAs in vitro.

C3 knockdown efficacy of siRNAs EJ0001, EJ0005, EJ0006 and EJ0007 was determined after transfection of 0.01-1 nM siRNA in Hep3B cells. The results are depicted in FIG. 11. After transfection with 1 nM, C3 mRNA knockdown is around 90% for all tested siRNAs and at 0.1 nM, knockdown is around 50% for EJ0001, EJ0006 and EJ0007. EJ0005 performs better with 80% knockdown at 0.1 nM.

For transfection of Hep3B cells with siRNAs, cells were seeded at a density of 8,000 cells/well into 96-well tissue culture plates. Transfection of siRNA was carried out with Atufect liposomal transfection reagent 24 h after seeding. The screen was performed in triplicates at 0.01, 0.1 and 1 nM siRNA concentration. An siRNA targeting Firefly Luciferase ("Luc") was used as control. After 24 h of incubation with siRNAs, medium was removed, cells were lysed and total RNA was extracted. C3 and PTEN mRNA levels were determined by TaqMan qRT-PCR. Each bar represents mean±SD from three technical replicates.

Example 14

Various siRNAs Targeting Mouse C3 are Active In Vitro.

Figure 12:
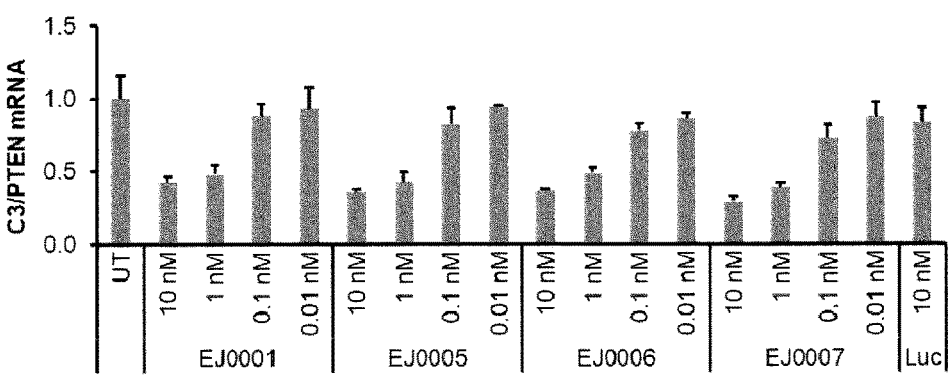
FIG. 12 shows mouse C3 mRNA knockdown efficiency by various siRNAs in vitro.

C3 knockdown efficacy of siRNAs EJ0001, EJ005, EJ0006 and EJ0007 was determined after transfection of 0.01-10 nM siRNA in AML12 cells. The results are depicted in FIG. 12. After siRNA transfection, a dose-dependent C3 mRNA knockdown with a maximum of around 60% is reached.

For transfection of AML12 cells, cells were seeded at a density of 6,000 cells/well into 96-well tissue culture plates. Transfection of siRNA was carried out with Atufect liposomal transfection reagent 24 h after seeding. The screen was performed with siRNAs targeting C3 in triplicates at 0.01, 0.1, 1 and 10 nM. An siRNA targeting Firefly Luciferase ("Luc") was used as control. After 24 h of incubation with siRNAs, medium was removed, cells were lysed, and total RNA was extracted. C3 and PTEN mRNA levels were determined by TaqMan qRT-PCR. Each bar represents mean±SD from three technical replicates.

Example 15

Various GalNAc-Conjugated siRNAs Targeting Mouse C3 are Active In Vitro.

Figure 13:
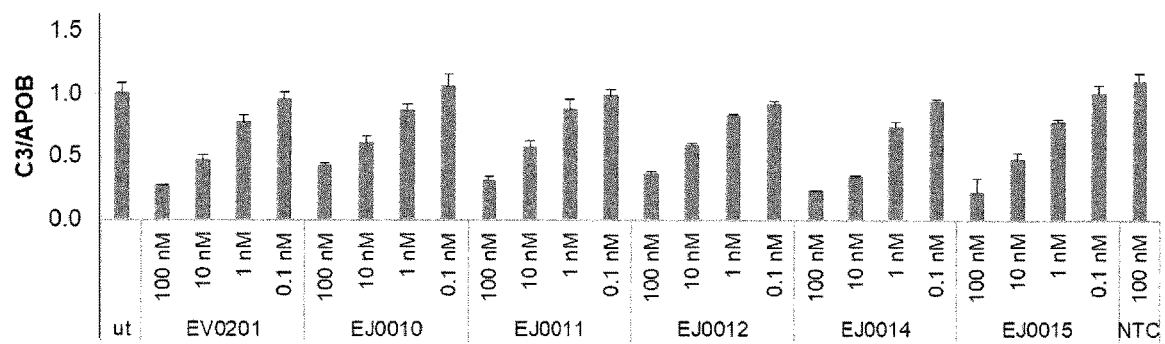
FIG. 13 shows C3 mRNA knockdown efficiency by various siRNA conjugates in mouse hepatocytes.

C3 mRNA knockdown efficiency of GalNAc siRNA conjugates EV0201, EJ0010, EJ0011, EJ0012, EJ0014 and EJ0015 was determined after receptor-mediated uptake in mouse primary hepatocytes. The results are depicted in FIG. 13. A dose-dependent knockdown with a maximum of around 75% was achieved.

Mouse primary hepatocytes were seeded at a density of 25,000 cells/well into 96-well tissue culture plates and treated with 100, 10, 1 and 0.1 nM GalNAc-conjugated siRNAs directly upon plating. A GalNAc-conjugated, scrambled sequence was used as non-targeting control (NTC). The cells were lysed after 24 h of incubation with GalNAc-conjugates and total RNA was extracted. C3 and APOB mRNA levels were determined by Taqman qRT-PCR. Each bar represents mean±SD from three technical replicates.

Example 16

Various GalNAc-Conjugated siRNAs Targeting Cynomolgus C3 are Active In Vitro.

Figure 14:
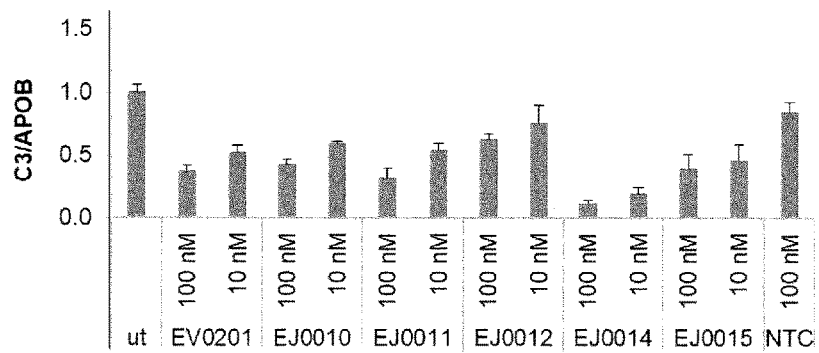
FIG. 14 shows C3 mRNA knockdown efficiency by various siRNA conjugates in cynomolgus hepatocytes.

C3 mRNA knockdown efficiency of GalNAc siRNA conjugates EV0201, EJ0010, EJ0011, EJ0012, EJ0014 and EJ0015 was determined after receptor-mediated uptake in cynomolgus primary hepatocytes. The results are depicted in FIG. 14. A dose-dependent knockdown with a maximum of around 90% was achieved.

Cynomolgus primary hepatocytes were seeded at a density of 36,500 cells/well into 96-well tissue culture plates and treated with 100 and 10 nM GalNAc-conjugated siRNAs directly upon plating. A GalNAc-conjugated, scrambled sequence was used as non-targeting control (NTC). The cells were lysed after 24 h of incubation with GalNAc-conjugates and total RNA was extracted. C3 and APOB mRNA levels were determined by Taqman qRT-PCR. Each bar represents mean±SD from three technical replicates.

Example 17

Variants of GalNAc-Conjugated siRNAs Repress C3 in Primary Mouse Hepatocytes.

Figure 15:
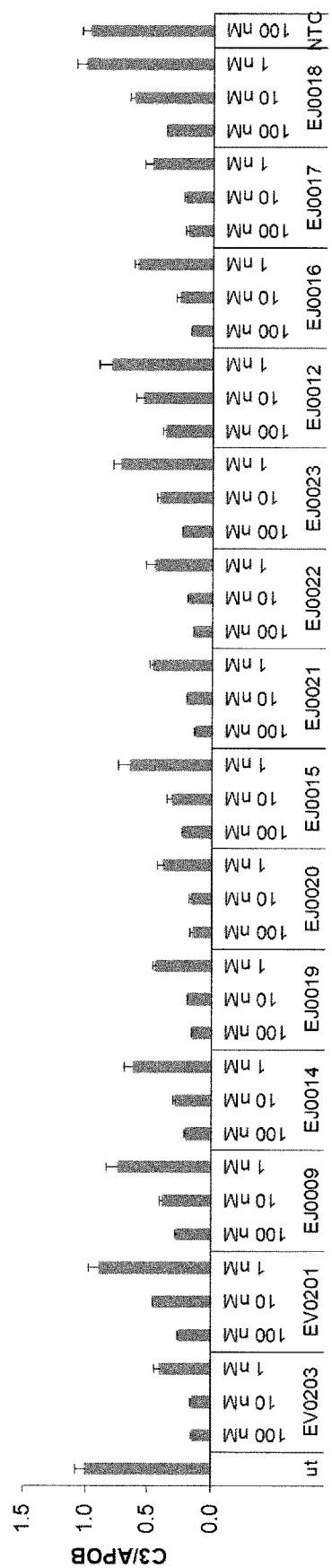
FIG. 15 shows C3 mRNA knockdown efficiency by siRNA conjugate variants in mouse hepatocytes.

C3 mRNA knockdown efficiency of GalNAc-siRNA conjugates EV0201 and variants thereof (EJ0009, EV0203), EJ0014 and variants thereof (EJ0019, EJ0020), EJ0015 and variants thereof (EJ0021-23) as well as EJ0012 and variants thereof (EJ0016-18) was determined after receptor-mediated uptake in mouse primary hepatocytes. The results are depicted in FIG. 15. A dose-dependent knockdown with a maximum of around 85% was achieved with some of the variants.

Mouse primary hepatocytes were seeded at a density of 25,000 cells/well into 96-well tissue culture plates and treated with 100, 10 and 1 nM GalNAc-conjugated siRNAs directly upon plating. A GalNAc-conjugated, scrambled sequence was used as non-targeting control (NTC). The cells were lysed after 24 h of incubation with GalNAc conjugates and total RNA was extracted. C3 and APOB mRNA levels were determined by Taqman qRT-PCR. Each bar represents mean±SD from three technical replicates.

Example 18

Figure 16:
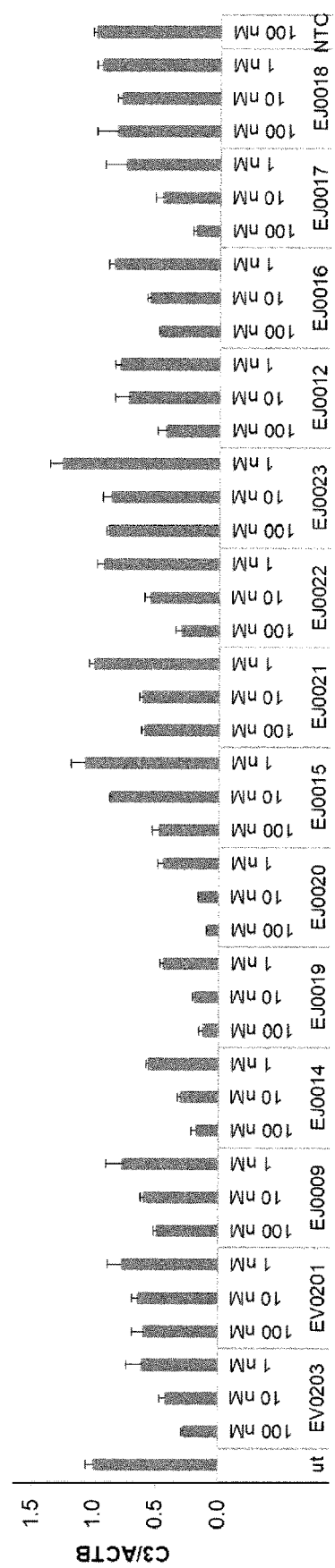
FIG. 16 shows C3 mRNA knockdown efficiency by siRNA conjugate variants in cynomolgus hepatocytes.

Variants of GalNAc-Conjugated siRNAs Repress C3 in Primary Cynomolgus Hepatocytes C3 mRNA knockdown efficiency of GalNAc-siRNA conjugates EV0201 and variants thereof (EJ0009, EV0203), EJ0014 and variants thereof (EJ0019, EJ0020), EJ0015 and variants thereof (EJ0021-23) as well as EJ0012 and variants thereof (EJ0016-18) was determined after receptor-mediated uptake in cynomolgus primary hepatocytes. The results are depicted in FIG. 16. A dose-dependent knockdown with a maximum of around 90% was achieved with some of the variants.

Cynomolgus primary hepatocytes were seeded at a density of 40,000 cells/well into 96-well tissue culture plates and treated with 100, 10 and 1 nM GalNAc-conjugated siRNAs directly upon plating. A GalNAc-conjugated, scrambled sequence was used as non-targeting control (NTC). The cells were lysed after 24 h of incubation with GalNAc conjugates and total RNA was extracted. C3 and ACTB mRNA levels were determined by Taqman qRT-PCR. Each bar represents mean±SD from three technical replicates.

Example 19

In Vitro Study Showing Knockdown of C3 mRNA in Murine Liver Tissue and Serum Protein after Single Subcutaneous Dosing of 1 or 3 mg/kg of GalNAc Conjugated C3 siRNA EJ0020.

Male C57BL/6N mice aged 8 weeks were obtained from Janvier, France. Animal experiments were performed according to ethical guidelines of the German Protection of Animals Act in its version of July 2013. Mice were randomized according to weight into groups of 4 mice. On day 0 of the study, animals received a single subcutaneous dose of 1 or 3 mg/kg siRNA dissolved in phosphate buffered saline (PBS) or PBS only as control. The viability, body weight and behaviour of the mice was monitored during the study without pathological findings. Serum samples were taken before the application, at day 7, day 14, day 28 and day 43. At day 43, the study was terminated, animals were euthanized, and liver samples were snap frozen and stored at −80° C. until further analysis.

Figure 17:
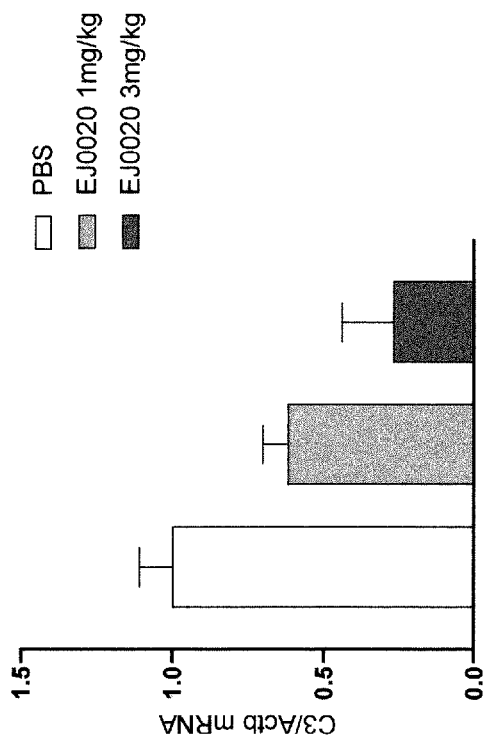
FIG. 17 shows relative C3 mRNA expression in % in murine liver 43 days after a single dosing of GalNAc conjugated C3 siRNA EJ0020.

For analysis, RNAs were isolated using the InviTrap Spin Tissue RNA Mini Kit from Stratec according to the manufacturer's protocol. qPCR was performed using C3 and Actin specific primer probe sets and Takyon™ One-Step Low Rox Probe 5× MasterMix dTTP on the QuantStudio6 device from Applied Biosystems in single-plex 384 well format. Expression was calculated using the delta delta Ct method and relative expression of C3 versus the house keeping gene normalized to PBS was used for comparisons. 38% C3 mRNA knock down was observed using 1 mg/kg siRNA EJ0020 and 73% C3 knock down using 3 mg/kg of the same siRNA. Results are shown in FIG. 17 (data are shown in bar charts as mean±SD (n=4 per group)).

Figure 18:
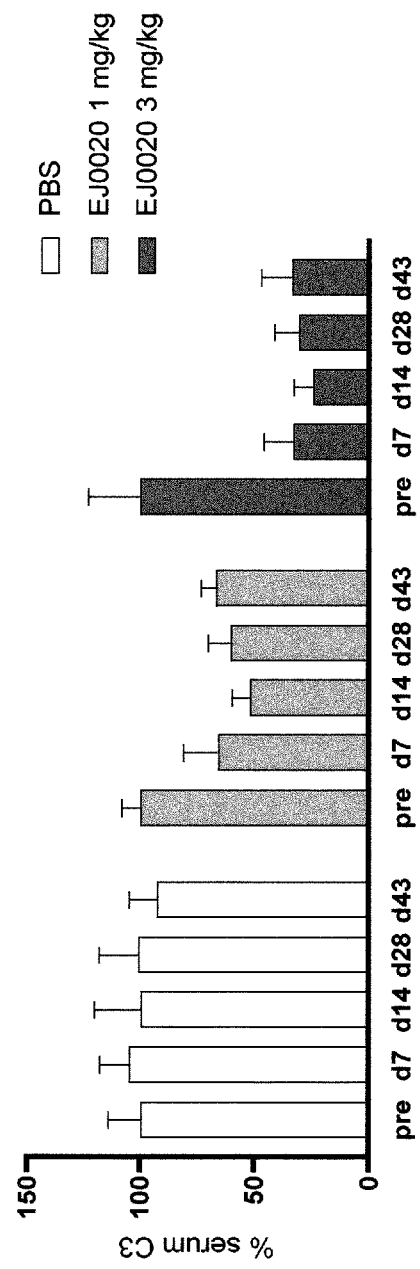
FIG. 18 shows relative C3 protein serum levels in % from mouse serum samples taken before, at day 7, day 14, day 28 and day 43 of the study after dosing of 1 or 3 mg/kg GalNAc conjugated C3 siRNA EJ0020.

C3 protein levels in serum were obtained using commercially available C3 ELISA Kits. The analyses were carried out according to the manufacturer's protocol, and C3 serum levels were calculated relative to the respective pre-dose levels. Results are shown in FIG. 18 (data are shown as means±SD (n=3 or 4 per group)).

Example 20

In Vitro Study in Primary Human Hepatocytes Showing C3 Knock Down Efficacy of Tested siRNA-GalNAc Conjugates at 1, 10 and 100 nM.

Figure 19:
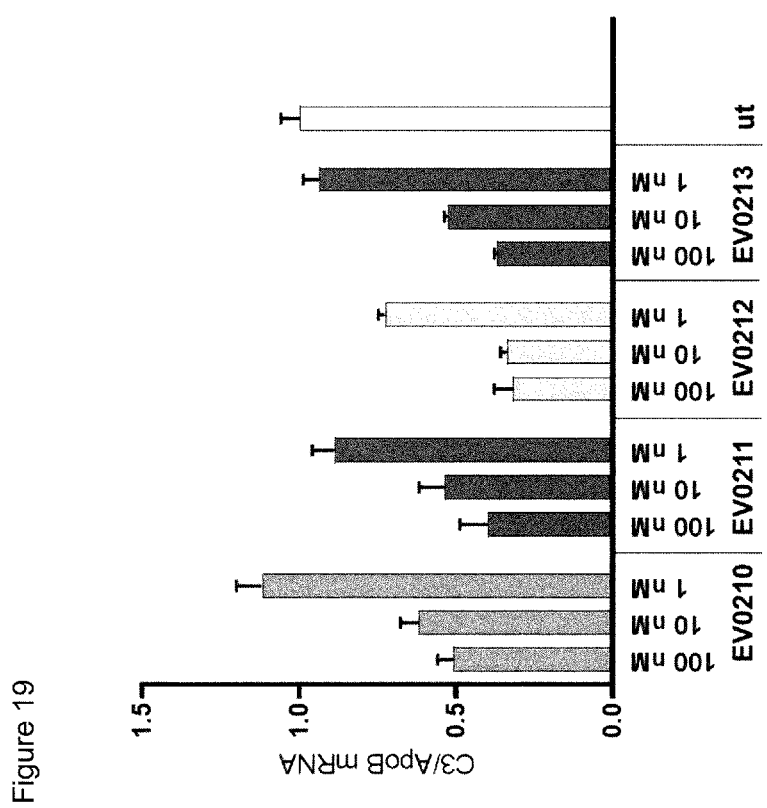
FIG. 19 shows expression of C3 mRNA in primary human hepatocytes after incubation with the GalNAc siRNA conjugates EV0210, EV0211, EV0212 and EV0213 at 1, 10 and 100 nM.

Expression of C3 mRNA after incubation with the GalNAc siRNA conjugates EV0210, EV0211, EV0212 and EV0213 at 1, 10 and 100 nM is shown in FIG. 19. The siRNA GalNAc conjugates are listed in Table 3. mRNA level of the gene APOB served as housekeeping control.

Human primary hepatocytes were seeded into collagen I-coated 96-well plates (Life Technologies) at a density of 40,000 cells per well. GalNAc-conjugated siRNAs were added immediately after plating to final siRNA concentrations of 100, 10 and 1 nM. Plates were then incubated at 37° C. in a 5% $CO_2$ atmosphere for 24 hours. Subsequently, cells were lysed, and RNA was isolated using InviTrap RNA Cell HTS96 Kit/C (Stratec).

Ten µl of RNA-solution was used for gene expression analysis by reverse transcription quantitative polymerase chain reaction (RT-qPCR) performed with amplicon sets/sequences for APOB (Eurogentec) and C3 (BioTez GmbH, Berlin, Germany), respectively. The RT-qPCR reactions were carried out with an ABI StepOne Plus (Applied Biosystems, part of Thermo Fisher Scientific, Massachusetts, USA) using standard protocols for RT-PCR (48° C. 30 min, 95° C. 10 min, 40 cycles at 95° C. 15 s followed by 60° C. 1 min). The data were calculated by using the comparative CT method also known as the 2-deltadelta Ct method.

SiRNAs EV0210, EV0211, EV0212 and EV0213 were able to inhibit C3 mRNA expression in primary human hepatocytes in a dose-dependent manner.

Example 21

In Vivo Study of the Efficacy of C3 siRNA GalNAc Conjugates in a Murine Disease Model of C3 Glomerulopathy (C3G).

Figure 20:
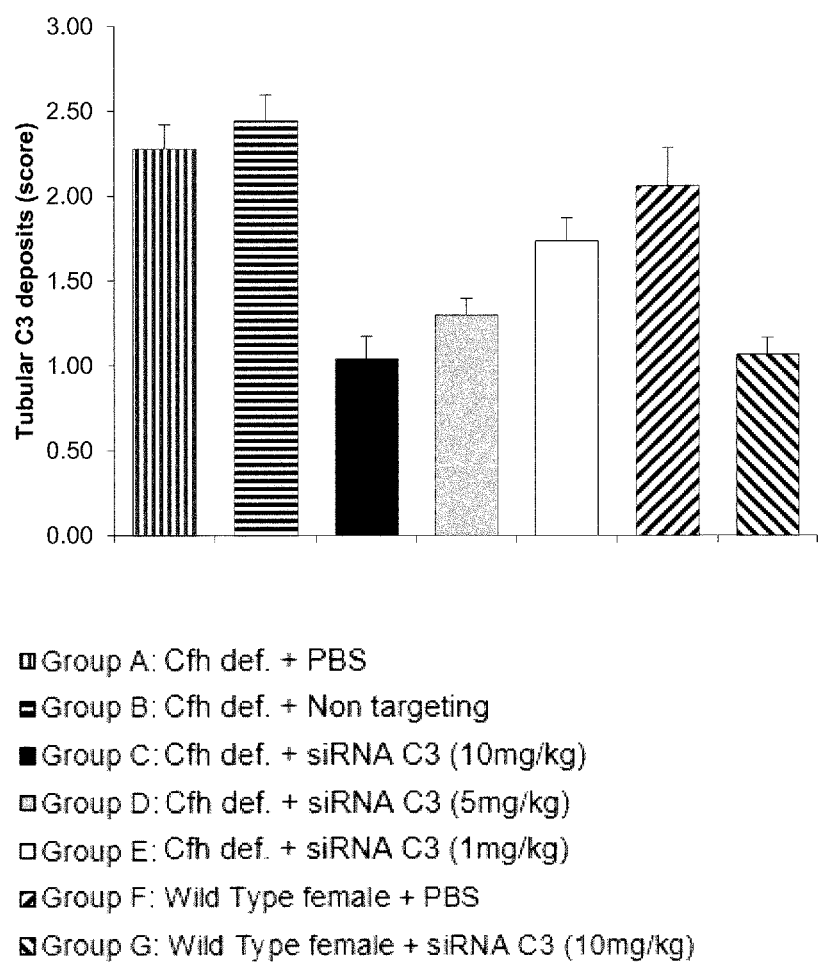
FIG. 20 shows the effect of treatment with different doses of a conjugated C3 siRNA on C3 tubular deposition in wild-type and C3G disease model mice ten days post treatment.
Figure 21:
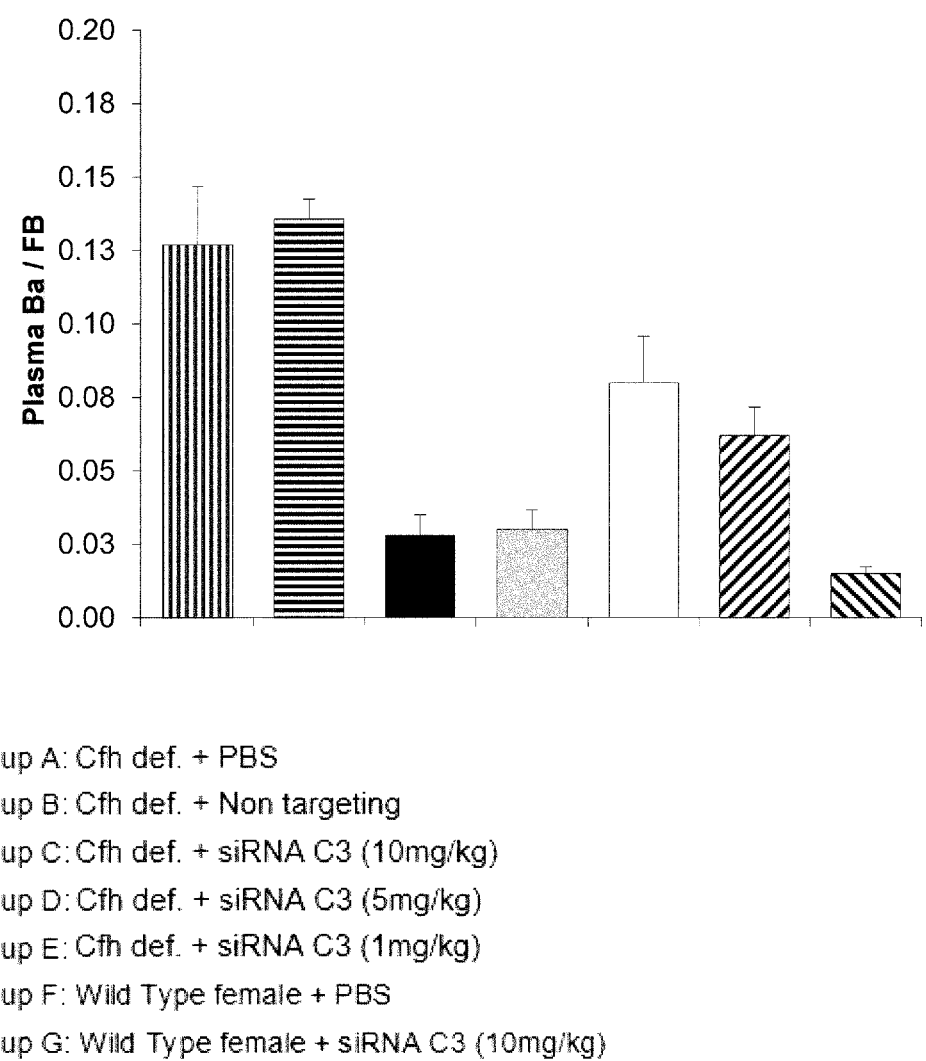
FIG. 21 shows the effect of treatment with different doses of a conjugated C3 siRNA on Complement Factor B fragmentation in wild-type and C3G disease model mice ten days post treatment.

EV0203 was tested in a murine disease model of C3 Glomerulopathy and in wild-type mice. Heterozygous complement factor H deficient mice (Cfh def.) were used as the C3 Glomerulopathy disease model. The animals were treated with a single dose of EV0203 or with controls (PBS or non-targeting siRNAs). The mice were sacrificed 10 days after treatment and tubular deposition of C3 was measured in the kidneys of the mice by C3 staining with an anti-C3 antibody and quantified (results are shown in FIG. 20). Complement factor B (FB) fragmentation, which is determined as the ratio of Ba fragments to full length FB, was also measured in the plasma by western blot and quantified—results are shown in FIG. 21. The results of the C3 staining show that tubular C3 deposits are significantly decreased in a dose-dependent manner by treatment with a conjugated C3 siRNA. The FB fragmentation data show that Cfh def. mice have increased levels of FB fragmentation compared to wild-type mice, but that this increased fragmentation level can be reduced by treatment with a conjugated C3 siRNA. Conjugated C3 siRNAs are therefore expected to be a powerful treatment for C3-related diseases and in particular for C3 Glomerulopathy and/or at least its symptoms.

Example 22

In Vivo Study of the Efficacy of Multiple Doses of a C3 siRNA GalNAc Conjugate in a Murine Disease Model of C3 Glomerulopathy (C3G).

Figure 22A:
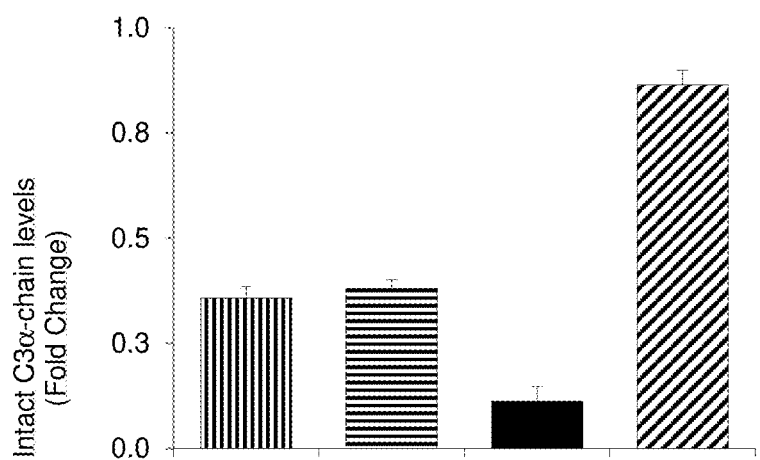
FIGS. 22A and 22B show the effect of treatment with multiple doses of a conjugated C3 siRNA on levels of C3α-chain and C3α-chain fragments in C3G disease model mice.
Figure 22B:
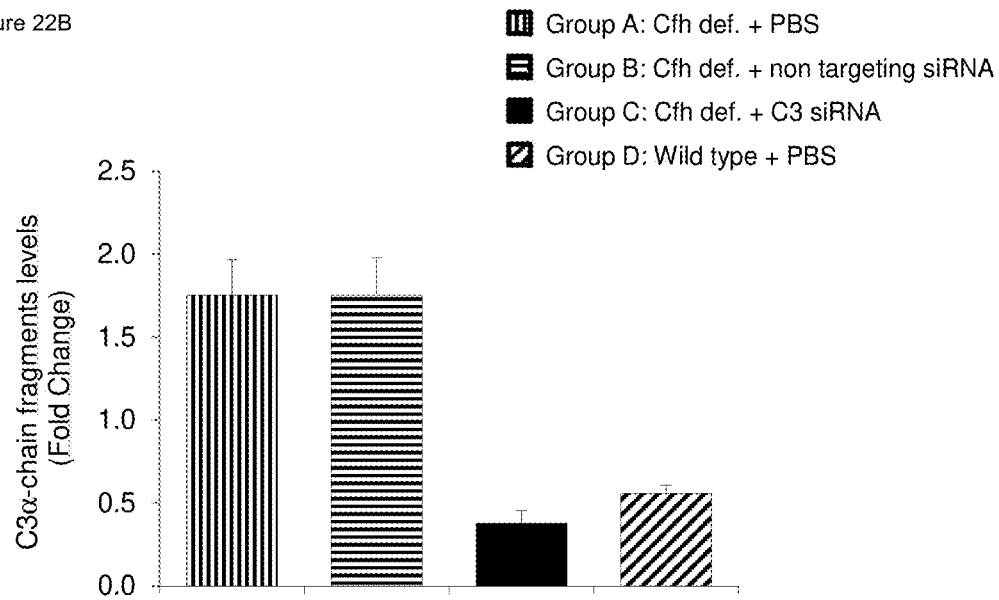
Figure 23:
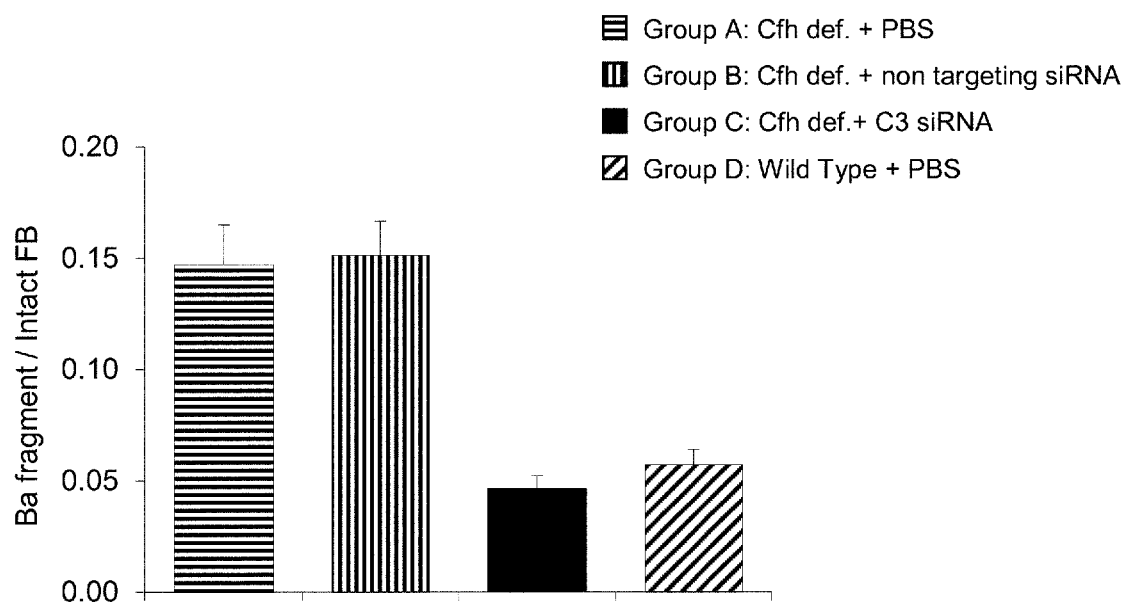
FIG. 23 shows the effect of treatment with multiple doses of a conjugated C3 siRNA on Complement Factor B fragmentation in C3G disease model mice.

EV0203 was tested in a murine disease model of C3 Glomerulopathy. Heterozygous complement factor H deficient mice (Cfh def.) were used as the C3 Glomerulopathy disease model. Seven- to eight-month-old mice were treated on the first day of the study and then monthly with 5 mg/kg of EV0203 or with PBS or a none-targeting siRNA as a control. Wild type mice treated with PBS were also used as a control. The mice were sacrificed three months after the start of the study (i.e., after three treatments with a conjugated C3 siRNA or a control). The levels of C3α-chain and C3α-chain fragments (activated C3 fragments) in the plasma were measured by western blot and quantified (results are shown in FIGS. 22A and 22B). Complement factor B (FB) fragmentation, which is determined as the ratio of Ba fragments to full length FB, was also measured in the plasma by western blot and quantified—results are shown in FIG. 23. These data confirm that conjugated C3 siRNAs are effective in reducing C3 fragment levels and FB fragmentation in aged mice.

Glomerular C3d deposits were also measured, by C3d staining. Three doses of the conjugated C3 siRNA were able to reduce glomerular C3d deposits of Cfh def. mice to levels similar to those of age-matched wild-type mice. Conjugated C3 siRNAs are therefore expected to be a powerful treatment for C3-related diseases and in particular for C3 Glomerulopathy and/or at least its symptoms.

Example 23

Conjugated C3 siRNAs from the above examples, including EV0210, EV0212 and EJ0020, were tested in vivo in healthy cynomolgus monkeys. The animals were treated once or multiple times with different doses of conjugated C3 siRNAs. Preliminary data from monkeys treated with the tested conjugated C3 siRNAs show reduced C3 protein levels in serum. These in vivo experiments are currently ongoing. Additional testing of conjugated C3 siRNAs in vivo in healthy cynomolgus monkeys is planned. After treatment once or multiple times with different doses of conjugated C3 siRNAs, C3 protein levels are measured in serum and C3 mRNA levels are measured in liver tissues. The C3 protein levels in serum and the C3 mRNA levels in the liver are both expected to be reduced after treatment with an effective dose of a conjugated C3 siRNA.

Statements

The following statements represent aspects of the invention.

1. A double-stranded nucleic acid for inhibiting expression of complement component C3, wherein the nucleic acid comprises a first strand and a second strand, wherein the first strand sequence comprises a sequence of at least 15 nucleotides differing by no more than 3 nucleotides from any one of the sequences SEQ ID NO: 370, 364, 365, 366, 368, 372, 377, 361, 95, 111, 125, 131, 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 97, 99, 101, 103, 105, 107, 109, 113, 115, 117, 119, 121, 123, 127, 129, 133 or 416.
2. The nucleic acid of statement 1, wherein
   (a) the first strand sequence comprises a sequence of at least 18 nucleotides differing by no more than 3 nucleotides from any one of the first strand sequences of Table 1 and optionally wherein the second strand sequence comprises a sequence of at least 18 nucleotides differing by no more than 3 nucleotides from the second strand sequence in the same line of the table;
   (b) the first strand sequence comprises a sequence of at least 18 nucleotides differing by no more than 1 nucleotide from any one of the first strand sequences of Table 1 and optionally wherein the second strand sequence comprises a sequence of at least 18 nucleotides differing by no more than 1 nucleotide from the second strand sequence in the same line of the table;
   (c) the first strand sequence comprises a sequence of at least 18 nucleotides of any one of the first strand sequences of Table 1 and optionally wherein the second strand sequence comprises a sequence of at least 18 nucleotides of the second strand sequence in the same line of the table; or
   (d) the first strand sequence consists of any one of the first strand sequences of Table 1 and optionally wherein the second strand sequence consists of the sequence of the second strand sequence in the same line of the table;

wherein Table 1 is:

| First strand sequence (SEQ ID NO:) | Second strand sequence (SEQ ID NO:) |
| --- | --- |
| 364 | 363 or 375 |
| 365 | 363 |
| 366 | 367 or 376 |
| 368 | 369 |
| 370 | 379 or 371, preferably 379 |
| 372 | 373 |
| 362 | 374 |
| 377 | 378 |
| 361 | 112 |
| 95 | 96 |
| 111 | 112 |
| 125 | 126 |
| 131 | 132 |
| 1 | 2 |
| 3 | 4 |
| 5 | 6 |
| 7 | 8 |
| 9 | 10 |
| 11 | 12 |
| 13 | 14 |
| 15 | 16 |
| 17 | 18 |
| 19 | 20 |
| 21 | 22 |
| 23 | 24 |
| 25 | 26 |
| 27 | 28 |
| 29 | 30 |
| 31 | 32 |
| 33 | 34 |
| 35 | 36 |
| 37 | 38 |
| 39 | 40 |
| 41 | 42 |
| 43 | 44 |
| 45 | 46 |
| 47 | 48 |
| 49 | 50 |
| 51 | 52 |
| 53 | 54 |
| 55 | 56 |
| 57 | 58 |
| 59 | 60 |
| 61 | 62 |
| 63 | 64 |
| 65 | 66 |
| 67 | 68 |
| 69 | 70 |
| 71 | 72 |
| 73 | 74 |
| 75 | 76 |
| 77 | 78 |
| 79 | 80 |
| 81 | 82 |
| 83 | 84 |
| 85 | 86 |
| 87 | 88 |
| 89 | 90 |

-continued

| First strand sequence (SEQ ID NO:) | Second strand sequence (SEQ ID NO:) |
|---|---|
| 91 | 92 |
| 93 | 94 |
| 97 | 98 |
| 99 | 100 |
| 101 | 102 |
| 103 | 104 |
| 105 | 106 |
| 107 | 108 |
| 109 | 110 |
| 113 | 114 |
| 115 | 116 |
| 117 | 118 |
| 119 | 120 |
| 121 | 122 |
| 123 | 124 |
| 127 | 128 |
| 129 | 130 |
| 133 | 134 |
| 416 | 26 |

3. The nucleic acid of any of the preceding statements, wherein the first strand sequence comprises the sequence of SEQ ID NO: 361 and optionally wherein the second strand sequence comprises a sequence of at least 15 nucleotides of the sequence of SEQ ID NO: 112; or wherein the first strand sequence comprises the sequence of SEQ ID NO: 95 and optionally wherein the second strand sequence comprises a sequence of at least 15 nucleotides of the sequence of SEQ ID NO: 96; or wherein the first strand sequence comprises the sequence of SEQ ID NO: 125 and optionally wherein the second strand sequence comprises a sequence of at least 15 nucleotides of the sequence of SEQ ID NO: 126; or wherein the first strand sequence comprises the sequence of SEQ ID NO: 131 and optionally wherein the second strand sequence comprises a sequence of at least 15 nucleotides of the sequence of SEQ ID NO: 132; or wherein the first strand sequence comprises the sequence of SEQ ID NO: 364 and optionally wherein the second strand sequence comprises a sequence of at least 15 nucleotides of the sequence of SEQ ID NO: 363 or 375; or wherein the first strand sequence comprises the sequence of SEQ ID NO: 365 and optionally wherein the second strand sequence comprises a sequence of at least 15 nucleotides of the sequence of SEQ ID NO: 363; or wherein the first strand sequence comprises the sequence of SEQ ID NO: 366 and optionally wherein the second strand sequence comprises a sequence of at least 15 nucleotides of the sequence of SEQ ID NO:367 or 376; or wherein the first strand sequence comprises the sequence of SEQ ID NO: 368 and optionally wherein the second strand sequence comprises a sequence of at least 15 nucleotides of the sequence of SEQ ID NO: 369; or wherein the first strand sequence comprises the sequence of SEQ ID NO: 370 and optionally wherein the second strand sequence comprises a sequence of at least 15 nucleotides of the sequence of SEQ ID NO: 371 or 379, preferably 379; or wherein the first strand sequence comprises the sequence of SEQ ID NO: 372 and optionally wherein the second strand sequence comprises a sequence of at least 15 nucleotides of the sequence of SEQ ID NO: 373 or 380; or wherein the first strand sequence comprises the sequence of SEQ ID NO: 362 and optionally wherein the second strand sequence comprises a sequence of at least 15 nucleotides of the sequence of SEQ ID NO: 374; or wherein the first strand sequence comprises the sequence of SEQ ID NO: 377 and optionally wherein the second strand sequence comprises a sequence of at least 15 nucleotides of the sequence of SEQ ID NO: 378; or wherein the first strand sequence comprises the sequence of SEQ ID NO: 416 and optionally wherein the second strand sequence comprises a sequence of at least 15 nucleotides of the sequence of SEQ ID NO: 26.

4. A double-stranded nucleic acid that is capable of inhibiting expression of complement component C3 for use as a medicament, wherein the nucleic acid comprises a first strand and a second strand.

5. The nucleic acid of any of the preceding statements, wherein the first strand and the second strand are separate strands and are each 18-25 nucleotides in length.

6. The nucleic acid of any of the preceding statements, wherein the first strand and the second strand form a duplex region of from 17-25 nucleotides in length.

7. The nucleic acid of any of the preceding statements, wherein the duplex region consists of 17-25 consecutive nucleotide base pairs.

8. The nucleic acid of any of the preceding statements, wherein said nucleic acid:
   a) is blunt ended at both ends;
   b) has an overhang at one end and a blunt end at the other end; or
   c) has an overhang at both ends.

9. The nucleic acid of any of the preceding statements, wherein the nucleic acid is a siRNA.

10. The nucleic acid of any of the preceding statements, wherein the nucleic acid mediates RNA interference.

11. The nucleic acid of any of the preceding statements, wherein at least one nucleotide of the first and/or second strand is a modified nucleotide.

12. The nucleic acid of any of the preceding statements, wherein at least nucleotides 2 and 14 of the first strand are modified by a first modification, the nucleotides being numbered consecutively starting with nucleotide number 1 at the 5' end of the first strand.

13 The nucleic acid of any of the preceding statements, wherein each of the even-numbered nucleotides of the first strand are modified by a first modification, the nucleotides being numbered consecutively starting with nucleotide number 1 at the 5' end of the first strand.

14. The nucleic acid of any of statements 12-13, wherein the odd-numbered nucleotides of the first strand are modified by a second modification, wherein the second modification is different from the first modification.

15. The nucleic acid of statements 12-14, wherein the nucleotides of the second strand in a position corresponding to an even-numbered nucleotide of the first strand are modified by a third modification, wherein the third modification is different from the first modification.

16. The nucleic acid of statements 12-15, wherein the nucleotides of the second strand in a position corresponding to an odd-numbered nucleotide of the first strand are modified by a fourth modification, wherein the fourth modification is different from the second modification and different from the third modification when a second and/or a third modification are present.

17. The nucleic acid of statements 12-14, wherein the nucleotide/nucleotides of the second strand in a position corresponding to nucleotide 11 or nucleotide 13 or nucleotides 11 and 13 or nucleotides 11-13 of the first strand is/are modified by a fourth modification and preferably wherein the nucleotides of the second strand that are not modified by a fourth modification are modified by a third modification.

18. The nucleic acid of statements 12-17, wherein the first modification is the same as the fourth modification if both modifications are present in the nucleic acid and preferably wherein the second modification is the same as the third modification if both modifications are present in the nucleic acid.

19. The nucleic acid of statements 12-18, wherein the first modification is a 2'-F modification; the second modification, if present in the nucleic acid, is preferably a 2'-OMe modification; the third modification, if present in the nucleic acid, is preferably a 2'-OMe modification; and the fourth modification, if present in the nucleic acid, is preferably a 2'-F modification.

20. The nucleic acid of any of the preceding statements, wherein each of the nucleotides of the first strand and of the second strand is a modified nucleotide.

21. The nucleic acid of any of the previous statements, wherein the first strand has a terminal 5' (E)-vinylphosphonate nucleotide at its 5' end and wherein the terminal 5' (E)-vinylphosphonate nucleotide is preferably linked to the second nucleotide in the first strand by a phosphodiester linkage.

22. The nucleic acid of any of the preceding statements, wherein the nucleic acid comprises a phosphorothioate linkage between the terminal two or three 3' nucleotides and/or 5' nucleotides of the first and/or the second strand and preferably wherein the linkages between the remaining nucleotides are phosphodiester linkages.

23. The nucleic acid of any of statements 1-21, comprising a phosphorodithioate linkage between each of the two, three or four terminal nucleotides at the 3' end of the first strand and/or comprising a phosphorodithioate linkage between each of the two, three or four terminal nucleotides at the 3' end of the second strand and/or a phosphorodithioate linkage between each of the two, three or four terminal nucleotides at the 5' end of the second strand and comprising a linkage other than a phosphorodithioate linkage between the two, three or four terminal nucleotides at the 5' end of the first strand.

24. The nucleic acid of statement 23, wherein the nucleic acid comprises a phosphorothioate linkage between each of the three terminal 3' nucleotides and/or between each of the three terminal 5' nucleotides on the first strand, and/or between each of the three terminal 3' nucleotides and/or between each of the three terminal 5' nucleotides of the second strand when there is no phosphorodithioate linkage present at that end.

25. The nucleic acid of statement 23, wherein all the linkages between the nucleotides of both strands other than the linkage between the two terminal nucleotides at the 3' end of the first strand and the linkages between the two terminal nucleotides at the 3' end and at the 5' end of the second strand are phosphodiester linkages.

26. The nucleic acid of any of the preceding statements, wherein the nucleic acid is conjugated to a ligand.

27. The nucleic acid of statement 26, wherein the ligand comprises (i) one or more N-acetyl galactosamine (GalNAc) moieties or derivatives thereof, and (ii) a linker, wherein the linker conjugates the at least one GalNAc moiety or derivative thereof to the nucleic acid.

28. The nucleic acid of any of statements 1-27, wherein the nucleic acid is conjugated to a ligand comprising a compound of formula (II):

$$[S-X^1-P-X^2]_3\text{-}A\text{-}X^3- \quad (II)$$

wherein:
S represents a saccharide, preferably wherein the saccharide is N-acetyl galactosamine;
$X^1$ represents $C_3$-$C_6$ alkylene or $(-CH_2-CH_2-O)_m(-CH_2)_2-$ wherein m is 1, 2, or 3;
P is a phosphate or modified phosphate, preferably a thiophosphate;
$X^2$ is alkylene or an alkylene ether of the formula $(-CH_2)_n-O-CH_2-$ where n=1-6;
A is a branching unit;
$X_3$ represents a bridging unit;
wherein a nucleic acid as defined in any of statements 1 to 27 is conjugated to $X^3$ via a phosphate or modified phosphate, preferably a thiophosphate.

29. The nucleic acid of any of statements 1-27, wherein the first strand of the nucleic acid is a compound of formula (V):

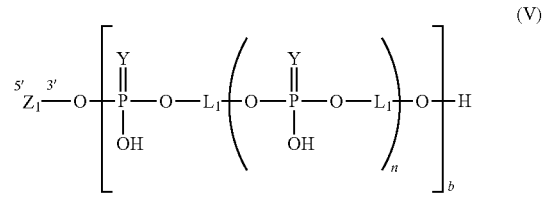

wherein b is 0 or 1; and
wherein the second strand is a compound of formula (VI):

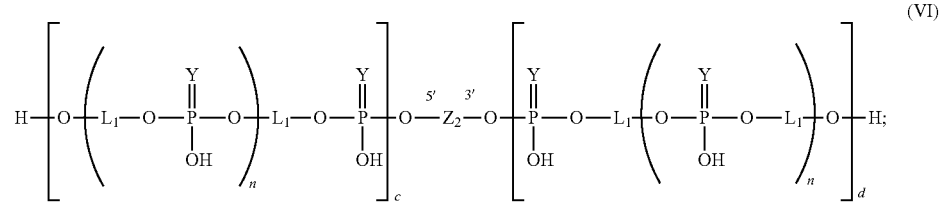

wherein:
c and d are independently 0 or 1;
$Z_1$ and $Z_2$ are respectively the first and second strand of the nucleic acid;
Y is independently O or S;
n is independently 0, 1, 2 or 3; and
$L_1$ is a linker to which a ligand is attached, wherein $L_1$ is the same or different in formulae (V) and (VI), and is the same or different within formulae (V) and (VI) when $L_1$ is present more than once within the same formula;

and wherein b+c+d is 2 or 3.

30. A composition comprising a nucleic acid of any of the previous statements and a solvent and/or a delivery vehicle and/or a physiologically acceptable excipient and/or a carrier and/or a salt and/or a diluent and/or a buffer and/or a preservative.

31. A composition comprising a nucleic acid of any of statements 1-29 and a further therapeutic agent selected from the group comprising an oligonucleotide, a small molecule, a monoclonal antibody, a polyclonal antibody and a peptide.

32. A nucleic acid of any of statements 1-3 or 5-29 or a composition of any of statements 30-31 for use as a medicament.

33. A nucleic acid of any of statements 1-29 or a composition of any of statements 30-32 for use in the prevention, decrease of the risk of suffering from, or treatment of a disease, disorder or syndrome.

34. The nucleic acid or composition of statement 33, wherein the disease, disorder or syndrome is a complement-mediated disease, disorder or syndrome.

35. The nucleic acid or composition of any of statements 33-34, wherein the disease, disorder or syndrome is associated with aberrant activation or over-activation of the complement pathway and/or with over-expression or ectopic expression or localisation or accumulation of C3.

36. The nucleic acid or composition of any of statements 33-35, wherein the disease, disorder or syndrome is:
    a) selected from the group comprising C3 Glomerulopathy (C3G), Paroxysmal Nocturnal Hemoglobinuria (PNH), atypical Hemolytic Uremic Syndrome (aHUS), Lupus nephritis, IgA nephropathy (IgA N), Cold Agglutinin Disease (CAD), Myasthenia gravis (MG), Primary Membranous Nephropathy, Immune Complex-mediated Glomerulonephritis (IC-mediated GN), post-Infectious Glomerulonephritis (PIGN), Systemic Lupus Erythematosus (SLE), Ischemia/reperfusion injury, age-related macular degeneration (AMD), Rheumatoid arthritis (RA), antineutrophil Cytoplasmic Autoantibodies-associated Vasculitis (ANCA-AV), dysbiotic periodontal Disease, Malarial Anaemia, Neuromyelitis Optica, Post-HCT/Solid Organ Transplant (TMAs), Guillain-Barré Syndrome, Membranous Glomerulonephritis, Thrombotic Thrombocytopenic Purpura and sepsis;
    b) selected from the group comprising C3 Glomerulopathy (C3G), Paroxysmal Nocturnal Hemoglobinuria (PNH), atypical Hemolytic Uremic Syndrome (aHUS), Lupus nephritis, IgA nephropathy (IgA N) and Primary Membranous Nephropathy;
    c) selected from the group comprising C3 Glomerulopathy (C3G), antineutrophil Cytoplasmic Autoantibodies-associated Vasculitis (ANCA-AV), atypical Hemolytic Uremic Syndrome (aHUS), Cold Agglutinin Disease (CAD), Myasthenia gravis (MG), IgA nephropathy (IgA N), Paroxysmal Nocturnal Hemoglobinuria (PNH);
    d) selected from the group comprising C3 Glomerulopathy (C3G), Cold Agglutinin Disease (CAD), Myasthenia gravis (MG), Neuromyelitis Optica, atypical Hemolytic Uremic Syndrome (aHUS), antineutrophil Cytoplasmic Autoantibodies-associated Vasculitis (ANCA-AV), IgA nephropathy (IgA N), Post-HCT/Solid Organ Transplant (TMAs), Guillain-Barré Syndrome, Paroxysmal Nocturnal Hemoglobinuria (PNH), Membranous Glomerulonephritis, Lupus nephritis and Thrombotic Thrombocytopenic Purpura
    e) selected from the group comprising C3 Glomerulopathy (C3G), Cold Agglutinin Disease (CAD) and IgA nephropathy (IgA N); or
    f) C3 Glomerulopathy (C3G).

37. Use of a nucleic acid of any of statements 1-29 or a composition of any of statements 30-31 in the prevention, decrease of the risk of suffering from, or treatment of a disease, disorder or syndrome, wherein the disease, disorder or syndrome is preferably C3 Glomerulopathy (C3G).

38. A method of preventing, decreasing the risk of suffering from, or treating a disease, disorder or syndrome comprising administering a pharmaceutically effective dose of a nucleic acid of any of statements 1-29 or 32-36 or a composition of any of statements 30-36 to an individual in need of treatment, preferably wherein the nucleic acid or composition is administered to the subject subcutaneously, intravenously or by oral, rectal or intraperitoneal administration.

Summary Tables

TABLE 3

Summary duplex table

| Duplex | Single Strands | Duplex | Single Strands | Duplex | Single Strands |
|---|---|---|---|---|---|
| EV0001 | EV0001A | EV0051 | EV0051A | EV0101 | EV0101A |
|  | EV0001B |  | EV0051B |  | EV0101B |
| EV0002 | EV0002A | EV0052 | EV0052A | EV0102 | EV0102A |
|  | EV0002B |  | EV0052B |  | EV0102B |
| EV0003 | EV0003A | EV0053 | EV0053A | EV0103 | EV0103A |
|  | EV0003B |  | EV0053B |  | EV0103B |
| EV0004 | EV0004A | EV0054 | EV0054A | EV0104 | EV0104A |
|  | EV0004B |  | EV0054B |  | EV0104B |
| EV0005 | EV0005A | EV0055 | EV0055A | EV0105 | EV0105A |
|  | EV0005B |  | EV0055B |  | EV0105B |
| EV0006 | EV0006A | EV0056 | EV0056A | EV0106 | EV0106A |
|  | EV0006B |  | EV0056B |  | EV0106B |
| EV0007 | EV0007A | EV0057 | EV0057A | EV0107 | EV0107A |
|  | EV0007B |  | EV0057B |  | EV0107B |
| EV0008 | EV0008A | EV0058 | EV0058A | EV0108 | EV0108A |
|  | EV0008B |  | EV0058B |  | EV0108B |

TABLE 3-continued

Summary duplex table

| Duplex | Single Strands | Duplex | Single Strands | Duplex | Single Strands |
|---|---|---|---|---|---|
| EV0009 | EV0009A EV0009B | EV0059 | EV0059A EV0059B | EV0109 | EV0109A EV0109B |
| EV0010 | EV0010A EV0010B | EV0060 | EV0060A EV0060B | EV0110 | EV0110A EV0110B |
| EV0011 | EV0011A EV0011B | EV0061 | EV0061A EV0061B | EV0111 | EV0111A EV0111B |
| EV0012 | EV0012A EV0012B | EV0062 | EV0062A EV0062B | EV0201 | EV0201A EV0201B |
| EV0013 | EV0013A EV0013B | EV0063 | EV0063A EV0063B | EV0202 | EV0201A EV0202B |
| EV0014 | EV0014A EV0014B | EV0064 | EV0064A EV0064B | EV0203 | EV0203A EV0201B |
| EV0015 | EV0015A EV0015B | EV0065 | EV0065A EV0065B | EV0204 | EV0203A EV0202B |
| EV0016 | EV0016A EV0016B | EV0066 | EV0066A EV0066B | EV0205 | EV0110A EV0205B |
| EV0017 | EV0017A EV0017B | EV0067 | EV0067A EV0067B | EV0206 | EV0110A EV0206B |
| EV0018 | EV0018A EV0018B | EV0068 | EV0068A EV0068B | EV0207 | EV0207A EV0205B |
| EV0019 | EV0019A EV0019B | EV0069 | EV0037A EV0069B | EV0208 | EV0207A EV0206B |
| EV0020 | EV0020A EV0020B | EV0070 | EV0038A EV0070B | EV0209 | EV0209A EV0205B |
| EV0021 | EV0021A EV0021B | EV0071 | EV0039A EV0071B | EV0312 | EV0312A EV0112B |
| EV0022 | EV0022A EV0022B | EV0072 | EV0040A EV0072B | EV0313 | EV0313A EV0313B |
| EV0023 | EV0023A EV0023B | EV0073 | EV0041A EV0073B | EJ0001 | EJ0001A EJ0001B |
| EV0024 | EV0024A EV0024B | EV0074 | EV0042A EV0074B | EJ0002 | EJ0002A EJ0001B |
| EV0025 | EV0025A EV0025B | EV0075 | EV0043A EV0075B | EJ0003 | EJ0003A EJ0001B |
| EV0026 | EV0026A EV0026B | EV0076 | EV0044A EV0076B | EJ0004 | EJ0004A EJ0004B |
| EV0027 | EV0027A EV0027B | EV0077 | EV0045A EV0077B | EJ0005 | EJ0005A EJ0005B |
| EV0028 | EV0028A EV0028B | EV0078 | EV0046A EV0078B | EJ0006 | EJ0006A EJ0006B |
| EV0029 | EV0029A EV0029B | EV0079 | EV0047A EV0079B | EJ0007 | EJ0007A EJ0007B |
| EV0030 | EV0030A EV0030B | EV0080 | EV0048A EV0080B | EJ0008 | EJ0001A EJ0008B |
| EV0031 | EV0031A EV0031B | EV0081 | EV0049A EV0081B | EJ0009 | EJ0001A EJ0009B |
| EV0032 | EV0032A EV0032B | EV0082 | EV0050A EV0082B | EJ0010 | EJ0002A EJ0010B |
| EV0033 | EV0033A EV0033B | EV0083 | EV0051A EV0083B | EJ0011 | EJ0004A EJ0011B |
| EV0034 | EV0034A EV0034B | EV0084 | EV0052A EV0084B | EJ0012 | EJ0012A EJ0012B |
| EV0035 | EV0035A EV0035B | EV0085 | EV0053A EV0085B | EJ0013 | EJ0005A EJ0013B |
| EV0036 | EV0036A EV0036B | EV0086 | EV0054A EV0086B | EJ0014 | EJ0006A EJ0014B |
| EV0037 | EV0037A EV0037B | EV0087 | EV0055A EV0087B | EJ0015 | EJ0007A EJ0015B |
| EV0038 | EV0038A EV0038B | EV0088 | EV0056A EV0088B | EJ0016 | EJ0016A EJ0012B |
| EV0039 | EV0039A EV0039B | EV0089 | EV0057A EV0089B | EJ0017 | EJ0017A EJ0017B |
| EV0040 | EV0040A EV0040B | EV0090 | EV0058A EV0090B | EJ0018 | EJ0018A EJ0017B |
| EV0041 | EV0041A EV0041B | EV0091 | EV0059A EV0091B | EJ0019 | EJ0019A EJ0014B |
| EV0042 | EV0042A EV0042B | EV0092 | EV0060A EV0092B | EJ0020 | EJ0020A EJ0020B |
| EV0043 | EV0043A EV0043B | EV0093 | EV0061A EV0093B | EJ0021 | EJ0021A EJ0015B |
| EV0044 | EV0044A EV0044B | EV0094 | EV0062A EV0094B | EJ0022 | EJ0022A EJ0022B |
| EV0045 | EV0045A EV0045B | EV0095 | EV0063A EV0095B | EJ0023 | EJ0023A EJ0022B |

TABLE 3-continued

Summary duplex table

| Duplex | Single Strands | Duplex | Single Strands | Duplex | Single Strands |
|---|---|---|---|---|---|
| EV0046 | EV0046A EV0046B | EV0096 | EV0064A EV0096B | EV0210 | EV0210A EV0210B |
| EV0047 | EV0047A EV0047B | EV0097 | EV0065A EV0097B | EV0211 | EV0211A EV0210B |
| EV0048 | EV0048A EV0048B | EV0098 | EV0066A EV0098B | EV0212 | EV0212A EV0211B |
| EV0049 | EV0049A EV0049B | EV0099 | EV0067A EV0099B | EV0213 | EV0213A EV0211B |
| EV0050 | EV0050A EV0050B | EV0100 | EV0068A EV0100B | | |

Summary abbreviations table— Table 4

| Abbreviation | Meaning |
|---|---|
| mA, mU, mC, mG | 2'-O-Methyl RNA nucleotides |
| 2'-OMe | 2'-O-Methyl modification |
| fA, fU, fC, fG | 2' deoxy-2'-F RNA nucleotides |
| 2'-F | 2'-fluoro modification |
| (ps) | phosphorothioate |
| (ps2) | phosphorodithioate |
| (vp) | Vinyl-(E)-phosphonate |
| (vp)-mU | |
| (vp)-mU-phos | |
| ivA, ivC, ivU, ivG | inverted RNA (3'-3') nucleotides |

-continued

| Abbreviation | Meaning |
|---|---|
| | Summary abbreviations table— Table 4 |
| ST23 | (structure: GalNAc sugar with NHAc, OH groups, linked via O-butyl-O tether) |
| ST23-phos | (structure: acetylated GalNAc with NHAc, OAc groups, linked via O-butyl-O to phosphoramidite with N(iPr)₂ and OCH₂CH₂CN) |
| ST43 (or C6XLT) | (structure: tris-branched triol with three propyloxy arms and one hexyloxy arm from a central quaternary carbon) |
| ST43-phos (or C6XLT-phos) | (structure: tris-DMT-protected C6XLT with phosphoramidite: NiPr₂, OCH₂CH₂CN) |

-continued
Summary abbreviations table— Table 4
| Abbreviation | Meaning |
|---|---|
| Ser(GN) (when at the end of a chain, one of the O--- is OH) | 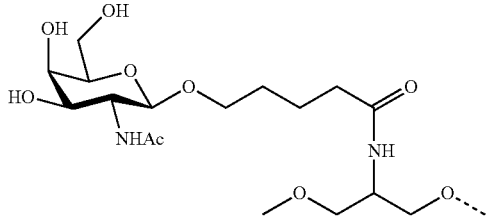 |
| [ST23(ps)]3 ST43 (ps) | 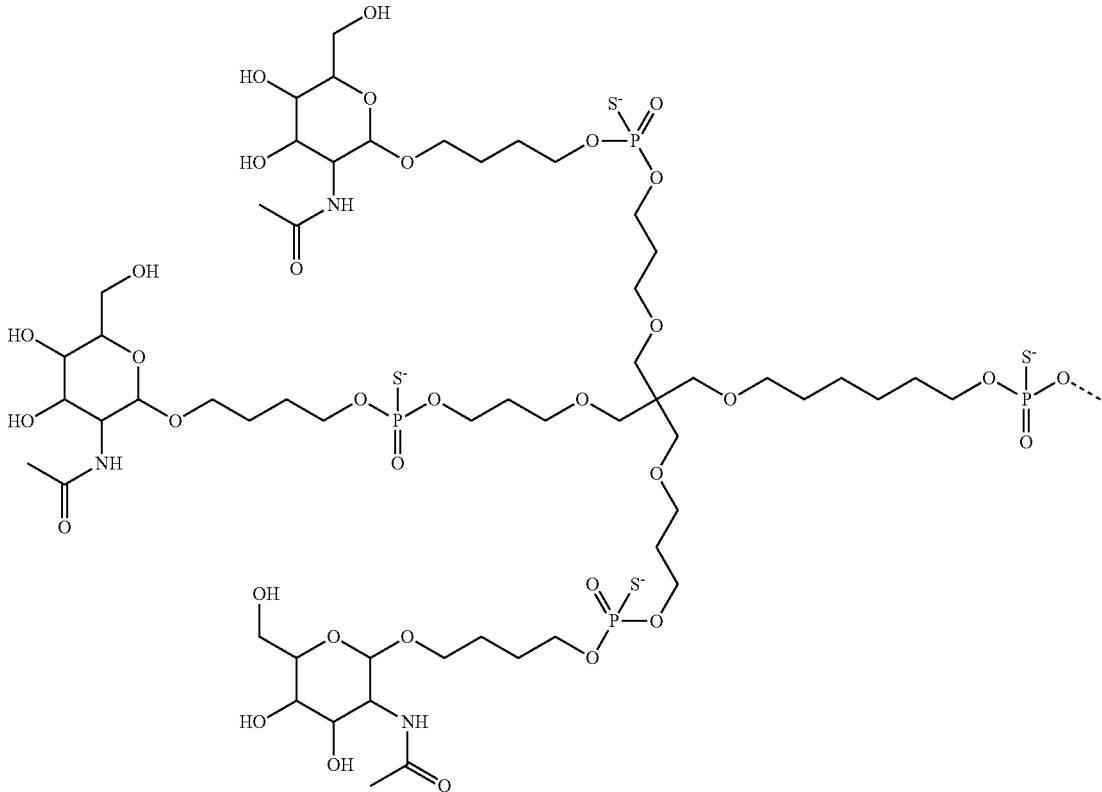 |

Summary abbreviations table— Table 4

| Abbreviation | Meaning |
|---|---|
| [ST23]3 ST43 | 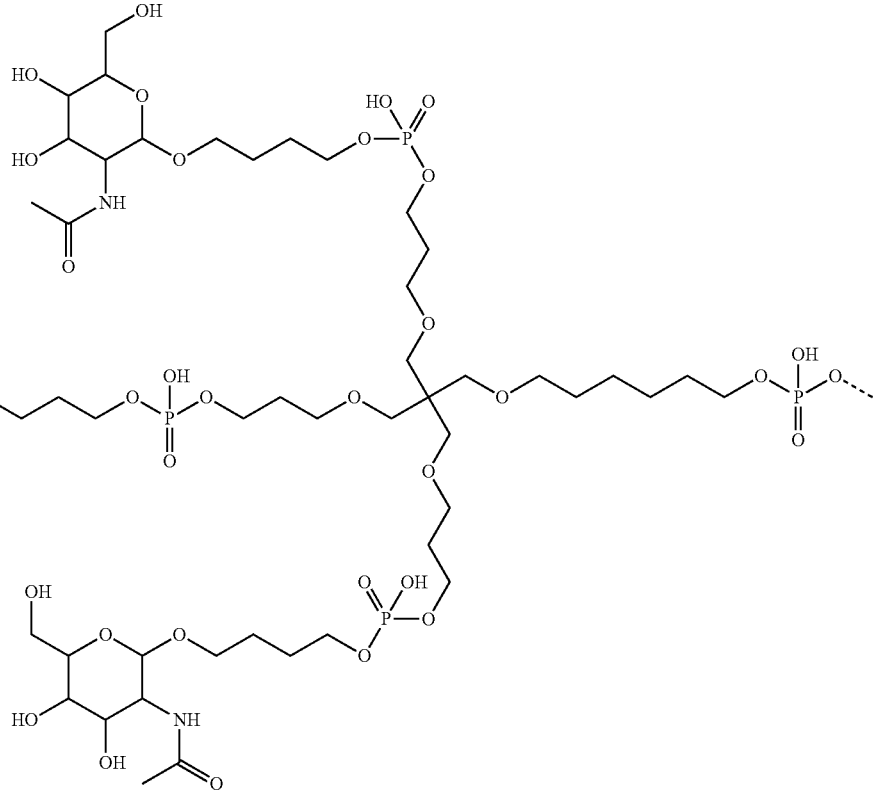 |

The abbreviations as shown in the above abbreviation table may be used herein. The list of abbreviations may not be exhaustive and further abbreviations and their meaning may be found throughout this document.

TABLE 5

Summary sequence table

| SEQ ID NO: | Name (A = 1st strand; B = 2nd strand) | Sequence 5'-3' | Unmodified sequence 5'-3' counterpart |
|---|---|---|---|
| 1 | EV0001Aun | UUUCAUAGUAGGCUCGGAU | UUUCAUAGUAGGCUCGGAU |
| 2 | EV0001Bun | AUCCGAGCCUACUAUGAAA | AUCCGAGCCUACUAUGAAA |
| 3 | EV0002Aun | UUUCUCUGUAGGCUCCACU | UUUCUCUGUAGGCUCCACU |
| 4 | EV0002Bun | AGUGGAGCCUACAGAGAAA | AGUGGAGCCUACAGAGAAA |
| 5 | EV0003Aun | UUAUAGAUGUAGUAGAAUU | UUAUAGAUGUAGUAGAAUU |
| 6 | EV0003Bun | AAUUCUACUACAUCUAUAA | AAUUCUACUACAUCUAUAA |
| 7 | EV0004Aun | AUGACAAAGGCAGUUCCCU | AUGACAAAGGCAGUUCCCU |
| 8 | EV0004Bun | AGGGAACUGCCUUUGUCAU | AGGGAACUGCCUUUGUCAU |
| 9 | EV0005Aun | AUCUGGUAGGGAGAGGUCA | AUCUGGUAGGGAGAGGUCA |
| 10 | EV0005Bun | UGACCUCUCCCUACCAGAU | UGACCUCUCCCUACCAGAU |
| 11 | EV0006Aun | UGUGUGUUGAUGCUGAGUU | UGUGUGUUGAUGCUGAGUU |

TABLE 5-continued

Summary sequence table

| SEQ ID NO: | Name (A = 1st strand; B = 2nd strand) | Sequence 5'-3' | Unmodified sequence 5'-3' counterpart |
|---|---|---|---|
| 12 | EV0006Bun | AACUCAGCAUCAACACACA | AACUCAGCAUCAACACACA |
| 13 | EV0007Aun | UAAUUGUUGGAGUUGCCCA | UAAUUGUUGGAGUUGCCCA |
| 14 | EV0007Bun | UGGGCAACUCCAACAAUUA | UGGGCAACUCCAACAAUUA |
| 15 | EV0008Aun | AGGAAGUUGACGUUGAGGG | AGGAAGUUGACGUUGAGGG |
| 16 | EV0008Bun | CCCUCAACGUCAACUUCCU | CCCUCAACGUCAACUUCCU |
| 17 | EV0009Aun | AUGAAGUCGGUGGUGAUGG | AUGAAGUCGGUGGUGAUGG |
| 18 | EV0009Bun | CCAUCACCACCGACUUCAU | CCAUCACCACCGACUUCAU |
| 19 | EV0010Aun | UUUACCACCAGCGAGCCCA | UUUACCACCAGCGAGCCCA |
| 20 | EV0010Bun | UGGGCUCGCUGGUGGUAAA | UGGGCUCGCUGGUGGUAAA |
| 21 | EV00HAun | UCUAUCUUCAGGGUCAUCU | UCUAUCUUCAGGGUCAUCU |
| 22 | EV00HBun | AGAUGACCCUGAAGAUAGA | AGAUGACCCUGAAGAUAGA |
| 23 | EV0012Aun | AUGUAGUUGCAGCAGUCCA | AUGUAGUUGCAGCAGUCCA |
| 24 | EV0012Bun | UGGACUGCUGCAACUACAU | UGGACUGCUGCAACUACAU |
| 25 | EV0013Aun | AAUAUAUUCAUGAGCUUCG | AAUAUAUUCAUGAGCUUCG |
| 26 | EV0013Bun | CGAAGCUCAUGAAUAUAUU | CGAAGCUCAUGAAUAUAUU |
| 27 | EV0014Aun | AAAUAUAUUCAUGAGCUUC | AAAUAUAUUCAUGAGCUUC |
| 28 | EV0014Bun | GAAGCUCAUGAAUAUAUUU | GAAGCUCAUGAAUAUAUUU |
| 29 | EV0015Aun | UCCUGCAUUACUGUGACCU | UCCUGCAUUACUGUGACCU |
| 30 | EV0015Bun | AGGUCACAGUAAUGCAGGA | AGGUCACAGUAAUGCAGGA |
| 31 | EV0016Aun | CAACAGAGUAGGGUAGCCG | CAACAGAGUAGGGUAGCCG |
| 32 | EV0016Bun | CGGCUACCCUACUCUGUUG | CGGCUACCCUACUCUGUUG |
| 33 | EV0017Aun | UCGAACAACAGAGUAGGGU | UCGAACAACAGAGUAGGGU |
| 34 | EV0017Bun | ACCCUACUCUGUUGUUCGA | ACCCUACUCUGUUGUUCGA |
| 35 | EV0018Aun | UUUCGAACAACAGAGUAGG | UUUCGAACAACAGAGUAGG |
| 36 | EV0018Bun | CCUACUCUGUUGUUCGAAA | CCUACUCUGUUGUUCGAAA |
| 37 | EV0019Aun | GUUUCAUCCAGGUAAUGCA | GUUUCAUCCAGGUAAUGCA |
| 38 | EV0019Bun | UGCAUUACCUGGAUGAAAC | UGCAUUACCUGGAUGAAAC |
| 39 | EV0020Aun | UUAUCUUUGGCUGUGGUCA | UUAUCUUUGGCUGUGGUCA |
| 40 | EV0020Bun | UGACCACAGCCAAAGAUAA | UGACCACAGCCAAAGAUAA |
| 41 | EV0021Aun | UGUUCAUUGAGCCAACGCA | UGUUCAUUGAGCCAACGCA |
| 42 | EV0021Bun | UGCGUUGGCUCAAUGAACA | UGCGUUGGCUCAAUGAACA |
| 43 | EV0023Aun | UUGGUAUUGAGCCAAGGCU | UUGGUAUUGAGCCAAGGCU |
| 44 | EV0023Bun | AGCCUUGGCUCAAUACCAA | AGCCUUGGCUCAAUACCAA |
| 45 | EV0024Aun | UUUAUUACAGGUGAGUUGA | UUUAUUACAGGUGAGUUGA |
| 46 | EV0024Bun | UCAACUCACCUGUAAUAAA | UCAACUCACCUGUAAUAAA |
| 47 | EV0025Aun | UUUCUGUUUCCGGUGCUGG | UUUCUGUUUCCGGUGCUGG |

TABLE 5-continued

Summary sequence table

| SEQ ID NO: | Name (A = 1st strand; B = 2nd strand) | Sequence 5'-3' | Unmodified sequence 5'-3' counterpart |
|---|---|---|---|
| 48 | EV0025Bun | CCAGCACCGGAAACAGAAA | CCAGCACCGGAAACAGAAA |
| 49 | EV0026Aun | UCAAGGAUCAUAGUGUUCU | UCAAGGAUCAUAGUGUUCU |
| 50 | EV0026Bun | AGAACACUAUGAUCCUUGA | AGAACACUAUGAUCCUUGA |
| 51 | EV0027Aun | AUCUCAAGGAUCAUAGUGU | AUCUCAAGGAUCAUAGUGU |
| 52 | EV0027Bun | ACACUAUGAUCCUUGAGAU | ACACUAUGAUCCUUGAGAU |
| 53 | EV0028Aun | UCAUACUUGGAGAUGUAUC | UCAUACUUGGAGAUGUAUC |
| 54 | EV0028Bun | GAUACAUCUCCAAGUAUGA | GAUACAUCUCCAAGUAUGA |
| 55 | EV0029Aun | UAUCGGAGAAGGCUUUGUC | UAUCGGAGAAGGCUUUGUC |
| 56 | EV0029Bun | GACAAAGCCUUCUCCGAUA | GACAAAGCCUUCUCCGAUA |
| 57 | EV0030Aun | AUGAUGAGGGUGUUCCUAU | AUGAUGAGGGUGUUCCUAU |
| 58 | EV0030Bun | AUAGGAACACCCUCAUCAU | AUAGGAACACCCUCAUCAU |
| 59 | EV0031Aun | UAUUGGUGAACUUUGAAAG | UAUUGGUGAACUUUGAAAG |
| 60 | EV0031Bun | CUUUCAAAGUUCACCAAUA | CUUUCAAAGUUCACCAAUA |
| 61 | EV0032Aun | AGCUUGUUCAGCUUUCCAU | AGCUUGUUCAGCUUUCCAU |
| 62 | EV0032Bun | AUGGAAAGCUGAACAAGCU | AUGGAAAGCUGAACAAGCU |
| 63 | EV0033Aun | UUUGUAUGAAGCAAUUCUC | UUUGUAUGAAGCAAUUCUC |
| 64 | EV0033Bun | GAGAAUUGCUUCAUACAAA | GAGAAUUGCUUCAUACAAA |
| 65 | EV0034Aun | GUCUUGUACACAUAGUCCA | GUCUUGUACACAUAGUCCA |
| 66 | EV0034Bun | UGGACUAUGUGUACAAGAC | UGGACUAUGUGUACAAGAC |
| 67 | EV0035Aun | UGCUCAAUGGCCAUGAUGU | UGCUCAAUGGCCAUGAUGU |
| 68 | EV0035Bun | ACAUCAUGGCCAUUGAGCA | ACAUCAUGGCCAUUGAGCA |
| 69 | EV0036Aun | UUGGCAUUCGUCCUCCUCG | UUGGCAUUCGUCCUCCUCG |
| 70 | EV0036Bun | CGAGGAGGACGAAUGCCAA | CGAGGAGGACGAAUGCCAA |
| 71 | EV0037Aun | GUCUGGAUGAAGAGGUACC | GUCUGGAUGAAGAGGUACC |
| 72 | EV0037Bun | GGUACCUCUUCAUCCAGAC | GGUACCUCUUCAUCCAGAC |
| 73 | EV0038Aun | UGUCUGGAUGAAGAGGUAC | UGUCUGGAUGAAGAGGUAC |
| 74 | EV0038Bun | GUACCUCUUCAUCCAGACA | GUACCUCUUCAUCCAGACA |
| 75 | EV0039Aun | UCUGUCUGGAUGAAGAGGU | UCUGUCUGGAUGAAGAGGU |
| 76 | EV0039Bun | ACCUCUUCAUCCAGACAGA | ACCUCUUCAUCCAGACAGA |
| 77 | EV0040Aun | CUUGUCUGUCUGGAUGAAG | CUUGUCUGUCUGGAUGAAG |
| 78 | EV0040Bun | CUUCAUCCAGACAGACAAG | CUUCAUCCAGACAGACAAG |
| 79 | EV0041Aun | AUGGUCUUGUCUGUCUGGA | AUGGUCUUGUCUGUCUGGA |
| 80 | EV0041Bun | UCCAGACAGACAAGACCAU | UCCAGACAGACAAGACCAU |
| 81 | EV0042Aun | AGAUGGUCUUGUCUGUCUG | AGAUGGUCUUGUCUGUCUG |
| 82 | EV0042Bun | CAGACAGACAAGACCAUCU | CAGACAGACAAGACCAUCU |
| 83 | EV0043Aun | GUAGAUGGUCUUGUCUGUC | GUAGAUGGUCUUGUCUGUC |

TABLE 5-continued

Summary sequence table

| SEQ ID NO: | Name (A = 1st strand; B = 2nd strand) | Sequence 5'-3' | Unmodified sequence 5'-3' counterpart |
|---|---|---|---|
| 84 | EV0043Bun | GACAGACAAGACCAUCUAC | GACAGACAAGACCAUCUAC |
| 85 | EV0044Aun | GUGUAGAUGGUCUUGUCUG | GUGUAGAUGGUCUUGUCUG |
| 86 | EV0044Bun | CAGACAAGACCAUCUACAC | CAGACAAGACCAUCUACAC |
| 87 | EV0045Aun | GGGGUGUAGAUGGUCUUGU | GGGGUGUAGAUGGUCUUGU |
| 88 | EV0045Bun | ACAAGACCAUCUACACCCC | ACAAGACCAUCUACACCCC |
| 89 | EV0046Aun | UAGGCUCGGAUCUUCCACU | UAGGCUCGGAUCUUCCACU |
| 90 | EV0046Bun | AGUGGAAGAUCCGAGCCUA | AGUGGAAGAUCCGAGCCUA |
| 91 | EV0047Aun | CUCGAAACUGGGCAGCACG | CUCGAAACUGGGCAGCACG |
| 92 | EV0047Bun | CGUGCUGCCCAGUUUCGAG | CGUGCUGCCCAGUUUCGAG |
| 93 | EV0048Aun | UUGGUGAAGUGGAUCUGGU | UUGGUGAAGUGGAUCUGGU |
| 94 | EV0048Bun | ACCAGAUCCACUUCACCAA | ACCAGAUCCACUUCACCAA |
| 95 | EV0049Aun | UCUUGGUGAAGUGGAUCUG | UCUUGGUGAAGUGGAUCUG |
| 96 | EV0049Bun | CAGAUCCACUUCACCAAGA | CAGAUCCACUUCACCAAGA |
| 97 | EV0050Aun | GUCUUGGUGAAGUGGAUCU | GUCUUGGUGAAGUGGAUCU |
| 98 | EV0050Bun | AGAUCCACUUCACCAAGAC | AGAUCCACUUCACCAAGAC |
| 99 | EV0051Aun | GGUGUCUUGGUGAAGUGGA | GGUGUCUUGGUGAAGUGGA |
| 100 | EV0051Bun | UCCACUUCACCAAGACACC | UCCACUUCACCAAGACACC |
| 101 | EV0052Aun | AACACCAUGAGGUCAAAGG | AACACCAUGAGGUCAAAGG |
| 102 | EV0052Bun | CCUUUGACCUCAUGGUGUU | CCUUUGACCUCAUGGUGUU |
| 103 | EV0053Aun | GAACACCAUGAGGUCAAAG | GAACACCAUGAGGUCAAAG |
| 104 | EV0053Bun | CUUUGACCUCAUGGUGUUC | CUUUGACCUCAUGGUGUUC |
| 105 | EV0054Aun | GUCACGAACACCAUGAGGU | GUCACGAACACCAUGAGGU |
| 106 | EV0054Bun | ACCUCAUGGUGUUCGUGAC | ACCUCAUGGUGUUCGUGAC |
| 107 | EV0055Aun | ACACAGAUCCCUUUCUUGU | ACACAGAUCCCUUUCUUGU |
| 108 | EV0055Bun | ACAAGAAAGGGAUCUGUGU | ACAAGAAAGGGAUCUGUGU |
| 109 | EV0058Aun | CCUUGCAGGAGAAUUCUGG | CCUUGCAGGAGAAUUCUGG |
| 110 | EV0058Bun | CCAGAAUUCUCCUGCAAGG | CCAGAAUUCUCCUGCAAGG |
| 111 | EV0059Aun | AGAGAGAAGACCUUGACCA | AGAGAGAAGACCUUGACCA |
| 112 | EV0059Bun | UGGUCAAGGUCUUCUCUCU | UGGUCAAGGUCUUCUCUCU |
| 113 | EV0060Aun | GAGUCGAUGGCGAUGAGGU | GAGUCGAUGGCGAUGAGGU |
| 114 | EV0060Bun | ACCUCAUCGCCAUCGACUC | ACCUCAUCGCCAUCGACUC |
| 115 | EV0061Aun | GCUUGGAACACCAUGAAGG | GCUUGGAACACCAUGAAGG |
| 116 | EV0061Bun | CCUUCAUGGUGUUCCAAGC | CCUUCAUGGUGUUCCAAGC |
| 117 | EV0062Aun | UCAUUUCCUUGGUCUCUU | UCAUUUCCUUGGUCUCUU |
| 118 | EV0062Bun | AAGAGACCAAGGAAAAUGA | AAGAGACCAAGGAAAAUGA |
| 119 | EV0063Aun | UGUGUCUGGAGCAAAGCCA | UGUGUCUGGAGCAAAGCCA |

TABLE 5-continued

Summary sequence table

| SEQ ID NO: | Name (A = 1st strand; B = 2nd strand) | Sequence 5'-3' | Unmodified sequence 5'-3' counterpart |
|---|---|---|---|
| 120 | EV0063Bun | UGGCUUUGCUCCAGACACA | UGGCUUUGCUCCAGACACA |
| 121 | EV0064Aun | AGGUAGAUGAUGAGGGUGU | AGGUAGAUGAUGAGGGUGU |
| 122 | EV0064Bun | ACACCCUCAUCAUCUACCU | ACACCCUCAUCAUCUACCU |
| 123 | EV0065Aun | UUGUAAUAGGCGUAGACCU | UUGUAAUAGGCGUAGACCU |
| 124 | EV0065Bun | AGGUCUACGCCUAUUACAA | AGGUCUACGCCUAUUACAA |
| 125 | EV0066Aun | GUUGUAAUAGGCGUAGACC | GUUGUAAUAGGCGUAGACC |
| 126 | EV0066Bun | GGUCUACGCCUAUUACAAC | GGUCUACGCCUAUUACAAC |
| 127 | EV0067Aun | GGGUCUUGUACACAUAGUC | GGGUCUUGUACACAUAGUC |
| 128 | EV0067Bun | GACUAUGUGUACAAGACCC | GACUAUGUGUACAAGACCC |
| 129 | EV0068Aun | CACUUGAUGGGCUGAUGA | CACUUGAUGGGCUGAUGA |
| 130 | EV0068Bun | UCAUCAGCCCAUCAAGUG | UCAUCAGCCCAUCAAGUG |
| 131 | EV0312Aun | AUUGUAAUAGGCGUAGACC | AUUGUAAUAGGCGUAGACC |
| 132 | EV0112Bun | GGUCUACGCCUAUUACAAU | GGUCUACGCCUAUUACAAU |
| 133 | EV0313Aun | AUGUAGAUGGUCUUGUCUG | AUGUAGAUGGUCUUGUCUG |
| 134 | EV0313Bun | CAGACAAGACCAUCUACAU | CAGACAAGACCAUCUACAU |
| 135 | EV0069Bun | GGUACCUCUUCAUCCAGAA | GGUACCUCUUCAUCCAGAA |
| 136 | EV0072Bun | CUUCAUCCAGACAGACAAA | CUUCAUCCAGACAGACAAA |
| 137 | EV0073Bun | UCCAGACAGACAAGACCAA | UCCAGACAGACAAGACCAA |
| 138 | EV0074Bun | CAGACAGACAAGACCAUCA | CAGACAGACAAGACCAUCA |
| 139 | EV0075Bun | GACAGACAAGACCAUCUAA | GACAGACAAGACCAUCUAA |
| 140 | EV0076Bun | CAGACAAGACCAUCUACAA | CAGACAAGACCAUCUACAA |
| 141 | EV0077Bun | ACAAGACCAUCUACACCCA | ACAAGACCAUCUACACCCA |
| 142 | EV0079Bun | CGUGCUGCCCAGUUUCGAA | CGUGCUGCCCAGUUUCGAA |
| 143 | EV0082Bun | AGAUCCACUUCACCAAGAA | AGAUCCACUUCACCAAGAA |
| 144 | EV0083Bun | UCCACUUCACCAAGACACA | UCCACUUCACCAAGACACA |
| 145 | EV0084Bun | CCUUUGACCUCAUGGUGUA | CCUUUGACCUCAUGGUGUA |
| 146 | EV0085Bun | CUUUGACCUCAUGGUGUUA | CUUUGACCUCAUGGUGUUA |
| 147 | EV0086Bun | ACCUCAUGGUGUUCGUGAA | ACCUCAUGGUGUUCGUGAA |
| 148 | EV0087Bun | ACAAGAAAGGGAUCUGUGA | ACAAGAAAGGGAUCUGUGA |
| 149 | EV0088Bun | AGGGAUCUGUGUGGCAGAA | AGGGAUCUGUGUGGCAGAA |
| 150 | EV0089Bun | AAUGCAGGACUUCUUCAUA | AAUGCAGGACUUCUUCAUA |
| 151 | EV0090Bun | CCAGAAUUCUCCUGCAAGA | CCAGAAUUCUCCUGCAAGA |
| 152 | EV0091Bun | UGGUCAAGGUCUUCUCUCA | UGGUCAAGGUCUUCUCUCA |
| 153 | EV0092Bun | ACCUCAUCGCCAUCGACUA | ACCUCAUCGCCAUCGACUA |
| 154 | EV0093Bun | CCUUCAUGGUGUUCCAAGA | CCUUCAUGGUGUUCCAAGA |
| 155 | EV0096Bun | ACACCCUCAUCAUCUACCA | ACACCCUCAUCAUCUACCA |

TABLE 5-continued

| SEQ ID NO: | Name (A = 1st strand; B = 2nd strand) | Sequence 5'-3' | Unmodified sequence 5'-3' counterpart |
|---|---|---|---|
| 156 | EV0098Bun | GGUCUACGCCUAUUACAAA | GGUCUACGCCUAUUACAAA |
| 157 | EV0099Bun | GACUAUGUGUACAAGACCA | GACUAUGUGUACAAGACCA |
| 158 | EV0100Bun | UCAUCAGCCCCAUCAAGUA | UCAUCAGCCCCAUCAAGUA |
| 159 | EV0001A | mU fU mU fC mA fU mA fG mU fA mG fG mC fU mC fG mG fA mU | UUUCAUAGUAGGCUCGGAU |
| 160 | EV0001B | fA mU fC mC fG mA fG mC fC mU fA mC fU mA fU mG fA mA fA | AUCCGAGCCUACUAUGAAA |
| 161 | EV0002A | mU fU mU fC mU fC mU fG mU fA mG fG mC fU mC fC mA fC mU | UUUCUCUGUAGGCUCCACU |
| 162 | EV0002B | fA mG fU mG fG mA fG mC fC mU fA mC fA mG fA mG fA mA fA | AGUGGAGCCUACAGAGAAA |
| 163 | EV0003A | mU fU mA fU mA fG mA fU mG fU mA fG mU fA mG fA mA fU mU | UUAUAGAUGUAGUAGAAUU |
| 164 | EV0003B | fA mA fU mU fC mU fA mC fU mA fC mA fU mC fU mA fU mA fA | AAUUCUACUACAUCUAUAA |
| 165 | EV0004A | mA fU mG fA mC fA mA fA mG fG mC fA mG fU mU fC mC fC mU | AUGACAAAGGCAGUUCCCU |
| 166 | EV0004B | fA mG fG mG fA mA fC mU fG mC fC mU fU mU fG mU fC mA fU | AGGGAACUGCCUUUGUCAU |
| 167 | EV0005A | mA fU mC fU mG fG mU fA mG fG mG fA mG fA mG fG mU fC mA | AUCUGGUAGGGAGAGGUCA |
| 168 | EV0005B | fU mG fA mC fC mU fC mU fC mC fC mU fA mC fC mA fG mA fU | UGACCUCUCCCUACCAGAU |
| 169 | EV0006A | mU fG mU fG mU fG mU fU mG fA mU fG mC fU mG fA mG fU mU | UGUGUGUUGAUGCUGAGUU |
| 170 | EV0006B | fA mA fC mU fC mA fG mC fA mU fC mA fA mC fA mC fA mC fA | AACUCAGCAUCAACACACA |
| 171 | EV0007A | mU fA mA fU mU fG mU fU mG fG mA fG mU fU mG fC mC fC mA | UAAUUGUUGGAGUUGCCCA |
| 172 | EV0007B | fU mG fG mG fC mA fA mC fU mC fC mA fA mC fA mA fU mU fA | UGGGCAACUCCAACAAUUA |
| 173 | EV0008A | mA fG mG fA mA fG mU fU mG fA mC fG mU fU mG fA mG fG mG | AGGAAGUUGACGUUGAGGG |
| 174 | EV0008B | fC mC fC mU fC mA fA mC fG mU fC mA fA mC fU mU fC mC fU | CCCUCAACGUCAACUUCCU |
| 175 | EV0009A | mA fU mG fA mA fG mU fC mG fG mU fG mG fU mG fA mU fG mG | AUGAAGUCGGUGGUGAUGG |
| 176 | EV0009B | fC mC fA mU fC mA fC mC fA mC fC mG fA mC fU mU fC mA fU | CCAUCACCACCGACUUCAU |
| 177 | EV0010A | mU fU mU fA mC fC mA fC mC fA mG fC mG fA mG fC mC fC mA | UUUACCACCAGCGAGCCCA |
| 178 | EV0010B | fU mG fG mG fC mU fC mG fC mU fG mG fU mG fG mU fA mA fA | UGGGCUCGCUGGUGGUAAA |
| 179 | EV0011A | mU fC mU fA mU fC mU fU mC fA mG fG mG fU mC fA mU fC mU | UCUAUCUUCAGGGUCAUCU |
| 180 | EV0011B | fA mG fA mU fG mA fC mC fC mU fG mA fA mG fA mU fA mG fA | AGAUGACCCUGAAGAUAGA |
| 181 | EV0012A | mA fU mG fU mA fG mU fU mG fC mA fG mC fA mG fU mC fC mA | AUGUAGUUGCAGCAGUCCA |
| 182 | EV0012B | fU mG fG mA fC mU fG mC fU mG fC mA fA mC fU mA fC mA fU | UGGACUGCUGCAACUACAU |
| 183 | EV0013A | mA fA mU fA mU fA mU fU mC fA mU fG mA fG mC fU mU fC mG | AAUAUAUUCAUGAGCUUCG |
| 184 | EV0013B | fC mG fA mA fG mC fU mC fA mU fG mA fA mU fA mU fA mU fU | CGAAGCUCAUGAAUAUAUU |
| 185 | EV0014A | mA fA mA fU mA fU mA fU mU fC mA fU mG fA mG fC mU fU mC | AAAUAUAUUCAUGAGCUUC |
| 186 | EV0014B | fG mA fA mG fC mU fC mA fU mG fA mA fU mA fU mA fU mU fU | GAAGCUCAUGAAUAUAUUU |
| 187 | EV0015A | mU fC mC fU mG fC mA fU mU fA mC fU mG fU mG fA mC fC mU | UCCUGCAUUACUGUGACCU |
| 188 | EV0015B | fA mG fG mU fC mA fC mA fG mU fA mA fU mG fC mA fG mG fA | AGGUCACAGUAAUGCAGGA |
| 189 | EV0016A | mC fA mA fC mA fG mA fG mU fA mG fG mG fU mA fG mC fC mG | CAACAGAGUAGGGUAGCCG |
| 190 | EV0016B | fC mG fG mC fU mA fC mC fC mU fA mC fU mC fU mG fU mU fG | CGGCUACCCUACUCUGUUG |
| 191 | EV0017A | mU fC mG fA mA fC mA fA mC fA mG fA mG fU mA fG mG fG mU | UCGAACAACAGAGUAGGGU |

TABLE 5-continued

Summary sequence table

| SEQ ID NO: | Name (A = 1st strand; B = 2nd strand) | Sequence 5'-3' | Unmodified sequence 5'-3' counterpart |
|---|---|---|---|
| 192 | EV0017B | fA mC fC mC fU mA fC mU fC mU fG mU fU mG fU mU fC mG fA | ACCCUACUCUGUUGUUCGA |
| 193 | EV0018A | mU fU mU fC mG fA mA fC mA fC mA fG mA fG mU fA fG mG | UUUCGAACAACAGAGUAGG |
| 194 | EV0018B | fC mC fU mA fC mU fC mU fG mU fU mG fU mU fC mG fA mA fA | CCUACUCUGUUGUUCGAAA |
| 195 | EV0019A | mG fU mU fU mC fA mU fC mC fA mG fU mA fA fU mG fC mA | GUUUCAUCCAGGUAAUGCA |
| 196 | EV0019B | fU mG fC mA fU mU fA mC fC mU fG mG fA mU fG mA fA mA fC | UGCAUUACCUGGAUGAAAC |
| 197 | EV0020A | mU fU mA fU mC fU mU fU mG fG mC fU mG fU mG fU fC mA | UUAUCUUUGGCUGUGGUCA |
| 198 | EV0020B | fU mG fA mC fC mA fC mA fG mC fC mA fA fA mG fA mU fA mA | UGACCACAGCCAAAGAUAA |
| 199 | EV0021A | mU fG mU fU mC fA mU fU mG fA mG fC mC fA mA fC mG fC mA | UGUUCAUUGAGCCAACGCA |
| 200 | EV0021B | fU mG fC mG fU mU fG mG fC mU fC mA fA fU mG mA fA mC fA | UGCGUUGGCUCAAUGAACA |
| 201 | EV0022A | mA fA mC fA mC fC mA fU mG fA mA fG mG fU mG fG mC fC mU | AACACCAUGAAGGUGGCCU |
| 202 | EV0022B | fA mG fG mC fC mA fC mC fU mU fC mA fU mG fG mU fG mU fU | AGGCCACCUUCAUGGUGUU |
| 203 | EV0023A | mU fU mG fG mU fA mU fU mG fA mG fC mC fA mA fG mG fC mU | UUGGUAUUGAGCCAAGGCU |
| 204 | EV0023B | fA mG fC mC fU mU fG mG fC mU fC mA fA fU mA fC mC fA mA | AGCCUUGGCUCAAUACCAA |
| 205 | EV0024A | mU fU mU fA mU fU mA fC mA fG mG fU mG fA mG fU mU fG mA | UUUAUUACAGGUGAGUUGA |
| 206 | EV0024B | fU mC fA mA fC mU fC mA fC mC fU mG fU mA fA mU fA mA fA | UCAACUCACCUGUAAUAAA |
| 207 | EV0025A | mU fU mU fC mU fG mU fU mU fC mC fG mG fU mG fC mU fG mG | UUUCUGUUUCCGGUGCUGG |
| 208 | EV0025B | fC mC fA mG fC mA fC mC fG mG fA mA fA mC fA mG fA mA fA | CCAGCACCGGAAACAGAAA |
| 209 | EV0026A | mU fC mA fA mG fG mA fU mC fA mU fA mG fU mG fU mU fC mU | UCAAGGAUCAUAGUGUUCU |
| 210 | EV0026B | fA mG fA mA fC mA fC mU fA mU fG mA fU mC fC mU fU mG fA | AGAACACUAUGAUCCUUGA |
| 211 | EV0027A | mA fU mC fU mC fA mA fG mG fA mU fC mA fU mA fG mU fG mU | AUCUCAAGGAUCAUAGUGU |
| 212 | EV0027B | fA mC fA mC fU mA fU mG fA mU fC mC fU mU fG mA fG mA fU | ACACUAUGAUCCUUGAGAU |
| 213 | EV0028A | mU fC mA fU mA fC mU fU mG fG mA fG mA fU mG fU mA fU mC | UCAUACUUGGAGAUGUAUC |
| 214 | EV0028B | fG mA fU mA fC mA fU mC fU mC fC mA fA mG fU mA fU mG fA | GAUACAUCUCCAAGUAUGA |
| 215 | EV0029A | mU fA mU fC mG fG mA fG mA fA mG fG mC fU mU fU mG fU mC | UAUCGGAGAAGGCUUUGUC |
| 216 | EV0029B | fG mA fC mA fA mA fG mC fC mU fU mC fU mC fC mG fA mU fA | GACAAAGCCUUCUCCGAUA |
| 217 | EV0030A | mA fU mG fA mU fG mA fG mG fG mU fG mU fU mC fC mU fA mU | AUGAUGAGGGUGUUCCUAU |
| 218 | EV0030B | fA mU fA mG fG mA fA mC fA mC fC mC fU mC fA mU fC mA fU | AUAGGAACACCCUCAUCAU |
| 219 | EV0031A | mU fA mU fU mG fG mU fG mA fA mC fU mU fU mG fA mA fA mG | UAUGGUGAACUUUGAAAG |
| 220 | EV0031B | fC mU fU mU fC mA fA mA fG mU fU mC fA mC fC mA fU mA fA | CUUUCAAAGUUCACCAUA |
| 221 | EV0032A | mA fG mC fU mU fG mU fU mC fA mG fC mU fU mU fC mC fA mU | AGCUUGUUCAGCUUUCCAU |
| 222 | EV0032B | fA mU fG mG fA mA fA mG fC mU fG mA fA mC fA mA fG mC fU | AUGGAAAGCUGAACAAGCU |
| 223 | EV0033A | mU fU mU fG mU fA mU fG mA fA mG fC mA fA fU mU fC mU fC | UUUGUAUGAAGCAAUUCUC |
| 224 | EV0033B | fG mA fG mA fA mU fU mG fC mU fU mC fA mU fA mC fA mA fA | GAGAAUUGCUUCAUACAAA |
| 225 | EV0034A | mG fU mC fU mU fG mU fA mC fA mU fA mG fU mC fC mA | GUCUUGUACAUAGUCCA |
| 226 | EV0034B | fU mG fG mA fC mU fA mU fG mU fA mC fA mA fG mA fC | UGGACUAUGUACAAGAC |
| 227 | EV0035A | mU fG mC fU mC fA mA fU mG fG mC fC mA fU mG fA mU fG mU | UGCUCAAUGGCCAUGAUGU |

TABLE 5-continued

Summary sequence table

| SEQ ID NO: | Name (A = 1st strand; B = 2nd strand) | Sequence 5'-3' | Unmodified sequence 5'-3' counterpart |
|---|---|---|---|
| 228 | EV0035B | fA mC fA mU fC mA fU mG fG mC fC mA fU mU fG mA fG mC fA | ACAUCAUGGCCAUUGAGCA |
| 229 | EV0036A | mU fU mG fG mC fA mU fU mC fG mU fC mC fU mC fU mC mG | UUGGCAUUCGUCCUCCUCG |
| 230 | EV0036B | fC mG fA mG fG mA fG mG fA mC fG mA fA mU fG mC fC mA fA | CGAGGAGGACGAAUGCCAA |
| 231 | EV0037A | mG fU mC fU mG fG mA fU mG fA mA fG mA fG mG fU mA fC mC | GUCUGGAUGAAGAGGUACC |
| 232 | EV0037B | fG mG fU mA fC mC fU mC fU mU fC mA fU mC fC mA fG mA fC | GGUACCUCUUCAUCCAGAC |
| 233 | EV0038A | mU fG mU fC mU fG mG fA mU fG mA fA fG mA fG mG fU mA fC | UGUCUGGAUGAAGAGGUAC |
| 234 | EV0038B | fG mU fA mC fC mU fC mU fU fC mA fU mC fC mA fG mA fC mA | GUACCUCUUCAUCCAGACA |
| 235 | EV0039A | mU fC mU fG mU fC mU fG mG fA mU fG mA fA fG mA fG mG fU | UCUGUCGGAUGAAGAGGU |
| 236 | EV0039B | fA mC fC mU fC mU fU mC fA mU fC mC fA mG fA mC fA mG fA | ACCUCUUCAUCCAGACAGA |
| 237 | EV0040A | mC fU mU fG mU fC mU fG mU fC mU fG mG fA mU fG mA fA mG | CUUGUCUGUCUGGAUGAAG |
| 238 | EV0040B | fC mU fU mC fA mU fC mC fA mG fA mC fA mG fA mC fA mA fG | CUUCAUCCAGACAGACAAG |
| 239 | EV0041A | mA fU mG fG mU fC mU fU mG fU mC fU mG fU mC fU mG mG fA | AUGGUCUUGUCUGUCUGGA |
| 240 | EV0041B | fU mC fC mA fG mA fC mA fG mA fA mG fA mC fC mA fU | UCCAGACAGACAAGACCAU |
| 241 | EV0042A | mA fG mA fU mG fG mU fC mU fU mG fU mC fU mG fU mC fU mG | AGAUGGUCUUGUCUGUCUG |
| 242 | EV0042B | fC mA fG mA fC mA fG mA fC mA fA mG fA mC fC mA fU mC fU | CAGACAGACAAGACCAUCU |
| 243 | EV0043A | mG fU mA fG mA fU mG fG mU fC mU fU mG fU mC fU mG fU mC | GUAGAUGGUCUUGUCUGUC |
| 244 | EV0043B | fG mA fC mA fG mA fC mA fA mG fA mC fC mA fU mC fU mA fC | GACAGACAAGACCAUCUAC |
| 245 | EV0044A | mG fU mG fU mA fG mA fU mG fG mU fC mU fU mG fU mC fU mG | GUGUAGAUGGUCUUGUCUG |
| 246 | EV0044B | fC mA fG mA fC mA fA mG fA mC fC mA fU mC fU mA fC mA fC | CAGACAAGACCAUCUACAC |
| 247 | EV0045A | mG fG mG fG mU fG mU fA mG fA mU fG mG fU mC fU mU fG mU | GGGGUGUAGAUGGUCUUGU |
| 248 | EV0045B | fA mC fA mA fG mA fC mC fA mU fC mU fA mC fA mC fC mC fC | ACAAGACCAUCUACACCCC |
| 249 | EV0046A | mU fA mG fG mC fU mC fG mG fA mU fC mU fU mC fC mA fC mU | UAGGCUCGGAUCUUCCACU |
| 250 | EV0046B | fA mG fU mG fG mA fA mG fA mU fC mC fG mA fG mC fC mU fA | AGUGGAAGAUCCGAGCCUA |
| 251 | EV0047A | mC fU mC fG mA fA mA fC mU fG mG fG mC fA mG fC mA fC mG | CUCGAAACUGGGCAGCACG |
| 252 | EV0047B | fC mG fU mG fC mU fG mC fC mC fA mG fU mU fU fC mG mA fG | CGUGCUGCCCAGUUUCGAG |
| 253 | EV0048A | mU fU mG fG mU fG mA fA mG fU mG fG mA fU mC fU mG fG mU | UUGGUGAAGUGGAUCUGGU |
| 254 | EV0048B | fA mC fC mA fG mA fU mC fC mA fC mU fU mC fA mC fC mA fA | ACCAGAUCCACUUCACCAA |
| 255 | EV0049A | mU fC mU fU mG fG mU fG mA fA mG fU mG fG mA fU mC fU mG | UCUUGGUGAAGUGGAUCUG |
| 256 | EV0049B | fC mA fG mA fU mC fC mA fC mU fU mC fA mC fC mA fA mG fA | CAGAUCCACUUCACCAAGA |
| 257 | EV0050A | mG fU mC fU mU fG mG fU mG fA mA fG mU fG mG fA mU fC mU | GUCUUGGUGAAGUGGAUCU |
| 258 | EV0050B | fA mG fA mU fC mC fA mC fU mU fC mA fC mC fA mA fG mA fC | AGAUCCACUUCACCAAGAC |
| 259 | EV0051A | mG fG mU fG mU fC mU fU mG fG mU fG mA fA mG fU mG fG mA | GGUGUCUUGGUGAAGUGGA |
| 260 | EV0051B | fU mC fC mA fC mU fU mC fA mC fC mA fA mG fA mC fA mC fC | UCCACUUCACCAAGACACC |
| 261 | EV0052A | mA fA mC fA mC fA mU fG mA fG mG fU mC fA mA fA mG fG | AACACCAUGAGGUCAAAGG |
| 262 | EV0052B | fC mC fU mU fU mG fA mC fC mU fC mA fU mG fG mU fG mU fU | CCUUUGACCUCAUGGUGUU |
| 263 | EV0053A | mG fA mA fC mA fC mC fA mU fG mA fG mG fU mC fA mA fA mG | GAACACCAUGAGGUCAAAG |

TABLE 5-continued

Summary sequence table

| SEQ ID NO: | Name (A = 1st strand; B = 2nd strand) | Sequence 5'-3' | Unmodified sequence 5'-3' counterpart |
|---|---|---|---|
| 264 | EV0053B | fC mU fU mU fG mA fC mC fU mC fA mU fG mG fU mG fU mU fC | CUUUGACCUCAUGGUGUUC |
| 265 | EV0054A | mG fU mC fA mC fG mA fA mC fA mC fC mA fU mG fA mG fG mU | GUCACGAACACCAUGAGGU |
| 266 | EV0054B | fA mC fC mU fC mA fU mG fG mU fG mU fU mC fG mU fG mA fC | ACCUCAUGGUGUUCGUGAC |
| 267 | EV0055A | mA fC mA fC mA fG mA fU mC fC mC fU fU mC fU mU fG mU | ACACAGAUCCCUUUCUUGU |
| 268 | EV0055B | fA mC fA mA fG mA fA mA fG mG fG mA fU mC fU mG fU mG fU | ACAAGAAAGGGAUCUGUGU |
| 269 | EV0056A | mG fU mC fU mG fC mC fA mC fA mC fA mG fA mU fC mC fC mU | GUCUGCCACACAGAUCCCU |
| 270 | EV0056B | fA mG fG mG fA mU fC mU fG mU fG mU fG mG fC mA fG mA fC | AGGGAUCUGUGUGGCAGAC |
| 271 | EV0057A | mG fA mU fG mA fA mG fA mA mG fU mC fC mU fG mC fA mU fU | GAUGAAGAAGUCCUGCAUU |
| 272 | EV0057B | fA mA fU mG fC mA fG mG fA mC fU mU fC mU fU mC fA mU fC | AAUGCAGGACUUCUUCAUC |
| 273 | EV0058A | mC fC mU fU mG fC mA fG mG fA mG fA mA fU mU fC mU fG mG | CCUUGCAGGAGAAUUCUGG |
| 274 | EV0058B | fC mC fA mG fA mA fU mU fC mU fC mC fU mG fC mA fA mG fG | CCAGAAUUCUCCUGCAAGG |
| 275 | EV0059A | mA fG mA fG mA fG mA fA mG fA mC fC mU fU mG fA mC fC mA | AGAGAGAAGACCUUGACCA |
| 276 | EV0059B | fU mG fG mU fC mA fA mG fG mU fC mU fU mC fU mC fU mC fU | UGGUCAAGGUCUUCUCUCU |
| 277 | EV0060A | mG fA mG fU mC fG mA fU mG fG mC fG mA fU mG fA mG fG mU | GAGUCGAUGGCGAUGAGGU |
| 278 | EV0060B | fA mC fC mU fC mA fU mC fG mC fC mA fU mC fG mA fC mU fC | ACCUCAUCGCCAUCGACUC |
| 279 | EV0061A | mG fC mU fU mG fG mA fA mC fA mC fC mA fU mG fA mA fG mG | GCUUGGAACACCAUGAAGG |
| 280 | EV0061B | fC mC fU mU fC mA fU mG fG mU fG mU fU mC fC mA fA mG fC | CCUUCAUGGUGUUCCAAGC |
| 281 | EV0062A | mU fC mA fU mU fU mU fC mC fU mU fG mG fU mC fU mC fU mU | UCAUUUUCCUUGGUCUCUU |
| 282 | EV0062B | fA mA fG mA fG mA fC mC fA mA fG mG fA mA fA mA fU mG fA | AAGAGACCAAGGAAAAUGA |
| 283 | EV0063A | mU fG mU fG mU fC mU fG mG fA mG fC mA fA mA fG mC fC mA | UGUGUCUGGAGCAAAGCCA |
| 284 | EV0063B | fU mG fG mC fU mU fU mG fC mU fC mC fA mG fA mC fA mC fA | UGGCUUUGCUCCAGACACA |
| 285 | EV0064A | mA fG mG fU mA fG mA fU mG fA mU fG mA fG mG fG mU fG mU | AGGUAGAUGAUGAGGGUGU |
| 286 | EV0064B | fA mC fA mC fC mC fU mC fA mU fC mU fA mC fC mU | ACACCCUCAUCAUCUACCU |
| 287 | EV0065A | mU fU mG fU mA fA mU fA mG fG mC fG mU fA mG fA mC fC mU | UUGUAAUAGGCGUAGACCU |
| 288 | EV0065B | fA mG fG mU fC mU fA mC fG mC mC fU mA fU mU fA mC fA mA | AGGUCUACGCCUAUUACAA |
| 289 | EV0066A | mG fU mU fG mU fA mA fU mA fG mG fC mG fU mA fG mA fC mC | GUUGUAAUAGGCGUAGACC |
| 290 | EV0066B | fG mG fU mC fU mA fC mG fC mC fU mA fU mU fA mC fA mA fC | GGUCUACGCCUAUUACAAC |
| 291 | EV0067A | mG fG mG fU mC fU mU fG mU fA mC fA mU fA mG fU mC | GGGUCUUGUACAUAGUC |
| 292 | EV0067B | fG mA fC mU fA mU fG mU fG mU fA mC fA mA fG mA fC mC fC | GACUAUGUGUACAAGACCC |
| 293 | EV0068A | mC fA mC fU mU fG mA fU mG fG mG fC mU fG mA fU mG fA | CACUUGAUGGGCUGAUGA |
| 294 | EV0068B | fU mC fA mU fC mA fG mC fC mC fC mA fU mC fA mA fG mU fG | UCAUCAGCCCCAUCAAGUG |
| 295 | EV0069B | mG mG mU mA mC mC fU fC fU mC mA mU mC mC mA mG mA irA | GGUACCUCUUCAUCCAGAA |
| 296 | EV0070B | mG mU mA mC mC mU fC fU fU mC mA mU mC mC mA mG mA mC irA | GUACCUCUUCAUCCAGACA |
| 297 | EV0071B | mA mC mC mU mC fU fU fC fA mU mC mC mA mG mA mC mA mG irA | ACCUCUUCAUCCAGACAGA |
| 298 | EV0072B | mC mU mU mC mA mU fC fC fA mG mA mC mA mG mA mC mA mA irA | CUUCAUCCAGACAGACAAA |
| 299 | EV0073B | mU mC mC mA mG mA fC fA fG mA mC mA mA mG mA mC mC mA irA | UCCAGACAGACAAGACCAA |

TABLE 5-continued

Summary sequence table

| SEQ ID NO: | Name (A = 1st strand; B = 2nd strand) | Sequence 5'-3' | Unmodified sequence 5'-3' counterpart |
|---|---|---|---|
| 300 | EV0074B | mC mA mG mA mC mA fG fA fC mA mA mG mA mC mC mA mU mC irA | CAGACAGACAAGACCAUCA |
| 301 | EV0075B | mG mA mC mA mG fC fA fA mG mA mC mC mA mU mC mU mA irA | GACAGACAAGACCAUCUAA |
| 302 | EV0076B | mC mA mG mA mC fA fG fA mC mC mA mU mU mA mC mA irA | CAGACAAGACCAUCUACAA |
| 303 | EV0077B | mA mC mA mA mG fC fC fA mU mC mU mA mC mA mC mC mC irA | ACAAGACCAUCUACACCCA |
| 304 | EV0078B | mA mG mU mG mG mA fA fG fA mU mC mC mG mA mG mC mC mU irA | AGUGGAAGAUCCGAGCCUA |
| 305 | EV0079B | mC mG mU mG mC mU fG fC fC mC mA mG mU mU mU mC mG mA irA | CGUGCUGCCCAGUUUCGAA |
| 306 | EV0080B | mA mC mC mA mG mA fU fC fC mA mC mU mU mC mA mC mC mA irA | ACCAGAUCCACUUCACCAA |
| 307 | EV0081B | mC mA mG mA mU mC fC fA fC mU mU mC mA mC mC mA mA mG irA | CAGAUCCACUUCACCAAGA |
| 308 | EV0082B | mA mG mA mU mC mC fA fC fU mU mC mA mC mC mA mA mG mA irA | AGAUCCACUUCACCAAGAA |
| 309 | EV0083B | mU mC mC mA mC mU fU fC fA mC mC mA mA mG mA mC mA mC irA | UCCACUUCACCAAGACACA |
| 310 | EV0084B | mC mC mU mU mU mG fA fC fC mU mC mA mU mG mG mU mG mU irA | CCUUUGACCUCAUGGUGUA |
| 311 | EV0085B | mC mU mU mU mG mA fC fC fU mC mA mU mG mG mU mG mU mU irA | CUUUGACCUCAUGGUGUUA |
| 312 | EV0086B | mA mC mC mU mC mA fU fG fG mU mG mU mU mC mG mU mG mA irA | ACCUCAUGGUGUUCGUGAA |
| 313 | EV0087B | mA mC mA mA mG mA fA fA fG mG mG mA mU mC mU mG mU mG irA | ACAAGAAAGGGAUCUGUGA |
| 314 | EV0088B | mA mG mG mG mA mU fC fU fG mU mG mU mG mG mC mA mG mA irA | AGGGAUCUGUGUGGCAGAA |
| 315 | EV0089B | mA mA mU mG mC mA fG fG fA mC mU mU mC mU mU mC mA mU irA | AAUGCAGGACUUCUUCAUA |
| 316 | EV0090B | mC mC mA mG mA mA fU fU fC mU mC mC mU mG mC mA mA mG irA | CCAGAAUUCUCCUGCAAGA |
| 317 | EV0091B | mU mG mG mU mC mA fA fG fG mU mC mU mU mC mU mC mU mC irA | UGGUCAAGGUCUUCUCUCA |
| 318 | EV0092B | mA mC mC mU mC mA fU fC fG mC mC mA mU mC mG mA mC mU irA | ACCUCAUCGCCAUCGACUA |
| 319 | EV0093B | mC mC mU mU mC mA fU fG fG mU mG mU mU mC mC mA mA mG irA | CCUUCAUGGUGUUCCAAGA |
| 320 | EV0094B | mA mA mG mA mG mA fC fC fA mA mG mG mA mA mA mA mU mG irA | AAGAGACCAAGGAAAAUGA |
| 321 | EV0095B | mU mG mG mC mU mU fU fG fC mU mC mC mA mG mA mC mA mC irA | UGGCUUUGCUCCAGACACA |
| 322 | EV0096B | mA mC mA mC mC mC fU fC fA mU mC mA mU mC mU mA mC mC irA | ACACCCUCAUCAUCUACCA |
| 323 | EV0097B | mA mG mG mU mC mU fA fC fG mC mC mU mA mU mU mA mC mA irA | AGGUCUACGCCUAUUACAA |
| 324 | EV0098B | mG mG mU mC mU mA fC fG fC mC mU mA mU mU mA mC mA mA irA | GGUCUACGCCUAUUACAAA |
| 325 | EV0099B | mG mA mC mU mA mU fG fU fG mU mA mC mA mA mG mA mC mC irA | GACUAUGUGUACAAGACCA |
| 326 | EV0100B | mU mC mA mU mC mA fG fC fC mC mA mU mC mA mA mG mU mA irA | UCAUCAGCCCCAUCAAGUA |
| 327 | EV0101A | mA (ps) fG (ps) mG fA mA fG mU fU mG fA mC fG mU fU mG fA mG (ps) fG (ps) mG | AGGAAGUUGACGUUGAGGG |
| 328 | EV0101B | [ST23 (ps)]3 ST43 (ps) fC mC fC mU fC mA fA mC fG mU fC mA fA mC fU mU fC (ps) mC (ps) fU | CCCUCAACGUCAACUUCCU |
| 329 | EV0102A | mA (ps) fA (ps) mU fA mU fA mU fU mC fA mU fG mA fG mC fU mU (ps) fC (ps) mG | AAUAUAUUCAUGAGCUUCG |
| 330 | EV0102B | [ST23 (ps)]3 ST43 (ps) fC mG fA mA fG mC fU mC fA mU fG mA fA mU fA mU (ps) fU (ps) mU | CGAAGCUCAUGAAUAUAUU |
| 331 | EV0103A | mA (ps) fU (ps) mG fA mU fG mA fG mG fG mU fG mU fC mC fU (ps) fA (ps) mU | AUGAUGAGGGUGUUCCUAU |
| 332 | EV0103B | [ST23 (ps)]3 ST43 (ps) fA mU fA mG fG mA fA mC fA mC fC mC fU mC fA mU (ps) fU (ps) fU | AUAGGAACACCCUCAUCAU |

TABLE 5-continued

Summary sequence table

| SEQ ID NO: | Name (A = 1st strand; B = 2nd strand) | Sequence 5'-3' | Unmodified sequence 5'-3' counterpart |
|---|---|---|---|
| 333 | EV0104A | mU (ps) fC (ps) mU fG mU fC mU fG mG fA mU fG mA fA mG fA mG (ps) fG (ps) mU | UCUGUCUGGAUGAAGAGGU |
| 334 | EV0104B | [ST23 (ps)]3 ST43 (ps) fA mC fC mU fC mU fU mC fA mU fC mC fA mG fA mC fA (ps) mG (ps) fA | ACCUCUUCAUCCAGACAGA |
| 335 | EV0105A | mG (ps) fU (ps) mA fG mA fU mG fG mU fC mU fU mG fU mC fU mG (ps) fU (ps) mC | GUAGAUGGUCUUGUCUGUC |
| 336 | EV0105B | [ST23 (ps)]3 ST43 (ps) fG mA fC mA fG mA fC mA fA mG fA mC fC mA fU mC fU (ps) mA (ps) fC | GACAGACAAGACCAUCUAC |
| 337 | EV0106A | mG (ps) fA (ps) mA fC mA fC mC fA mU fG mA fG mG fU mC fA mA (ps) fA (ps) mG | GAACACCAUGAGGUCAAAG |
| 338 | EV0106B | [ST23 (ps)]3 ST43 (ps) fC mU fU mU fU mA fC mC fU mC fA mU fG mG fU mG mG fU mG (ps) fU (ps) mU (ps) fC | CUUUGACCUCAUGGUGUUC |
| 339 | EV0107A | mA (ps) fG (ps) mA fG mA fG mA fA mG fA mC fC mU fU mG fA mC (ps) fC (ps) mA | AGAGAGAAGACCUUGACCA |
| 340 | EV0107B | [ST23 (ps)]3 ST43 (ps) mU fG mG fU mC fA mA fG mG fU mC fU mU fC mU fC mU fC mU fC (ps) fC (ps) mU | UGGUCAAGGUCUUCUCUCU |
| 341 | EV0108A | mC (ps) fU (ps) mU fG mU fC mU fG mU fC mU fG mG fA mU fG mA (ps) fA (ps) mG | CUUGUCUGUCUGGAUGAAG |
| 342 | EV0108B | [ST23 (ps)]3 ST43 (ps) mC mU mU mC mA mU fC fC fA mG mA mC mA mG mA mC mA mA irA | CUUCAUCCAGACAGACAAA |
| 343 | EV0109A | mG (ps) fU (ps) mA fG mA fU mG fG mU fC mU fU mG fU mC fU mG (ps) fU (ps) mC | GUAGAUGGUCUUGUCUGUC |
| 344 | EV0109B | [ST23 (ps)]3 ST43 (ps) mG mA mC mA mG mA mC fA fA mG mA mC mC mA mU mC mU mA mA irA | GACAGACAAGACCAUCUAA |
| 345 | EV0110A | mU (ps) fC (ps) mU fU mG fG mU fG mA fA mG fU mG fG mA fU mC (ps) fU (ps) mG | UCUUGGUGAAGUGGAUCUG |
| 346 | EV0110B | [ST23 (ps)]3 ST43 (ps) mC mA mG mA mU mC fC mA fC mU mU mC mA mC mA mA mG irA | CAGAUCCACUUCACCAAGA |
| 347 | EV0111A | mG (ps) fU (ps) mU fG mU fA mA fU mA fG mG fC mG fU mA fG mA (dsy) fG (dsy) mC | GUUGUAAUAGGCGUAGACC |
| 348 | EV0111B | [ST23 (ps)]3 ST43 (ps) mG mG mU mC mU mA fC fG fC mC mU mA mU mU mA mC mA mA irA | GGUCUACGCCUAUUACAAA |
| 349 | EV0312A | mA (ps) fU (ps) mU fG mU fA mA fU mA fG mG fC mG fU mA fG mA (ps) fC (ps) mC | AUUGUAAUAGGCGUAGACC |
| 350 | EV0112B | [ST23 (ps)]3 ST43 (ps) fG mG fU mC fU mA fC mG fC mC fU mA fU mU fA mC fA (ps) mA (ps) fU | GGUCUACGCCUAUUACAAU |
| 351 | EV0313A | mA (ps) fU (ps) mG fU mA fG mA fU mG fG mU fC mU fU mG fU mC (ps) fU (ps) mG | AUGUAGAUGGUCUUGUCUG |
| 352 | EV0313B | [ST23 (ps)]3 ST43 (ps) fC mA fG mA fC mA fA mG fA mC fC mA fU mC fU mA fC (ps) mA (ps) fU | CAGACAAGACCAUCUACAU |
| 353 | EV0201A | mU (ps) fG (ps) mA fG mA fG mA fA mG fA mC fC mU fU mG fA mC (ps) fC (ps) mA | UGAGAGAAGACCUUGACCA |
| 354 | EV0201B | [ST23 (ps)]3 ST43 (ps) mU mG mG mU mC mA fA fG fG mU mC mU mU mC mU mC mU (ps) mC (ps) mU | UGGUCAAGGUCUUCUCUCU |
| 355 | EV0202B | Ser(GN) (ps) mU (ps) mG (ps) mG mU mC mA fG fG mU mC mU mU mC mU (ps) mC (ps) mU (ps) Ser (GN) | UGGUCAAGGUCUUCUCUCU |
| 356 | EV0203A | (vp)-mU fG mA fG mA fG mA fA mG fA mC fC mU fU mG fA mC (ps) fC (ps) mA | UGAGAGAAGACCUUGACCA |

TABLE 5-continued

Summary sequence table

| SEQ ID NO: | Name (A = 1st strand; B = 2nd strand) | Sequence 5'-3' | Unmodified sequence 5'-3' counterpart |
|---|---|---|---|
| 357 | EV0205B | [ST23 (ps)]3 ST43 (ps) mC mA mG mA mU mC fC fA fC mU mU mC mA mC mC mA mA (ps) mG (ps) mA | CAGAUCCACUUCACCAAGA |
| 358 | EV0206B | Ser(GN) (ps) mC (ps) mA (ps) mG mA mU mC fC fA fC mU mU mC mA mC mC mA mA (ps) mG (ps) mA (ps) Ser (GN) | CAGAUCCACUUCACCAAGA |
| 359 | EV0207A | (vp)-mU (ps) fC (ps) mU fU mG fG mU fG mA fA mG fU mG fG mA fU mC (ps) fU (ps) mG | UCUUGGUGAAGUGGAUCUG |
| 360 | EV0209A | (vp)-mU fC mU fU mG fG mU fG mA fA mG fU mG fG mA fU mC (ps) fU (ps) mG | UCUUGGUGAAGUGGAUCUG |
| 361 | EV0201Aun | UGAGAGAAGACCUUGACCA | UGAGAGAAGACCUUGACCA |
| 362 | EJ0001Aun | UGAGAGAAGACCUUGACCA | UGAGAGAAGACCUUGACCA |
| 363 | EJ0001Bun | UGGUCAAGGUCUUCUCUCU | UGGUCAAGGUCUUCUCUCU |
| 364 | EJ0002Aun | UGAGAGACGACCUUGACCA | UGAGAGACGACCUUGACCA |
| 365 | EJ0003Aun | UGAGAGAAUACCUUGACCA | UGAGAGAAUACCUUGACCA |
| 366 | EJ0004Aun | UGAGAGAAGACCUUGACCG | UGAGAGAAGACCUUGACCG |
| 367 | EJ0004Bun | CGGUCAAGGUCUUCUCUCU | CGGUCAAGGUCUUCUCUCU |
| 368 | EJ0005Aun | AUGAGCUUCGUAGAGAUUC | AUGAGCUUCGUAGAGAUUC |
| 369 | EJ0005Bun | GAAUCUCUACGAAGCUCAU | GAAUCUCUACGAAGCUCAU |
| 370 | EJ0006Aun | UUGUAGUAGCGGAUCUUGG | UUGUAGUAGCGGAUCUUGG |
| 371 | EJ0006Bun | CCAAGAUCCGCUACUACAC | CCAAGAUCCGCUACUACAC |
| 372 | EJ0007Aun | UUCUGUCUGGAUGAAGAGG | UUCUGUCUGGAUGAAGAGG |
| 373 | EJ0007Bun | CCUCUUCAUCCAGACAGAC | CCUCUUCAUCCAGACAGAC |
| 374 | EJ0009Bun | UGGUCAAGGUCUUCUCUCA | UGGUCAAGGUCUUCUCUCA |
| 375 | EJ0010Bun | UGGUCAAGGUCGUCUCUCA | UGGUCAAGGUCGUCUCUCA |
| 376 | EJ0011Bun | CGGUCAAGGUCUUCUCUCA | CGGUCAAGGUCUUCUCUCA |
| 377 | EJ0012Aun | UGAGAGACGACCUUGACCG | UGAGAGACGACCUUGACCG |
| 378 | EJ0012Bun | CGGUCAAGGUCGUCUCUCA | CGGUCAAGGUCGUCUCUCA |
| 379 | EJ0014Bun | CCAAGAUCCGCUACUACAA | CCAAGAUCCGCUACUACAA |
| 380 | EJ0015Bun | CCUCUUCAUCCAGACAGAA | CCUCUUCAUCCAGACAGAA |
| 381 | EJ0001A | mU (ps) fG (ps) mA fA mG mA fA mG fA mC fC mU fU mG fA mC (ps) fC (ps) mA | UGAGAGAAGACCUUGACCA |
| 382 | EJ0001B | mU (ps) mG (ps) mG mU mC mA fA fG fG mU mC mU mU mC mU (ps) mC (ps) mU | UGGUCAAGGUCUUCUCUCU |
| 383 | EJ0002A | mU (ps) fG (ps) mA fG mA fG mA fC mG fA mC fC mU fU mG fA mC (ps) fC (ps) mA | UGAGAGACGACCUUGACCA |
| 384 | EJ0003A | mU (ps) fG (ps) mA fG mA fG mA fA mU fA mC fC mU fU mG fA mC (ps) fC (ps) mA | UGAGAGAAUACCUUGACCA |
| 385 | EJ0004A | mU (ps) fG (ps) mA fG mA fG mA fA mC fC mU fU mG fA mC (ps) fC (ps) mG | UGAGAGAAGACCUUGACCG |
| 386 | EJ0004B | mC (ps) mG (ps) mG mU mC mA fA fG fG mU mC mU mU mC mU (ps) mC (ps) mU | CGGUCAAGGUCUUCUCUCU |

TABLE 5-continued

Summary sequence table

| SEQ ID NO: | Name (A = 1st strand; B = 2nd strand) | Sequence 5'-3' | Unmodified sequence 5'-3' counterpart |
|---|---|---|---|
| 387 | EJ0005A | mA (ps) fU (ps) mG fA mG fC mU fU mC fG mU fA mG fA mG fA mU (ps) fU (ps) mC | AUGAGCUUCGUAGAGAUUC |
| 388 | EJ0005B | mG (ps) mA (ps) mA mU mC mU fC fU fA mC mG mA mA mG mC mU mC (ps) mA (ps) mU | GAAUCUCUACGAAGCUCAU |
| 389 | EJ0006A | mU (ps) fU (ps) mG fU fA fG mU fA mG fC mG fG mA fU mC fU mU (ps) fG (ps) mG | UUGUAGUAGCGGAUCUUGG |
| 390 | EJ0006B | mC (ps) mC (ps) mA mA mG mA fU fC fC mG mC mU mA mC mU mA mC (ps) mA (ps) mC | CCAAGAUCCGCUACUACAC |
| 391 | EJ0007A | mU (ps) fU (ps) mC fU mG fU mC fU mG fG mA fU mG fA mA fG mA (ps) fG (ps) mG | UUCUGUCUGGAUGAAGAGG |
| 392 | EJ0007B | mC (ps) mC (ps) mU mC mU fC fA fU mC mA mG mA mC mA mG (ps) mA (ps) mC | CCUCUUCAUCCAGACAGAC |
| 393 | EJ0008B | [ST23 (ps)]3 ST43 (ps) mU mG mG mU mC mA fA fG fG mU mC mU mU mC mU mC mU (ps) mC (ps) mU | UGGUCAAGGUCUUCUCUCU |
| 394 | EJ0009B | [ST23 (ps)]3 ST43 (ps) mU mG mG mU mC mA fA fG fG mU mC mU mU mC mU mC mU (ps) mC (ps) mA | UGGUCAAGGUCUUCUCUCA |
| 395 | EJ0002A | mU (ps) fG (ps) mA fG mA fG mA fC mG fA mC fC mU fU mG fA mC (ps) fC (ps) mA | UGAGAGACGACCUUGACCA |
| 396 | EJ0010B | [ST23 (ps)]3 ST43 (ps) mU mG mG mU mC mA fA fG fG mU mC mG mU mC mU mC mU (ps) mC (ps) mA | UGGUCAAGGUCGUCUCUCA |
| 397 | EJ0011B | [ST23 (ps)]3 ST43 (ps) mC mG mG mU mC mA fA fG fG mU mC mU mU mC mU mC mU (ps) mC (ps) mA | CGGUCAAGGUCUUCUCUCA |
| 398 | EJ0012A | mU (ps) fG (ps) mA fG mA fG mA fC mG fA mC fC mU fU mG fA mC (ps) fC (ps) mG | UGAGAGACGACCUUGACCG |
| 399 | EJ0012B | [ST23 (ps)]3 ST43 (ps) mC mG mG mU mC mA fA fG fG mU mC mG mU mC mU mC mU (ps) mC (ps) mA | CGGUCAAGGUCGUCUCUCA |
| 400 | EJ0013B | [ST23 (ps)]3 ST43 (ps) mG mA mA mU mC mU fC fU fA mC mG mA mA mG mC mU mC (ps) mA (ps) mU | GAAUCUCUACGAAGCUCAU |
| 401 | EJ0014B | [ST23 (ps)]3 ST43 (ps) mC mC mA mA mG mA fU fC fC mG mC mU mA mC mU mA mC (ps) mA (ps) mA | CCAAGAUCCGCUACUACAA |
| 402 | EJ0015B | [ST23 (ps)]3 ST43 (ps) mC mC mU mC mU mU fC fA fU mC mC mA mG mA mC mA mG (ps) mA (ps) mA | CCUCUUCAUCCAGACAGAA |
| 403 | EJ0016A | (vp)-mU fG mA fG mA fG mA fC mG fA mC fC mU fU mG fA mC (ps) fC (ps) mG | UGAGAGACGACCUUGACCG |
| 404 | EJ0017A | (vp)-mU fG mA fG mA fG mA fC mG fA mC fC mU fU mG fA mC fC (ps2) mG | UGAGAGACGACCUUGACCG |
| 405 | EJ0017B | [ST23]3 ST43 mC (ps2) mG mG mU mC mA fA fG fG mU mC mG mU mC mU mC mU mC (ps2) mA | CGGUCAAGGUCGUCUCUCA |
| 406 | EJ0018A | mU (ps) fG (ps) mA fG mA fG mA fC mG fA mC fC mU fU mG fA mC fC (ps2) mG | UGAGAGACGACCUUGACCG |
| 407 | EJ0017B | [ST23]3 ST43 mC (ps2) mG mG mU mC mA fA fG fG mU mC mG mU mC mU mC mU mC (ps2) mA | CGGUCAAGGUCGUCUCUCA |
| 408 | EJ0019A | (vp)-mU fU mG fU mA fG mU fA mG fC mG fG mA fU mC fU mU (ps) fG (ps) mG | UUGUAGUAGCGGAUCUUGG |
| 409 | EJ0020A | (vp)-mU fU mG fU mA fG mU fA mG fC mG fG mA fU mC fU mU fG (ps2) mG | UUGUAGUAGCGGAUCUUGG |
| 410 | EJ0020B | [ST23]3 ST43 mC (ps2) mC mA mA mG mA fU fC fC mG mC mU mA mC mU mA mC mA (ps2) mA | CCAAGAUCCGCUACUACAA |

TABLE 5-continued

Summary sequence table

| SEQ ID NO: | Name (A = 1st strand; B = 2nd strand) | Sequence 5'-3' | Unmodified sequence 5'-3' counterpart |
|---|---|---|---|
| 411 | EJ0021A | (vp)-mU fU mC fU mG fU mC fU mG fG mA fU mG fA mA fG mA (ps) fG (ps) mG | UUCUGUCUGGAUGAAGAGG |
| 412 | EJ0022A | (vp)-mU fU mC fU mG fU mC fU mG fG mA fU mG fA mA fG (ps2) mG | UUCUGUCUGGAUGAAGAGG |
| 413 | EJ0022B | [ST23]3 ST43 mC (ps2) mC mU mC mU mU fC fA fU mC mC mA mG mA mC mA mG mA (ps2) mA | CCUCUUCAUCCAGACAGAA |
| 414 | EJ0023A | mU (ps) fU (ps) mC fU mG fU mC fU mG fG mA fU mG fA mA fG mA fG (ps2) mG | UUCUGUCUGGAUGAAGAGG |
| 415 | EJ0022B | [ST23]3 ST43 mC (ps2) mC mU mC mU mU fC fA fU mC mC mA mG mA mC mA mG mA (ps2) mA | CCUCUUCAUCCAGACAGAA |
| 416 | EV0210Aun | UAUAUAUUCAUGAGCUUCG | UAUAUAUUCAUGAGCUUCG |
| 417 | EV0210A | mU (ps) fA (ps) mU fA mU fA mU fU mC fA mU fG mA fG mC fU mU (ps) fC (ps) mG | UAUAUAUUCAUGAGCUUCG |
| 418 | EV0210B | [ST23 (ps)]3 ST43 (ps) mC mG mA mA mG mC fU fC fA mU mG mA mA mU mA mU mA (ps) mU (ps) mU | CGAAGCUCAUGAAUAUAUU |
| 419 | EV0211A | (vp)-mU fA mU fA mU fA mU fU mC fA mU fG mA fG mC fU mU (ps) fC (ps) mG | UAUAUAUUCAUGAGCUUCG |
| 420 | EV0212A | (vp)-mU fA mU fA mU fA mU fU mC fA mU fG mA fG mC fU mU fC (ps2) mG | UAUAUAUUCAUGAGCUUCG |
| 421 | EV0211B | [ST23]3 ST43 mC (ps2) mG mA mA mG mC fU fC fA mU mG mA mA mU mA mU mA mU (ps2) mU | CGAAGCUCAUGAAUAUAUU |
| 422 | EV0213A | mU (ps) fA (ps) mU fA mU fA mU fU mC fA mU fG mA fG mC fU mU fC (ps2) mG | UAUAUAUUCAUGAGCUUCG |
| 423 | EJ0020B without ligand | mC (ps2) mC mA mA mG mA fU fC fC mG mC mU mA mC mU mA mC mA (ps2) mA | CCAAGAUCCGCUACUACAA |
| 424 | EV0211B without ligand | mC (ps2) mG mA mA mG mC fU fC fA mU mG mA mA mU mA mU mA mU (ps2) mU | CGAAGCUCAUGAAUAUAUU |
| 425 | EV0210B without ligand | mC mG mA mA mG mC fU fC fA mU mG mA mA mU mA mU mA (ps) mU (ps) mU | CGAAGCUCAUGAAUAUAUU |

The invention claimed is:

1. A double-stranded nucleic acid for inhibiting expression of complement component C3, wherein the nucleic acid comprises a first strand and a second strand, wherein:
the first strand sequence comprises a sequence of 5' (vp)-mU fU mG fU mA fG mU fA mG fC mG fG mA fU mC fU mU fG (ps2) mG 3' (SEQ ID NO: 409) and the second strand sequence comprises a sequence of 5'mC (ps2) mC mA mA mG mA fU fC fC mG mC mU mA mC mU mA mC mA (ps2) mA 3' (SEQ ID NO: 423).

2. The nucleic acid of claim 1, wherein the first strand sequence consists of SEQ ID NO: 409.

3. The nucleic acid of claim 1, wherein the second strand consists of SEQ ID NO: 423.

4. The nucleic acid of claim 1, wherein the first strand consists of SEQ ID NO: 409 and the second strand consists of SEQ ID NO: 423.

5. The nucleic acid of claim 1, wherein the nucleic acid is conjugated to a ligand.

6. The nucleic acid of claim 5, wherein the ligand comprises (i) one or more N-acetyl galactosamine (GalNAc) moieties or derivatives thereof, and (ii) a linker, wherein the linker conjugates the at least one GalNAc moiety or derivative thereof to the nucleic acid.

7. A composition comprising a nucleic acid of claim 1 and a solvent and/or a delivery vehicle and/or a physiologically acceptable excipient and/or a carrier and/or a salt and/or a diluent and/or a buffer and/or a preservative and/or a further therapeutic agent selected from the group consisting of an oligonucleotide, a small molecule, a monoclonal antibody, a polyclonal antibody and a peptide.

8. The nucleic acid of claim 5, having the structure

9. The nucleic acid of claim 5, wherein the ligand is conjugated to the 5' end of the second strand.

10. The nucleic acid of claim 5, wherein the second strand consists of SEQ ID NO: 423 or SEQ ID NO: 410.

11. The nucleic acid of claim 5, wherein the first strand consists of SEQ ID NO: 409.

12. The nucleic acid of claim 5, wherein the first strand consists of SEQ ID NO: 409 and the second strand consists of SEQ ID NO: 410 or SEQ ID NO: 423.

13. The nucleic acid of claim 8, wherein the second strand consists of SEQ ID NO: 423.

14. The nucleic acid of claim 8, wherein the second strand consists of SEQ ID NO: 410.

15. The nucleic acid of claim 8, wherein the first strand consists of SEQ ID NO: 409.

16. The nucleic acid of claim 8, wherein the first strand consists of SEQ ID NO: 409 and the second strand consists of SEQ ID NO: 423 or SEQ ID NO: 410.

17. The nucleic acid of claim 8, wherein the ligand is conjugated to the 5' end of the second strand.

18. The nucleic acid of claim 12, wherein the ligand is conjugated to the 5' end of the second strand.

19. The nucleic acid of claim 16, wherein the ligand is conjugated to the 5' end of the second strand.

20. A method of preventing, decreasing the risk of suffering from, or treating a disease, disorder or syndrome comprising administering a pharmaceutically effective amount of a nucleic acid of claim 1 to an individual in need of treatment, wherein the disease, disorder or syndrome is selected from the group consisting of C3 Glomerulopathy (C3G), Cold Agglutinin Disease (CAD) and IgA nephropathy (IgA N), Paroxysmal Nocturnal Hemoglobinuria (PNH),

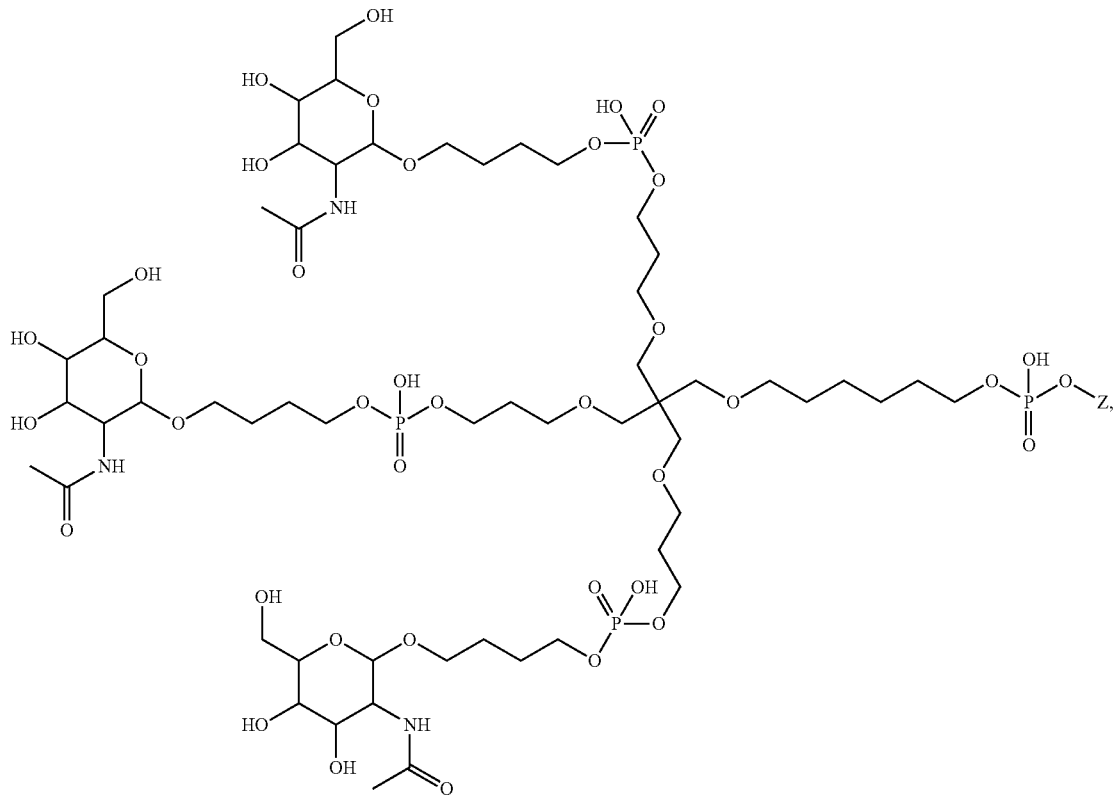

wherein Z represents the nucleic acid according to claim 1.

age-related macular degeneration (AMD), antineutrophil cytoplasmic autoantibodies-associated vasculitis (ANCA-AV), and lupus nephritis.

21. The method of claim 20, wherein the first strand consists of SEQ ID NO: 409.

22. The method of claim 20, wherein the second strand consists of SEQ ID NO: 423.

23. The method of claim 20, wherein the second strand consists of SEQ ID NO: 410.

24. The method of claim 20, wherein the first strand consists of SEQ ID NO: 409 and the second strand consists of SEQ ID NO: 423 or SEQ ID NO: 410.

25. The method of claim 20, wherein the nucleic acid is conjugated to a ligand and has the following structure:

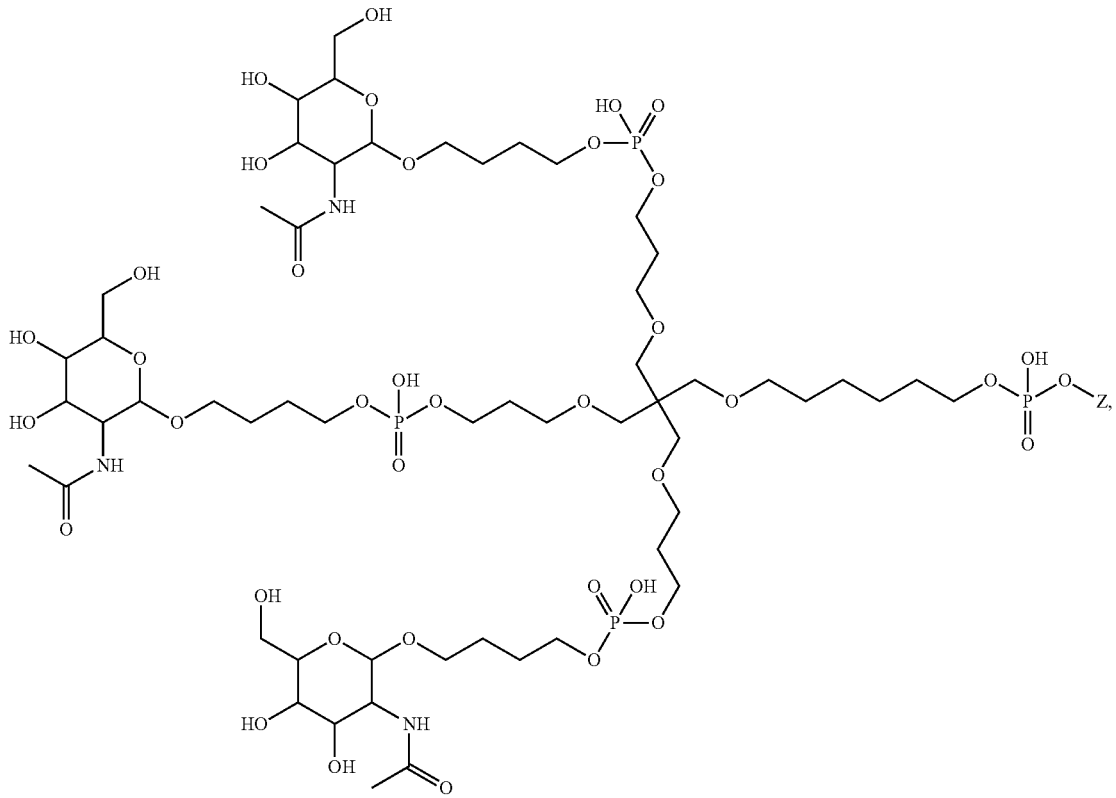

wherein Z represents the nucleic acid according to claim 1.

26. The method of claim 25, wherein the first strand of the nucleic acid consists of SEQ ID NO: 409.

27. The method of claim 25, wherein the second strand of the nucleic acid consists of SEQ ID NO: 423.

28. The method of claim 25, wherein the second strand of the nucleic acid consists of SEQ ID NO: 410.

29. The method of claim 25, wherein the first strand of the nucleic acid consists of SEQ ID NO: 409 and the second strand of the nucleic acid consists of SEQ ID NO: 423 or SEQ ID NO: 410.

* * * * *